(12) United States Patent
Doranz et al.

(10) Patent No.: US 8,574,590 B2
(45) Date of Patent: Nov. 5, 2013

(54) LIPOPARTICLES COMPRISING PROTEINS, METHODS OF MAKING, AND USING THE SAME

(75) Inventors: Benjamin J. Doranz, Narberth, PA (US); Sharon Willis, Wayne, PA (US); Eric Ross, Philadelphia, PA (US); Tiffani Anne Greene, Cherry Hill, NJ (US)

(73) Assignee: Integral Molecular, Inc., Philadelphia, PA (US)

( * ) Notice: Subject to any disclaimer, the term of this patent is extended or adjusted under 35 U.S.C. 154(b) by 1304 days.

(21) Appl. No.: 10/901,399

(22) Filed: Jul. 28, 2004

(65) Prior Publication Data

US 2005/0123563 A1 Jun. 9, 2005

Related U.S. Application Data

(60) Provisional application No. 60/491,477, filed on Jul. 30, 2003, provisional application No. 60/491,633, filed on Jul. 30, 2003, provisional application No. 60/498,755, filed on Aug. 29, 2003, provisional application No. 60/502,478, filed on Sep. 12, 2003, provisional application No. 60/509,677, filed on Oct. 7, 2003, provisional application No. 60/509,608, filed on Oct. 7, 2003, provisional application No. 60/509,575, filed on Oct. 7, 2003.

(51) Int. Cl.
*A61K 39/12* (2006.01)
*A61K 39/21* (2006.01)

(52) U.S. Cl.
USPC .......................... 424/204.1; 424/208.1; 435/5

(58) Field of Classification Search
None
See application file for complete search history.

(56) References Cited

U.S. PATENT DOCUMENTS

| | | | |
|---|---|---|---|
| 5,175,099 | A | 12/1992 | Wills |
| 6,376,236 | B1 | 4/2002 | Dubensky et al. |
| 6,583,121 | B1 | 6/2003 | Johnston et al. |
| 2002/0183247 | A1 * | 12/2002 | Doms et al. ................. 514/8 |

FOREIGN PATENT DOCUMENTS

| | | |
|---|---|---|
| WO | 96/16087 | 5/1996 |
| WO | WO 01/02551 | 1/2001 |

OTHER PUBLICATIONS

Hoffman TL. et al "A biosensor assay for studying ligand-membrane receptor interactions: Binding of antibodies and HIV-1 Env to chemokine receptors" PNAS 2000, 97: 11215-11220.*
Seifert R. et al "GPCR-G alpha fusion proteins: molecular analysis of receptor-G-protein coupling". Trends Pharmacol Sci. Sep. 1999; 20(9):383-9).*
Milligan G et al. "Chimaeric G alpha proteins: their potential use in drug discovery". Trends Pharmacol Sci. Mar. 1999;20(3):118-124.*
Martinez X. et al. "CD4-Independent protective cytotoxic T cells induced in early life by a non-replicative delicery system based on virus-like particles" Virology 305, 428-435 (2003).*
McEwen DP et a. "Fluorescent BODIPY-GTP analogs: real-time measurement of nucleotide binding to G proteins". Anal Biochem. Apr. 1, 2001;291(1):109-17.*
Mills K. et al "HIV p24-specific helper T cell clones from immunized primates recognize highly conserved regions of HIV-1". J Immunol. Mar. 1, 1990;144(5):1677-83.*
Morikawa Y. et al. "In vitro processing of human immunodeficiency virus type 1 Gag virus-like particles" Virology, Jul. 5, 2000;272(2):366-74.*
Chen, "Influenza Virus Hemagglutinin and Neuraminidase, but Not the Matrix Protein, Are Required for Assembly and Budding of Plasmid-Derived Virus-Like Particles" J. Virology, 81(13):7111-7123, 2007.*
Adamson CS, et al. "A block in virus-like particle maturation following assembly of murine leukaemia virus in insect cells." Virology. Sep. 30, 2003;314(2):488-96.*
Adamson CS Erratum to "A block in virus-like particle maturation following assembly of murine leukaemia virus in insect cells." Virology. Dec. 20, 2003;317(2):384-6.*
Adamson CS. et al. Erratum to "A block in virus-like particle maturation following assembly of murine leukaemia virus in insect cells" [Virology 314 (2003) 488-496]in Virology. Dec. 20, 2003;317(2):384-6.*
Kim, J-S. et al. "Development of a packaging cell line for propagation of replication-deficient adenovirus vector" Experimental and Molecular Medicine, vol. 33, No. 3, 145-149, Sep. 2001.*
Okimoto at al., "VSV-G envelope glycoprotein forms complexes with plasmid DNA and MLV retrovirus-like particles in cell-free conditions and e3nhances DNA transfection," *Molecular Therapy*, (Sep. 2001); 4(3) 232-238.
Rice et al., "Inhibition of HIV-1 replication in alveolar macrophages by adenovirus gene transfer vectors," *Am J Respir Cell Miol Biol.*, Aug. 2002; 27(2):214-219.
Shiver et al., "Replication-incompetent adenoviral vaccine vect 415(6869):331-5or elicits effective anti-immunodeficiency-virus immunity," *Nature* (Jan. 2002).
Adamson et al., "A block in virus-like particle maturation following assembly of murine leukaemia virus in insect cells," *Virology* (2003) vol. 314, pp. 488-496.
Andrawiss et al., "Murine leukemia virus particle assembly quantitated by fluorescence microscopy: role of Gag-Gag interactions and membrane association," (2003) *J Virol* vol. 77, pp. 11651-11660.
Arthur et al., "Chemical Inactivation of Retroviral Infectivity by Targeting Nucleocapsid Protein Zinc Fingers: A Candidate SIV Vaccine," *AIDS Research and Human Retroviruses*, 1998, vol. 14, Supp. 3, pp. S311-S319.
Ausubel et al., (2001). Current Protocols in Molecular Biology.
Balliet et al., "Efficient infection mediated by viral receptors incorporated into retroviral particles," *Journal of Virology* (1998), vol. 72, pp. 671-676.

(Continued)

*Primary Examiner* — Stacy B. Chen
(74) *Attorney, Agent, or Firm* — Pepper Hamilton LLP

(57) ABSTRACT

The present invention relates to lipoparticles. The invention also relates to producing lipoparticles. The invention further relates to lipoparticles comprising a viral structural protein. The invention further relates to a lipoparticle comprising a membrane protein, and the lipoparticle can be attached to a sensor surface. The invention further relates to methods of producing and using the lipoparticle to, inter alia, assess protein binding interactions.

19 Claims, 33 Drawing Sheets

(56) References Cited

OTHER PUBLICATIONS

Baribaud et al., "Antigenically distinct conformations of CXCR4," *Journal of Virology* (2001) vol. 75, pp. 8957-8967.
Bartlett et al., "Fluorescent viral vectors: a new technique for the pharmacological analysis of gene therapy," *Nat Med* (1998), vol. 4, pp. 635-637.
Bastiani et al., "Host cell-dependent alterations in Envelope components of human immunodeficiency virus type 1 virions," *Journal of Virology*, 1997, vol. 71, pp. 3444-3450.
Bechor et al., "Recombinant microorganisms as environmental biosensors: pollutants detection by *Escherichia coli* bearing fabA'::lux fusions," *J Biotechnol.* (2002) 14;94(1)125-32.
Belgrader, et al., "PCR detection of bacteria in seven minutes," *Science*, (1999) 284, 449-450.
Belgrader, et al, "A reusable flow-through polymerase chain reaction instrument for the continuous monitoring of infectious biological agents," *Anal Chem* 2003, vol. 75, pp. 3446-3450.
Belkin, S. "Microbial whole-cell sensing systems of environmental pollutants," *Curr Opin Microbiol*, 2003, vol. 6, pp. 206-212.
Bennett et al., "Amino Acids Encoded Downstream of *gag* Are Not Required by Rous Sarcoma Virus Protease During Gag-Mediated Assembly," *Journal of Virology*, 1991, vol. 65, No. 1, pp. 272-280.
Berger et al., "Chemokine receptors as HIV-I coreceptors: Roles in viral entry, tropism, and disease," *Annu Rev Immunol*, (1999), vol. 17, pp. 657-700.
Bergman, et al., "Vesicular stomatitis virus expressing a chimeric Sindbis glycoprotein containing an Fc antibody binding domain targets to Her2/neu overexpressing breast cancer cells," *Virology* (2003), vol. 316, pp. 337-347.
Berson, et al., "A seven-transmembrane domain receptor involved in fusion and entry of T-cell-tropic human immunodeficiency virus type 1 strains," *Journal of Virology* 1996, vol. 70, pp. 6288-6295.
Bieganski et al., "Stabilization of active recombinant retroviruses in an amorphous dry state with trehalose," *Biotechnol Prog*,(1998), vol. 14, pp. 615-620.
Bieri et al, "Micropatterned immobilization of a G protein-coupled receptor and direct detection of G protein activation," *Nature Biotechnology* (1999), vol. 17, pp. 1105-1108.
Blanpain et al., "Multiple charged and aromatic residues in CCR5 amino-terminal domain are involved in high affinity binding of both chemokines and HIV-1 Env protein," *Journal of Biological Chemistry* (1999), vol. 274, pp. 34719-34727.
Bradley et al, "Anthrax toxin receptor proteins," *Biochem Pharmacol* (2003), vol. 65, pp. 309-314.
Caffrey, "A lipid's eye view of membrane protein crystallization in mesophases," *Curr Opin Struct Biol* (2000), vol. 10, pp. 486-497.
Canziani et al., "Exploring biomolecular recognition using optical biosensors," *Methods* (1999), vol. 19, pp. 253-269.
Caplen et al., "Adeno-retroviral chimeric viruses as in vivo transducing agents," *Gene Ther* (1999), vol. 6, pp. 454-459.
Capobianchi et al., "A Simple and Reliable Method to Detect Cell Membrane Proteins on Infectious Human Immunodeficiency Virus Type 1 Particles," *The Journal of Infection Diseases*, 1994, vol. 169, pp. 886-889.
Carfi et al., "Crystallization and preliminary diffraction studies of the ectodomain of the envelope glycoprotein D from herpes simplex virus 1 alone and in complex with the ectodomain of the human receptor," *HveA. Acta Crystallogr D Biol Crystallogr* (2002), vol. 58, pp. 836-838.
Carfi et al., "Herpes simplex virus glycoprotein D bound to the human receptor," *HveA. Mol Cell* (2001), vol. 8, pp. 169-179.
Caterina et al., "The capsaicin receptor: a heat-activated ion channel in the pain pathway," *Nature* (1997), vol. 389, pp. 816-824.
Chabot et al., "N-linked glycosylation of CXCR4 masks coreceptor function for CCR5-dependent human immunodeficiency virus type 1 isolates," *J Virol* (2000), vol. 74, pp. 4404-4413.
Chan, "Fluorescence resonance energy transfer analysis of cell surface receptor interactions and signaling using spectral variants of the green fluorescent protein," *Cytometry* (2001), vol. 44, pp. 361-368.
Chroboczek et al., "The Sequence of the Genome of Adenovirus Type 5 and Its Comparison With the Genome of Adenovirus Type 2," *Virology*, 1992, vol. 186, pp. 280-285.
Clapham, "TRP channels as cellular sensors," *Nature* (2003), vol. 426, pp. 517-524.
Cocchi et al., "Identification of RANTES, MIP-1a, and MIP-lb as the major HIV-suppressive factors produced by $CD8^+T$ cells," *Science* (1995), vol. 270, pp. 1811-1815.
Conway et al., "The Use of Biosensors to Study GPCR Function: Applications for High-Content Screening," *Receptors and Channels*, 2002, vol. 8, pp. 331-341.
Cooper et al., "Direct and sensitive detection of a human virus by rupture event scanning," *Nat Biotechnol* (2001), vol. 19, pp. 833-837.
Cooper et al., "A vesicle capture sensor chip for kinetic analysis of interactions with membrane-bound receptors," *Analytical Biochemistry* (2000), vol. 277, pp. 196-205.
Cooper et al., "Surface plasmon resonance analysis at a supported lipid monolayer," *Biochimica et Biophysica Acta* (1998), vol. 1373, pp. 101-111.
Coorssen et al., "Quantitative femto-to attomole Munuriodetection of regulated secretory vesicle proteins critical to exocytosis," *Anal Biochem* (2002), vol. 307, pp. 54-62.
Crump et al., "Solution structure and basis for functional activity of stromal cell-derived factor-1; dissociation of CXCR4 activation from binding and inhibition of HIV-1," EMBO (1997), vol. 16, pp. 6996-7007.
Cunningham et al., "Colorimetric resonant reflection as a direct biochemical assay technique," *Sensors and Actuators* (2002a), vol. B81, pp. 316-328.
Cunningham et al., "A plastic colorimetric resonant optical biosensor for multiparallel detection of label-free biochemical interactions," *Sensors and Actuators* (2002b), vol. B85, pp. 219-226.
Dalton et al., "Vesicular stomatitis virus glycoprotein containing the entire green fluorescent protein on its cytoplasmic domain is incorporated efficiently into virus particles," *Virology* (2001), vol. 279, pp. 414-421.
Day et al., "Direct comparison of binding equilibrium, thermodynamic, and rate constants determined by surface- and solution-based biophysical methods," *Protein Science* (2002), vol. 11, pp. 1017-1025.
Dettenhofer et al., "Highly purified human immunodeficiency virus type 1 reveals a virtual absence of Vif in virions," *J Virol* (1999), vol. 73, pp. 1460-1467.
Deutsch, C. "Potassium channel ontogeny," *Annu Rev Physiol* (2002), vol. 64, pp. 19-46.
Dickinson et al., "A Chemical-Detecting System Based on a Cross-Reactive Optical Sensor Array," *Nature*, 1996, vol. 382, pp. 697-700.
Doranz, "The Use of Envelope for HIV Therapeutics: From Vaccines to Co-Receptors," *Emerging Therapeutic Targets*, 2000, vol. 4, No. 4, pp. 423-437.
Doranz et al., "Use of a gp120 binding assay to dissect the requirements and kinetics of human immunodeficiency virus fusion events," *Journal of Virology* (1999a), vol. 73, pp. 10346-10358.
Doranz et al., "A small-molecule inhibitor directed against the chemokine receptor CXCR4 prevents its use as an HIV-1 coreceptor," *Journal of Experimental Medicine* (1997a), vol. 186, pp. 1395-1400.
Doranz et al., "Two distinct CCR5 domains can mediate coreceptor usage by human immunodeficiency virus type 1," *Journal of Virology* (1997b), vol. 71, pp. 6305-6314.
Doranz et al., "Identification of CXCR4 domains that support coreceptor and chemokine receptor functions," *Journal of Virology* (1999b), vol. 73, pp. 2752-2761.
Doranz et al., "A dual-tropic primary HIV-1 isolate that uses fusin and the b-chemokine receptors CKR-5, CKR-3, and CKR-2b as fusion cofactors," *Cell* (1996), vol. 85, pp. 1149-1158.
Doyle et al., "The structure of the potassium channel: molecular basis of K+ conduction and selectivity," *Science* (1998), vol. 280, pp. 69-77.
Drews, "Genomic sciences and the medicine of tomorrow," *Nature Biotechnology*, 1996, vol. 14, pp. 1516-1518.

(56) References Cited

OTHER PUBLICATIONS

Duisit et al., "Functional characterization of adenoviral/retroviral chimeric vectors and their use for efficient screening of retroviral producer cell lines," *Human Gene Therapy* (1999), vol. 10, pp. 189-200.
Edinger et al., "Differential utilization of CCR5 by macrophage and T-cell tropic SIV strains," *Proceedings of the National Academy of Sciences*, USA (1997), vol. 94, pp. 4005-4010.
Eidne et al., "Applications of novel resonance energy transfer techniques to study dynamic hormone receptor interactions in living cells," *Trends Endocrinol Metab* (2002), vol. 13, pp. 415-421.
Endres et al., "Targeting of HIV- and SIV-infected cells by CD4-chemokine receptor pseudotypes," *Science* (1997), vol. 278, pp. 1462-1464.
Evans et al., "New turf for CFP/YFP FRET imaging of membrane signaling molecules," *Neuron* (2003), vol. 38, pp. 145-147.
Fang et al., "Membrane protein microarrays," *J Am Chem Soc* (2002), vol. 124, pp. 2394-2395.
Farzan et al., "Tyrosine sulfation of the amino terminus of CCR5 facilitates HIV-1 entry," *Cell* (1999), vol. 96, pp. 667-676.
Gheysen et al., "Assembly and Release of HIV-1 Precursor PR55$^{gag}$ Virus-Like Particles From Recombinant Baculovirus-Infected Insect Cells.," *Cell*, 1989, vol. 59, pp. 103-112.
Giaimis et al., "Flow cytometry distinction between adherent and phagocytized yeast partides," *Cytometry*, 1994, vol. 17, pp. 173-178.
Gonzalez et al., "Voltage Sensing by Fluorescence Resonance energy Transfer in Single Cells," *Biophysical Journal*, 1995, vol. 69(4), pp. 1272-1280.
Graham et al. "A prospective seroepidemiologic study on dengue in children four to nine years of age in Yogyakarta, Indonesia I," *Am J Trop Med Hyg*, 1995, vol. 61, pp. 412-419.
Baik et al., "HIV and SIV gp120 binding does not predict coreceptor function," *Virology* (1999) 259:267-273.
Galameau et al., "Beta-lactamase protein fragment complementation assays as in vivo and in vitro sensors of protein protein interactions," *Nat Biotechnol* (2002), vol. 20, pp. 619-622.
Wong et al., "Direct measurement of a tethered ligand-receptor interaction potential," *Science* (1997) 275:820-822.
Hunter et al., "The adjuvant activity of nonionic block polymer surfactants," *Journal of Immunology* (1981) 127(3):1273-1250.
Gomez-Reino et al., "Association of rheumatoid arthritis with a functional chemokine receptor, CCR5," *Arthritis & Rheumitism* (1999), vol. 42, pp. 989-992.
Sparacio et al., "Membrane fusion between retroviral particles: host-range extension and vaccine prospects," *Virology* (2000) 271:248-252.
Sparacio et al., "Inter-retroviral fusion mediated by human immunodeficiency virus or murine leukemia virus glycoproteins: independent of cellular membranes and membrane vesicles," *Virology* (2002) 294:305-311.
Gubler, D. J., "Dengue and dengue hemorrhagic fever," *Clin Microbial Rev* (1998), vol. 11, pp. 480-496.
Gubler et al., "Emergence of epidemic dengue/dengue hemorrhagic fever as a public health problem in the Americas," *Infect Agents Dis* (1993), vol. 2, pp. 383-393.
Harlow E, Lane D. (1988) *Antibodies: A Laboratory Manual.* Cold Spring Harbor Laboratory Press, Cold Spring Harbor, N.Y.
Haugland RP. (2003) *Molecular Probes handbook of fluorescent probes and research chemicals.* 9th ed. Spence MTZ, ed.
Hanson et al., "Green fluorescent protein variants as ratiometric dual emission pH sensors. 1. Structural characterization and preliminary application," *Biochemistry* (2002), vol. 41, pp. 15477-15488.
Harlow, E., and Lane, D. (1989). Antibodies: A Laboratory Manual (Cold Spring Harbor, Cold Spring Harbor Press).
Haruyama, T., "Micro- and nanobiotechnology for biosensing cellular responses," *Adv Drug Deliv Rev* (2003), vol. 55, pp. 393-401.
Haugland, R. P. (2003). Handbook of Fluorescent Probes and Research Chemicals (Eugene, OR, Molecular Probes, Inc.).
Hemmila et al., "Novel detection strategies for drug discovery," *Drug Discov Today* (2002), vol. 7, pp. S150-S156.

Infrared spectroscopy of supported lipid monolayer, bilayer and multibilayer membranes, *Chemistry and Physics of Lipids* (1998) 96:69-80.
Heyse et al., "Incorporation of rhodopsin in laterally structured supported membranes: observation of transducin actiation with spatially and time-resolved surface plasmon resonance," *Biochemistry* (1998), vol. 37, pp. 507-522.
Hoffman et al., "A biosensor assay for studying ligand-membrane receptor interactions: Binding of antibodies and HIV-1 Env to chemokine receptors," *Proceedings of the National Academy of Sciences*, USA (2000), vol. 97, pp, 11215-11220.
Hoffman et al., "Stable exposure of the coreceptor-binding site in a CD4-independent HIV-1 envelope protein," *Proceedings of the National Academy of Sciences*, USA (1999), vol. 96, pp. 6359-6364.
Hughes et al., "Morphogenic capabilities of human immunodeficiency virus type 1 gag and gag-pol proteins in insect cells," *Virology* (1993), vol. 193, pp. 242-255.
Iqbal et al., "A review of molecular recognition technologies for detection of biological threat agents," *Biosens Bioelectron* (2000), vol. 15, pp. 549-578.
Jendelova et al., "Magnetic resonance tracking of transplanted bone marrow and embryonic stem cells labeled by iron oxide nanoparticles in rat brain and spinal cord," *J Neurosci Res* (2004), vol. 76, pp. 232-243.
Ji et al., "Synthesis and application of submicrometer fluorescence sensing particles for lysosomal pH measurements in murine macrophages," *Anal Chem* (2000), vol. 72, pp. 3497-3503.
Ji et al., "Molecular oxygen-sensitive fluorescent lipobeads for intracellular oxygen measurements in murine macrophages," *Anal Chem* (2001), vol. 73, pp. 3521-3527.
Jiang et al., "Crystal structure and mechanism of a calcium-gated potassium channel," *Nature* (2002), vol. 417, pp. 515-522.
Jiang et al., "X-ray structure of a voltage-dependent K+ channel," *Nature* (2003), vol. 423, pp. 33-41.
Karube et al.,"Immobilized cells used for detection and analysis," *Curr Opin Biotechnol*, 1994, vol. 5, pp. 54-59.
Karacostas et al., "Human immunodeficiency virus-like particles produced by a vaccinia virus expression vector," *Proc Natl Acad Sci U S A*(1989), vol. 86, pp. 8964-8967.
Karlsson et al., "Flow-mediated on-surface reconstitution of G-protein coupled receptors for applications in surface plasmon resonance biosensors," *Analytical Biochemistry* (2002), vol. 300, pp. 132-138.
Yuan et al., "Expression, purification, and characterization of a biologically active bovine enterokinase catalytic subunit in *Escherichia coli*," *Protein Expression and Purification* (2002) 25:300-304.
Khromykh et al., "Encapsidation of the flavivirus kunjin replicon RNA by using a complementation system providing Kunjin virus structural proteins in trans," *J Virol* (1998), vol. 72, pp. 5967-5977.
Khromykh et al., "Subgenomtic replicons of the flavivirus Kunjin: construction and applications," *J Virol* (1997), vol. 71, pp. 1497-1505.
Kimple et al., "RGS12 and RGS14 GoLoco motifs are G alpha(i) interaction sites with guanine nucleotide dissociation inhibitor Activity," *J Biol Chem* (2001), vol. 276, pp. 29275-29281.
Kiselyov et al., "Signalling specificity in GPCR-dependent Ca2+ signalling," *Cell Signal* (2003), vol. 15, pp. 243-253.
Klaassen et al., "Large-scale production and purification of functional recombinant bovine rhodopsin with the use of the baculovirus expression system," *Biochem J* (1999), vol. 342, ( Pt 2), pp. 293-300.
Knipe, D. M., and Howley, P. M., eds. (2001). Fields Virology, 4 edn (Philadelphia, Lippincott Williams & Wilkins).
Lalani et al., "Secreted poxvirus chemokine binding proteins," *Journal of Leukocyte Biology*, 1997, vol. 62, pp. 570-576.
Luker et al., "Optimizing Luciferase Protein Fragment Complementation for Bioluminescent Imaging of Protein-Protein Interactions in Live Cells and Animals," *Methods in Enzymology*, 2002, vol. 385, pp. 349-360.
Le Doux et al., "Complexation of retrovirus with cationic and anionic polymers increases the efficiency of gene transfer," *Hum Gene Ther* (2001), vol. 12, pp. 1611-1621.
Lee et al., "An intricate web: Chemokine receptors, HIV-1, and hematopoiesis," *Stem Cells* (1998), vol. 16, pp. 79-88.

(56) References Cited

OTHER PUBLICATIONS

Lee et al., "Epitope mapping of CCR5 reveals multiple conformational states and distinct but overlapping structures involved in chemokine and coreceptor function," *Journal of Biological Chemistry* (1999), vol. 274, pp. 9617-9626.

Leopold et al., "Dynein- and microtubule-mediated translocation of adenovirus serotype 5 occurs after endosomal lysis," *Hum Gene Ther* (2000), vol. 11, pp. 151-165.

Li et al., "Production of infectious recombinant Moloney murine leukemia virus particles in BHK cells using Semliki Forest virus-derived RNA expression vectors," *Proc Natl Acad Sci U S A* (1996), vol. 93, pp. 11658-11663.

Lin et al., "A label-free optical technique for detecting small molecule interactions," *Biosens Bioelectron* (2002), vol. 17, pp. 827-834.

Lin, X., "Construction of new retroviral producer cells from adenoviral and retroviral vectors," *Gene Therapy* (1998), vol. 5, pp. 1251-1258.

Lu et al., "T1-T1 interactions occur in ER membranes while nascent Kv peptides are still attached to ribosomes," *Biochemistry* (2001), vol. 40, pp. 10934-10946.

Lu, et al., "Evolution of HIV-1 coreceptor usage through interactions with distinct CCR5 and CXCR4 domains," *Proceedings of the National Academy of Sciences*, USA (1997), vol. 94, pp. 6426-6431.

Wu et al., "Bioassay of prostate-specific antigen (PSA) using microcantilevers," *Nature Biotechnology* (2001) 19:856-860.

Lundstrom, K., "Alphaviruses as expression vectors," *Curr Opin Biotechnol* (1997), vol. 8, pp. 578-582.

Lundstrom, K. "Semliki Forest virus vectors for rapid and high-level expression of integral membrane proteins," *Biochim Biophys Acta* (2003), vol. 1610, pp. 90-96.

Lundstrom et al., "Semliki Forest virus vectors: efficient vehicles for in vitro and in vivo gene delivery," *FEBS Lett* (2001), vol. 504, pp. 99-103.

Ma et al., "Submicrometric lipobead-based fluorescence sensors for chloride ion measurements in aqueous solution," *Anal Chem* (2004), vol. 76, pp. 569-575.

Malmborg et al., "Selection of binders from phage displayed antibody libraries using the BIAcore biosensor," *Journal of Immunological Methods* (1996), vol. 198, pp. 51-57.

Massoud et al., "Retroviral vectors bearing IgG-binding motifs for antibody-mediated targeting of vascular endothelial growth factor receptors," *Int J Mol Med* (2001), vol. 8, pp. 335-343.

Massotte, D., "G protein-coupled receptor overexpression with the baculovirus-insect cell system: a tool for structural and functional studies," *Biochim Biophys Acta* (2003), vol. 1610, pp. 77-89.

Massoud et al., "Molecular imaging in living subjects: seeing fundamental biological processes in a new light," *Genes Dev* (2003), vol. 17, pp. 545-580.

Massoud et al., "Molecular imaging of homodimeric protein-protein interactions in living subjects," *Faseb J.* (2004) 18(10):1105-1107.

McDonald et al., "Visualization of the intracellular behavior of HIV in living cells," *Journal of Cell Biology* (2002), vol. 159, pp. 441-452.

McDonald et al., "Recruitment of HIV and its receptors to dendritic cell-T cell junctions," *Science* (2003), vol. 300, pp. 1295-1297.

McKnight et al., "Inhibition of human immunodeficiency virus fusion by a monoclonal antibody to a coreceptor (CXCR4) is both cell type and virus strain dependent," *Journal of Virology* (1997), vol. 71, pp. 1692-1696.

McNamara et al., "Synthesis, characterization, and application of fluorescence sensing lipobeads for intracellular pH measurements," *Anal Chem* (2001), vol. 73, pp. 3240-3246.

Milligan, "Construction and Analysis of Function of G Protein-Coupled Receptor-G Protein Fusion Proteins," *Methods in Enzymology*, 2002, vol. 343, pp. 260-273.

Michnick, S. W., "Exploring protein interactions by interaction-induced folding of proteins from complementary peptide fragments," *Curr Opin Struct Biol* (2001), vol. 11, pp. 472-477.

Milligan, G., "Insights into ligand pharmacology using receptor-G protein fusion proteins," *Trends Pharmacol Sci* (2000), vol. 21, pp. 24-28.

Sundberg et al., "High-throughput and ultra-high-throughput screening: solution- and cell-based approaches," *Curr. Opn. in Biotechnology* (2000)11:47-53.

Milligan, G., "Principles: extending the utility of [35S]GTP gamma S binding assays," *Trends Pharmacol Sci* (2003), vol. 24, pp. 87-90.

Molinari et al., "Promiscuous coupling at receptor-Galpha fusion proteins. The receptor of one covalent complex interacts with the alpha-subunit of another," *J Biol Chem* (2003), vol. 278, pp. 15778-15788.

Monath, T. P., "Dengue: the risk to developed and developing countries," *Proc Natl Acad Sci U S A* (1994), vol. 91, pp. 2395-2400.

Montana et al., "Dual-wavelength ratiometric fluorescence measurements of membrane potential," *Biochemistry* (1989), vol. 28, pp. 4536-4539.

Moore et al., "Mechanism of GTP hydrolysis by p21N-ras catalyzed by GAP: studies with a fluorescent GTP analogue," *Biochemistry* (1993), vol. 32, pp. 7451-7459.

Morizono et al., "Antibody-directed targeting of retroviral vectors via cell surface antigens," *J. Virol* (2001), vol. 75, pp. 8016-8020.

Morris et al., "Physiological regulation of G protein-linked signaling," *Physiol Rev* (1999), vol. 79, pp. 1373-1430.

Murakami et al., "A small molecule CXCR4 inhibitor that blocks T cell line-tropic HIV-1 infection," *Journal of Experimental Medicine* (1997), vol. 186, pp. 1389-1393.

Nollert et al., "Crystallization of Membrane Proteins in Cubo," *Methods in Enzymology*, 2002, vol. 343, pp. 183-199.

Nollert et al., "Climbing Mount Everest, The CPCR Way," *DDT: Targets*, 2004, vol. 3, No. 1, pp. 2-4.

Nakamura et al., "Antibody-targeted cell fusion," *Nat Biotechnol* (2004), vol. 22, pp. 331-336.

Nedelkov et al., "Analysis of native proteins from biological fluids by biomolecular interaction analysis mass spectrometry (BIA/MS): exploring the limit of detection, identification of non-specific binding and detection of multi-protein complexes," *Biosensors & Bioelectronics* (2001a), vol. 16, pp. 1071-1078.

Nedelkov et al., "Delineation of in vivo assembled multiprotein complexes via biomolecular interaction analysis mass spectrometry," *Proteomics* (2001b), vol. 1, pp. 1441-1446.

Nedelkov et al., "Design of buffer exchange surfaces and sensor chips for biosensor mass spectrometry," *Proteomics* (2002), vol. 2, pp. 441-446.

Nguyen et al., "Calcium ion fluorescence detection using liposomes containing Alexa-labeled calmodulin," *Anal Bioanal Chem* (2002), vol. 374, pp. 69-74.

Nyambi, et al., "A virus binding assay for studying the antigenic landscape on intact, native, primary human immunodeficiency virus-type 1," *J Immunol Methods* (2001), vol. 253, pp. 253-262.

Oben et al., "A simple quantitative fluorimetric assay of in vitro phagocytosis in human neutrophils," *J Immunol Methods*, 1988, vol. 112, pp. 99-103.

Nolkrantz et al., "Functional screening of intracellular proteins in single cells and in patterned cell arrays using electroporation," *Anal. Chem.* (2002) 74:4300-4305.

Ono et al., "Role of the gag matrix domain in targeting human immunodeficiency virus type 1 assembly," *Journal of Virology* (2000) 74(6):2855-2866.

Orentas et al., "Association of Host Cell Surface Adhesion Receptors and Other Membrane Proteins With HIV and SIV," *AIDS Research and Human Retroviruses*, 1993, vol. 9, No. 11, pp. 1157-1165.

Ohno et al., "Retrovirus vectors displaying the IgG-binding domain of protein A," *Biochem Mol Med* (1997), vol. 62, pp. 123-127.

Ohno et al., "Cell-specific targeting of Sindbis virus vectors displaying IgG-binding domains of protein A," *Nat Biotechnol* (1997), vol. 15, pp. 763-767.

O'Neil et al., "Virus harvesting and affinity-based liquid chromatography. A method for virus concentration and purification," *Biotechnology* (N Y) (1993), vol. 11, pp. 173-178.

Opella et al., "Structure determination of membrane proteins by NMR spectroscopy," *Biochem Cell Biol* (2002), vol. 80, pp. 597-604.

Marrero et al., "Electroporation of pp60c-src antibodies inhibits the angiotensin II activation of phospholipase C-γl in rat aortic smooth muscle cells," *Journal of Biological Chemistry* (1995) 270(26):15734-15738.

(56) References Cited

OTHER PUBLICATIONS

Overton et al., "G-protein-coupled receptors function as oligomers in vivo," *Curr Biol* (2000), vol. 10, pp. 341-344.
Overton et al., "Use of fluorescence resonance energy transfer to analyze oligomerization of G-protein-coupled receptors expressed in yeast," *Methods* (2002), vol. 27, pp. 324-332.
Martinez et al., "CD4-independent protective cytotoxic T-cells induced in early life by a non-replicative delivery system based on virus-like particles," *Virology* (2003) 305:428-435.
Perticarari et al. "A new flow cytometric assay for the evaluation of phagocytosis and the oxidative burst in whole blood," *J Immunol Methods* (1994) 170, 117-124.
Prior et al., "Inactivation and Purification of Human Immunodeficiency Virus-1 as Antigen for the Treatment of HIV-1 Infection," *BioPharm*, 1996, pp. 22-34.
Prior et al., "Process Development for the Manufacture of Inactivated HIV-1," *BioPharm*, 1995, pp. 25-35.
Palczewski et al., "Crystal structure of rhodopsin: A G protein-coupled receptor," *Science* (2000), vol. 289, pp. 739-745.
Pang et al., "Development of Dengue virus type 2 replicons capable of prolonged expression in host cells," *BMC Microbiol* (2001), vol. 1, p. 18.
Park et al., "Integration of cell culture and microfabrication technology," *Biotechnol Prog* (2003), vol. 19, pp. 243-253.
Pebay-Peyroula et al., "X-ray structure of bacteriorhodopsin at 2.5 angstroms from microcrystals grown in lipidic cubic phases," *Science* (1997), vol. 277, pp. 1676-1681.
Peled et al., "Dependence of human stem cell engraftment and repopulation of NOD/SCID mice on CXCR4," *Science* (1999), vol. 283, pp. 845-848.
Pelletier et al., "An in vivo library-versus-library selection of optimized protein-protein interactions," *Nat Biotechnol* (1999), vol. 17, pp. 683-690.
Pelletier et al., "Oligomerization domain-directed reassembly of active dihydrofolate reductase from rationally designed fragments," *Proc Natl Acad Sci U S A* (1998), vol. 95, pp. 12141-12146.
Penfold et al., "Cytomegalovirus encodes a potent alpha chemokine," *Proceedings of the National Academy of Sciences, USA* (1999), vol. 96, pp. 9839-9844.
Perticarari et al., "A new flow cytometric assay for the evaluation of phagocytosis and the oxidative burst in whole blood," *J Immunol Methods* (1994), vol. 170, pp. 117-124.
Pham et al., "Concentration of viral vectors by co-precipitation with calcium phosphate," *J Gene Med* (2001), vol. 3, pp. 188-194.
Pindel et al., "Purification and cloning of a broad substrate specificity human liver carboxylesterase that catalyzes the hydrolysis of cocaine and heroin," *J Biol Chem* (1997), vol. 272, pp. 14769-14775.
Plasek et al., "Slow fluorescent indicators of membrane potential: a survey of different approaches to probe response analysis," *J of Photochemistry and Photobiology* (1996), vol. 33, pp. 101-124.
Michael et al., "Randomly ordered addressable high-density optical sensor arrays," *Anal. Chem.* (1998) 70:1242-1248.
Lipovsek et al., "In-vitro protein evolution by ribosome display and mRNA display," *J. of. Immunological Methods* (2004) 290:51-67.
Ragsdale et al., "An improved spectrofluorometric assay for quantitating yeast phagocytosis in cultures of murine peritoneal macrophages," *J Immunol Methods*, 1989, vol. 123, pp. 259-267.
Rohr et al., "Multiple Site Optical Recording of Transmembrane Voltage (MSORTV) in Patterned Growth Heart Cell Cultures: Assessing Electrical Behavior, With Microsecond Resolution, on a Cellular and Subcellular Scale," *Biophysical Journal*, 1994, vol. 67, pp. 1301-1315.
Royer et al., "Expression and extracellular release of human immunodeficiency virus type 1 Gag precursors by recombinant baculovirus-infected cells," *J Virol*, 1992, vol. 66, pp. 3230-3235.
Ramsey et al., "Adenovirus vectors as transcomplementing templates for the production of replication defective retroviral vectors," *Biochem Biophys Res Commun* (1998), vol. 246, pp. 912-919.

Ray et al., "Optical bioluminescence and positron emission tomography imaging of a novel fusion reporter gene in tumor xenografts of living mice," *Cancer Res* (2003), vol. 63, pp. 1160-1165.
Remmers, A. E., "Detection and quantitation of heterotrimeric G proteins by fluorescence resonance energy transfer," *Anal Biochem* (1998), vol. 257, pp. 89-94.
Remmers et al., "Partial G protein activation by fluorescent guanine nucleotide analogs. Evidence for a triphosphate-bound but inactive state," *J Biol Chem* (1996), vol. 271, pp. 4791-4797.
Remmers et al., "Fluorescent guanine nucleotide analogs and G protein activation," *J Biol Chem* (1994), vol. 269, pp. 13771-13778.
Remy et al., "Regulation of apoptosis by the Ft1 protein, a new modulator of protein kinase B/Akt," *Mol Cell Biol* (2004), vol. 24, pp. 1493-1504.
Richieri et al., "Characterization of highly purified, inactivated HIV-1 particles isolated by anion exchange chromatography," *Vaccine* (1998), vol. 16, pp. 119-129.
Rider et al., "A B cell-based sensor for rapid identification of pathogens," *Science* (2003), vol. 301, pp. 213-215.
Rowe et al., "Array biosensor for simultaneous identification of bacterial, viral, and protein analytes," *Anal Chem* (1999), vol. 71, pp. 3846-3852.
Rex, "Pore formation induced by the peptide melittin in different lipid vesicle membranes," *Biophysical Chemistry* (1996) 58:75-85.
Rui et al., "Transfer of anti-TFAR19 monoclonal antibody into HeLa cells by in situ electroporation can inhibit the apoptosis," *Life Sciences* (2002)1771-1778.
Rucker et al.,"Regions in b-chemokine receptors CCR5 and CCR2b that determine HIV-1 cofactor specificity," *Cell* (1996), vol. 87, pp. 437-446.
Salamon et al., "Surface Plasmon Resonance Spectroscopy Studies of Membrane Proteins: Transducin Binding and Activation by Rhodopsin Monitored in Thin Membrane Films," *Biophysical Journal*, 1996, vol. 71m pp. 283-294.
Salamon et al., "Coupled Plasmon-Waveguide Resonators: A New Spectroscopic Tool for Probing Proteolipid Film Structure and Properties," *Biophysical Journal*, 1997, vol. 73, pp. 2791-2797.
Sambrook J, et al. (1989) *Molecular Cloning: A Laboratory Manual*. (2nd ed.) Cold Spring Harbor Laboratory Press, Cold Spring, NY.
Sambrook J, Russel DW. (2001) *Molecular Cloning: A Laboratory Manual*. (3rd ed.) Cold Spring Harbor Laboratory Press. Cold Spring, NY.
Schertler et al., "Projection Structure of Rhodopsin," *Letters to Nature*, 1993, vol. 362, pp. 770-772.
Salamon et al., "Coupled Plasmon-Waveguide Resonance Spectroscopy Studies of the Cytochrome *b6f*/Plastocyanin System in Supported Bilayer Membranes," *Biophysical Journal* (1998) 75:1874-1885.
Suomalainen et al., "Incorporation of Homologous and Heterologous Proteins Into the Envelope of Moloney Murine Leukemia Virus," *Journal of Virology*, 1994, pp. 4879-4889.
Salamon et al., "Plasmon resonance studies of agonist/antagonist binding to the delta-opioid receptor: new structural insights into receptor-ligand interactions," *Biophysical Journal* (2000), vol. 79, pp. 2463-2474.
Salamon et al., "Conformational changes in rhodopsin probed by surface plasmon resonance spectroscopy," *Biochemistry* (1994), vol. 33, pp. 13706-13711.
Graier et al., "Submaximal stimulation of porcine endothelial cells causes focal $Ca^{2+}$ elevation beneath the cell membrane," *Journal of Physiology* (1998) 506.1:109-125.
Sawai et al., "A novel method of cell-specific mRNA transfection," *Mol Genet Metab* (1998), vol. 64, pp. 44-51.
Schatzlein et al., "Phage derived peptides for targeting of doxorubicin conjugates to solid tumours," *J Control Release* (2001), vol. 74, pp. 357-362.
Schertler et al., "Projection structure of rhodopsin," *Nature* (1993), vol. 362, pp. 770-772.
Seisenberger et al., "Real-time single-molecule imaging of the infection pathway of an adeno-associated virus," *Science* (2001), vol. 294, pp. 1929-1932.

(56) References Cited

OTHER PUBLICATIONS

Shi et al., "Construction and characterization of subgenomic replicons of New York strain of West Nile virus," *Virology* (2002), vol. 296, pp. 219-233.
Smith et al., "Poxvirus genomes encode a secreted, soluble protein that preferentially inhibits beta chemokine activity yet lacks sequence homology to known chemokine receptors," *Virology* (1997), vol. 236, pp. 316-327.
Smith, J. C., "Potential-sensitive molecular probes in membranes of bioenergetic relevance," *Biochimica et Biophysica Acta* (1990), vol. 1016, pp. 1-28.
Snitkovsky et al., "A TVA-single-chain antibody fusion protein mediates specific targeting of a subgroup A avian leukosis virus vector to cells expressing a tumor-specific form of epidermal growth factor receptor," *J Virol* (2000), vol. 74, pp. 9540-9545.
Stadel et al., "Orphan G-protein coupled receptors: a neglected opportunity for pioneer drug discovery," *Trends Pharmacol Sci* (1997), vol. 18, pp. 430-437.
Stanley, M., "An introduction to FRET, with an emphasis on the optics involved," *Chroma* (2003), *Application Notes* No. 6. pp. 1-14.
Tertoolen et al., "Dimerization of receptor protein-tyrosine phosphatase alpha in living cells," *BMC Cell Biol* (2001) vol. 2, p. 8.
Torrent et al., "Transgene amplification and persistence after delivery of retroviral vector and packaging functions with E1/E4-deleted adenoviruses," *Cancer Gene Ther* (2000), vol. 7, pp. 1135-1144.
Torres et al., "Membrane proteins: the 'Wild West' of structural biology," *Trends Biochem Sci* (2003), vol. 28, pp. 137-144.
Townsend et al., "Combining anatomy and function: the path to true image fusion," *Eur Radiol* (2001), vol. 11, pp. 1968-1974.
Venema et al., "Quantitative measurement of cationic fluxes, selectivity and membrane potential using liposomes multilabelled with fluorescent probes," *Biochimica et Biophysica Acta*, 1993, vol. 1146, pp. 87-96.
Varnayski et al., "Noncytopathic flavivirus replicon RNA-based system for expression and delivery of heterologous genes," *Virology* (1999), vol. 255, pp. 366-375.
Vaughn et al., "Dengue viremia titer, antibody response pattern, and virus serotype correlate with disease severity," *J Infect Dis* (2000), vol. 181, pp. 2-9.
Vogt et al., "The genetic structure of RNA tumor viruses," *Ann. Rev. Genet.* (1977) 11:203-238.
Vilardaga et al., "Measurement of the millisecond activation switch of G protein-coupled receptors in living cells," *Nat Biotechnol* (2003), vol. 21, pp. 807-812.
Wakabayashi et al., "Comparison of Human Papillomavirus Type 16L1 Chimeric Virus-Like Particles Versus L1/L2 Chimeric Virus-Like Particles in Tumor Prevention," *Intervirology*, 2002, vol. 45, pp. 300-307.
Weeks BL, et al., "A microcantilever-based pathogen detector," *Scanning* (2003) 25:297-299.
White DO, Fenner FJ. (1994) *Medical Virology* (4th ed.) Academic Press, San Diego, CA.
Weldon, Jr., et al., "Incorporation of Chimeric Gag Protein Into Retroviral Particles," *Journal of virology*. 1990, pp. 4169-4179.
Wiley DC. (1985) Viral Membranes. In: *Virology*. BN Fields, ed. Raven Press, New York, NY. pp. 45-68.
Willis, "Retro-Secretion of Recombinant Proteins," *Nature*, 1989, vol. 340, pp. 323-324.
Walde et al., "Enzymes inside lipid vesicles: preparation, reactivity and applications," *Biomol Eng* (2001), vol. 18, pp. 143-177.
Weclewicz et al., "Specific interactions between retrovirus Env and Gag proteins in rat neurons," *J Virol* (1998), vol. 72, pp. 2832-2845.
Werten et al., "Progress in the analysis of membrane protein structure and function," *FEBS Lett* (2002), vol. 529, pp. 65-72.
Williams, "Biotechnology match making: screening orphan ligands and receptors," *Current Opinion in Biotechnology* (2000), vol. 11, pp. 42-46.
Williams et al., "The integration of SPR biosensors with mass spectrometry: possible applications for proteome analysis," *Trends in Biotechnology* (2000), vol. 18, pp. 45-48.

Jenny et al., "A critical review of the methods for cleavage of fusion proteins with thrombin and factor Xa," *Protein Expression & Purification* (2003)31:1-11.
Li et al., "Synthesis of polyethylene glycol (PEG) derivatives and PEGylated-peptide biopolymer conjugates," *Biomacromolecules* (2003) 4:1055-1067.
Wise et al., "Target validation of G-protein coupled receptors," *Drug Discovery Today* (2002) vol. 7, pp. 235-246.
Wu et al., "Immunofluorescent labeling of cancer marker Her2 and other cellular targets with semiconductor quantum dots," *Nat Biotechnol* (2003), vol. 21, pp. 41-46.
Wurm et al., "Large-scale transient expression in mammalian cells for recombinant protein production," *Curr Opin Biotechnol* (1999), vol. 10, pp. 156-159.
Yamada et al., "Lentivirus vector purification using anion exchange HPLC leads to improved gene transfer," *Biotechniques* (2003), vol. 34, pp. 1074-1078, 1080.
Yamshchikov et al., "Assembly of SIV virus-like particles containing envelope proteins using a baculovirus expression system," *Virology* (1995), vol. 214, pp. 50-58.
Yao et al., "Virus-like particle and DNA-based candidate AIDS vaccines," *Vaccine* (2003), vol. 21, pp. 638-643.
Yao et al., Production and characterization of simian—human immunodeficiency virus-like particles, *AIDS Res Hum Retroviruses* (2000), vol. 16, pp. 227-236.
Yoshida et al., "VSV-G-pseudotyped retroviral packaging through adenovirus-mediated inducible gene expression," *Biochem Biophys Res Commun* (1997), vol. 232, pp. 379-382.
Zemanova et al., "Endothelin receptor in virus-like particles: ligand binding observed by fluorsecence fluctuation spectroscopy," *Biochemistry*, 2004, 20;43(28):9021-9028.
Zhang et al., "Creating new fluorescent probes for cell biology," *Nat Rev Mol Cell Biol*, 2002, vol. 3, pp. 906-918.
Zhu et al., "Electron tomography analysis of envelope glycoprotein trimers on HIV and simian immunodeficiency virus virions," Proc Natl Acad Sci U S A 2003, 100, 15812-15817.
HTS Biosystems website. www.htsbiosystems.com (cited Aug. 2004).
Current Protocols in Human Genetics, 1995, *Fields Virology*. (3rd ed.) Fields et al., eds. Lippincott-Raven Publishers, Philadelphia, PA.
Gosalia et al., "Printing chemical libraries on microarrays for fluid phase nanoliter reactions," *PNAS* (2003) 100(15):8721-8726.
Schubert et al., Insertion of the human immunodeficiency virus CD4 receptor into the envelope of vesicular stomatitis, J. Virology, 66(3): 1579-1589 (1992).
Choe H., et al., The beta-chemokine receptors CCR3 and CCR5 facilitate infection by primary HIV-1 isolates, Cell, 85:1135-1148 (1996).
Office Action Mailed Nov. 17, 2004 for U.S. Appl. No. 10/032,311 entitled "Lipoparticle comprising a protein and methods of making and using the same".
Office Action Mailed Jun. 2, 2005 for U.S. Appl. No. 10/032,311 entitled "Lipoparticle comprising a protein and methods of making and using the same".
Office Action Mailed Mar. 22, 2006 for U.S. Appl. No. 10/032,311 entitled "Lipoparticle comprising a protein and methods of making and using the same".
Office Action Mailed Oct. 17, 2006 for U.S. Appl. No. 10/032,311 entitled "Lipoparticle comprising a protein and methods of making and using the same".
Final Office Action Mailed Apr. 9, 2007 for U.S. Appl. No. 10/032,311 entitled "Lipoparticle comprising a protein and methods of making and using the same".
Sedlik et al., Recombinant parvovirus-like particles as an antigen carrier: A novel nonreplicative exogenous antigen to elicit protective antiviral cytotoxic T cells, PNAS, vol. 94, pp. 7503-7508 (1997).
Narayan , P., et al., Expression of functional lutropin/choriogonadotropin receptor in the baculovirus system, Molecular and Cellular Endocrinology, 1996;117:95-100.

(56) References Cited

OTHER PUBLICATIONS

Margulies, B. J., et al., Identification of the Human Cytomegalovirus G Protein-Coupled Receptor Homologue Encoded by UL33 in Infected Cells and Enveloped Virus Particles, Virology;1996;225:111-125.

Loisel, T. P., et al., Recovery of homogenous and functional Beta2-adrenergic receptors from extracellular baculovirus particles, Nature Biotechnology, Nov. 1997;15:1300-1304.

Hayashi, I., et al., Selective Reconstitution and Recovery of Functional Gamma-Secretase Complex on Budded Baculovirus Particles, Journal of Biological Chemistry, Sep. 3, 2004;279(36):38040-38046.

Masuda, K., et al., A Combinatorial G Protein-coupled Receptor Reconstitution System on Budded Baculovirus, Journal of Biological Chemistry, Jul. 4, 2003;278(27):14552-24562.

Notice of Allowability and Reasons for Allowance for U.S. Appl. No. 10/032,311, Dec. 10, 2009.

\* cited by examiner

FIGURE 1
A.
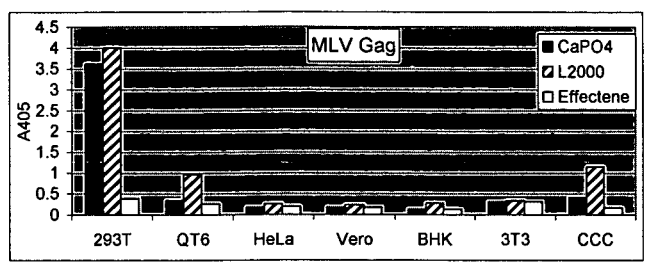
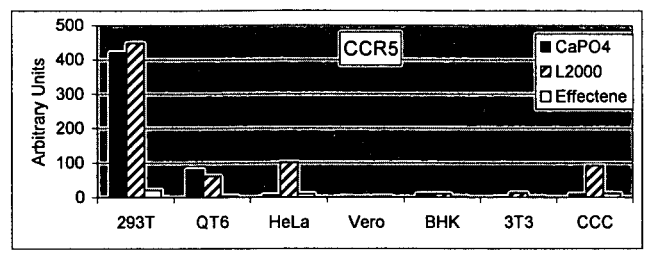
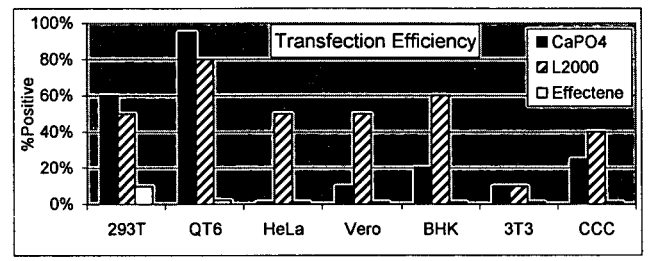
B. CCR5 Dot Blot
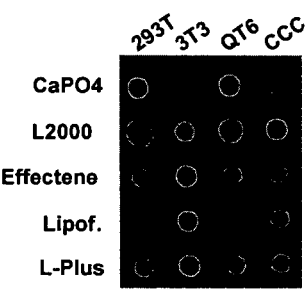

FIGURE 2
A.  B. 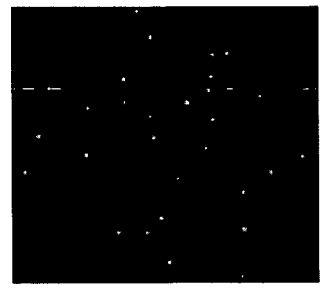 C. 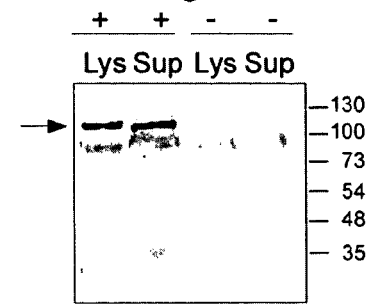

FIGURE 3
A. CXCR4 MAb 12G5 dilutions
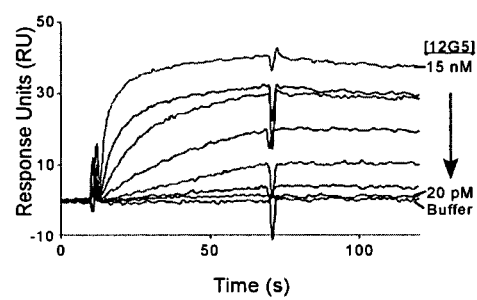
B. MAb $K_D$ comparison
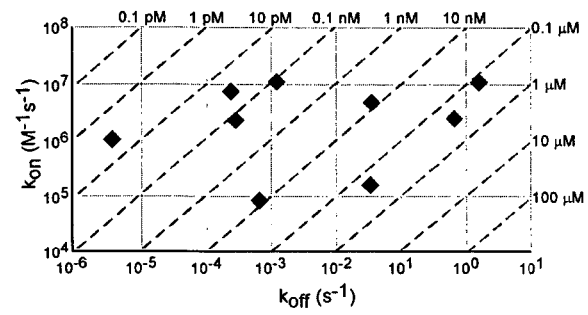

FIGURE 4.
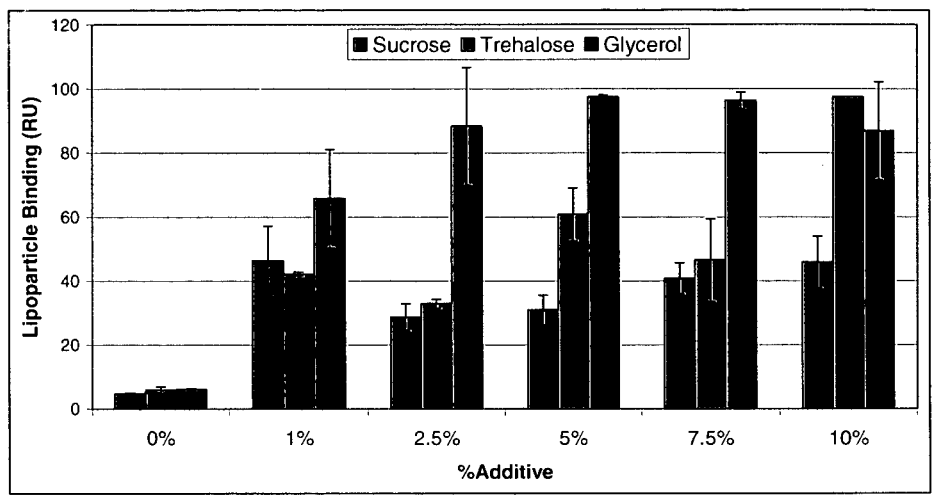
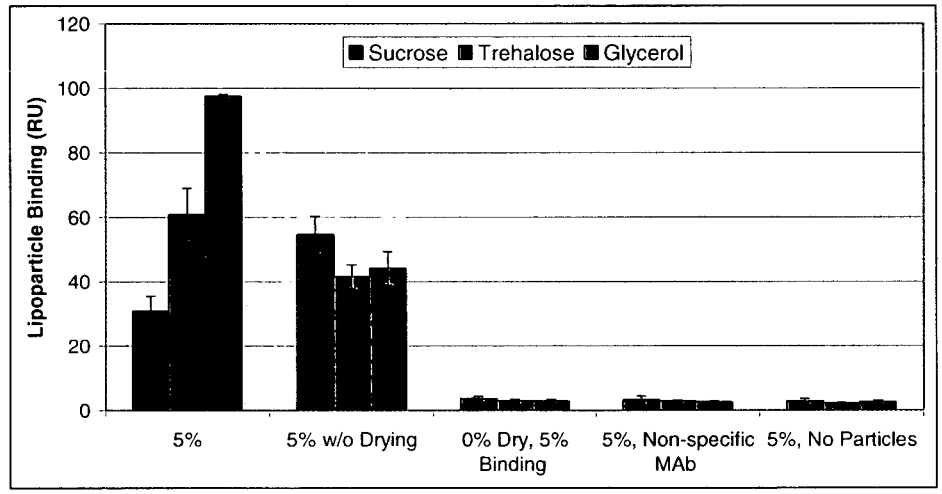

B.

FIGURE 15 (Sheet 1 of 3)
Dynamic Light Scattering
A. 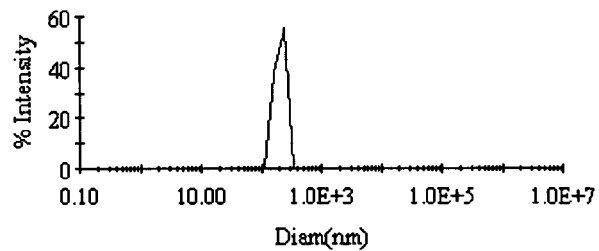
B. 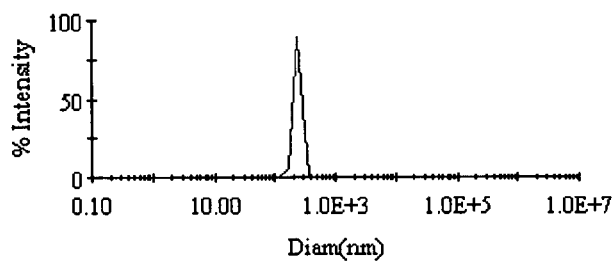
C. 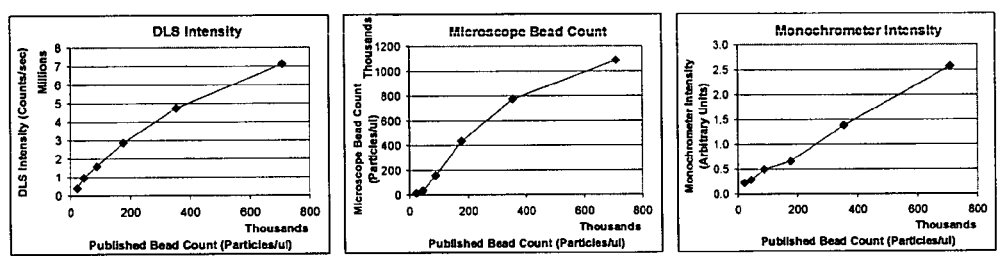
D. 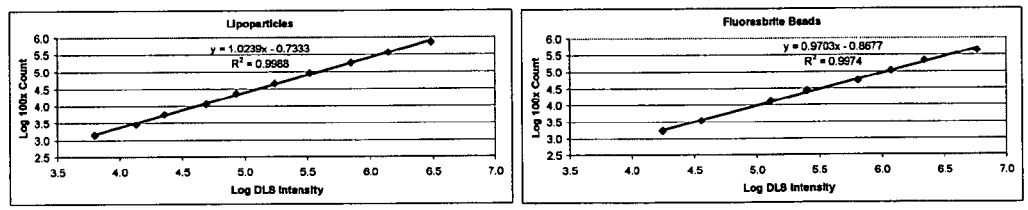

FIGURE 15
E.
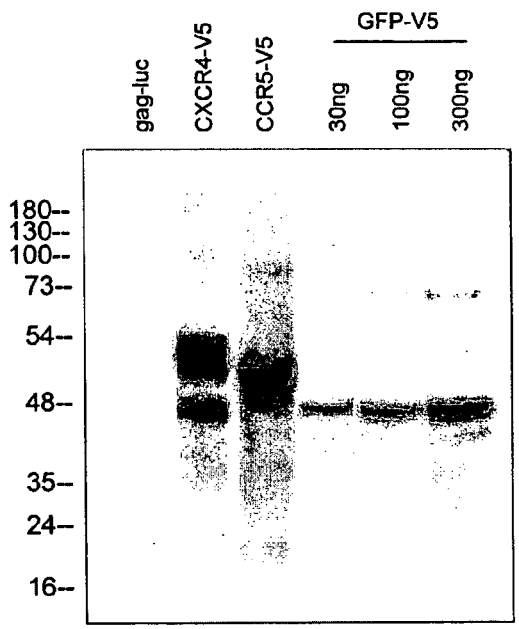
F.
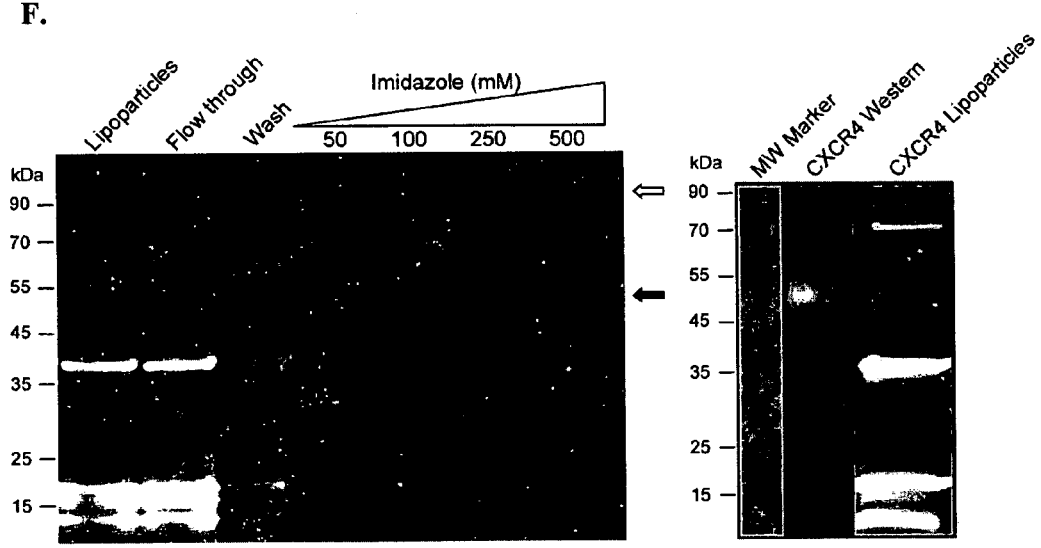
G.
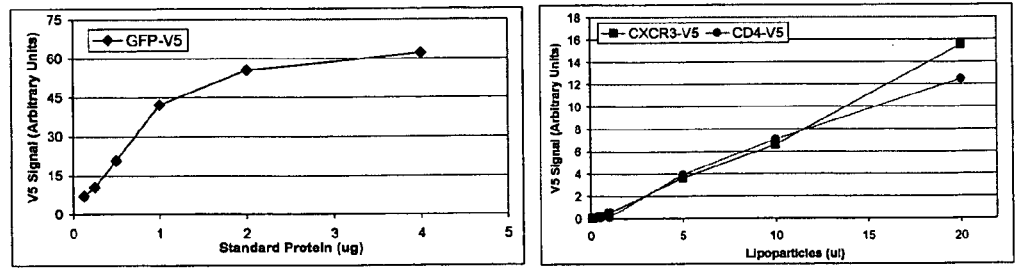

FIGURE 15 (Sheet 3 of 3)
H.
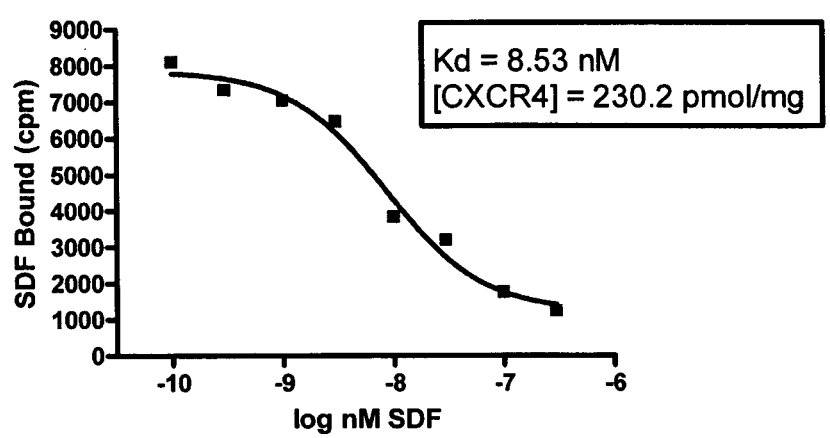
I.
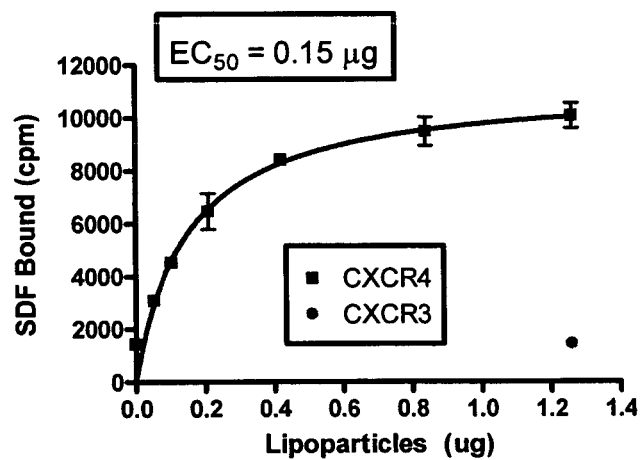

FIGURE 16.
VELISA Binding Detection
A.
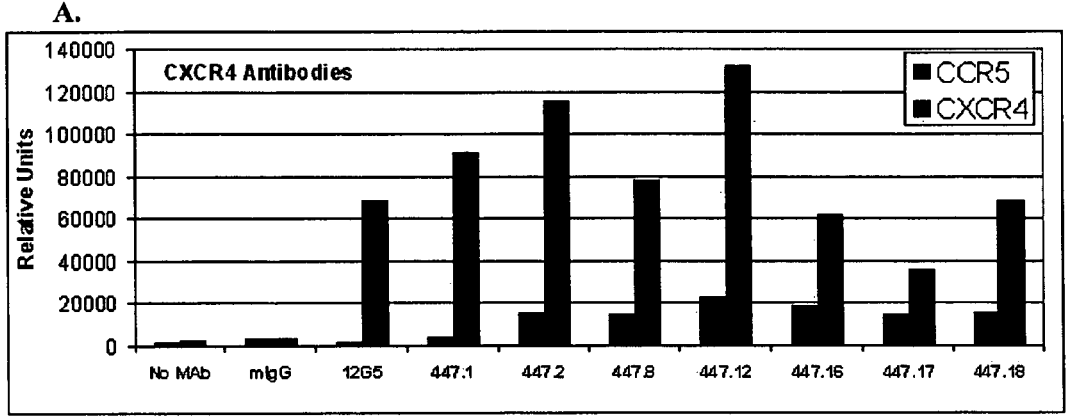
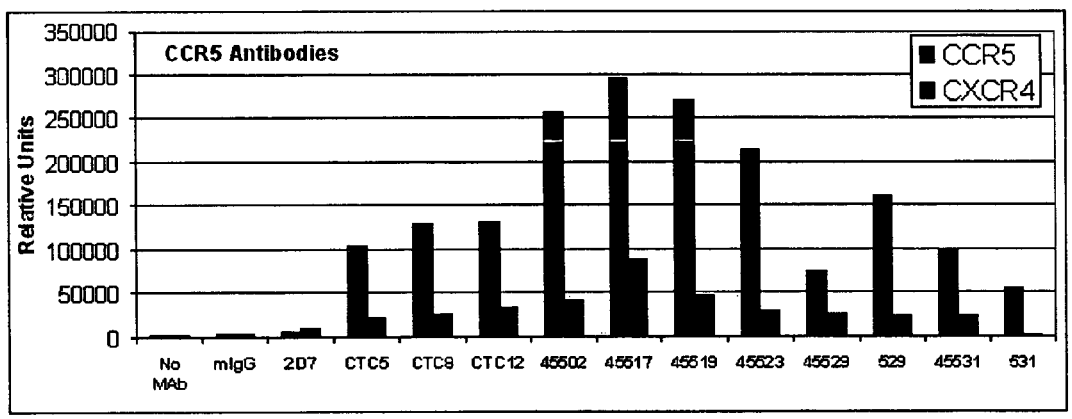
B.
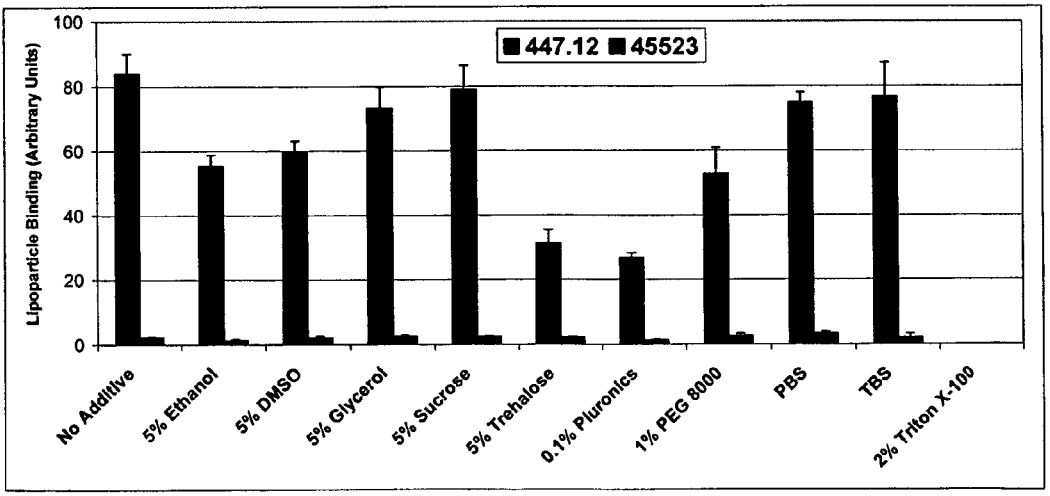

FIGURE 19
A.
B.
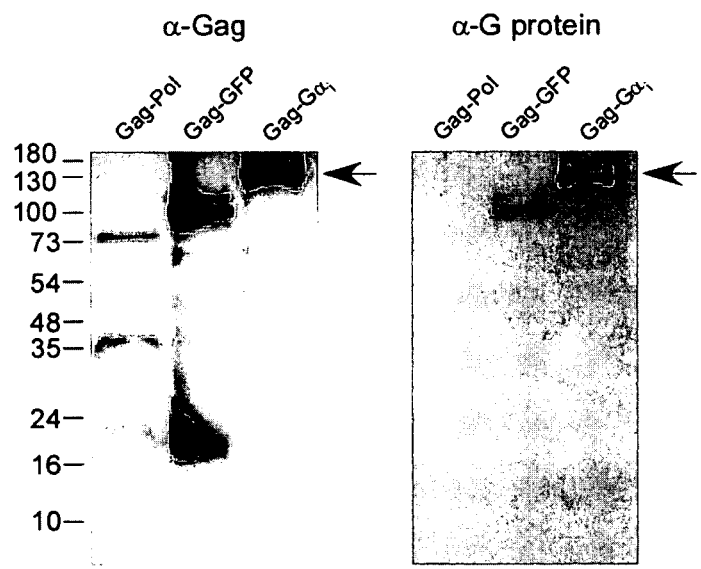

WGA-agarose beads          ProA-agarose beads

LIPOPARTICLES COMPRISING PROTEINS, METHODS OF MAKING, AND USING THE SAME

CROSS-REFERENCE TO RELATED APPLICATIONS

This application claims the benefit of U.S. Provisional Application Ser. No. 60/491,477, filed Jul. 30, 2003, U.S. Provisional Application Ser. No. 60/491,633, filed Jul. 30, 2003, U.S. Provisional Application Ser. No. 60/498,755, filed Aug. 29, 2003, U.S. Provisional Application Ser. No. 60/502,478, filed Sep. 12, 2003, U.S. Provisional Application Ser. No. 60/509,677, filed Oct. 7, 2003, U.S. Provisional Application Ser. No. 60/509,608, filed Oct. 7, 2003, and U.S. Provisional Application Ser. No. 60/509,575, filed Oct. 7, 2003, each of which is herein incorporated by reference in its entirety.

GOVERNMENT SUPPORT

This invention was made with U.S. Government support (NIH Grants No. GM64924, GM68322, and RR16832) and the U.S. Government may therefore have certain rights in the invention.

BACKGROUND OF THE INVENTION

Ligand interactions with membrane proteins are responsible for a multitude of cell adhesion, signaling, and regulatory events. This diversity of function makes membrane proteins important drug targets. G-protein coupled receptors (GPCRs) are one family of membrane proteins that comprise nearly half of existing drug targets (Drews (1996), Nat. Biotechnol., 11:1516-1518, Stadel, et al. (1997), Trends Pharmacol. Sci., 18:430-437, Wise, et al. (2002), Drug Discovery Today, 7:235-246). Another 5% of drug targets are comprised of membrane-embedded ion channels, and many of the remaining targets are also membrane proteins. These topologically complex membrane proteins span the lipid bilayer of the cell multiple times and usually serve as receptors to mediate communication between a cell's function and its exterior environment. Drugs targeting membrane proteins include antipsychotics, antihistamines, beta-blockers, anti-migraine drugs, anti-ulcer drugs, and analgesics.

Despite their importance, proteins that span the membrane multiple times present a unique set of challenges for ligand binding and drug discovery studies because they require a lipid environment to maintain native structure. For example, GPCRs weave in and out of the cell membrane seven times, so cannot be extracted from the lipid bilayer without disrupting their structure. While detergent conditions can occasionally be found that allow native structure to be maintained in solution, this is an empirical and very time-consuming process, and even then stability is only transient.

As a result, interaction studies involving membrane proteins typically use whole cells or vesicles derived from cell membranes, where the protein of interest is but a minor component, making both adequate sensitivity and specificity more difficult to achieve. Living cells are cumbersome to grow, must be maintained in a high protein (serum) environment, and present a moving target as receptors are internalized, altered by intracellular events, and recycled. Cells also have severe limitations in their application to biosensors and other microfluidic devices, most notably in their size, sensitivity to environmental conditions, and heterogeneous cell surface. Membrane vesicles, prepared by mechanically disrupting cells, are a common source of membrane protein for many drug screens currently conducted. However, membrane vesicles are heterogeneous, impure, and not particularly stable. The receptors within them may be misoriented, a minor component of total protein, and derived from intracellular organelles.

Thus, there remains a need for the development of a broad methodology that permits the rapid purification of a wide spectrum of membrane and cellular proteins. The present invention satisfies this need. Further, there is a need for assays that permit the study of membrane protein interactions, and the present invention also satisfies this need. Further, there is a need for vesicles that facilitate the elicitation of an immune response against membrane proteins to be mounted, particularly for the generation of monoclonal antibodies, humoral response, cellular response, and vaccines, and the present invention also satisfies this need. The present invention fulfills these needs as well others.

Human pathogens enter their host cells, and eventually kill or weaken them, using cellular receptors. In nearly all cases, these cellular receptors are membrane proteins on the cell surface. Identifying these membrane proteins and linking infectious agents to their receptors offers direct insight into disease pathogenesis. For example, HIV uses a fusion co-receptor, typically either the chemokine receptors CXCR4 or CCR5 (Doranz (2000), Emerging Therapeutic Targets, 4:423-437). Strains of HIV that use the co-receptor CXCR4 are correlated with increased disease pathogenicity, while strains that use the co-receptor CCR5 are responsible for transmission of the virus. Preventing receptor binding is a common strategy for treating or preventing pathogen infection.

Cellular receptors are not only involved in pathogen binding, fusion, and entry, but are also involved with other pathogenic processes. For example, many pathogens encode toxins that facilitate virulence of the pathogen. Examples include anthrax toxin (Bradley, et al. (2003), Biochem Pharmacol, 65:309-314), HHV8-encoded chemokines (vMIP-2) (Holst, et al. (2003), Contrib Microbiol, 10:232-252), cytomegalovirus chemokine UL146 (Penfold, et al. (1999), Proc. Natl. Acad. Sci. USA, 96:9839-9844), and pox virus-encoded chemokine inhibitors (vCCI, M-T1, M-T7) (Lalani, et al. (1997), J. Leukoc. Biol., 62:570-576, Smith, et al. (1997), Virology, 236:316-327). In many cases, identifying and inhibiting these toxins and their receptors can explain the lethal effects of the pathogen and neutralize their actions.

The techniques currently used to identify pathogen receptor interactions are generally slow and laborious. In many cases, such techniques require transfection of individual receptors, the growth of cells, and the use of the pathogen in its infectious form. In other cases, protein interactions are detected using immunoprecipitation, Western blotting, or radiolabeled proteins. For example, the HIV co-receptors CCR5 and CXCR4 were identified over ten years after HIV and its primary receptor, CD4, were discovered.

Optical biosensors are a class of instruments that can detect affinities of intramolecular interaction from picomolar to micromolar concentrations, in real-time, and without labels. Biosensors can also yield pharmacological information (kinetic and equilibrium binding constants) that other assays cannot (see (Canziani, et al. (1999), Methods, 19:253-269, Day, et al. (2002), Protein Science, 11:1017-1025) for review). Biosensors have been integrated into both drug discovery and diagnostics.

The most widely used optical biosensor, the BIACORE™, is based on surface plasmon resonance (SPR), which measures changes in refractive index at the sensor surface. The BIACORE platform consists of a flow cell with three inert walls (sides and floor) and a gold ceiling that is chemically modified to attach biomolecules. During usage, binding of protein in solution to tethered protein on the biosensor surface is monitored by changes in refractive index at the chip surface. A number of new biosensor devices are emerging that operate on similar principles.

Biosensors can also operate by measuring changes in spectroscopic measurements, such as reflectance, absorbance, transmission, or resonance. For example, microcantilever-based biosensors operate by detecting mechanical deflections of light reflecting from microcantilevers. The microcantilevers can be conjugated with an antibody, a protein, a ligand, a small molecule, a peptide, or a lipoparticle. The binding partner that deflects the cantilever can also be an antibody, a protein, a ligand, a small molecule, a peptide, or a lipoparticle.

Other biosensors are based on surface plasmon resonance and operate using an array format (on the world wide web at htsbiosystems.com). Other biosensors are based on colorimetric diffraction grating and operate using an array format (Cunningham, et al. (2002), Sensors and Actuators, B81:316-328, Cunningham, et al. (2002), Sensors and Actuators, B85: 219-226, Lin, et al. (2002), Biosens Bioelectron, 17:827-834). Other biosensors are based on acoustic resonators (Cooper, et al. (2001), Nat Biotechnol, 19:833-7).

Such biosensors, however, have not been widely suitable for membrane proteins because: 1) biosensor detection signals are a function of distance from the surface and structures larger than 200 nm yield poor signals (e.g. cells, membrane vesicles), 2) the purity of molecules tethered to the biosensor surface is directly proportional to the signal-to-noise ratio, 3) the use of microfluidic channels limits the size of flow components, 4) the nature of biosensor detection restricts nearly all such devices to soluble molecules, and 5) removal of membrane proteins from their native lipid environment destroys their structure.

Only a handful of proof-of-concept studies have detected binding to membrane proteins using optical biosensors, but not using lipoparticles (Bieri, et al. (1999), Nat. Biotechnol., 17:1105-1108, Cooper, et al. (2000), Analytical Biochemistry, 277:196-205, Cooper, et al. (1998), Biochim Biophys Acta, 1373: Heyes, et al. (1998), Biochemistry, 37:507-522, Karlsson, et al. (2002), Analytical Biochemistry, 300:132-138, Salamon, et al. (2000), Biophysical Journal, 79:2463-2474, Salamon, et al. (1994), Biochemistry, 33:13706-13711, Salamon, et al. (1996), Biophysical Journal, 71:283-294). All of these studies used detergent-solubilized membrane proteins, and most focused on one prototype protein where solubilization conditions have been well studied (rhodopsin). Detergent-solubilized membrane proteins have been used to investigate membrane protein interactions, although this approach has significant drawbacks. As discussed previously, G-protein coupled receptors (GPCRs) weave in and out of the cell membrane seven times, and thus cannot be extracted from the lipid bilayer without disrupting their structure.

Doms et al. (U.S. Patent Publication 2002/0183247 A1) discusses using biosensors to detect interactions between membrane proteins on lipoparticles and their binding partners, however improvements are still needed.

Thus, there remains a need for improved methods for using membrane proteins with optical biosensors. One aspect of the present invention is to use arrays of membrane proteins in conjunction with optical biosensors to recreate the cell surface in vitro. This will result in a product that will consist of a biosensor chip containing the thousands of membrane proteins encoded by the human genome. There is also a need for improved methods and techniques to identify receptors for viral entry. There is also a need for improved methods of identifying receptors for ligands or drugs. There is also a need for improved methods of identifying unknown pathogens or substances in a sample. The present invention satisfies these needs and others.

Biological probes comprise one or both of two basic functional features: a targeting component and a reporting component. The targeting component interacts with the structure or molecule of interest and defines the ability of the probe to discriminate target structures or events. The reporting component signals target interaction and defines detection parameters such as sensitivity. Most biological probes in current use (e.g. antibodies, fluorescent proteins, ion-sensitive dyes) are single molecule structures, and thus usually possess a single reporting domain and either no or one targeting domain.

Molecules designed to detect the presence of specific biological targets or report the occurrence of biological events are known broadly as molecular probes. Traditional imaging probes comprise a recognition component (in this context defined as a "targeting" domain) which binds to a target molecule, and a signaling component (in this context defined as a "reporter") which illuminates it (reviewed in (Massoud, et al. (2003), Genes Dev, 17:545-80, Molecular Probes Handbook (2003), Zhang, et al. (2002), Nat Rev Mol Cell Biol, 3:906-18)). The most widely used reporters emit an electromagnetic signal in the visual spectrum (bioluminescence or fluorescence), but radioactive and magnetic signals are also of medical importance for imaging techniques such as autoradiography, positron emission tomography (PET), and magnetic resonance imaging (MRI). Examples of visual reporters include fluorescent proteins, luminescent substrates, quantum dots, and fluorescent dyes. Biological probes incorporating these types of reporters are used to physically map cell structures and tissue architecture, as well as to monitor (and correlate) biological functions. The cellular structures and events that are emerging as important targets of molecular probes include subcellular components involved in gene transcription, cell growth and proliferation, cell migration and second messenger pathways.

With the increasing need to monitor smaller targets, and to dissect complex cellular functions at greater resolution, has arisen a requirement for the development of more sophisticated probes with improved localization and reporting characteristics. Cells are able to interpret the meaning of individual signaling events, for example, because each is part of a larger cellular response which includes sequential second messenger activity and spatial localization of signaling components. In contrast, most of the probes used in research and diagnostics to interpret such cell events rely on simple end-point measurements of a single event, target, or phenomenon (e.g. fluctuations in cytosolic calcium), and often fail to resolve the target to a sub-cellular location. The two most important characteristics of emerging biomedical imaging strategies are the ability to localize and align structural and functional information at tissue, cellular and sub-cellular levels, and the ability to exploit 'multimodal' detection systems (more than one reporter being simultaneously detected or correlated). Improvements in these properties can allow superior spatial localization of abnormalities in vivo, as well as structure-function correlation on the subcellular level (Massoud, et al. (2003), Genes Dev, 17:545-80). These 'new generation' probes are playing an increasingly important role in defining molecular events in the fields of cancer biology, cell biology, and gene therapy, for example in the detection of tumor markers and in tracking the delivery and function of gene therapy vectors (Jendelova, et al. (2004), J Neurosci Res, 76:232-43, Ray, et al. (2003), Cancer Res, 63:1160-5, Townsend, et al. (2001), Eur Radiol, 11:1968-74, Wu, et al. (2003), Nat Biotechnol, 21:41-6). Most existing single-molecule probes possess inherent limitations in these properties due to difficulties in integrating complex targeting and reporting systems. Although multiple probes can be introduced to simultaneously detect several events, most reporters cannot be targeted to desired cellular or subcellular structures to more accurately differentiate signaling events. Those probes that can be localized (e.g. fluorescent antibodies) usually contain only a small number (1-4) of reporter fluorophores per molecule, limiting signal amplification and detection.

A major obstacle in constructing improved imaging probes is not simply the development of new reporter molecules, but the development of a suitably sophisticated format in which complex and multiple reporters can be linked, and, importantly, controlled for target localization. Probes that can be spatially localized at the nanometer scale, that can amplify infrequent signals, and that can compartmentalize multiple reporters simultaneously, could have a major impact on developing subcellular and nano-scale applications in biomedical research and diagnostics.

A variety of foreign soluble proteins can also be incorporated into retroviruses. The incorporation of green fluorescent protein (GFP) into retroviruses has been used in a number of studies to understand aspects of the retroviral lifecycle such as budding, assembly, and infection (Andrawiss, et al. (2003), J Virol, 77:11651-60, Dalton, et al. (2001), Virology, 279: 414-421, McDonald, et al. (2002), J. Cell Biol., 159: McDonald, et al. (2003), Science, 300:1295-7). In addition, labeling of viruses with fluorescent reporters has been used on several occasions to understand the early stages of virus fusion, endocytosis, and nuclear migration (Bartlett, et al. (1998), Nat Med, 4:635-7, Leopold, et al. (2000), Hum Gene Ther, 11:151-65, McDonald, et al. (2002), J. Cell Biol., 159: McDonald, et al. (2003), Science, 300:1295-7). An additional study demonstrated proof-of-concept incorporation of a different foreign protein fused to Gag (cytochrome c from yeast) (Weldon, et al. (1990), J Virol, 64:4169-79, Wills (1989), Nature, 340:323-4; U.S. Pat. No. 5,175,099). Probes attached to viruses have been limited to antibodies or fluorescent proteins that typically have limited life-spans and have never reported anything more than the location of the virus. Similar work has also been performed to study the phagocytosis of fluorescent yeast and bacteria (a product currently sold by Molecular Probes as 'BioParticles') (Giaimis, et al. (1994), Cytometry, 17:173-8, Haugland (2003), Oben, et al. (1988), J Immunol Methods, 112:99-103, Perticarari, et al. (1994), J Immunol Methods, 170:117-24, Ragsdale, et al. (1989), J Immunol Methods, 123:259-67), but virus-based bioparticles have never been developed. The incorporation of proteins of desired specificity and function into retroviruses has never been pursued for probe purposes.

There has been a desire and long-felt need for vehicles that can encapsulate and target multimodal probes to be used in the imaging field (Massoud, et al. (2003), Genes Dev, 17:545-80). The use of liposomes and related lipid structures is one approach that others have pursued. For example, synthetic beads conjugated with lipids have been used to create fluorescent sensors for pH, chloride, calcium, and oxygen that have been used to probe intracellular compartments and phagocytic pathways (a critical component of the immune response against infections) (Ji, et al. (2000), Anal Chem, 72:3497-503, Ji, et al. (2001), Anal Chem, 73:3521-7, Ma, et al. (2004), Anal Chem, 76:569-75, McNamara, et al. (2001), Anal Chem, 73:3240-6, Nguyen, et al. (2002), Anal Bioanal Chem, 374:69-74). However, the implementation of such probes has generally been limited to materials (usually synthetic dyes) that can be encapsulated within a lipid bilayer. Functional enzymes and membrane proteins have been much more difficult to capture within such structures (Walde, et al. (2001), Biomol Eng, 18:143-77). Moreover, synthetic lipid vesicles are difficult to localize and often lack the stability necessary for wide-spread application.

The specificity of membrane proteins can be controlled, in part, by engineering membrane proteins to bind antigen-specific antibodies. The antibody-binding (Z) domain of Staphylococcal Protein A (ProA) binds the constant, Fc, domain of IgG. Membrane-anchored antibodies and antibody-containing structures (ZZ-TM fusion proteins) have been incorporated into cells and viruses, primarily for use in targeting of gene therapy vectors (Bergman, et al. (2003), Virology, 316: 337-47, Masood, et al. (2001), Int J Mol Med, 8:335-43, Morizono, et al. (2001), J Virol, 75:8016-20, Nakamura, et al. (2004), Nat Biotechnol, 22:331-6, Ohno, et al. (1997), Biochem Mol Med, 62:123-7, Ohno, et al. (1997), Nat Biotechnol, 15:763-7, Sawai, et al. (1998), Mol Genet Metab, 64:44-51, Snitkovsky, et al. (2000), J Virol, 74:9540-5). In all of the published cases, ZZ-TM fusion proteins bound antibody in the appropriate orientation for targeting of retroviruses to cells expressing complementary antigen.

The use of fluorescently-labeled beads as a solid substrate for binding reactions has recently become a popular replacement for traditional 96-well plates in such techniques as immunoassays and competitive binding assays. By flowing beads and their associated protein reactants through a kinetic fluidics system, and by incorporating into the beads a number of different dyes that can be detected after excitation at different wavelengths of light, sample throughput has been increased by allowing the simultaneous detection of multiple analytes (multiplex analysis).

Thus, there is a need for improvements in the performance of probes in the areas described above to allow superior spatial localization of abnormalities in vivo, as well as structure-function correlation on the subcellular level, and already have applications in the fields of cancer biology, cell biology, and gene therapy, for example in the detection of tumor markers and in tracking the delivery and function of gene therapy vectors. There is also a need for probes that can be spatially localized, that can amplify infrequent signals, and that can compartmentalize multiple reporters simultaneously. There is also a need to generate probes that can generate multimodal signals. The present invention satisfies the needs as well as others.

Ion channels are membrane-bound proteins which control the flow of ions across biological membranes, either through passive or active transport mechanisms. In the context of cell electrophysiology, ion channels are the primary molecular mechanism by which cells maintain a membrane potential. Membrane potential is generated and maintained by concentration gradients of charged ions such as sodium, potassium, chloride, hydrogen, and calcium, across the otherwise impermeable cell membrane. The membrane potential of a cell can change in the course of signaling, development, differentiation of function, and pathology.

Electrical potential differences are present across the plasma membrane of most living prokaryotic and eukaryotic cells, and also between the cytosol and the interior of organelles such as chloroplasts and mitochondria. As a consequence of ion concentration gradients that are maintained by active transport processes, the electrical membrane potential of some resting cells is approximately −70 mV, with the cell interior electrically negative with respect to the exterior. The membrane potential is reduced to zero when the plasma membrane is ruptured by chemical or physical agents. When a membrane is permeable to only a single ion species (the simplest theoretical model), the membrane potential is given by the Nernst equation: $V=-(RT/zF)*\ln([I]_{in}/[I]_{out})$ where R is the gas constant, T is the absolute temperature, z is the ion valency, F is Faraday's constant, I is the cation concentration. The value of RT/F is 25.7 mV at 25° C.

A change in membrane potential in the positive direction is called a depolarization. Conversely, a change in membrane potential in the negative direction is called a hyperpolarization. Depolarization of the cell membrane during the action potential of a nerve or muscle cell typically results in the cell interior transiently becoming electrically positive with respect to the exterior, as Na-channels open, Na+ rushes in, and membrane potential approaches the $V_{ion}$ of Na+, +60 mV. Voltage-gated K-channels will open when there is sufficient depolarization, allowing K+ to rush out and bringing the membrane potential back to its resting value, approximately the $V_{ion}$ of K+.

Membrane potential is often measured by electrophysiological methods in which glass microelectrodes are inserted into or onto cells (e.g. voltage clamp, patch clamp) to directly measure the difference in electrical potential across the cell membrane. Many biological structures, however, are not readily amenable to microelectrode measurement, such as sub-cellular organelles and neuronal processes. Moreover, microelectrode techniques are difficult to automate for drug discovery applications.

In these cases, fluorescent dyes and probes that measure electrical membrane potential represent an alternative. Fluorescent dyes that can measure membrane potential were first employed in the 1970s, and have evolved in capability, speed of response, and sensitivity for the past thirty years (Cohen, et al. (1978), Rev Physiol Biochem Pharmacol, 83:35-88, Molecular Probes Handbook (2002), Plasek, et al. (1996), J of Photochemistry and Photobiology, 33:101-124, Smith (1990), Biochim Biophys Acta, 1016:1-28). Numerous studies have shown that optically and electrically recorded action potentials are identical in shape, and fluorescent dyes are now a well-accepted methodology for measuring electrical potential across a membrane. Since a single ion channel can facilitate the flux of a million ions per second, membrane potential change can be detected with high sensitivity even in cases of limited quantities of ion channel.

Many biological compartments, despite their importance in biology, are not readily amenable to ion or voltage measurements using conventional technologies. For example, some intracellular organelles are too small to seal with a microelectrode and cannot be readily labeled with a fluorescent dye or probe independent of the rest of the cell. Similarly, synaptic junctions are dynamic structures with budding vesicles, interstitial gaps, and secreted neurotransmitters and ions that cannot be easily isolated from the structure as a whole.

Thus, there remains a need for the development of an improved methodology that permits the study of ion channels and/or transporter proteins. The present invention satisfies this need. Further, there is a need for assays that permit the study of ion channel inhibitors and/or activators, and the present invention also satisfies this need as well others.

Viral vaccines are made in several ways, but all are significantly different than the lipoparticle. At least half a dozen different successful virus vaccine systems (summarized in Table 1) give support for using small particles to induce immune responses. Lipoparticles are unique because they are able to incorporate membrane proteins which are not part of the viral genome.

TABLE 1

Killed virus vaccines (Field's Virology).
Enveloped indicates whether virus is surrounded by a lipid bilayer.

| Virus Vaccine | Enveloped | Type of Vaccine |
| --- | --- | --- |
| Hepatitis A | − | Whole inactivated virus |
| Hepatitis B | + | Recombinant virus-like particles |
| Influenza A and B | + | Disrupted virus |
| Japanese encephalitis virus | + | Whole inactivated virus |
| Poliovirus | − | Whole inactivated virus |
| Rabies | + | Whole inactivated virus |

Parvovirus-like particles (VLPs) and have been used to induce cytotoxic T lymphocyte (CTL) responses. This technology involves linking an antigen to the viral particle, which is significantly different than the lipoparticle which incorporates a membrane protein of interest into the lipid membrane of the cell. The Parvovirus VLP technology does not involve a lipid bilayer and therefore cannot allow a membrane protein to maintain its structure. Martinez et al (2003) used a recombinant VLP carrying a CD8(+) T cell determinant to successfully induce an immune response in mouse neonates (Martinez et al (2003) Virology. 2003; Jan. 20; 305(2):428-35). Wakabayashi et al (2002) fused the HPV16 E7 antigen to the major and minor capsid proteins (L1 and L2) of chimeric human papillomavirus (HPV) virus-like particles (cVLPs) (Wakabayashi et al Intervirology. 2002; 45(4-6):300-7). Mice vaccinated with this cVLP successfully generated a specific CTL response.

Antibodies are also useful in determining structure and function of a polypeptide, and can also be used as therapeutics. Polyclonal antibodies are a mixture of many antibodies recognizing different epitopes of an antigen. It is possible to isolate one of these antibodies and amplify it by fusing the antibody cell to an immortal tumor cell, forming a hybridoma. Amplification of the hybridoma results in a clonal population of cells that secrete antibodies which are identical; these antibodies recognize the same epitope on the same antigen, and are known as monoclonal antibodies (Mabs). Because of their specificity to a single epitope, Mabs that recognize non-linear epitopes (epitopes formed by a conformational structure of sequentially separated amino acids) are sensitive probes of subtle conformational changes brought about by either mutational alterations or variations in physical/chemical conditions.

Historically, it has been difficult to generate good Mabs to many integral membrane proteins. Traditional methods of immunization using purified proteins or peptides have limited application to membrane-bound receptors in which removal of the protein from a lipid environment results in complete loss of conformation. While antibodies can be elicited against peptides derived from extracellular sequences of topologically complex receptors, such antibodies often react with the native receptor inefficiently. The use of whole cells has been used with success for the development of some antibodies to complex receptors (Lee, et al. (1999), J. Biol. Chem., 274: 9617-9626), but has a number of limitations. For example, many receptors, especially when over expressed within a cell, can reduce cell health, cause cell death, be cycled away from the cell surface, aggregate, denature, or have difficulty being translated, leading to poor expression. In addition, the protein of interest is typically a minor component on the cell surface, and the numbers of Mabs elicited by this approach is typically small.

The chemokine receptors CCR5 and CXCR4 serve as examples of integral membrane proteins which are difficult to generate Mabs against. CCR5 and CXCR4 are GPCRs that in addition to their normal functions in the immune system are also used by HIV to infect cells. Due to their importance for virus infection, considerable effort has been spent on developing immunological reagents to these and related receptors. Some of the first CCR5 and CXCR4 receptor antibodies were obtained via immunization with peptides (Doranz, et al. (1997), J. Virol., 71:6305-6314). However, second-generation antibodies obtained following immunization of mice with cells over-expressing the receptor of interest supplanted these first generation antibodies (Lee, et al. (1999), J. Biol. Chem., 274:9617-9626). While such an approach is labor intensive and only a very small fraction of hybridomas target the desired receptor, it is now clear that presentation of GPCRs in their native conformation is essential for the generation of effective Mabs. The solved structure of bovine rhodopsin, a 7 transmembrane (7TM) receptor, as well as structure-function studies on a variety of 7TM receptors including CCR5 and CXCR4, indicate that the extracellular domains of these proteins are conformationally complex. In addition, disulfide bonds link the amino terminal domain of these receptors with the third extracellular loop, and the first with the second extracellular loops. Thus, it is not surprising that the epitopes recognized by many Mabs are composed of residues from multiple extracellular domains of the receptor. Therefore, the native conformation of the receptor as it resides in the membrane can be of critical importance not just for its function, but also for the elicitation of specific, high affinity Mabs.

The antigenic structures of topologically complex proteins such as GPCRs, amino acid transporters, and ion channels are critically influenced by the lipid environment; a large fraction of the protein's mass, sometimes even a majority, is embedded in the lipid bilayer. Attempts to reconstitute such receptors in artificial membranes have proven difficult, though not impossible. In our experience, the most useful Mabs to 7TM proteins have thus far come from using cells for immunization that express the receptors in their native conformation. While this approach has proven successful for the generation of Mabs to the chemokine receptors CXCR4, APJ, CCR2, CCR3, and CCR5, it has proven difficult for the generation of Mabs to the chemokine receptors XCR1 (the Lymphotactin receptor), CCR4, CCR7, CCR8, and CX3CR1 (the Fractalkine receptor). In addition, most attempts have failed to produce high affinity Mabs to topologically complex receptors such as glucose transporters (e.g. Glut4), ion channels (e.g. Kv1.3), and amino acid transporters (e.g. MCAT1).

Thus, there is a need for compositions that facilitate the elicitation of an immune response against native membrane protein structures, particularly for the generation of monoclonal antibodies, of humoral response, of cellular response, and for vaccines, and the present invention also satisfies this need. The present invention fulfills these needs as well others.

Protein transfection is defined as the internalization of an exogenous protein into a target cell's cytoplasm or nucleus. While similar to DNA transfection in that both processes ultimately introduce exogenous protein into a cell, protein transfection differs by bypassing the transcription and translation machinery needed for protein production from DNA. Furthermore, by introducing a foreign protein directly into the target cell, protein transfection introduces the protein faster than DNA transfection and bypasses potential complications of DNA transfection and protein synthesis, such as undesired or incorrect RNA splicing variations, protein folding, and post-translational modifications.

Current applications for protein transfection include studying proteins that are inherently toxic to cells, that are involved in signaling cascades within cells, and that are downstream cascade regulators. For example, antibodies transfected into the cytoplasm can be used to inhibit or modify downstream signaling cascade effectors (Marrero 1995; Rui 2002). Additionally, fluorescent ligands and substrates can be transfected into a target cell's cytoplasm or nucleus to study a signaling pathway of interest (Nolkrantz 2002).

Previous protein transfection techniques include microinjection, myristylation of amino termini, protein encapsulation by various lipid formulations, such as those comprising cationic lipids, and the use of peptides that bind to the protein that is being transfected (e.g. Protein Transduction Domains (PTDs). Current commercial kits include Pro-Ject (Pierce Biotechnology, Inc.) and Profect (Targeting Systems) both using lipid-based technologies, and Chariot™, protein delivery reagent, (Active Motif) using PTD technology. Other methods of protein transfection include the HIV Tat protein. However, current methods still do not resolve the problems of transfecting membrane proteins into a cell. Most, if not all, membrane proteins require proper folding and structure to be active. The current methods of transfecting membrane proteins are inadequate and can be improved.

Thus, there is a need for new and improved protein transfection methods and compositions to introduce proteins into cells. The present invention fulfills this need as well as others.

Viruses are of great significance to the field of medicine, but there are few techniques for quantifying and characterizing viruses due to their exceptionally small size. Most viruses are between 30 nm and 1 μm, too small for direct visualization under a light microscope or with the use of most cellular detection methods. Quantification of viruses can be especially difficult, with most researchers relying on infectious assays for quantification, an assay that typically takes several days, requires live virus, and detects only infectious virions. Many infectious viruses are produced along with 10 to 100-fold more non-infectious viruses, and these non-infectious viruses are rarely quantified (Knipe, et al. (2001)). Visualization of fluorescent viruses has been used in some cases to overcome these obstacles (Leopold, et al. (2000), Hum Gene Ther, 11:151-65, McDonald, et al. (2002), J. Cell Biol., 159: McDonald, et al. (2003), Science, 300:1295-7, Seisenberger, et al. (2001), Science, 294:1929-32).

In addition, the proteins that reside on the surface of lipid-enveloped viruses are also difficult to detect and quantify. Previous research has disclosed methods of detecting some membrane proteins on the surface of intact HIV and SIV virions (Bastiani, et al. (1997), J. Virol., 71:3444-3450, Capobianchi, et al. (1994), J Infect Dis, 169:886-9, Nyambi, et al. (2001), J Immunol Methods, 253:253-62, Orentas, et al. (1993), AIDS Res Human Retroviruses, 9:1157-1165). In addition, research has demonstrated the detection of membrane proteins on a virus-like particle using confocal microscopy (Zemanova, et al. (2004), Biochemistry). However, many membrane proteins can be relatively sparse, difficult to detect, and even more difficult to quantify on an absolute basis (Coorssen, et al. (2002), Anal Biochem, 307:54-62). Yet such membrane proteins, such as the native viral envelope protein on HIV, gp160, can be central to the infectious life cycle of the virus and the pathogenesis of the disease it causes.

Furthermore, membrane proteins compose a complex structure that is often dependent on the lipid bilayer in which they reside. Methods to measure the structural state of the membrane protein within an enveloped virus are needed. When the protein of interest is Envelope, infection assays have been used, but in cases where the membrane protein does not mediate viral entry other methods are needed.

Currently, the most commonly employed assays for protein interactions include radioimmunoassays, competitive protein binding assays, and enzyme-linked immunoassays. All of these, however, suffer from a number of drawbacks: they are expensive, labor-intensive, time-consuming, and have not been used to study membrane proteins without the use of whole cells or membrane vesicles derived from cells. One of the major limitations to many in vitro analyses of protein binding is the requirement for the protein(s) of interest to be structurally intact and in solution in order for appropriate interaction with receptor to occur. Many proteins of interest, including the receptors of many viral envelope proteins, are integrated into cell membranes. These proteins are notoriously difficult to purify and solubilize in their structurally-intact form, limiting the ability to work with them. As such, laboratory techniques involving such proteins are either non-existent or involve laborious preparatory steps.

Thus, there remains a need for new and/or improved methods for detecting and quantifying viruses, viral particles, virus like particles and lipoparticles. There is also a need for new and/or improved methods and techniques to detect and quantify the membrane proteins that reside in viruses, viral particles, and lipoparticles. There is also a need for improved methods of identifying proteins, antibodies, ligands, or drugs that bind to these membrane proteins. The present invention satisfies these needs and others.

Sensors capable of detecting infectious agents and/or of detecting a serological reaction in people exposed to dangerous pathogens, are desired for rapid detection and diagnosis of infectious disease, for screening for environmental and food contaminants, and for efficient biodefense screening and response procedures (reviewed in (Iqbal, et al. (2000), Biosens Bioelectron, 15:549-78)). Flaviviruses, for example, are a group of positive-stranded RNA viruses that have a global impact resulting from their widespread distribution and ability to cause disease in humans and economically important domestic animals. Several members of this genus, such as dengue virus (DEN) and West Nile virus (WNV), are considered emerging or re-emerging pathogens because of the rapid annual increase in the rate at which they encounter humans and cause disease (Gubler (1998), Clin Microbiol Rev, 11:480-96). With 50 million cases of related illness reported annually, DEN infection has become the most significant source of arthropod-borne viral disease in humans (Gubler, et al. (1993), Infect Agents Dis, 2:383-93, Monath (1994), Proc Natl Acad Sci USA, 91:2395-400). Both DEN and WNV are emerging biodefense pathogens (category A and B, respectively) for which the development of diagnostics, therapeutics, and vaccines are the focus of considerable effort. The development of a DEN vaccine is particularly challenging because sequential exposure to different serotypes of DEN actually increases (rather than attenuates) the likelihood of developing dengue hemorrhagic fever in response to infection (Burke, et al. (1988), Am J Trop Med Hyg, 38:172-80, Graham, et al. (1999), Am J Trop Med Hyg, 61:412-9, Sangkawibha, et al. (1984), Am J Epidemiol, 120:653-69, Vaughn, et al. (2000), J Infect Dis, 181:2-9, Winter, et al. (1968), Am J Trop Med Hyg, 17:590-599). For such pathogens, characterizing not only the magnitude, but also the breadth, persistence, and specificity of the humoral response is an important component of evaluating candidate vaccines and understanding pathogenesis in infected individuals.

Conventional laboratory techniques used to detect pathogens and antibodies in blood serum and other samples include ELISA, PCR, and cell culture (Belgrader, et al. (1999), Science, 284:449-50, Belgrader, et al. (2003), Anal Chem, 75:3114-8, Rowe, et al. (1999), Anal Chem, 71:3846-52). A common limitation of these techniques is the time and complexity of the assays themselves, which usually require extensive sample handling. This renders them unsuitable for rapid screening of samples, for automation, and for portability for field applications. Recent directions in the development of alternative techniques for pathogen detection reflect these limitations in traditional technology, and the need for increased simplicity, reliability, and rapidity for methods that detect both biodefense pathogens and antibodies that target them.

Increasingly, biosensor systems are utilizing living cells, and their complex sensing and signaling mechanisms, for assays such as pathogen detection (Bechor, et al. (2002), J Biotechnol, 94:125-32, Belkin (2003), Curr Opin Microbiol, 6:206-12, Conway, et al. (2002), Receptors Channels, 8:331-41, Haruyama (2003), Adv Drug Deliv Rev, 55:393-401, Kamei, et al. (2003), Biotechnol Lett, 25:321-5, Karube, et al. (1994), Curr Opin Biotechnol, 5:54-9, Park, et al. (2003), Biotechnol Prog, 19:243-53). Cell-based biosensors are already being exploited in diagnostic and screening tests, including some for biodefense pathogens. For example, a technique was reported (Rider, et al. (2003), Science, 301:213-5) in which B-cells were used to report the presence of clone-specific pathogens. These cells were transfected with a calcium-sensitive bioluminescent protein that was sensitive to fluctuations in cytosolic calcium resulting from B-cell receptor (BCR) signaling. Cell-based assays of this sort show improvements in fidelity, simplicity, and speed when compared with traditional pathogen detection techniques. However, despite their advantages compared with traditional methods, assays that utilize living cells are limited in three main areas: 1) Dependence on living cells that require high maintenance and specialized tissue culture facilities, rendering miniaturization (due to cell size and environmental requirements) and field application impractical or impossible. 2) Limitation in flexibility of antigen recognition due to the clonal nature of cell pathogen-receptors (such as BCRs), requiring extensive cell line development for detection of diverse pathogens or of mutants and variants. 3) Susceptibility to false positives resulting from reliance on a single pathogen receptor, and on detection of a single downstream (and often promiscuous) signaling event (e.g. $Ca^{++}$ flux). There is a need for the development of pathogen (and ligand) biosensors that can utilize cell-sensing and signaling machinery in a flexible and cell-free format in order to overcome these limitations.

Sensors that take advantage of the signaling capacity of single-transmembrane (1-TM) proteins, such as BCRs and kinase-activating receptors, have not been utilized outside of laboratory-based live-cell assays. Cells have been required for both the maintenance of the native structure of 1-TM proteins (which is reliant upon the presence of the cell membrane), and for the retention of cellular signaling pathways that can be linked to a measurable reporter. 1-TM receptors typically comprise an extracellular ligand recognition domain, a transmembrane domain that crosses the cell membrane once and anchors the protein to the cell surface, and one or more intracellular domains which interact directly or indirectly with cytosolic signaling proteins. Functionally, many 1-TM receptors mediate their signaling activities through a common mechanism—ligand-induced receptor cross-linking. For example, BCRs exist as unliganded monomers on the cell surface that, when cross-linked by an appropriate antigen, form clusters on the cell surface. Clustering and cross-linking of 1-TM receptors induces a cascade of phosphorylation events that recruits adaptors and other accessory proteins to the receptor complex, ultimately activating multiple signaling pathways such as calcium/calmodulin, phospholipase C, Ras, and MAPK. The ability to easily manipulate 1-TM pathogen and ligand recognition elements, and link them to signaling and reporter (output) pathways in cell-free vehicles, could enable new types of pathogen sensors to be developed, exhibiting many of the advantages of live-cell assays, but without their practical limitations.

One method of measuring protein-protein interactions is by fluorescent resonance energy transfer (FRET). When complementary fluorescent reporters are brought into close proximity, the transfer of fluorescent energy from an excited donor (CFP) to an acceptor (YFP) results in fluorescence emission by the acceptor (Stanley (2003), Chroma Application Note No. 6). The transfer of energy is by non-radiative dipole-dipole interaction, making FRET efficiency highly dependent upon fluorochrome pair proximity (within 5 nm), and thus an excellent indicator of proximity. FRET strategies have been used on numerous occasions within cells and cell-based biosensors to measure interactions between membrane proteins (Chan, et al. (2001), Cytometry, 44:361-8, Minor (2003), Curr Opin Drug Discov Devel, 6:760-5, Overton, et al. (2000), Curr Biol, 10:341-4, Overton, et al. (2002), Methods, 27:324-32, Tertoolen, et al. (2001), BMC Cell Biol, 2:8). A similar system using a luminescent and fluorescent pair is also available (BRET).

Thus there is a need for improved molecules and methods for the detection of antigens and ligands. The present invention fulfils these needs as well as others.

G protein coupled receptors (GPCRs) are a large family of cell surface receptors with an assortment of ligands and diverse biological actions. The importance of GPCRs in cellular function, their diversity, and their accessibility to exogenous agents make them an important focus of research into disease processes and drug discovery.

GPCR activation events are communicated to cell signaling pathways via GTP-binding proteins (G proteins) associated with the intracellular domain of the receptor. GPCRs constitute the largest group of drug targets today, highlighting their importance in biological research and in disease pathways. However, GPCRs are structurally complex, spanning the cell membrane seven times. Removal from the cell membrane usually destroys the receptor's native structure which is maintained by the environment of the lipid bilayer. GPCRs are thus extremely difficult to purify and manipulate experimentally, and their study relies on whole cells or isolated cell membranes. However, these formats suffer from poor receptor purity, stringent environmental requirements, and an inability to be miniaturized, prohibiting their application to emerging micro- and nano-scale detection technologies. Methods for assaying GPCR activation that can be applied to microfluidic drug-screening devices are needed.

Although GPCRs respond to a wide variety of extracellular ligands, they mediate intracellular communication through common signaling pathways (Kiselyov, et al. (2003), Cell Signal, 15:243-53, Morris, et al. (1999), Physiol Rev, 79:1373-430). The intracellular domains of GPCRs are coupled to a heterotrimeric complex of membrane-associated GTP-binding proteins (G proteins). Nearly all GPCRs initiate their signaling pathway through the action of G proteins, which transmit the GPCR activation signal to intracellular effectors. The G protein complex consists of $G\alpha$, $G\beta$, and $G\gamma$ subunits, each of which occur as a number of ligand- and signal-specific isotypes. For example, the Go family includes Gi, Gs, Gq, and $G_{12}$ isotypes, and a family such as Gi is composed of several sub-members (Gi, Go, Gt, Ggus, and Gz). In the inactive state, the $G\alpha$ subunit binds GDP and maintains the GPCR in a ligand-receptive conformation. GPCR stimulation by an agonist induces $G\alpha$ to exchange GDP for GTP. The now activated G protein subunits dissociate and activate signaling cascades that release second messengers such as cAMP and intracellular calcium. These second messengers exert their biological effects by modifying cellular processes such as gene expression, ion balance, and the release of bioactive substances. The hydrolysis of GTP to GDP by $G\alpha$ returns the G proteins to their inactive state, attenuating and eventually terminating the signal. Multiple accessory proteins, such as arrestins and GTPase-activating proteins (GAPs), modify these downstream signaling events. A number of studies have created GPCR-G protein fusion proteins (Milligan (2000), Trends Pharmacol Sci, 21:24-8, Milligan (2002), Method in Enzymology: G Protein Pathways Part A, 343:260-273, Molinari, et al. (2003), J Biol Chem, 278:15778-88).

GPCR activation is traditionally measured experimentally by monitoring one or more of the participants of these signaling cascades. Fluorescently or radioactively labeled GPCRs, G-proteins, and guanine nucleotides, have all been cited as potential reporters of intracellular signaling events (Eidne, et al. (2002), Trends Endocrinol Metab, 13:415-21, Hemmila, et al. (2002), Drug Discov Today, 7:S150-6, Kimple, et al. (2001), J Biol Chem, 276:29275-81, Milligan (2003), Trends Pharmacol Sci, 24:87-90, Moore, et al. (1993), Biochemistry, 32:7451-9, Remmers (1998), Anal Biochem, 257:89-94, Remmers, et al. (1996), J Biol Chem, 271:4791-7, Remmers, et al. (1994), J Biol Chem, 269:13771-8). However, 'endpoint' messengers such as calcium flux or cAMP production are not stimulated by a number of important GPCRs and G proteins, and as such, the ligands and functions of many GPCRs remain unknown.

Thus there is a need for improved methods for detecting GPCR activation to overcome the current constraints by being simple, flexible, and applicable to a wide range of GPCRs and G-proteins. The present invention fulfils these needs as well as others.

Proteins that span the membrane multiple times present a unique set of challenges for structural analyses such as x-ray crystallography. As a result, the structure of only a handful of multiple-spanning membrane proteins has been determined at high resolution (for example, see (Jiang, et al. (2002), Nature, 417:515-22, Jiang, et al. (2003), Nature, 423:33-41, Palczewski, et al. (2000), Science, 289:739-45, Pebay-Peyroula, et al. (1997), Science, 277:1676-1681) (approximately 40 unique membrane protein structures compared to 3,000 unique soluble protein structures) (Nollert, et al. (2004), DDT: Targets, 3:2-4, Werten, et al. (2002), FEBS Lett, 529:65-72), and the vast majority of these proteins are relatively simple, prokaryotic proteins (52 of 67 total membrane protein structures are of bacterial origin) (Werten, et al. (2002), FEBS Lett, 529:65-72).

Structural studies of any protein typically require the protein to be expressed at high levels, solubilized for manipulation, and purified to near complete homogeneity. Integral membrane proteins present difficulties in all three of these requirements. While soluble (secreted or cytoplasmic) proteins can be expressed at high levels within traditional E. coli and insect cell expression systems, membrane proteins have been less successful, in part because these systems lack many of the (poorly understood) folding, membrane insertion, and trafficking mechanisms used to express higher-order eukaryotic membrane proteins. Oligomeric membrane proteins present even greater difficulties, as co-expression of subunits and assembly systems are required for efficient production of structurally intact functional units. In addition, the membrane surface area of cells is limited, restricting the quantity of membrane protein that can be expressed in any given cell (e.g. compared to secreted and intracellular proteins). Exemplifying this limitation, rhodopsin, the sole GPCR for which the crystal structure has been determined, was derived from natural tissue (bovine retinas) that contain unusually large amounts of the protein (Palczewski, et al. (2000), Science, 289:739-45). Comparable natural sources for other membrane proteins are rarely available. Despite these difficulties, however, several membrane proteins have been successfully expressed at high levels, often using baculovirus insect cell expression systems (Klaassen, et al. (1999), Biochem J, 342 (Pt 2):293-300, Lundstrom (2003), Biochim Biophys Acta, 1610:90-6, Massotte (2003), Biochim Biophys Acta, 1610: 77-89, Nollert, et al. (2004), DDT: Targets, 3:2-4). Mammalian expression systems, such as semliki forest virus (SFV), have also been used to obtain large quantities of membrane proteins (Lundstrom (1997), Curr Opin Biotechnol, 8:578-82, Lundstrom (2003), Biochim Biophys Acta, 1610:90-6, Lundstrom, et al. (2001), FEBS Lett, 504:99-103, Wurm, et al. (1999), Curr Opin Biotechnol, 10:156-9). Just as importantly, advances in crystallization have extended the useful life of limited quantities of protein by miniaturizing crystallization trials (2 mg of protein is often now sufficient for an entire trial).

Despite the successful large-scale expression of at least some membrane proteins, membrane proteins are still difficult to crystallize. A primary reason for this disparity is because once expressed, membrane proteins face another obstacle—purification to homogeneity. While soluble proteins can be readily purified from the cellular media (in the case of secreted proteins) or soluble cell fractions (in the case of cytoplasmic proteins), membrane proteins remain embedded within the cell where they are difficult to extract. A significant portion of many membrane protein molecules, sometimes even a majority of the protein, is embedded within the plasma membrane lipid bilayer. GPCRs for example, possess seven distinct transmembrane domains, making large portions of these proteins hydrophobic and the protein as a whole topologically complex. Removal of GPCRs (and most other multi-spanning membrane proteins) from their lipid bilayer usually results in loss of their native structure. Because 95% of the cell's membrane content is inside the cell (nucleus, mitochondria, endoplasmic reticulum, golgi, etc.), purification of plasma membrane proteins is not trivial. Detergents can allow solubilization of some membrane proteins in their native state, but this is an empirical and very time-consuming process, and even then stability is only transient. Finding a detergent that keeps a membrane protein structurally intact, in micelle form, and stable enough for purification is difficult; finding one that is selective enough to accomplish these things in the presence of a large amount of contaminating lipid and protein limits the choices of detergent even further. Finally, even when membrane proteins can be expressed and purified from cells using detergents, cell lysates will contain a heterogeneous mix of the membrane protein of interest in various stages of synthesis, folding, and processing.

Therefore, there is a need for innovations that focus primarily on the development of methods for membrane protein preparation. A novel method that can enable the purification of large quantities of homogeneous membrane protein could have a major impact on drug discovery and membrane protein research.

Baculovirus vectors are commonly used to express high quantities of membrane proteins in their correctly folded, natively processed forms (Carfi, et al. (2002), Acta Crystallogr D Biol Crystallogr, 58:836-8, Carfi, et al. (2001), Mol Cell, 8:169-79, Klaassen, et al. (1999), Biochem J, 342 (Pt 2):293-300, Massotte (2003), Biochim Biophys Acta, 1610: 77-89). Baculovirus systems are limited to particular cell types (most commonly insect Sf9 or High Five cells), but result in very high levels of expression from the polyhedrin promoter in serum-free growth conditions. Insect cell-derived proteins are routinely used in crystallography studies, a result of their combined high protein yield and ability to produce correctly folded and processed eukaryotic proteins. Baculovirus vectors expressing Gag (from HIV and from MLV retroviruses) have previously been used to study retroviral assembly mechanisms (Adamson, et al. (2003), Virology, 314:488-96, Gheysen, et al. (1989), Cell, 59:103-12, Hughes, et al. (1993), Virology, 193:242-55, Royer, et al. (1992), J Virol, 66:3230-5, Yamshchikov, et al. (1995), Virology, 214:50-8, Yao, et al. (2003), Vaccine, 21:638-43, Yao, et al. (2000), AIDS Res Hum Retroviruses, 16:227-36, Zemanova, et al. (2004), Biochemistry).

Vaccinia virus vectors are one of the most potent expression systems within mammalian cells. Vaccinia is capable of infecting nearly any cell type and expresses high amounts of protein driven from an internal vaccinia promoter (synthetic early-late promoter). Both transcription and translation of vaccinia genes occur in the infected cell's cytoplasm, enabling high level expression of nearly any protein. Vaccinia expressing Gag proteins have previously been described as a means of studying retroviral assembly and budding (Karacostas, et al. (1989), Proc Natl Acad Sci USA, 86:8964-7). Vaccinia vectors can be easily produced by recombination between a specially engineered plasmid (psC60) and a wild type strain of the virus (WR), followed by plaque purification. Advantages of vaccinia also include native mammalian cell processing and trafficking. Replication-deficient vaccinia virus MVA can also be used to reduce virus-induced toxicity and the presence of live virus.

Alphaviruses, such as semliki forest virus (SFV), have proven to be among the most robust mammalian expression systems described to date, especially for correctly folded and processed eukaryotic membrane proteins (Lundstrom (1997), Curr Opin Biotechnol, 8:578-82, Lundstrom (2003), Biochim Biophys Acta, 1610:90-6, Lundstrom, et al. (2001), FEBS Lett, 504:99-103, Wurm, et al. (1999), Curr Opin Biotechnol, 10:156-9). Their utility reflects three major attributes. First, the genetic organization of the SFV genome allows the introduction of heterologous genes in place of genes encoding the viral structural proteins, where they are under the control of an internal sub-genomic promoter (26S). Second, RNAs encoded by alphavirus vectors (called replicons) are capable of cytoplasmic replication in transduced cells. Replication of the replicon RNA in the cytoplasm effectively increases the number of templates for transcription and bypasses mRNA nuclear export limitations, resulting in high-level gene expression. Finally, when SFV structural genes are provided in trans, SFV replicons can be packaged into virus particles capable of single-round infection of virtually any cell type. SFV vectors expressing Gag (from HIV and from MLV retroviruses) have previously been used to study viral assembly and to produce more effective vaccines (L1, et al. (1996), Proc Natl Acad Sci USA, 93:11658-63, Suomalainen, et al. (1994), J Virol, 68:4879-89, Weclewicz, et al. (1998), J Virol, 72:2832-45). While SFV is capable of high levels of protein expression within hours of infection, the virus normally kills infected cells within several days. Mutations of SFV have been characterized that delay or prevent cytotoxicity that can be used (Lundstrom, et al. (2001), FEBS Lett, 504:99-103). Numerous alternative alphavirus expression systems exist (pSFV-help, Invitrogen) and/or are emerging (producer cells with capsid-E1-E2/3) that continue to improved ease of use and viral titer.

Recombinant adenovirus expressing Gag has previously been developed as a means of producing retroviruses for gene therapy (Caplen, et al. (1999), Gene Ther, 6:454-9, Duisit, et al. (1999), Human Gene Therapy, 10:189-2000, Lin (1998), Gene Therapy, 9:1251-1258, Ramsey, et al. (1998), Biochem Biophys Res Commun, 246:912-9, Torrent, et al. (2000), Cancer Gene Ther, 7:1135-44, Yoshida, et al. (1997), Biochem Biophys Res Commun, 232:379-82).

SUMMARY OF THE INVENTION

The present invention provides lipoparticles comprising a viral protein component and a cellular protein, wherein said viral protein component consists essentially of a viral structural protein.

In some embodiments, the present invention provides lipoparticles comprising a viral protein component and a cellular protein, wherein said cellular protein is an unmodified protein, and wherein said lipoparticle is reverse transcription incompetent.

The present invention also provides lipoparticles comprising an unmodified viral structural protein and a cellular protein, provided that the only viral proteins in said lipoparticle are structural proteins.

In some embodiments, the present invention provides lipoparticles comprising a viral structural protein and a native cellular protein, provided that the only viral proteins in said lipoparticle are structural proteins.

The present invention provides compositions comprising an isolated lipoparticle of any attached to a biosensor surface.

In some embodiments, the present invention provides lipoparticles comprising a viral protein component, a cellular protein and a G-protein.

In some embodiments, the present invention provides methods of identifying modulators of a GPCR comprising: a) contacting a lipoparticle comprising a GPCR and a G-protein with a test compound; and b) measuring GPCR activity.

In some embodiments, the present invention provides methods for producing a lipoparticle comprising: a) contacting a cell with nucleic acid encoding an unmodified viral structural protein and a cellular protein; and b) culturing said cell under conditions resulting in production of said lipoparticle, provided that the only viral protein encoded by said nucleic acid is a structural protein.

In some embodiments, the present invention provides methods for producing a lipoparticle comprising: a) contacting a cell having a membrane protein of interest with an adenovirus encoding at least a viral Gag protein; and b) culturing said cell under conditions resulting in production of said lipoparticle.

In some embodiments, the present invention provides methods for producing a lipoparticle comprising: a) contacting a cell with an adenoviral vector encoding at least a viral Gag protein and a cellular protein or an adenoviral vector encoding at least a viral Gag protein and a nucleic acid encoding said cellular protein; and b) culturing said cell under conditions resulting in production of said lipoparticle.

In some embodiments, the present invention provides chimeric viral vectors comprising adenoviral nucleic acid and retroviral nucleic acid, provided that said retroviral nucleic acid comprises a sequence encoding Gag, but does not comprise a sequence encoding the envelope, promoter, or packaging signal of the retrovirus.

In some embodiments, the present invention provides methods of eliciting an immune response in a subject comprising administering lipoparticles to said subject.

The present invention also provides methods of assessing the binding interaction of a protein with a ligand, said method comprising contacting a lipoparticle comprising said protein, wherein said lipoparticle is attached to a substrate, with a ligand of said protein; and detecting any change in said substrate compared with any change in an otherwise identical substrate wherein said lipoparticle is not contacted with said ligand; wherein detecting a change in said substrate wherein said lipoparticle is contacted with said ligand compared with said otherwise identical substrate wherein said lipoparticle is not contacted with said ligand assesses said binding interaction of said protein with said ligand.

The present invention also provides methods of identifying potential ligands of a protein, said method comprising contacting a lipoparticle comprising said protein, wherein said lipoparticle is attached to a substrate, with a test ligand and detecting any change in said substrate compared with any change in an otherwise identical substrate wherein said lipoparticle is not contacted with said ligand; wherein detecting a change in said substrate wherein said lipoparticle is contacted with said ligand compared with said otherwise identical substrate wherein said lipoparticle is not contacted with said ligand identifies a ligand.

The present invention also provides methods of identifying a compound that affects binding between a ligand and a protein, said method comprising contacting said compound with said ligand; contacting said compound/ligand complex with a lipoparticle comprising said protein, wherein said lipoparticle is attached to a substrate; and detecting any change in said substrate compared with any change in an otherwise identical substrate wherein said compound is not contacted with said ligand and said ligand is contacted with said lipoparticle; wherein detecting a change in said substrate when said compound is contacted with said ligand compared with said otherwise identical substrate wherein said ligand is contacted with said lipoparticle assesses said effect of said compound.

In some embodiments, the present invention provides methods of detecting a ligand of a protein in a test sample, said method comprising contacting a lipoparticle comprising said protein, wherein said lipoparticle is attached to a substrate with a test sample; and detecting any change in said substrate compared with any change in an otherwise identical substrate wherein said lipoparticle is not contacted with said test sample; wherein detecting a change in said substrate wherein said lipoparticle is contacted with said ligand compared with said otherwise identical substrate wherein said lipoparticle is not contacted with said test sample indicates the presence of said ligand in said test sample.

In some embodiments, the present invention provides immunogens comprising a lipoparticle.

The present invention also provides methods of eliciting an immune response to a protein, said method comprising the introduction of a lipoparticle to an animal.

In some embodiments, the present invention provides methods of eliciting an immune response to a protein, said method comprising the introduction of a lipoparticle to an animal.

In some embodiments, the present invention provides methods of determining the structure of a membrane protein comprising: a) isolating a membrane protein from a lipoparticle containing said membrane protein; and b) determining said structure of said membrane protein; wherein said membrane protein is not a viral envelope protein.

In some embodiments, the present invention provides methods of determining the structure of a protein comprising: a) isolating a protein from a lipoparticle containing said membrane protein; and b) determining said structure of said protein; wherein said protein comprises a Gag fusion protein.

In some embodiments, the present invention provides compositions comprising an array of lipoparticles attached to a surface.

In some embodiments, the present invention provides methods of detecting an infectious pathogen in a sample comprising the steps of: a) contacting the sample with an array of lipoparticles attached to a surface, wherein said array of lipoparticles comprises membrane proteins that interact with various infectious pathogens; and b) detecting an interaction with said array of lipoparticles; wherein said detection of said interaction indicates the presence of an infectious pathogen.

In some embodiments, the present invention provides methods of determining the presence of a substance in a sample comprising the steps of: a) contacting the sample with an array of lipoparticles attached to a surface, wherein said lipoparticles comprise membrane proteins that interact with said substance; and b) detecting an interaction with said array of lipoparticles; wherein said detection of said interaction indicates the presence of said substance.

In some embodiments, the present invention provides methods of identifying an inhibitor of a binding activity of a substance to a membrane protein comprising the steps of: a. contacting said substance with an array of lipoparticles comprising said membrane protein attached to a surface to which said substance normally binds, in the presence of a potential inhibitor; and b. detecting an interaction of said substance with said array; wherein if an interaction is detected, then said potential inhibitor does not inhibit said binding and if an interaction is not detected then said potential inhibitor inhibits said binding.

In some embodiments, the present invention provides methods for spotting lipoparticles, viruses, or virus-like particles in an array format onto a surface comprising including in the spotting medium a preservative.

In some embodiments, the present invention provides methods of identifying a binding partner of a membrane protein comprising: a) contacting a surface coated with lipoparticles, viruses, or virus-like particles comprising said membrane protein with an array comprising potential binding partners; and b) detecting binding of potential binding partner to said membrane protein.

In some embodiments, the present invention provides lipoparticles comprising a viral protein component and a cellular protein, wherein said viral protein component consists essentially of a viral structural protein, wherein said cellular protein is an ion channel protein or transporter protein.

In some embodiments, the present invention provides methods to determine membrane protein function in a lipoparticle, virus, or virus-like particle comprising a membrane protein, wherein said lipoparticle, virus, or virus-like particle further comprises a detectable agent, wherein measuring either an increase or decrease in the detectable agent is used to determine the membrane protein function.

In some embodiments, the present invention provides methods of identifying a stimulator of a membrane protein comprising: a) contacting a lipoparticle comprising said membrane protein and a detectable agent with a compound; and b) measuring any change in the detectable agent; wherein said change in the detectable agent is used to indicate that said compound is a stimulator.

In some embodiments, the present invention provides methods of identifying an inhibitor of a known stimulator of an ion channel protein or a transporter protein within a lipoparticle, wherein said lipoparticle comprises an ion channel or transporter, comprising the steps of: a) contacting said lipoparticle with said stimulator; b) contacting said lipoparticle with a test compound; c) measuring the function of said ion channel protein or transporter protein.

In some embodiments, the present invention provides methods of detecting changes in ion concentration in a location comprising: a) microinjecting lipoparticles comprising a membrane protein and a detectable agent to said location; and b) detecting changes in ion concentration by measuring said change in said detectable agent.

In some embodiments, the present invention provides immunogenic compositions comprising a lipoparticle comprising a protein of interest and at least one immunostimulatory component.

In some embodiments, the present invention provides methods of producing antibodies against a protein comprising: a) administering a immunogenic composition comprising said protein to an animal; and b) isolating said antibodies.

In some embodiments, the present invention provides methods of identifying a binding partner of a membrane protein comprising: a) contacting a lipoparticle, virus, or virus-like particle comprising said membrane protein with a library, wherein said library comprises more than one potential binding partner; b) detecting the binding of said binding partner to said membrane protein.

In some embodiments, the present invention provides methods of transfecting a protein into a cell comprising contacting said cell with a lipoparticle comprising said protein.

In some embodiments, the present invention provides methods of transfecting a protein into a cell comprising contacting said cell with a lipoparticle comprising a viral protein component and said protein, wherein said viral protein component consists essentially of a viral structural protein.

In some embodiments, the present invention provides methods of correcting a protein defect in an individual comprising administering a cell transfected with a lipoparticle.

In some embodiments, the present invention provides particles comprising a fluorophore wherein said fluorophore changes fluorescence in response to pH, membrane potential, oxidation state, NO level, ion concentration, ATP concentration, protein interaction, or combinations thereof and wherein said particle is less than 1 μm In some embodiments, the present invention provides lipoparticles comprising a Gag fusion protein and exogenous membrane protein, wherein said Gag fusion protein comprises a fluorescent protein or an enzymatic protein.

In some embodiments, the present invention provides lipoparticles comprising a modified lipid.

In some embodiments, the present invention provides lipoparticles comprising at least one of a radioactive molecule, a magnetic substance, a paramagnetic substance, a biotinylated molecule, an avidin-like molecule, gold, or combinations thereof and optionally a fluorophore.

In some embodiments, the present invention provides methods of incorporating a molecule into a lipoparticle, virus or a virus-like particle comprising contacting an AM-ester form of said molecule with a lipoparticle comprising an esterase.

In some embodiments, the present invention provides methods of incorporating a molecule into a lipoparticle, virus or a virus-like particle comprising contacting a soluble form of said molecule with said lipoparticle and performing electroporation, sonication, or vortexing.

In some embodiments, the present invention provides methods of inducing pores in a lipoparticle comprising incubating said lipoparticle with a pore-forming peptide, an alkane, or a detergent.

In some embodiments, the present invention provides methods of attaching a molecule to a lipoparticle, virus, or virus-like particle comprising contacting a modified molecule with said lipoparticle, virus, or virus-like particle, wherein said lipoparticle, virus, or virus-like particle is able to bind to said modified molecule.

In some embodiments, the present invention provides methods of determining binding of a compound to a lipoparticle, virus, or virus-like particle comprising a) contacting said compound with said lipoparticle; and b) determining if said compound binds to said lipoparticle, wherein said compound or said compound and said lipoparticle comprises a fluorescent label.

In some embodiments, the present invention provides methods of detecting the presence of an antigen in a sample comprising: a) contacting a lipoparticle comprising a binding partner for said antigen with said sample; and b) detecting a signal in said sample; wherein said detection of said signal indicates the presence of said antigen.

In some embodiments, the present invention provides methods of hybridizing an oligonucleotide to a target sequence in a lipoparticle, virus, or virus-like particle comprising contacting said oligonucleotide with said lipoparticle, virus, or virus-like particle comprising said target sequence under conditions that permit hybridization of said oligonucleotide to said target sequence.

In some embodiments, the present invention provides methods of detecting lipoparticle fusion comprising: a) contacting a lipoparticle, virus, or virus-like particle containing a fusigenic membrane protein with a lipoparticle comprising a receptor for said fusigenic membrane protein; and b) detecting said fusion; wherein said lipoparticle, virus, or virus-like particle comprises at least one reporter that is detectable upon fusion.

In some embodiments, the present invention provides lipoparticles, viruses, or virus-like particles attached to a bead, wherein said lipoparticle is attached to said bead via WGA, PEI, avidin-biotin interaction, poly-lysine interaction, or covalent coupling.

In some embodiments, the present invention provides methods for calculating the number of lipoparticles, viruses, or virus-like particles in a sample comprising: a) labeling said particles with a fluorophore; b) detecting said labeled particles, and c) counting said particles.

In some embodiments, the present invention provides methods for calculating the quantity of particles, wherein said particles are lipoparticles, viruses, or virus-like particles comprising: a) measuring a detectable properties of a particle sample; and b) determining said quantity of particles by a correlation of amount of said properties to an amount of said particles.

In some embodiments, the present invention provides methods for detecting the structural integrity of a membrane protein within a particle comprising a) contacting said particle with a molecule that binds to said membrane protein; and b) detecting binding of said molecule to said particle; wherein binding of said molecule to said particle is indicative that the structural integrity of said membrane protein is intact.

In some embodiments, the present invention provides methods for determining the purity of a particle, wherein said particle is a lipoparticle, virus, or virus-like particle preparation comprising: a) quantifying number of particles in said preparation; b) quantifying total protein concentration in said preparation; and c) determining said purity by dividing the total protein concentration by the number of particles; and d) dividing the number obtained from step c) by the theoretical protein weight of said particle, wherein a value of about 1 is indicative of a pure sample and a value greater than 1 is indicative of a sample that is not completely pure.

In some embodiments, the present invention provides lipoparticles comprising at least one fusion protein, wherein said fusion protein comprises at least one binding domain, at least one transmembrane domain, and at least one reporter domain.

In some embodiments, the present invention provides methods of detecting the presence of an antigen in a sample comprising contacting said sample with at least one lipoparticle comprising a binding partner wherein said particle comprises at least one fusion protein comprising at least one binding domain, at least one transmembrane domain, and at least one reporter domain and detecting the signal from said lipoparticle.

In some embodiments, the present invention provides devices comprising at least one lipoparticle and capable of being used to perform the method described herein.

BRIEF DESCRIPTION OF THE DRAWINGS

FIGS. 1A and B: A. Lipoparticles were produced in the cell types indicated on the x-axis, including human HEK-293T and HeLa, quail QT6, monkey Vero, hamster BHK, mouse NIH-3T3, and cat CCC cells. Samples were collected after two days and assayed for MLV Gag, CCR5, or transfection efficiency using a lacZ reporter transfected in parallel. B. Dot blot results of CCR5 expression from a separate experiment with improved sensitivity and additional transfection modalities are shown. Cells were transfected using multiple reagents, including CaPO4, Lipofectamine 2000, Effectene, Lipofectamine, and Lipofectamine Plus. Samples were also assayed for Gag by ELISA with results similar to that in panel A (data not shown).

FIG. 2: Lipoparticles were produced in NIH-3T3 cells using an Adenovirus expression vector. An Adenovirus vector expressing a Gag-GFP fusion protein (Ad-Gag-GFP) was constructed using Invitrogen's Gateway kit and used to infect murine NIH-3T3 cells. Expression of Gag-GFP is confirmed by the presence of fluorescent cells 48 h post-infection (A). The Gag-GFP fusion protein has been previously constructed and tested in a pcDNA3 plasmid vector, and the GFP fusion protein does not interfere with lipoparticle production. The presence of GFP enables lipoparticles to be visualized using a 100× objective under epifluorescent illumination. The presence of lipoparticles produced from NIH-3T3 cells was confirmed by visualizing Gag-GFP particles (B). Lipoparticle production was further confirmed using western blot analysis of lysate (lys) and supernatant (sup) from NIH-3T3 cells either infected or not infected with Ad-Gag-GFP using an anti-Gag rabbit sera (C).

FIGS. 3A and B. Antibody binding to lipoparticles on a biosensor. (A) Lipoparticles containing CXCR4 were coupled to the surface of a BIACORE biosensor C1 chip. MAb concentrations down to 20 pM were detected (3-fold serial dilutions of the conformation-sensitive 12G5 MAb). Data are reference-subtracted (non-specific lipoparticles), and the data fit a bivalent interaction model. (B) Plot of 'apparent' $k_{on}$ vs $k_{off}$ for nine different (bivalent) MAbs against CXCR4 and CCR5. Each kinetic data point is derived from a dilution series of the MAb binding to captured lipoparticles (similar to the left panel). Points falling on the same diagonal line have the same $K_D$. Each binding series fit a bivalent binding model, and $K_D$ was calculated using the ratio of $k_{off}$ over $k_{on}$.

FIG. 4. Lipoparticles were lyophilized in the presence of 0-10% sucrose, trehalose, or glycerol, as indicated, and tested for binding to a CXCR4 conformation-specific monoclonal antibody (447.08) or control surfaces (a non-specific MAb) by VELISA. The presence of bound Gag in the lipoparticles was detected with a rabbit anti-Gag sera and quantitated by ELISA on an AlphaInnotech Fluorchem 8900. Non-lyophilized lipoparticles with the same amount of additive ('5% w/o Drying') were also included as a positive control. Negative controls included additive added after drying without additive ('0% Dry, 5% Binding'), a non-specific antibody ('5%, Non-specific MAb'), and no particles. Results indicate that lipoparticles lyophilized in the presence of additives retain the structure of the membrane protein CXCR4.

FIG. 15A-I. A and B. Dynamic Light Scattering. Purified lipoparticles were analyzed by dynamic light scattering using a Proterion DyanPro dynamic light scattering measuring device (A). Lipoparticles in this experiment measured 207.4 nm in diameter with a polydispersity of 18.1%. 200 nm beads were used as a control (B) and measured 235.9 nm in diameter with a polydispersity of 8.3%. It should be noted that the modeling assumptions used by the DLS software likely amplify the estimated diameter by about 25% due to the surface composition of viral particles versus theoretical hard spheres. C. 200 nm YG Fluoresbrite beads (Polysciences) were quantified in four different ways. The beads were quantified by converting weight to particles/ul by Polysciences (manufacturer's specification). The beads were then quantified by dynamic light scattering (left panel), imaging the fluorescent beads with a 100× objective and a hemocytometer under epifluorescent illumination (middle panel), and by monochrometer intensity at a wavelength of 540 nm excitation and 570 nm emission (right panel). All results were correlated with each other and are plotted against the published bead count from the manufacturer. D. Lipoparticles (left panel) and 200 nm YG Fluoresbrite beads (right panel) were counted by 100× imaging with a microscope and subjected to dynamic light scattering to obtain intensity values (counts/sec). The results from these analyses are plotted on a log scale over a wide range of values and are indicative of high correlation between the counts and the DLS intensity. The relationship between particle counts and intensity values can be related with a simple equation, as shown. E. Purified lipoparticles containing the GPCRs CXCR4 and CCR5 were analyzed by western blot. The GPCRs contained a V5 epitope tag. On the same western blot was run a purified and quantified protein standard (GFP-V5) that also contained the same V5 epitope tag. Using the standard, we were able to estimate the quantity of Shaker in the lipoparticle preparation. F. Lipoparticles containing the GPCR CXCR4 were purified using $Ni^{+2}$ beads (purity increasing from left to right) and visualized by SDS-PAGE gel and Sypro (Molecular Probes) staining of all proteins (left panel). The filled arrow represents CXCR4 monomer and the unfilled arrow indicates CXCR4 dimer. A faint ~43 kDa band is also seen, which likely represents CXCR4 without full glycosylation, as seen previously (Berson, et al. (1996), J. Virol., 70:6288-6295). The CXCR4 protein contains C-terminal V5 and His tags, and represents 5.7-6.3% of the total protein in the lanes. The major 'contaminant' bands shown in the starting material and flow-through are Gag structural proteins (capsid, matrix, and nucleocapsid) that compose the lipoparticle internal structure. A separate preparation of CXCR4 lipoparticles was prepared and similarly visualized by Sypro (right lane) and western blot (middle lane) (right panel). G. A dot blot was performed by spotting dilutions of a standard protein (purified GFP protein containing a V5 epitope tag) and dilutions of two different lipoparticle preparations with receptors containing the identical V5 tag. The dot blot filter was probed with an anti-V5 antibody and quantitated. The results of the quantitation enable quantitation of the amount of receptor per ul of lipoparticle. H. Lipoparticles were used for ligand binding competition assays using radiolabeled SDF1α (the cognate ligand for CXCR4). The concentration of CXCR4 in the lipoparticles achieved a concentration of 230.2 pmol/mg protein, much greater than typical concentrations in cells or membrane vesicles. Results are representative of two similar experiments. I. A titration curve of radiolabeled SDF1α binding to increasing amounts of CXCR4 lipoparticles was conducted. The amount of lipoparticles required to achieve a half-maximal signal ($EC_{50}$) for the amount of radioligand added was 0.15 ug, again demonstrating the high concentration of structurally intact CXCR4 in the lipoparticles. No non-specific binding to CXCR3 was detected. Results shown were performed in duplicate and are representative of two similar experiments.

FIG. 16A-B. A. VELISA Binding Detection. Lipoparticles containing either CCR5 or CXCR4 were used in a VELISA assay by binding lipoparticles to ELISA wells coated with antibodies against either CXCR4 (top panel) or CCR5 (bottom panel). Bound lipoparticles were lysed, analyzed for Gag protein, and quantified in relative units of chemiluminescence. B. CXCR4-containing lipoparticles were bound to an anti-CXCR4 MAb (447.12) or a non-specific anti-CCR5 MAb (45523) in the presence or absence of various additives, as indicated. Most additives had little or no effect on binding, as measured by VELISA. Additives such as Triton X-100 detergent, however, completely destroyed lipoparticle structure and binding, as expected.

FIG. 19. A. A Gag-G protein fusion protein was transfected into cells. The cell lysate (L) and cell supernatant (S) from this transfection was run on an SDS-PAGE gel and probed for Gag. The negative control 293T cells indicate no background activity. The full-length and processed Gag is shown for comparison (pCGP). Three different clones of the Gag-G protein (Gi) fusion are shown, with each containing the Gag-G protein fusion protein in both the lysate and the supernatant (i.e. in lipoparticles). B. Purified lipoparticles containing a Gag-G protein fusion protein were analyzed by western blot by probing using an anti-Gag antibody (left panel) or an anti-G protein (Gi) antibody (right panel). Results indicate that purified lipopaticles produced using the Gag-G protein fusion protein incorporate G protein. Lipoparticles made with Gag-Pol and with Gag-GFP are shown for comparison.

DETAILED DESCRIPTION OF THE INVENTION

Figure 5:
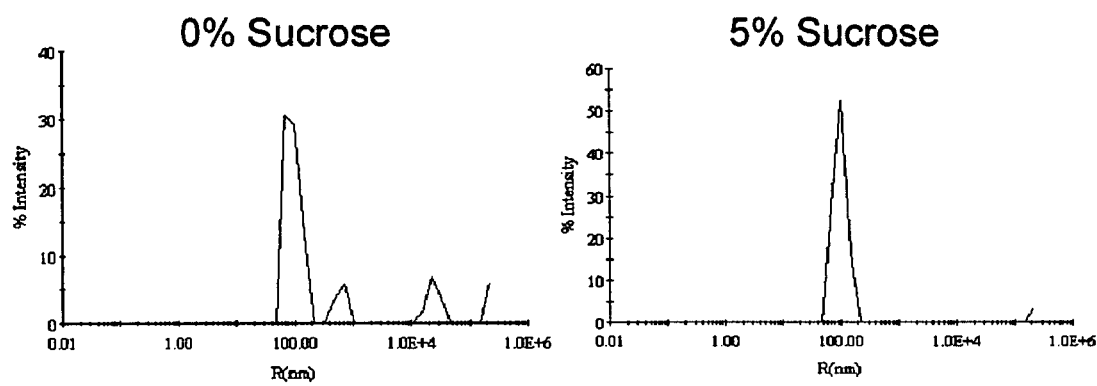
FIG. 5. Lipoparticles were lyophilized in the presence of 0% or 5% sucrose, as indicated, and analyzed using dynamic light scattering. Lipoparticles lyophilized in the absence of sucrose demonstrated multiple high molecular weight peaks, while lipoparticles lyophilized in the presence of sucrose demonstrated a single, monomodal peak similar to the unlyophilized starting material.

The methods, modifications, and compositions disclosed herein can be applied to or incorporated into lipoparticles, viruses (e.g. non-enveloped (e.g. adenovirus) and/or enveloped viruses (e.g. influenza)), virus-like particles, and the like.

The lipoparticle is based on retrovirus structures and enables structurally intact cellular proteins to be purified away from the cell. Briefly, when a retrovirus is produced from a cell, the protein core of the virus buds through the membrane of the cell. As a consequence, the virus becomes enwrapped by the cellular membrane. Once the membrane 'pinches' off, the virus particle is free to diffuse. Normally, the virus also produces its own membrane protein (Envelope) that is expressed on the cell surface and that becomes incorporated into the virus. However, if the gene for the viral membrane protein is deleted, virus assembly and budding can still occur. Under these conditions, the membrane enwrapping the virus contains a number of cellular proteins.

In a 1997 manuscript published in *Science*, the incorporation of membrane proteins (the GPCRs CCR5 and CXCR4) into retroviral pseudotype particles (Endres, et al. (1997), Science, 278:1462-1464) was demonstrated. A follow-up paper in the *Journal of Virology* demonstrated that a more complex receptor, an amino acid transporter that spans the membrane fourteen times (MCAT-1), could also be incorporated into retroviral pseudotypes and retain its structural and functional integrity (Balliet, et al. (1998), J. Virol., 72:671-676). In both cases, the structural integrity of the membrane proteins was verified using functional assays (viral fusion) and conformationally-sensitive antibodies.

In a 2000 paper published in PNAS, it was demonstrated that a number of complex proteins, including GPCRs, can be incorporated into lipoparticles and attached to the BIACORE biosensor (Hoffman, et al. (2000), Proc. Natl. Acad. Sci. USA, 97:11215-11220). Binding of antibodies, peptides, and proteins to these receptors exhibited appropriate specificity, and structural integrity of the receptors was maintained. An affinity of interaction between a protein and its receptor (HIV gp120 and CXCR4) of approximately 500 nM was also measured. This affinity is sufficiently weak so as to render previous standard binding assays unable to detect the interaction (Doranz, et al. (1999), J. Virol., 73:10346-10358, Doranz, et al. (1999), J. Virol., 73:2752-2761). The affinity with which different HIV-1 gp120 proteins bind to chemokine receptors can be an important determinant of viral pathogenesis, so measuring these interactions has enabled practitioners to begin correlating binding affinity with disease progression. The use of the lipoparticle made this possible, and provides a clear example where use of this novel approach has proven its worth. Work with the GPCRs CCR5 and CXCR4 has, to date, been directly applicable to other membrane proteins. Over twenty different membrane proteins have been incorporated into virus-based lipoparticles, including GPCRs, ion channels, transporters, and Type I and Type II single transmembrane proteins.

Lipoparticles were purified using sucrose cushions, as described previously (Balliet, et al. (1998), J. Virol., 72:671-676, Endres, et al. (1997), Science, 278:1462-1464, Hoffman, et al. (2000), Proc. Natl. Acad. Sci. USA, 97:11215-11220). Lipoparticles can also be purified using a number of methods that are often used to purify retroviruses (Arthur, et al. (1998), AIDS Res Human Retroviruses, 3:S311-9, Ausubel, et al. (2001), Current Protocols in Molecular Biology, Dettenhofer, et al. (1999), J Virol, 73:1460-7, Le Doux, et al. (2001), Hum Gene Ther, 12:1611-21, O'Neil, et al. (1993), Biotechnology (NY), 11:173-8, Pham, et al. (2001), J Gene Med, 3:188-94, Prior, et al. (1995), BioPharm, 25-35, Prior, et al. (1996), BioPharm, 22-34, Richieri, et al. (1998), Vaccine, 16:119-129, Yamada, et al. (2003), Biotechniques, 34:1074-8, 1080).

In some embodiments, unwanted proteins from the cell surface are also present on the surface of lipoparticles, but these can be minimized by over-expression of the receptor of interest and by the use of non-human cell types for production. It should be noted that traditional sources of membrane proteins—cells and membrane vesicles—also have heterogeneous protein populations, and that lipoparticles have a much greater density of conformationally intact receptor.

The production of lipoparticles comprising cellular virus receptors and membrane spanning proteins using enveloped viruses is described in US 2002/0183247A1, the entire contents of which is hereby incorporated by reference. Lipoparticles can also be produced using non-enveloped viruses as described herein.

The production of lipoparticles, however, has been limited by, for example, inefficient cellular transduction systems, bottlenecks in virus production within a cell, premature cleavage of viral polyproteins by overexpression of retroviral protease, and inefficient cell growth chambers dictated by cellular transfection techniques. The present invention provides systems and methods that overcome these difficulties.

In some embodiments of the present invention, a "chimeric" viral genome is constructed that contains nucleic acid sequences from a virus whose structural protein forms the core of a lipoparticle. In one embodiment, the virus structural protein is the Gag polyprotein of a retrovirus such as, but not limited to, murine leukemia virus, rous sarcoma virus, HIV, SIV, avian leukemia virus, equine anemia virus, and the like.

This chimeric virus may be used to transduce or transfect a producer host cell. The producer host cell may contain a membrane protein of interest that is naturally expressed on its cell surface. Alternatively, the producer host cell may be induced or treated in such a way as to express a membrane protein of interest on its cell surface. Alternatively, the producer host cell may be transduced or transfected, for example by plasmid transfection or by viral vector infection, in order to express a membrane protein on its cell surface. The result of a) the structural proteins of the lipoparticle, and b) the membrane protein of interest being expressed on the cell surface, enables lipoparticles to be formed that comprise a viral core protein and the membrane protein of interest. The resulting lipoparticle need not contain reverse transcriptase, integrase, an expressed cellular transgene, a genomic packaging signal (psi), or a viral genome, although such constituents in some embodiments can be present. The resulting lipoparticle need not be infectious, capable of entering a cell, capable of replicating, capable of expressing a gene, capable of reverse transcription, or capable of integrating in a host's genome, although it may possess such functions.

The invention relates to a lipoparticle which comprises a membrane protein. The lipoparticle allows presentation of a membrane protein while preserving the membrane protein's biological structure, such that the interaction of the protein with its cognate ligand can be studied. In certain embodiments, the lipoparticle comprises a plurality of membrane proteins.

The invention also relates to methods of making the lipoparticle of the invention including, but not limited to, a method involving using a viral vector such as, but not limited to, adenovirus or Semliki forest virus, to express the structural proteins at high levels within a desired producer cell.

The invention also relates to methods of making the lipoparticle of the invention including, but not limited to, a method involving using a viral vector such as, but not limited to, adenovirus or Semliki forest virus, to express the structural proteins of the virus and a separate vector, such as, but not limited to, adenovirus, alphavirus (e.g. Semliki forest virus) or a plasmid, to express the desired membrane and/or cellular protein at high levels within a desired producer cell. The invention also relates to methods of making the lipoparticle of the invention to a method involving using a viral vector such as, but not limited to, adenovirus or Semliki forest virus, to express both the structural proteins of the virus and the desired membrane and/or cellular protein at high levels within a desired producer cell.

The invention also relates to methods of using the lipoparticle of the invention to induce an immune response, with the immune response being used to derive monoclonal antibodies or membrane protein-specific antisera. In some embodiments the immune response may be protective against infectious diseases, against autoimmune diseases, or against cancer, by eliciting a humoral (antibody) response or a T-cell (CTL) response.

The invention also relates to methods of using the lipoparticle of the invention to assess protein-protein binding interactions using methods such as, but not limited to, microfluidics-based assays or biosensors.

Composition

A "lipoparticle," as that term is used herein, means a small particle of about ten nanometers to about one micrometer, comprising an external lipid bilayer further comprising a protein. The lipoparticle may also be about ten nm to about 500 nm, about 100 to about 500 nm, about 200 to about 400 nm, about 300 to about 399 nm, about 500 nm to about 1000 nm, about 600 to about 900 nm, or about 700 to about 800 nm. The lipoparticle does not encompass cell membrane vesicles, which are typically produced using empirical methods and which are usually heterogeneous in size. The lipoparticle also does not encompass liposomes, which typically lack core proteins that induce their formation. In some embodiments, the lipoparticle is dense, spherical, and/or homogeneous in size.

The core, or interior, of the lipoparticle is not a crucial feature of the invention and can comprise any viral structural protein. Lipoparticles of the invention can be made using, without limitation thereto, a virus (e.g. a retrovirus (e.g., HIV, MLV, RSV, and the like), a vesicular stomatitis virus, and the like. The core protein can be derived from any number of viral or synthetic sources. In the preferred embodiment, the core consists of a viral structural protein that is sufficient to mediate budding of a virus-like particle from the cell, taking a small piece of membrane and the proteins within it with the particles. In some embodiments the core protein is Gag or functional fragment thereof. In some embodiments, Gag does not comprise a heterologous tag. In some embodiments, Gag does not bind to the membrane protein that is incorporated into the lipoparticle. In some embodiments, the membrane protein that is incorporated into the lipoparticle does not have a heterologous tag. In some embodiments, the membrane protein that is incorporated into the lipoparticle does not bind to Gag.

A functional fragment of Gag is any fragment of Gag that is sufficient to produce a lipoparticle when expressed in a producer cell.

Enveloped virus particles can be produced that are missing one or more of the ordinary components of such particles, such as a portion of the genome of the enveloped virus (Volt et al., 1977, Annu. Rev. Genet. 11:203-238; Hanafusa, 1977, In: *Comprehensive Virology*, vol. 10, Fraenkel-Conrat et al., eds., Plenum Press, New York, pp. 401-483). Such virus particles are referred to herein as 'defective.' Lipoparticles comprising such a defective particle and a membrane protein are included in the present invention. It is contemplated that the omission of one or more components of such particles provides an opportunity to substitute an additional component in place of the missing component. In addition, numerous viruses known in the art are able to accommodate the presence of an additional component without deletion of a component of the virus. By way of example, the additional component may be a nucleic acid, an antisense nucleic acid, a gene, a protein, a peptide, Vpr protein, an enzyme, an intracellular antagonist of HIV, a radionucleotide, a cytotoxic compound, an antiviral agent, an imaging agent, and the like.

In another embodiment, the defective virus facilitates the production of the lipoparticle. For example, the retroviral gag gene is necessary and sufficient for budding of a retrovirus-like particle. The retroviral genes pol (including protease) and env, the packaging signal psi, and the long terminal repeats (LTRs) need not be present for production of a lipoparticle. In some embodiments, these sequences are not present. Indeed, the elimination of the protease protein (part of the pol gene) can enhance retroviral budding by avoiding premature cleavage of Gag when the protease is overexpressed. Similarly, substitution of the viral LTR promoter with a stronger promoter can enhance production. Elimination of all of these genes and the packaging signal (psi) makes production of replication competent, fusigenic, or infectious particles highly unlikely.

Thus, the lipoparticles may comprise a simple membrane in which a protein of interest can be embedded while maintaining the normal structure, function, or both, of the protein. However, in some embodiments, the membrane protein may not retain a detectable function in a lipoparticle since this is partly determined by intracellular pathways that may or may not be present inside the lipoparticle. However, in some embodiments, the membrane protein maintains its structure compared with the native protein when present in the membrane of a cell.

The lipoparticle may comprise a single membrane protein or a plurality of membrane proteins. By way of example, a lipoparticle may comprise a membrane protein that is CD4, CCR5, CXCR4, ICAM-1, ICAM-2, ICAM-3, CR3, CR4, CD43, CD44, CD46, CD55, CD59, CD63, CD71, a chemokine receptor, Tva, and MCAT-1. In some embodiments, the viral vector comprises Tva, MCAT-1, CD4, CCR5, CXCR4, both CD4 and CCR5, or both CD4 and CXCR4. However, the invention is not limited to these molecules. Indeed, the data disclosed in Balliet, et al. (Balliet, et al. (1998), J. Virol., 72:671-676) demonstrated the successful incorporation of Tva and MCAT-1 into MLV (murine leukemia virus) lipoparticles, which demonstrated that type 1 (i.e., single-spanning proteins) and an amino acid transporter (fourteen transmembrane domains), respectively, and not just multiple membrane spanning proteins such as GCPRs, can be embedded in the lipoparticles while preserving their native binding ability. Preservation of binding ability relative to the protein as typically present in the cell membrane can be assessed by functional assays, such as, but not limited to, the biosensor assays exemplified herein.

Although the Examples described herein disclose viral vectors that comprise one or two membrane proteins, one skilled in the art is enabled by the teaching provided herein to produce a viral vector comprising any number of membrane proteins in the lipoparticle. Indeed, one skilled in the art, based on the disclosure provided herein, would appreciate that the invention encompasses any membrane protein and any protein typically present in a membrane can be inserted into the lipoparticles of the invention thereby presenting the protein in its native conformation and/or preserving its binding affinity of a cognate ligand or binding partner. In some embodiments, a protein that is not normally targeted to the membrane can also be incorporated into the membrane of the lipoparticle. This may be done by having a fusion protein that comprises a protein of interest and a signal peptide that directs it to the membrane. In some embodiments, a signal peptide is removed, which allows the protein to be targeted to the plasma membrane. In some embodiments, the protein will be targeted to be a membrane protein. As used herein, the phrase "targeted to be a transmembrane protein" refers to a protein that is not normally a membrane protein but is then modified so that is becomes a membrane protein. In some embodiments, the protein is targeted so that it attaches to the membrane but does not traverse the membrane. In some embodiments, the protein is targeted to and attached to the extracellular side of the plasma membrane but does not span the membrane.

In addition, the inclusion of two or more proteins that form a complex, quaternary structure (e.g. homo- or hetero-oligomers) can be useful for drug discovery targeting or antibody production. In some embodiments, the protein is associated with the membrane either through non-covalent interactions with the membrane itself or through an interaction with another protein that is attached to the membrane.

In some embodiments, a lipoparticle comprises a multiple membrane spanning protein that spans the lipid bilayer at least twice. In some embodiments, the lipoparticle comprises a membrane protein that spans the membrane at least 3, at least 4, at least 5, at least 6, at least 7, at least 8, at least 9, at least 10, at least 11, at least 12, at least 13, or at least 14 times. The skilled artisan would understand, based upon the disclosure provided herein, that the invention encompasses a plethora of such complex proteins which traverse a membrane multiple times. Further, the invention provides a novel system comprising a lipid bilayer where one or more such proteins can interact to form, e.g., homo and/or heterodimers, or otherwise interact with other membrane proteins or itself similarly to such interactions in the native membrane where the proteins typically reside.

Multiple membrane spanning proteins include, but are not limited to, G protein-coupled receptors (GPCRs) (also known as 7-transmembrane receptors, 7TM) that span the membrane seven times, e.g., CCR5, CXCR4, CCR3, mu-opioid receptor, as well as transporters (proteins that transport molecules such as, but not limited to, amino acids or carbohydrates, across a membrane), ion channels, and the like.

As noted elsewhere herein, the invention encompasses a lipoparticle comprising a variety of membrane proteins, including combinations of proteins, which can form complexes when present in the lipoparticle. Such complexes include, but are not limited to, complexes of proteins that function together, e.g., CD4 and CCR5, CD4 and CXCR4, and the like. The lipoparticle can comprise MCAT-1, an amino acid transporter that spans the membrane 14 times, and ion channels that span the membrane 6 times, e.g., K-channel KCNH2. All of these proteins have a similar feature: they span the membrane at least once. Many of these span the membrane multiple times.

In addition, some complexes (e.g. homo and hetero-oligomers) interact only when in a lipid membrane and so retain their quaternary structure (formed by multiple subunits or proteins) only when in a lipid membrane. The lipoparticle of the invention encompasses incorporation of these proteins as well.

The membrane protein within the lipoparticle can be one which is cognate to a viral envelope protein which is displayed on the surface of a cell with which it is desired to fuse the lipoparticle, in which case the membrane protein is defined as a cellular virus receptor. The membrane protein may be any protein which is cognate to a viral envelope protein. Preferably, the membrane protein is cognate to a retroviral envelope protein, more preferably, it is cognate to a viral envelope protein of a virus selected from the group consisting of HIV, SIV, RSV, and ecotropic MLV. In some embodiments, the membrane protein is, but no limited to, CD4, CCR5, CXCR4, ICAM-1, ICAM-2, ICAM-3, CR3, CR4, CD43, CD44, CD46, CD55, CD59, CD63, CD71, a chemokine receptor, Tva, and MCAT-1. In some embodiments, the first virus receptor protein is selected from the group consisting of CD4, CCR5, CXCR4, Tva, and MCAT-1.

In addition to these membrane proteins, which have been exemplified herein, other protein types and categories are encompassed in the invention and include, but are not limited to, the following: cytoplasmic domains of proteins (e.g., active conformations, G-protein coupling domains, kinase motifs of proteins such as EGF-receptor, and the like); organelle proteins (e.g., nuclear transporters, mitochondrial receptors, endoplasmic reticulum and Golgi membrane proteins); and multimeric complexes (e.g., dimers and trimers, viral envelope proteins, hetero-oligomers, and the like). More specifically, membrane proteins of the invention include, but are not limited to, GPCRs (e.g., CCR8, XCR1, CX3CR1), transporters (e.g., glucose transporter), ion channels (e.g., K-channel Kv1.3 tetramers), tetrameric Type II protein (e.g., DC-SIGN tetramers), constitutively active GPCRs (e.g., HHV8 ORF74), viral proteins (e.g., HIV gp160, hepatitis C E1-E2 Envelope protein, expressed on endoplasmic reticulum membrane).

The lipoparticle can comprise non-membrane proteins. In some embodiments, a lipoparticle can comprise water soluble proteins that interact with a membrane receptor of interest. For example, a lipoparticle comprising a GCPR can be made with or without G-proteins, the intracellular subunits (alpha, beta, gamma) that couple to the receptor and mediate signaling. Other intracellular proteins are also included, such as Lck (interacts with CD4), arrestins, and β-adrenergic receptor kinase. These intracellular proteins can influence extracellular protein structure and can be important for formation of lipoparticles comprising complex membrane proteins that interact with soluble intracellular proteins. These proteins can be incorporated into lipoparticles either in their native form or by targeting them for lipoparticle incorporation by e.g. inclusion of signal sequences or lipid moiety tags.

In some embodiments a lipoparticle comprises a membrane protein and a cellular protein that binds to the membrane protein. In some embodiments, the cellular protein is a G-protein. In some embodiments the membrane protein is a GPCR. In some embodiments, the G-protein is G$\alpha$, G$\beta$, or G$\gamma$. In some embodiments, the G-protein is from the G$\alpha_i$ family (G$\alpha_t$, G$\alpha_{gust}$, G$\alpha_{i1}$,), G$\alpha_{i2}$ family (G$\alpha_{i3}$, G$\alpha_{o1}$, G$\alpha_{o2}$, G$\alpha_z$), G$\alpha_s$ family (G$\alpha_s$, G$\alpha_{olf}$), G$\alpha_q$ family (G$\alpha_q$, G$\alpha_{11}$, G$\alpha_{14}$,), G$\alpha_{15/16}$, or G$\alpha_{12/13}$ family (G$\alpha_{12}$, G$\alpha_{13}$). In some embodiments, the G-protein is G$\beta_1$, G$\beta_2$, G$\beta_3$, G$\beta_4$, or G$\beta_5$. In some embodiments, the G-protein is G$\gamma_1$, G$\gamma_2$, G$\gamma_3$, G$\beta_8$, or G$\gamma_{8olf}$/G$\gamma_9$.

The membrane protein that is incorporated into the lipoparticle can be a modified membrane protein. As used herein the term "modified membrane protein" refers to a protein that contains a portion of sequence that is not normally found in the unmodified membrane protein. In some embodiments, the portion is at least 5, at least 10, at least 15, at least 20, at least 25, at least 30, at least 40, at least 50 amino acid residues in length. In some embodiments, the portion is contiguous. In some embodiments, the modified membrane protein comprises a fluorescent protein. In some embodiments, the modified membrane protein comprises CFP, YFP, GFP, eGFP, BFP, CFP, dsRED or a combination thereof.

In some embodiments, the modified GPCR comprises a fluorescent protein in an intracellular loop of the G-protein. The structure of 7-transmembrane proteins is well known to one of ordinary skill in the art and the intracellular loops and the sequences comprising the cytoplasmic tail can be identified by analyzing the sequence. In some embodiments, the fluorescent protein is present in the third intracellular loop, at the cytoplasmic tail, or combinations thereof.

A GPCR protein comprising a fluorescent protein at the third intracellular loop and the cytoplasmic tail can be used to measure GPCR activation. When a ligand binds to a GPCR the cytoplasmic tail changes in spatial relationship to the intracellular loops and when these components comprise fluorescent proteins a change fluorescent energy transfer can be measured, which indicates that the GPCR is activated.

In some embodiments, the G-protein is a modified G-protein. A "modified G-protein" is a G-protein that comprises a portion of amino acid sequence that is not found in the unmodified or native G-protein sequence. In some embodiments, the modified G-protein comprises a fusion protein, a fluorescent protein, a linker, or a protease cleavage sequence.

The fusion G-protein can be a combination of the G-protein with a portion of another non-G-protein sequence. This fusion protein can, in some embodiments, assist in the incorporation or localization of the G-protein into the lipoparticle or to the cellular membrane of the lipoparticle. In some embodiments, the portion is a fragment or the entire sequence of another non-G-protein sequence. In some embodiments, the fusion-G-protein comprises Gag. The fusion protein can also comprise a membrane protein in addition to the G-protein. In some embodiments, the membrane protein is a single transmembrane protein. In some embodiments, the single transmembrane protein is CD4. The G-protein can also be fused to the GPCR itself. A G-protein can also comprise a fluorescent protein. In some embodiments, the G-protein comprises a fluorescent protein on its N-terminus, C-terminus, or both. The fluorescent protein of the G-protein can interact with a fluorescent fusion GPCR. The interaction of the two fluorescent proteins can be measured and a change in fluorescence can be used to measure GPCR activity.

Any of these fusion proteins can also comprise a linker sequence or a cleavage site. In some embodiments, the linker sequence comprises at least 5, at least 10, at least 15, or at least 20 residues. In some embodiments, the linker sequence comprises a poly-alanine sequence, an alpha helical structure, a beta-turn structure, or a beta sheet structure. The poly-alanine sequence can comprise about 5, about 10, about 15, or about 20 alanines. The linker sequence can provide flexibility between the two proteins allowing freedom of movement and functionality.

The cleavage site can be any site recognized by a cellular or non-cellular protease. In some embodiments, the protease is a viral (e.g. retroviral) protease. In some embodiments, the protease cleavage site comprises SAAWP (SEQ ID NO:1), TAAYP (SEQ ID NO:2), SAAFP (SEQ ID NO:3), SVAYP (SEQ ID NO:4), SAGYP (SEQ ID NO:5), DDDKX (SEQ ID NO:6) or EEEKX (SEQ ID NO:7) and the like. In some embodiments, the lipoparticle comprises the protease that is able to cleave the fusion protein comprising the cleavage site. Examples of proteases include retroviral proteases, such as for example, HIV SIV, MLV, RSV, and ALV proteases, enterokinase. Other kinases can be found on the world wide web at delphi.phys.univ-tours.fr/Pro-lysis/ec.html and on the world wide web at neuro.wusthedu/neuromuscular/mother/degrade.htm.

In some embodiments, a lipoparticle comprising a GPCR and a G-protein further comprises a dye. The dye can also be used to measure GPCR activity. In some embodiments, the dye is voltage sensitive or pH sensitive. Examples of dyes that can be used are described herein.

In some embodiments, the lipoparticles of the present invention comprise a GTP analog. A GTP analog can either be hydrolysable or non-hydrolysable. In some embodiments the GTP analog is a fluorescent analog. A fluorescent GTP analog can be used to measure GPCR or G-protein activity by measuring a change in fluorescent that occurs when the analog either binds to a G-protein or is cleaved by the G-protein. Examples of GTP analogs include, but are not limited to, GTPγS, MANT-GTP, MANT-GMPPNP, BODIPY-FL-GTP, BODIPY-R6G-GTP, BODIPY-TR-GTP, BODIPY FL GMP-PNP, BODIPY FL GTP-γ-S thioester, TNP-GTP (2'-(or 3'-) O-(trinitrophenyl)guanosine 5'-triphosphate), BzBzGTP (2'-(or 3'-)O-(4-benzoylbenzoyl)guanosine 5'-triphosphate), S-(DMNPE-caged) GTP-γ-S, or Europium-GTPγS.

The G-proteins can be added to the lipoparticles in any manner that allows the G-protein to interact with a GPCR. In some embodiments, this includes, but is not limited to, overexpressing the G-protein in a cell that produces lipoparticles. The production of lipoparticles is described herein. G-proteins can be overexpressed in a cell by, but not limited to, transfection, either transiently or stably.

G-proteins can also be added to a lipoparticle by contacting the lipoparticle with purified G-protein. In some embodiments, holes or pores are made in the lipoparticle which allows the G-protein to enter the lipoparticle. In some embodiments, holes or pores are made by electroporation. Lipoparticles can also be permeabilized by using methods that involve ATP, EDTA, Ca++, $Ca_3(PO_4)_2$, DEAE-dextran, polyethylene-glycol, I-14402 (a cell-loading reagent), *S. aureus* alpha-toxin, melittin, or streptolysin-O. In some embodiments, lipoparticles are permeabilized by agitation, vortexing, or sonication. In some embodiments, method of the pores are induced by a pore-forming peptide, an alkane, a detergent, and the like.

G-proteins can also be incorporated into the lipoparticles by using a G protein-Gag fusion protein. The fusion protein can contain an amino acid linker to allow adequate mobility of the G protein component for its interaction with incorporated GPCRs. The Gag-G protein fusion protein can be created by fusing a G protein to a Gag protein. In some embodiments, the fusion occurs at residue 1955 of MoMLV Gag.

In some embodiments G protein isotypes, such as $G\alpha_i$, $G\alpha_s$, $G\alpha_q$, and $G\alpha_{12}$, are incorporated into lipoparticles.

G-protein can also be incorporated into lipoparticles by fusing them to partner GPCRs which are then incorporated into the lipoparticle membrane. A G-protein isotype can be fused to a GPCR at the membrane protein's C-terminus. The GPCR-G protein fusion protein is incorporated into lipoparticles using techniques to produce lipoparticles as described herein and elsewhere.

G-proteins can also be incorporated into lipoparticles by fusing them to a non-GPCR transmembrane protein that can be incorporated into the lipoparticle, and that serves to anchor the G proteins to the inner membrane. A G-protein isotype can be fused to the C-terminus (cytoplasmic) of a single transmembrane protein (e.g. CD4). Alternatively, a fusion protein may contain a truncated version of CD4 with a shorter C-terminus that can also be constructed and incorporated. The single transmembrane-G protein fusion protein can be incorporated into lipoparticles using techniques as described herein.

The present invention also provides methods for producing lipoparticles comprising a G-protein and a membrane protein comprising: a) contacting a lipoparticle comprising a GPCR with a protein comprising a G-protein; and b) incubating said mixture under conditions resulting in production of said lipoparticle. In some embodiments the G-protein is contacted by sonication, pore-forming peptidation (e.g. melittin), electroporation, transfection and the like. In some embodiments, the G-protein is an essentially pure G-protein.

In some embodiments, the present invention provides methods of identifying modulators of a GPCR comprising: a) contacting a lipoparticle comprising a GPCR and a G-protein with a test compound; and b) measuring GPCR activity; wherein an increase in GPCR activity indicates that the test compound is an activator of GPCR activity or a decrease in GPCR activity indicates that the test compound is an inhibitor of GPCR activity. In some embodiments, the GPCR or G-protein is a modified GPCR or a modified G-protein. In some embodiments, the modified GPCR is a fusion protein as described above. The lipoparticles can also comprise a hydrolysable or non-hydrolysable analog that can be fluorescently labeled. In some embodiments, a GTP analog is GTP.

By using a lipoparticle that comprises a GPCR, a G-protein, a GTP analog, or combinations and subcombinations thereof, the GPCR signaling activity can be measured by measuring changes in fluorescence that occur when proteins come in contact with one another. For example, as described above, if the GPCR and/or the G-protein is a fusion protein comprising a fluorescent protein, the changes in fluorescence indicates a change in GPCR activity. If the GTP analog is fluorescently labeled, when it binds to the G-protein, a change in fluorescence will occur, which is indicative of GPCR signaling activity. The changes in fluorescence can be easily measured using standard techniques and equipments, such as a fluorometer. Dyes can also be used to measure GPCR activity. The dyes can be, for example, pH sensitive or voltage sensitive. The lipoparticles can be suspended in a concentrated solution of a fluorescent dye (e.g. di-4-ANEPPS), which diffuses preferentially into the lipid bilayer of cell membranes and is incorporated into the lipoparticles. Examples of alternative voltage-sensitive fluorescent dyes include, but are not limited to, di-4-ANEPPS ($C_{28}H_{36}N_2O_3S$), di-8-ANEPPS, rhodamine 421, oxonol VI, JC-1, DiSC3(5), and the like (Molecular Probes, Inc.). The dyes can be measured ratiometrically, responding to increases in membrane potential with a decrease in fluorescence excited at approximately 440 nm and an increase in fluorescence excited at 530 nm. In some embodiments, the GPCR is CXCR4 and the G-protein subunit is $G\alpha_z$. However, any GPCRs, G proteins, membrane potential-responsive fluorescent probes, or pH-responsive probes can also be used. To test the function of the GPCR, the lipoparticles can be contacted or exposed to a GPCR agonist. Ligand binding by the GPCR results in a change in the structural conformation of the receptor associated with G-protein dissociation. This results in a change in the electrical potential across the lipoparticle membrane, causing a detectable signal emission from the dye probe. In some embodiments, fluorescence emission is not altered in null-lipoparticles, or in lipoparticles treated with a GPCR antagonist. In some embodiments, fluorescence is measured in real-time, beginning prior to the addition of the agonist. In some embodiments, fluorescence is measured using a Perkin Elmer LS-50B fluorometer.

lipoparticles can also comprise a GPCR (i.e. CXCR4), a G-protein subunit (e.g. $G\alpha_z$), a GTP analog, an ion channel, or combinations thereof. In some embodiments, the ion channel is an inwardly-rectifying potassium channels (GIRK), such as Kir3.x. A fluorescent dye (e.g. di-4-ANEPPS) can be loaded into this lipoparticle. In some embodiments, the dye fluoresces in a lipid environment and its fluorescence spectrum changes in response to fluctuations in membrane potential. The presence of the GPCR and the G-protein subunit CXCR4 and $G\alpha_z$ in lipoparticles can be verified by Western blot using anti-G protein and anti-GPCR antibodies. One skilled in the art would recognize that alternative GPCRs, G proteins, and membrane potential-responsive fluorescent probes could also be used. To test their function, the labeled lipoparticles are exposed to a GPCR agonist. In some embodiments, stimulation of the GPCR causes dissociation of the G protein from GPCR and activation of the ion channel. The resultant movement of ions causes an alteration to the lipoparticle membrane potential, leading to a change in the fluorescence of the dye. In some embodiments, fluorescence emission is not altered in null-lipoparticles or in lipoparticles treated with a GPCR antagonist. Fluorescence can be measured in real-time before and after adding the agonist. Thus, lipoparticles can also be used to measure GPCR activation of ion channel activation.

Method of Generating the Lipoparticle of the Invention

The method of making a lipoparticle involves using a cell. Hence in some embodiments the method of making the lipoparticle involves expression of at least a competent portion of the genome of an enveloped virus in a cell.

As used herein, the term "competent portion" refers to the portion of the virus that is sufficient to cause the budding of lipoparticle from a cell.

In some embodiments the lipoparticle comprises a membrane protein of interest. The membrane protein may be a normal component of the cell or it may be provided exogenously to the cell using, for example, transfection, viral infection, or other known molecular biology techniques.

In some embodiments of the making of the lipoparticle, at least a competent portion of the genome of a virus is provided to a producer cell which comprises a membrane protein, and the producer cell is thereafter incubated under conditions which permit expression of the gene products encoded by the competent portion of the virus genome. These gene products include factors which facilitate the generation of the lipoparticle. In some embodiments, the gene products facilitate the association of the capsid-like particle with the cell membrane. In some embodiments, the virus is an adenovirus. In some embodiments, the virus is an alphavirus, such as semliki forest virus. In some embodiments, the virus is a baculovirus. In some embodiments, the virus is a vaccinia virus or a herpes virus.

The producer cell need not normally comprise the desired membrane protein of interest. Thus, in another example of making the lipoparticle of the invention, a producer cell is provided with at least a competent portion of the genome of a virus and a membrane protein of interest, and is thereafter incubated under conditions which permit formation of a lipoparticle of the invention comprising a membrane protein. This method, therefore, does not employ a producer cell which naturally comprises the membrane protein of interest.

For lipoparticles that will be produced for long-periods of time, cell lines can be established that both produce the competent portion of a viral genome and express high quantities of the membrane protein desired. In some embodiments, to be converted to producer cells for lipoparticles, human primary cells can comprise the MLV structural gene gag and/or the membrane protein of interest. Stable cells that express either the MLV structural gene gag or the membrane protein of interest can be complemented with the other lipoparticle component. These genes can be delivered either by plasmid transfection, retroviral infection, adenoviral infection, or other common means of genetic transduction. For example, a stable cell line expressing a membrane protein of interest can be infected with an adenoviral construct expressing MLV gag in order to produce lipoparticles. Different existing gene delivery systems can be combined to produce new, and possibly more powerful, gene delivery constructs.

The present invention also provides for the use of viral vectors such as adenovirus and semliki forest virus to produce MLV structural genes within cells that naturally express membrane proteins of interest, for example, but not limited to primary cells, hybridomas, stem cells, treated cells, or cell lines.

Capture of naturally expressed membrane proteins can result in populations of membrane proteins that better represent native membrane protein structure. For example, some proteins are modified after translation, and this modification may depend on factors within the cell. For example, CCR5 is sulfated on Tyrosine 11 and this sulfation is known to alter its structure and make it more competent for interaction with HIV-1 Envelope proteins. Similarly, CXCR4 is glycosylated, and if this glycosylation is removed, additional structures of CXCR4 are exposed. Different cell types are known to have different conformations of the CXCR4 membrane protein, although it is not clear why some conformations are more prevalent on some cell types. Other cell types can be induced (e.g. with hormones, growth factors, cytokines, or chemicals) to differentiate or change, often resulting in a change in the membrane proteins at the surface of the cell. Different cell types can also contain different transcriptional splice variants of the same gene. For example, CCR2 has two cell-type specific splice variants, CCR2a and CCR2b, which have differences in their C-terminus.

Other cell-specific interactions can also alter the epitopes of membrane proteins. For example, the coupling of G-proteins to a receptor can change the conformation of the membrane protein (GPCR) that the G-proteins bind. Similarly, binding of the membrane protein CD4 by the intracellular protein Lck can influence the location and function of CD4. One skilled in the art would recognize that lipoparticles can be generated from any cell type by over-expressing a retroviral Gag protein and harvesting the lipoparticles that are generated from these cells. The MLV Gag protein can be introduced using either DNA plasmid transfection or using Ad-Gag infection.

As used herein, the term "Ad-Gag" refers to an adenovirus that expresses the Gag protein. In some embodiments, the Ad-Gag adenovirus may also express other proteins, such as a protein that is incorporated into the lipoparticle.

In some embodiments, Ad-gag is used to infect a cell type of interest, the adenovirus expresses the gag gene and lipoparticles are produced, and as the lipoparticles particles bud from the surface of the cell, they incorporate the membrane proteins naturally expressed or exogenously expressed on the surface of the cell. Adenoviral vectors are an attractive choice for the transfer of the MLV gag gene into target cells since they have proven gene transfer efficiency and can accommodate a large insert. Lipoparticles derived from primary cells function as a stable source of membrane proteins from these cells, without the limitations of living cells, protein degradation, or contaminant proteins. Lipoparticles are especially useful if the primary cells have a limited lifespan. Such lipoparticles can be used to make MAbs against the membrane proteins, discover drugs against the membrane proteins, or to identify orphan receptors on the cells. Primary cells with interesting characteristics, such as the ability to bind a ligand of interest, are of especial note in using the lipoparticles for identifying orphan receptors or unidentified receptors.

The cell type is not a critical factor and may be any cell of interest. For example, the cell type used to produce lipoparticles in order to capture their native membrane proteins can include cell lines, primary cells, non-transfectable cell types, or hybridomas. As used herein, the term "non-transfectable cell type" refers to a cell type that is unable to efficiently take up exogenous DNA via chemical or liposomal mediated transfected (i.e. calcium phosphate mediated and Lipofectin™, transfection reagent, mediated transfection, and the like). In the case of hybridomas, the membrane protein of interest can be a membrane-bound antibody that would be incorporated into the lipoparticle. In other embodiments, the antibody can be a whole antibody or a fragment of an antibody such as a Fab fragment, an immunoglobulin-fusion protein, a single-chain Fv, an Fc-fusion protein, or combinations thereof. One skilled in the art will also recognize that the membrane protein need not be naturally expressed within the cell type at all periods of time. The cell type can be induced, chemically or genetically, or treated (e.g. differentiated) in order to express the desired membrane protein. For example, heat shock can induce expression of a novel set of membrane proteins on the surface of many cells. In other cases, DMSO, hormones, hypertonic shock, growth factors, or other means can induce a cell type to express a different set of membrane proteins.

Moreover, the invention further includes a composition comprising a lipoparticle comprising a protein that spans a membrane at least once, where the lipoparticle is attached to a sensor surface. Such proteins can interact to form complexes or otherwise interact while present in the lipoparticle lipid bilayer.

One skilled in the art would appreciate, based on the disclosure provided herein, that the lipoparticle can comprise any membrane protein, i.e., any protein that typically is associated with a membrane. In some embodiments, the lipoparticle comprises a multiple membrane spanning protein. That is, the protein spans the membrane at least twice. Such multiple membrane spanning proteins encompass a wide plethora of membrane proteins including, but not limited to, the 7 transmembrane receptor proteins (e.g., G-protein coupled receptor proteins, GPCRs, which include chemokine receptors), ion channels, transporters (such as amino acid transporter MCAT-1, and the like). However, the lipoparticles may also comprise proteins that are targeted to the membrane by virtue of a signal peptide, whereas the protein would not normally be present at the membrane.

In other embodiments making a lipoparticle further comprises providing an additional component to the producer cell, whereby, upon formation of the lipoparticle, the lipoparticle comprises the additional component. The additional component may be any molecule which can be provided to the cytoplasm or the membrane of the producer cell. By way of example, the additional component may be a nucleic acid, an antisense nucleic acid, a gene, a protein, a peptide, Vpr protein, an enzyme, an intracellular antagonist of HIV, a radionucleotide, a cytotoxic compound, an antiviral agent, an imaging agent, or the like.

Inclusion of the additional component in the lipoparticle may be accomplished by directly coupling the additional component to the competent portion of the genome of the virus. For instance, if the competent portion of the genome is provided to the producer cell in the form of a plasmid, the plasmid may comprise a gene encoding an imaging agent or a reporter molecule, such as luciferase or green fluorescence protein. Inclusion of the additional component in the lipoparticle of the invention may also be accomplished by directly coupling the additional component to a nucleic acid encoding the membrane protein. For example, if the membrane protein is provided to the producer cell in the form of a DNA molecule encoding the same, an additional component comprising a protein may be provided to the producer cell by including the sequence of a gene encoding the protein in the DNA molecule, prior to provision thereof to the producer cell.

The additional component may also be provided directly to the membrane or the cytoplasm of the producer cell by, for example, including the additional component in the extracellular medium of the producer cell.

It will be appreciated by one skilled in the art that the genes chosen to construct a lipoparticle, such as a retroviral gag gene and/or a desired membrane/cellular protein gene, can be delivered to a cell in any number of ways. In some embodiments, the method of nucleic acid transduction involves DNA transfection, such as by calcium phosphate precipitation, lipid-based transfection, electroporation, microinjection, or other methods of DNA delivery. In another embodiment, the genes of interest are stably incorporated into the cell of interest by transducing or transfecting the cell with the genes of interest and then selecting cells that express desired levels of the genes of interest.

In some other embodiments, the method of gene transduction involves infection of a desired cell with a viral vector. The viral vector can be composed of any number of common viral vector gene delivery systems, such as adenovirus, adeno-associated virus, herpes virus, retrovirus, vaccinia virus, or alphavirus. Some of the most versatile viral vectors available are adenovirus vectors that are capable of infecting nearly any cell type and expressing high levels of a desired gene. Adenovirus has previously been used by others to produce large amounts of infectious retroviral vectors by placing the retroviral structural genes (gag and pol) inside an adenoviral vector (Duisit et al., 1999; Lin, 1998). However, this system has never been used to produce non-infectious retroviral particles comprising membrane proteins, and the quantity of particles (not just infectious units) has never been reported. Adenovirus-based production of lipoparticles allows convenient gene transduction into a wide variety of cell types (including non-human cells), but also enables more convenient cell growth within roller bottles and/or continuous flow systems. Alternative viral transduction vectors are also available (e.g. vaccinia, bacculovirus, semliki forest virus, adeno-associated virus).

In other embodiments, the vector is a chimeric viral vector. A chimeric viral vector contains viral nucleic acid sequences from two different types of viruses. In some embodiments, the chimeric viral genome includes nucleic acid sequences from a "primary" virus that allows for transfection of a variety of cells, including, but not limited to primary cells, stem cells, hybridomas, cell lines, and the like. The chimeric viral genome also includes nucleic acid sequences from a "secondary" virus. In some embodiments these secondary virus sequences is the retroviral (e.g. MLV) gag gene. In some embodiments the primary virus is adenovirus. In some embodiments, this viral vector comprises an adenovirus that expresses retroviral gag (Ad-gag). In some embodiments, the viral vector comprises an adenovirus that expresses both the retroviral gag and pol genes (Ad-gag/pol). In some embodiments, the viral vector comprises an adenovirus that expresses gag and the protease fragment of the pol gene (Ad-gag/PR). In some embodiments, the chimeric viral vector comprises nucleic acid sequences from an adenovirus, a retrovirus, and a nucleic acid molecule encoding a cellular protein. In some embodiments, the chimeric viral vector comprises a sequence encoding Gag, but doe not comprise a sequence encoding the envelope, promoter, or packaging signal of a retrovirus. In some embodiments, a chimeric viral vector does not comprise a retroviral sequence that encodes a functional pol gene.

The following can be performed to construct and package a chimeric virus for infection of producer host cells and production of secondary virus. Methods for constructing a recombinant Adenovirus are well described in the literature (Ausubel, et al. (2001), Current Protocols in Molecular Biology), and several kits are available to construct such a chimeric virus (Invitrogen, Clontech). In one embodiment, a chimeric viral genome is prepared by first isolating the constituent nucleic acids. The nucleic acids are then joined, for example, using restriction endonuclease sites at the ends of the molecule. The recombinant molecule is ligated into a suitable plasmid or vector. Methods for preparing a recombinant nucleic acid are known by those skilled in the art (see Sambrook et al., Molecular Cloning. A Laboratory Manual (2d ed. 1989), (Ausubel, et al. (2001), Current Protocols in Molecular Biology)). In another embodiment, chimeric viral genomes are constructed using transfer vectors and homologous recombination.

Any primary virus can be used as the source for the primary viral genome in the chimeric virus. In some embodiments, the primary virus has a broad host range. Primary viruses include, e.g., adenoviruses, adeno-associated virus, retrovirus, alpha virus, vaccina viruses, and herpes simplex viruses (HSV). In some embodiments, primary virus nucleic acid sequences include those derived from the family Adenoviridae (White & Fenner, Medical Virology (4th ed., 1994)). One embodiment of the primary virus is a primary viral genome derived from the strain adenovirus 5 (for the sequence of adenovirus 5, see Chroboczek et al., Virology 186: 280-285 (1992)).

Typically, the chimeric virus is replication deficient (it cannot produce additional primary virus) and lacks a gene required for replication or packaging. For example, adenoviral vectors usually have the E1A gene deleted from their genome. This gene is essential for viral replication and is complemented by the packaging cell line 293. Thus, a replication deficient chimeric viral genome is packaged after introduction of the viral genome into 293 cells. Other genes that are commonly deleted in adenovirus vectors are E1B and E3.

In some embodiments, the adenoviral vector can be used to express both the structural protein (i.e. gag) and the desired membrane/cellular protein. In some other embodiments, two different adenoviruses are used to express the structural protein and the desired membrane/cellular protein. In some embodiments, cells can be infected with equivalent quantities of Adenovirus-Gag and Adenovirus-cellular protein, but the ratios of the two viruses can be varied in order to express more cellular protein per lipoparticle (e.g. a cellular protein:Gag vector ratio of 3:1) or to produce more particles relative to receptor (e.g. a cellular protein:Gag ratio of 1:3). In some embodiments the ratio of Ad-cellular protein to Ad-Gag is about 1:100, about 1:10, about 1:5, about 1:4, about 1:3, about 1:2, about 1:1, about 2:1, about 3:1, about 4:1, about 5:1, about 10:1, or about 100:1.

In making the lipoparticle, the identity of the producer cell which is used is not critical. In some embodiments, the cell is an immortalized cell line, such as HEK-293, HEK-293T, Cos, HeLa, CHO, 3T3, QT6, Cf2TH, CCC, Vero, or BHK. In some other embodiments, the cell is a non-human, human, stem, or hybridoma cell. The production of a human membrane protein in a non-human cell type provides the opportunity to study that membrane protein isolated away from components that it might otherwise naturally interact with. In some embodiments the human membrane protein is incorporated into a lipoparticle produced from a mouse cell type. In some embodiments the cell type is from the same species that is used for lipoparticle immunization. By using a cell type that is from the species that is used for immunization, the immune response would be focused on the membrane protein instead of membrane proteins from the producer cell. Cell types that can be used for lipoparticles to use in immunization can be any cell type, but in some embodiments the cell type is derived from a Balb-c mouse.

In another embodiment, the cell is a primary cell type derived from animal tissue such as liver, spleen, brain, pancreas, intestine, skin, or bone. In another embodiment, the cell is a stem cell in which the cell is capable of differentiating into a number of type-specific cells. In another embodiment, the cell is a differentiable cell type in its pre-differentiated form or in its post-differentiated form. The production of lipoparticles from a cell before and after differentiation would provide the means to compare membrane proteins from these two cellular conditions. As used herein, the term "primary cell" refers to a cell that has not been immortalized or is not immortalized (i.e. will undergo a finite number of cell divisions, usually less than 100, but can be more.)

The production of lipoparticles from many cell types can be difficult without a high efficiency means of gene transduction. In some cases, plasmid transfection can achieve high efficiency gene transduction (>50% of cells). In other cases, plasmid transfection is inadequate or is prohibitively expensive to perform. For example, many primary cell types are not readily transfected with calcium phosphate or other means of plasmid transfection. In these cases, viral vectors can provide a means to express the structural proteins of a lipoparticle (e.g. Gag) and/or the membrane protein of interest within the cell type of interest. Many viral vectors can be used, including adenovirus, adeno-associated virus, herpes virus, retrovirus, vaccinia virus, or alphavirus. In some embodiments, adenovirus is used to express the gag gene of a retrovirus. In some embodiments, a retroviral vector is used to express the gag gene of another retrovirus. In some embodiments, the retroviral vector is a lentiviral vector that is capable of entering and expressing within quiescent cells. The use of these viral vectors to express the genes used in the lipoparticle enables a number of new cell types to be used in the production of lipoparticles.

In some embodiments, structural proteins from other virus families can be used. Examples of other virus families include, but are not limited to, alphavirus, arenavirus, arterivirus, bornavirus, bunyavirus, coronavirus, filovirus, flavivirus, hepadnavirus, herpesvirus, orthomyxovirus, paramyxovirus, poxvirus, retrovirus, rhabdovirus, togavirus, adenovirus, astrovirus, calcivirus, papillomavirus, parvovirus, picornaviridae, polyomavirus, reovirus. In some embodiments, structural proteins besides gag can be used. Examples of other structural proteins include, but is not limited to, nucleoprotein (NP), nucleocapsid, nucleoprotein (N), capsid protein, C protein, hepatitis delta antigen), Core proteins (i.e., A3L, A4/5L, A10L, D2L, D3R, or F17/18R), and the like.

Depending on the structural protein that is used, the protein can influence where the lipoparticle will bud from. In some embodiments the lipoparticle will bud from the golgi apparatus, the endoplasmic reticulum intermediate compartment, the endoplasmic reticulum, the plasma membrane, or the rough endoplasmic reticulum.

Conditions that enable formation of lipoparticles are well known in the art. These conditions may vary depending upon the properties of the producer cell and the virus used. A number of references exist which describe conditions which are useful for culturing particular enveloped viruses (*Fields Virology*, 3rd ed., Fields et al., eds., Lippincott-Raven Publishers, Philadelphia, Pa.). Particular non-limiting examples are provided herein of conditions which are useful to enable formation of lipoparticles.

Conditions which enable formation of lipoparticles include conditions that enable expression of the competent portion of the genome of the virus, conditions under which a membrane protein is present in the membrane of the producer cell, and conditions which enable the formation of lipoparticles from the components of a producer cell which has been provided with the competent portion of the genome. Details regarding processes by which enveloped viral particles are formed following provision to a cell of a competent portion of the genome of an enveloped virus have been described in the art, for instance by Wiley (1985, in *Virology*, Fields et al., ed., Raven Press, New York, 45-52).

Lipoparticles can be produced in at least two different ways. First, production of large amounts of particles for high-demand applications (e.g. high throughput screening), and second, production of small amounts of particles for limited use applications (e.g. testing of new receptors). By choosing the appropriate production components, discussed below, both production scales can be accommodated while balancing differing needs for speed, cost, and up-front labor.

Although 150 mm dishes or flasks are used in many viral production protocols for production of non-infectious virus, more efficient systems exist. In particular, cell factories (Nunc™) with multi-tiered growth layers can be used for large-scale production. Another alternative is to use roller bottles, which can achieve 5-10 times the surface area of a large dish. 293 cells are notoriously difficult to grow (poor adhesion) and transfect (poor efficiency) in roller bottles, but alternative production conditions (described below) can make roller bottles more feasible. Finally, for stable cells that secrete proteins or viruses, continuous flow systems have proven highly efficient. Cells within a continuous flow chamber cannot be transfected, but for some transduction mechanisms (e.g. adenovirus infection, stable cells) such culture conditions may be ideal.

The method of production of lipoparticles can be greatly influenced by the cell type and gene transduction methodology used. For example, calcium phosphate transfection is efficient in only some cell types, such as HEK-293, and usually requires growing cells in an adherent fashion (e.g. within plates or flasks). More efficient means of growing cells for transduction and lipoparticle production, such as spinner flasks and bioreactors, require non-adherent cells and also require transduction mechanisms more amenable to such growth conditions. In these cases, viral vectors can provide a means to express the structural proteins of a lipoparticle (e.g. Gag) and/or the membrane and/or cellular protein of interest within the cell type of interest under the growth conditions desired. The use of a viral vector for gene transduction enables any number of cellular growth vessels and conditions to be employed that will not interfere with transduction or lipoparticle production. Many of these conditions are more convenient or amenable to large-scale production. In one embodiment, adenovirus is used to transduce the genes of interest into cells grown within a bioreactor. In another embodiment, the cells can be grown and transduced in a spinner-flask. In another embodiment, the cells can be grown and transduced in plates, flasks, roller bottles, or cell factories. The use of viral vectors to express the genes used in the lipoparticle enables a number of new methods of cell growth to be used in the production of lipoparticles. Virus-based production of lipoparticles would not only allow convenient gene transduction into a wide variety of cell types (including non-human cells), but also enable more convenient cell growth within roller bottles and/or continuous flow systems.

In some embodiments, the lipoparticle is produced according to the methods described in US 2002/0183247A1, the entire contents of which are hereby incorporated by reference.

Applications

In some embodiments, lipoparticles can be used for isolating membrane receptor drug targets. Structurally complex targets include G-protein coupled receptors (GPCRs), ion channels, and molecular transporters that are involved in cell-cell recognition, cell-adhesion, lipid interactions, and protein-protein interactions. More importantly, lipoparticles can also be applied to targets that are difficult or impossible to work with using traditional systems. For example, targets will include proteins that are toxic to cells, difficult to express, are highly charged, have intractable or no identified ligand, or that are located on intracellular membranes. Lipoparticles can address each of these limitations. The production of lipoparticles using viral vectors will allow better lipoparticles to be produced, since difficult membrane proteins, even those residing on primary cells, can be incorporated into lipoparticles. The types of targets that can include the following, but are not limited to the following examples.

Successful targets such as GPCRs, ion channels, and transporters may comprise a major target class. Lipoparticles may include members of this class that are toxic to cells, have weak or no ligands, or that are difficult to express or work with.

Some targets that are located on the cell surface are relatively simple transmembrane molecules, spanning the lipid bilayer only once, yet are functional only in a multimeric complex composed of two or more molecules. This complex can either be a complex of one molecule with other identical molecules (a homocomplex) or with different molecules (a heterocomplex). Important molecules that fall into this class include receptor kinases such as EGF, integrins, and most viral envelope proteins.

Ninety-five percent of a cell's membrane structures are estimated to lie within the cell, in organelles such as the mitochondria, nucleus, golgi, and endoplasmic reticulum (ER). These membranes are filled with regulatory receptors and transporters, but have traditionally been inaccessible for drug screening. Lipoparticles will be able to be used to isolate these intracellular integral membrane proteins on the surface of a lipoparticle, thereby making them amenable to drug screening, binding assays, and protein interaction mapping.

In some embodiments, lipoparticles can be used for the development of lead drug compounds to complex targets. Applications within the drug discovery pipeline include, without limitation, the following.

Mapping the network of which proteins bind to which receptors is a critical step in defining optimal targets of the proteome. Mapping proteomic interactions and ligand fishing can be an application for lipoparticles.

High throughput screening methods used today are fast, but are usually limited to biologically manageable targets such as soluble molecules (e.g. enzymes) and readily accessible cell-surface molecules. Proteins that are toxic to cells, are difficult to express, are highly charged, have intractable or no identified ligand, or that are located on intracellular membranes are not amenable to most high throughput screens available today. Lipoparticles can address each of these limitations.

Simple yes/no binding information is not sufficient for lead optimization. Data-rich information such as selectivity, specificity, affinity, and kinetics of interaction are standard measurements used to refine a drug candidate, but are not easily obtained, especially for difficult targets. The use of lipoparticles on biosensors and data-rich detection devices enables more information to be gathered during lead optimization.

Lipoparticles permit specificity of interaction to be measured using highly sensitive detection devices and using lipoparticles that mimic cell surface molecules that are known to influence absorption, distribution, metabolism, elimination, and toxicology (ADMET) properties.

The lipoparticles can also be used to assess the binding of the membrane protein presented in the lipid bilayer of the particle with a test component, and/or to assess the effect of a test compound on the binding of the protein with a cognate ligand. This is because, as more fully set forth elsewhere herein, the protein embedded in the lipoparticle retains its ability to bind with its cognate ligand(s) and because the protein, now present in a lipoparticle, can be used in assays where soluble proteins or whole cells cannot be used, such as assays where the protein of interest must be bound to a support or substrate, including, but not limited to, an assay using a microfluidic device, e.g., a biosensor assay.

In some embodiments, a lipoparticles is attached to a surface and then is contacted with a ligand and the biosensor detects the binding to the membrane protein in the lipoparticle. The detection can be by surface plasmon resonance, colorimetric diffraction grating, deflection of microcantilevers (Wu, G., et al., Nature Biotechnology 19, 856-860; Weeks B L et al., Scanning. 2003 November-December; 25(6):297-9), or acoustic wave response (Cooper, M. A., et. al. (2001). Nature Biotechnology 19, 833-837). Or in some embodiments, the ligand is attached to a surface that is part of a sensor and this is contacted with a lipoparticle and the binding is detected. The detection can be by surface plasmon resonance, colorimetric diffraction grating, deflection of microcantilevers, or acoustic wave response. In some embodiments, the ligand and lipoparticle are contacted in solution.

Biosensor devices are designed to measure the interaction between biological molecules. Typically, biosensors measure direct interactions between a protein of interest and potential ligands (proteins, antibodies, peptides, small molecules) that may bind to it. Biosensors are typically highly sensitive and can work with and detect even very weak or very small quantity interactions. Biosensor devices have been constructed that consist of optical chips, fiber optics, spectrometer detectors, microchannel chips, nanowells, and microcantilevers, acoustic wave devices. In some embodiments, the assay comprises using a biosensor device wherein the device is a surface plasmon resonance biosensor device.

In some embodiments, the lipoparticle is attached to a sensor surface, where a "sensor surface" is any substrate where a change in a property of the substrate mediated by the contacting of the surface with a molecule or compound is detected and can be compared to the surface in the absence of such contacting. However, in other embodiments, the lipoparticle is already attached to a sensor surface. While the sensor surface can be a biosensor chip as exemplified herein, the sensor surface is not limited to such a chip. A sensor surface also includes any biosensor chip that is disclosed herein (e.g., a BIACORE C1 chip, a F1 chip, and the like), known in the art, or to be developed in the future. Such sensor surfaces include, but are not limited to, a glass substrate comprising a coating of, e.g., gold, which can further comprise, for instance, a dextran matrix. However, the invention is not limited to any particular sensor surface. The important feature of such a surface is that a change in a characteristic of the sensor surface e.g., its refractive index, can be detected, preferably by an instrument connected to the sensor surface, such that data or information from the sensor can be assessed thus detecting the change, or lack of change, of the characteristic of the surface.

However, the present invention is not limited to any particular assay. Rather, the present invention encompasses any assay where the protein of interest is a membrane component and where study of the binding of the protein with a ligand requires, or is facilitated by, presenting the protein in the context of a lipid bilayer and/or attaching the protein to a support or solid substrate. Such assays include, but are not limited to, assays using a microfluidic device, an optical biosensor, PATIR-FTIR spectroscopy, which is a type of biosensor using total internal reflection Fourier-transform infrared spectroscopy (1998, Chem. Phys. Lipids 96:69-80), CPRW Biosensor (Coupled plasmon-waveguide resonance (CPWR) spectroscopy as described in Salamon et al. (1997, Biophys J. 73:2791-2197) and Salamon et al. (1998, Biophys J. 75:1874-1885), Multipole Coupling Spectroscopy (MCS) as described in Signature Biosciences, on the worldwide web at signaturebio.com, Fiber optic biosensors (Illumina) as described in Walt (2000, Science 287:451-452) and Dickinson et al. (1996, Nature 382:697-700), Michaels (1998, Analytical Chemistry 70:1242-1248), Lab-on-a-chip microfluidics (manufactured by, e.g., Caliper and Aclara) as described in Sundberg et al. (Current Opin. in Biotech. 11:47-53), and Bousse et al. (1999, Electrokinetic Microfluidic Systems, SPIE Microfluidic Devices and Systems II 3877:2-8, Sep. 20, 1999-Sep. 21, 1999), Microchannels (Gyros' microchannels etched into a Compact Disc-based device) as described on the worldwide web at gyros.com, Microcantilevers (Protiveris) as described in Tamayo et al., 2001, Ultramicroscopy. 86:167-173), Wu et al. (2001, Nature Biotechnol. 19:856-860), Confocal microscopy and nanowell detection as described in Hunt et al. (International Publication No. WO 01/02551), and Microwell binding assays. The aforementioned, as well as similar assays known in the art or to be developed in the future, are encompassed in the invention.

In some embodiments, a sensor surface comprises a 96-well, 384-well, 1536-well, a nano-well, optical fiber, or slide format. In some embodiments, the surface comprises gold, glass, plastic, or a combination thereof.

The nature of the instrument or the particular surface to which the lipoparticle is attached is not crucial. That is, while a derivatized gold surface or a short carboxy detran matrix can be used to attach the lipoparticle thereto, the invention is in no way limited to these surfaces; instead, the invention includes any surface that can be used in a microfluidic device to assess the interaction of proteins. Such substrates include, but are not limited to, a plethora of biosensor "chips" that are commercially available, and others surfaces that are known in the art, or such surfaces as will be developed in the future.

As discussed above, lipoparticles can be used for the presentation of structurally intact membrane proteins for antibody generation. Antibodies are now in use throughout the biotechnology industry as therapeutics, diagnostics, and research and development reagents, and are a part of vaccine elicitation.

The lipoparticle allows the stable presentation of structurally intact membrane proteins within a particulate format that is suitable for antigen presentation. That is, because the structure of complex membrane proteins can be maintained using the lipoparticle, the present invention provides for methods of using lipoparticles comprising a membrane protein of interest as an immunogenic vector for production of antibodies that specifically bind with the membrane protein. In some embodiments, the antibodies produced by this method can bind with the protein in its native structure and thus can provide a method for producing antibodies that can, for instance, inhibit protein function by steric blocking of important sites on the protein and/or antibodies that can affect protein function by allosteric effect. The production of lipoparticles using viral vectors will allow better lipoparticles to be produced for antibody purposes, since additional cell types (e.g. non-human mouse cells) can be used for incorporation of human membrane proteins.

The particulate nature of lipoparticles makes them comparable to killed-virus vaccines currently used to successfully elicit immune responses (e.g. humoral and cellular). The ability to place non-viral molecules within such an immunogen allows lipoparticles to have direct application to both preventative and therapeutic vaccines. In some embodiments, the use of lipoparticles as an immunogen will elicit a cytotoxic T-cell response as well as a humoral (antibody) response, both of which can be important components of research and for vaccine purposes.

The lipoparticle has additional uses beyond the applications described above. Even if expressed at low levels within tissues or cell lines, lipoparticles can be used to purify and concentrate targets to enable drug discovery without the use of the cDNA clone. The production of lipoparticles using viral vectors will allow lipoparticles to be produced using cell types with naturally occurring sources of desired membrane proteins. Lipoparticles also represent a method for purifying membranes and membrane proteins from any cell type, without lysing the cell and without contamination from such membrane preparation techniques (e.g. intracellular membranes, inverted membranes). Lipoparticles are stable and present correctly oriented membrane proteins.

Existing array technology is largely focused on oligonucleotide or cDNA arrays. More recent arrays have included antibody and protein arrays, but are limited to proteins that can be chemically stabilized on a surface while maintaining their structural integrity, requirements that exclude integral membrane proteins. Lipoparticles can be used to present integral membrane proteins on a surface while maintaining their structural integrity. With an estimated 3,000-6,000 integral membrane proteins in the entire human genome, it is possible that the entire repertoire of cell-surface receptors can be spotted on a single array, thus mimicking the cell surface. Integration of such array technology with biosensors would create a detection system that recreates the cell surface in vitro. Such arrays would be used for mapping protein-protein interactions and drug screening.

Determination of the structure of integral membrane proteins is complicated by the multiple hydrophobic membrane spanning domains of this class of proteins. Because lipoparticles can be constructed with purified receptor, they offer the opportunity to decipher the structure of the receptors in their native state. An NMR-based approach has substantial promise for this application and could have a major impact on the ability to design drugs against integral membrane proteins. In addition, an NMR-based approach is also capable of determining the structure of ligands bound to their cognate receptors.

The initial focus of the biotechnology industry was on the development of proteins that could be directly used for therapeutic intervention. Proteins such as insulin, growth hormone, and IL-2 are examples of soluble molecules that are now in therapeutic use. Nearly all proteins in development today as therapeutics are soluble molecules. Yet many molecules that could have biological efficacy are not released from the cell membrane. Other molecules function only as homo- or hetero-dimers, and all molecules exhibit a greater avidity (and therefore potency) when presented as part of a multimeric complex. Lipoparticles can address these issues to enable a new class of proteins to be used as therapeutics. Moreover, the surface chemistry of lipoparticles can be altered to give proteins embedded within them a longer circulation half-life in vivo.

Lipoparticles may be used to deliver a composition to a target cell. This composition delivery method is particularly useful when it is desired to deliver a composition specifically to a cell which comprises a viral envelope protein on its surface. Specific examples of such a target cell include, but are not limited to, a cell infected with an enveloped virus, such as HIV, SIV, RSV, or ecotropic MLV. A target cell may also be a cell infected with another enveloped virus vector of the invention or a cell which has fused with an enveloped virus vector other than the enveloped virus vector of the invention.

As set forth herein, the lipoparticle comprising a membrane protein of interest can be used in a wide variety of applications. In some embodiments, the lipoparticle can be used in assays relating to, for example, but not limited to, drug screening, peptide screening, agonist versus antagonist discrimination, ADMET studies, structure-activity relationships studies, vaccine development, food testing, chemical sensing, light sensing, content release, monoclonal antibody production, fusion studies, phage display methods, ligand "fishing" or identification, protein interaction mapping, various diagnostics, and production of artificial cells, among many others. Such uses would be understood by the skilled artisan to be encompassed in the invention based upon the disclosure provided herein.

The present invention also provides for kits that comprise a lipoparticle comprising a membrane protein, and/or compositions of the invention, an applicator, and instructional materials which describe use of the compound to perform the methods of the invention. Although exemplary kits are described below, the contents of other useful kits will be apparent to the skilled artisan in light of the present disclosure. Each of these kits is included within the invention.

In some embodiments, the kits of the present invention described herein weigh less than 50 pounds, 20 pounds, 10 pounds, 5 pounds, 3, pounds, 2 pounds, or 1 pound.

In one aspect, the invention provides for kits for assessing the binding interaction of a membrane protein with a ligand. The kit comprises a lipoparticle comprising a membrane protein, a ligand of the membrane protein, and a substrate to which the lipoparticle can be attached. The kit further comprises an applicator, which applicator can be used to attach the lipoparticle to the substrate and/or for applying the ligand such that the ligand is contacted with the lipoparticle comprising the membrane protein. Such an applicator includes, but is not limited to, a pipette, an injection device, a dropper, and the like.

In some embodiments, the kit comprises a lipoparticle already attached to a substrate with or without the ligand being bound to the membrane protein. The substrate can then be examined using methods well known in the art to detect any change in the substrate mediated by or associated with the ligand binding with its cognate membrane receptor present in the lipoparticle.

In one aspect, the surface includes a wide variety of sensor surfaces, such as, but not limited to, a plethora of biosensor chips that are known in the art or to be developed in the future.

The present invention also provides for kits for identifying a potential ligand of a membrane protein. The kit comprises a lipoparticle comprising a membrane protein. In some embodiments, the kit comprises a lipoparticle that is attached to a surface and can also comprise a lipoparticle that is provided separately from the surface, which is also provided in the kit. In other embodiments, the kit further comprises a test ligand, or a plurality of such ligands, such as, but not limited to, a library of test ligands to be assessed for their ability to specifically bind with the membrane protein present in the lipoparticle.

The present invention also encompasses a kit where the lipoparticle is provided physically separated from a ligand and where the ligand is already bound with the lipoparticle. Similarly, the present invention encompasses a kit where the lipoparticle is provided physically separated from the surface, as well as a kit where the lipoparticle is provided attached to the surface. Further, the present invention also encompasses a kit with all possible permutations such that the ligand can be bound with the lipoparticle which is, in turn, attached to the surface, or each is provided separately, or any permutation thereof.

The present invention also provides for kits for identifying a compound that affects binding between a ligand and a protein (i.e., a receptor). The kit comprises a lipoparticle comprising a protein and a surface to which the lipoparticle can be attached. In some embodiments, the kit comprises a lipoparticle and a surface that are provided separately or where the lipoparticle is provided already attached to the surface.

The invention also provides for kits to produce lipoparticles. In some embodiments the kit comprises a producer cell, at least one viral vector, and/or producer cell media. The vector may comprise a viral vector that is amenable to cloning a membrane spanning protein of interest into the vector. In some embodiments, the kit comprises a viral vector that expresses Gag. In some embodiments, the kit comprises a virus that is ready to infect a cell, wherein the virus expresses a viral structural core protein such as, but not limited to Gag. In some embodiments, the virus is an adenovirus.

Viral expression systems provide a convenient, scalable, and reproducible method for lipoparticle production. By using such viral expression systems to both produce Lipoparticles and express membrane proteins, high levels of membrane protein can be produced and captured within the lipoparticle. In some embodiments, simultaneous infection with recombinant virus vectors expressing Gag and a membrane protein can be performed, but in some embodiments, staggered infections can be used. For example, expression of CXCR4 prior to Gag expression may ensure that high levels of CXCR4 are incorporated into all lipoparticles (which begin to be produced only once Gag is introduced). Similarly, reinfection (expression boosts) may result in further improvements in membrane protein production. In some embodiments, mixed expression systems can be employed for lipoparticle production (e.g. adenovirus expressing Gag and SFV expressing CXCR4).

In addition to x-ray crystallization studies, a number of alternative structural analyses have also been used with membrane proteins and may be used with lipoparticle-derived membrane proteins, including cryo-EM (Henderson, et al. (1990), J Mol Biol, 213:899-929), projection maps (Schertler, et al. (1993), Nature, 362:770-2), lipidic cubic phase (Nollert, et al. (2002), Methods Enzymol, 343:183-99), 2D crystallization, solution NMR, solid-state NMR (Opella, et al. (2002), Biochem Cell Biol, 80:597-604), atomic force microscopy (Werten, et al. (2002), FEBS Lett, 529:65-72), and electron tomography (Werten, et al. (2002), FEBS Lett, 529:65-72, Zhu, et al. (2003), Proc Natl Acad Sci USA, 100:15812-7) (reviewed in (Torres, et al. (2003), Trends Biochem Sci, 28:137-44)). In addition, a host of structural techniques applicable to membrane proteins in lipid bilayers are emerging (Caffrey (2000), Curr Opin Struct Biol, 10:486-97). Several of these techniques (e.g. cryo-EM and tomography) utilize membrane proteins embedded in lipid bilayers, and have already been applied to the low resolution examination of whole-retroviral membrane protein structures (Zhu, et al. (2003), Proc Natl Acad Sci USA, 100:15812-7). The structure of ligands, peptides, or proteins binding to membrane proteins within the lipoparticle can be determined, for example by solution or solid-state NMR, X-ray crystallography, cryo-EM, projection maps, lipidic cubic phase, 2D crystallization, atomic force microscopy or electron tomography. The lipoparticle offers significant advantages for all of these structural studies.

In some embodiments, the structure of ligands bound to lipoparticles, ligands bound to membrane proteins, membrane proteins, and other proteins can be determined by, for example, x-ray crystallography, cryo-EM, projection maps, lipidic cubic phase, 2D crystallization, solution Nuclear Magnetic Resonance, solid-state Nuclear Magnetic Resonance, atomic force microscopy, electron tomography and the like.

For example, membrane proteins within lipoparticles are structurally intact and derived from a homogeneous source.

Because of the mechanism of lipoparticle production, only proteins in their fully-processed native form on the plasma-membrane are isolated. In contrast, lysates from cells will contain a membrane protein of interest in all stages of synthesis, folding, and processing. Many of these proteins will not retain their native structure and complicate structural analyses by introducing significant heterogeneity.

Additionally, the lipoparticle facilitates separation of membrane proteins from contaminating cellular structures. lipoparticles are harvested in culture supernatant, and can be readily separated from debris using simple centrifugation or chromatography steps. The use of lipoparticles as a starting material provides a higher quality protein source for subsequent purification steps. Purification techniques and reagents that might not be successful when starting with whole cells might succeed with lipoparticles.

Also, membrane protein can be produced from cells indefinitely. Traditional membrane protein expression systems using cells must be terminally harvested. Lipoparticle production itself is not toxic to cells, so lipoparticles can be harvested multiple times over long periods of time. In effect, the lipoparticle mimics the production of secreted protein, providing a greater surface area of plasma membrane from which to capture membrane proteins as new plasma membrane is generated and released with lipoparticles.

Methods and Devices for Detecting Proteins

In a 2000 paper published in PNAS, it was demonstrated that a number of complex proteins, including GPCRs, can be incorporated into lipoparticles and attached to the BIACORE biosensor (Hoffman, et al. (2000), Proc. Natl. Acad. Sci. USA, 97:11215-11220). Binding of antibodies, peptides, and proteins to these receptors exhibited appropriate specificity, and structural integrity of the receptors was maintained. An affinity of interaction between a protein and its receptor (HIV gp120 and CXCR4) of approximately 500 nM was also measured. This affinity is sufficiently weak so as to render previous standard binding assays unable to detect the interaction (Doranz, et al. (1999), J. Virol., 73:10346-10358, Doranz, et al. (1999), J. Virol., 73:2752-2761). The affinity with which different HIV-1 gp120 proteins bind to chemokine receptors can be an important determinant of viral pathogenesis, so measuring these interactions has enabled practitioners to begin correlating binding affinity with disease progression. The use of the lipoparticle made this possible, and provides a clear example where use of this novel approach has proven its worth. Work with the GPCRs CCR5 and CXCR4 has, to date, been directly applicable to other membrane proteins. Over twenty different membrane proteins have been incorporated into virus-based lipoparticles, including GPCRs, ion channels, transporters, and Type I and Type II single transmembrane proteins.

In some embodiments, the present invention relates to a composition comprising an array of lipoparticles attached to a surface or a sensor surface. In some embodiments, the present invention relates to a composition comprising an array of viral particles attached to a surface or a sensor surface. In some embodiments, the present invention relates to an array of pseudotypes attached to a sensor surface. In some embodiments, the present invention relates to a composition comprising an array of at least 1 lipoparticle and at least 1 pseudotype. In some embodiments, the present invention relates to a composition comprising at least 1 lipoparticle, at least 1 pseudotype, at least 1 viral particle, or combinations thereof.

As used herein, the term "array" refers to a group of at least 2 members. In some embodiments, an array comprises at least 3, at least 4, at least 5, at least 6, at least 7, at least 8, at least 9, at least 10, at least 11, at least 15, at least 50, at least 95, at least 96, at least 384, at least 1,000, at least 5,000, or at least 10,000 members. As used herein, the term "member" refers to a lipoparticle, virus, pseudotype, as well as empty positions.

As used herein the term "positions" refers to distinct locations on a sensor surface to which a lipoparticle, pseudotype, or viral particle may be attached.

As used herein, the term "array of lipoparticles" refers to a group of lipoparticles.

In some embodiments, an array of lipoparticles comprises least 2, at least 3, at least 4, at least 5, at least 6, at least 7, at least 8, at least 9, at least 10, at least 15, at least 20, at least 30, at least 40, at least 50, at least 60, at least 70, at least 80, at least 90, at least 95, at least 96, at least 100, at least 200, at least 300, at least 384, at least 500, at least 1,000, at least 2,000, at least 5,000, or at least 10,000 positions.

In some embodiments, the array of lipoparticles comprises at least 2, at least 3, at least 4, at least 5, at least 6, at least 7, at least 8, at least 9, at least 10, at least 15, at least 20, at least 30, at least 40, at least 50, at least 60, at least 70, at least 80, at least 90, at least 95, at least 96, at least 100, at least 200, at least 300, at least 384, at least 500, at least 1,000, at least 2,000, at least 5,000, or at least 10,000 lipoparticles.

In some embodiments, the group of lipoparticles comprises at least two lipoparticles that have different compositions. Therefore, in some embodiments, an array of lipoparticles refers to a heterogeneous group of lipoparticles rather than a homogenous (i.e. a group of lipoparticles where all the lipoparticles contain the exact same membrane protein or exogenously expressed protein).

In some embodiments, an array of lipoparticles comprises least 2, at least 3, at least 4, at least 5, at least 6, at least 7, at least 8, at least 9, at least 10, at least 15, at least 20, at least 30, at least 40, at least 50, at least 60, at least 70, at least 80, at least 90, at least 95, at least 96, at least 100, at least 200, at least 300, at least 384, at least 500, at least 1,000, at least 2,000, at least 5,000, or at least 10,000 different lipoparticles. In some embodiments, an array of lipoparticles comprises 95 or 96 different lipoparticles.

In some embodiments, the array of lipoparticles is arranged such that the spacing of the lipoparticles occurs along a horizontal axis and a vertical axis, wherein each axis comprises at least 2 positions, such that the array is 2×2. In some embodiments, the array is in the arrangement of 8×12 (e.g. 96 well plate), 16×24 (e.g. 384 well plate), or 32×48 (e.g. 1536 well plate).

In some embodiments, an array of lipoparticles comprises 96 positions. In some embodiments, an array of lipoparticles comprises 96 lipoparticles attached to a sensor surface. In some embodiments, an array of lipoparticles comprises 95 lipoparticles attached to a sensor surface and one empty position on the sensor.

In some embodiments, an array of lipoparticles attached to a sensor surface comprises at least one position on the sensor surface that is left empty. In some embodiments, at least 2, at least 3, at least 4, at least 5, at least 10, at least 20, at least 30, at least 40, at least 50, at least 60, at least 70, at least 80, at least 90, at least 91, at least 92, at least 93, at least 94, or at least 95 positions are left empty.

As used herein the term "an array of lipoparticles attached to a sensor surface" refers to a group of lipoparticles that is attached to a sensor surface and can include empty positions. In some embodiments the lipoparticles can be attached to the sensor surface by covalent bonds, ionic bonds, hydrophobic interactions, affinity interactions, hydrophilic interactions, chemical crosslinking, and the like. The exact method used to attach the lipoparticles to the sensor surface is not essential to the invention, as long as the integrity of the lipoparticles is, maintained.

The present invention also provides method of identifying a binding partner of a membrane protein comprising contacting a surface coated with a lipoparticle comprising the membrane protein with an array comprising the binding partner. In some embodiments, the surface may also be coated with a virus. By coating a surface with the same lipoparticle an array of other molecules can be screened to determine if a member of the array can bind to the lipoparticle. Thus, while the lipoparticle composition is uniform the members of the array are not and thus, a large number of molecules can be screened against the surface that is coated with the lipoparticles. Methods of coating a molecule on a surface can routinely be done (see, for example, Gosalia D N, Diamond S L. *Proc Natl Acad Sci USA*. (2003) Jul. 22; 100(15):8721-6.)

As used herein, the term "sensor surface" is any substrate where a change in a property of the substrate mediated by the contacting of the surface with a molecule or compound is detected and can be compared to the surface in the absence of such contacting. In some embodiments, a lipoparticle can be attached to a surface and then an interaction between a lipoparticle and a substrate is detected by another mechanism. In some embodiments, the substrate is attached to a surface.

While the sensor surface can be in the form of a chip as exemplified herein, the sensor surface is not limited to such a chip. Instead, the skilled artisan would appreciate, based on the disclosure provided herein, that a sensor surface includes not only any biosensor chip that is disclosed herein (e.g., a BIACORE C1 chip, a F 1 chip, and the like), but also any biosensor chip presently known in the art, or to be developed in the future. Such sensor surfaces include, but are not limited to, a glass substrate comprising a coating of, e.g., gold, which can further comprise, for instance, a dextran matrix. The present invention is not limited to any particular sensor surface. The important feature of such a surface is that a change in a characteristic of the sensor surface e.g., its refractive index, can be detected, preferably by an instrument connected to the sensor surface, such that data or information from the sensor can be assessed thus detecting the change, or lack of change, of the characteristic of the surface.

Example of biosensors and detection systems include, but are not limited to, biosensors and systems created by Biacore™, Protiveris™, Luna™, Illumina™, SRU Biosystems™, Akubio™, Applied Biosystems™, Graffinity™, and HTS Biosystems™.

One skilled in the art will recognize that the optical biosensor is but a detection mechanism. Optical biosensor technology is a growing field with increasing sophistication, and the present invention can be practiced using a wide variety of biosensors. The present invention can be practiced using any biosensor, including biosensors based on arraying the samples to an alternative surface (such as a glass slide), or biosensors which have been reduced in size.

In some embodiments, the sensor surface comprises a sensor, a biosensor, an optical fiber, or a microfluidic device. The mechanism by which an optical biosensor measures the interaction is also not essential to the invention and can include any method. In some embodiments, an optical biosensor measures an interaction by surface plasmon resonance (SPR), colorimetric diffraction grating, chemiluminescence, fluorescence, and the like.

In some embodiments the sensor surface can also comprise a 96-well, 384-well, 1536-well, a nano-well, optical fiber, or slide format. In some embodiments, the sensor surface comprises gold, glass, plastic, or a combination thereof. However, the exact materials that comprise the sensor surface is not essential as long as the sensor surface enables the detection or an interaction, and that such information can be assessed thus detecting the interaction, or change, the lack of interaction, or change.

The membrane proteins can be either cloned or obtained from commercial or academic sources and produced in lipoparticles as described herein. The structural integrity of membrane proteins within each batch of lipoparticles can be tested using conformationally-sensitive MAbs and/or ligands, depending on availability.

The present invention also provides methods for detecting the structural integrity of a membrane protein within a particle (e.g. virus particle or lipoparticle) comprising contacting the particle with a molecule that binds to the membrane protein; and detecting binding of the molecule to the particle, wherein the binding of the molecule to the particle is indicative that the structural integrity of the membrane protein is intact. In some embodiments, the molecule is an antibody, conformation-dependent antibody, ligand (e.g. toxin), agonist, or antagonist. In some embodiments, the method comprises a centrifugation step. In some embodiments, the method of detection comprises a Virus-Detection ELISA, an antibody detection Viral ELISA, a sensor, flow-cytometry, immunofluorescence staining, centrifugation, or combinations thereof.

In some embodiments, a lipoparticle has only one exogenous membrane protein. Some lipoparticles, can, however, contain more than one exogenous membrane protein. In some embodiments, the exogenous membrane protein can be any membrane protein. In some embodiments, the exogenous membrane protein is both alpha and beta dystroglycan, and the like.

The lipoparticles can be incorporated into the BIND™ biosensor detection system from SRU Biosystems (Woburn, Mass.). BIND is a label-free biosensor with continuous biosensor gratings that is compatible with industry-standard 96-well and 384-well plates and microarray slides. SRU's technology is based on a colorimetric diffractive grating surface that, when illuminated with white light, is designed to reflect only a single wavelength. When molecules are attached to the surface, the reflected wavelength (color) is shifted due to the change of the optical path of light that is coupled into the grating. SRU's biosensors have picomolar sensitivity, and are not based on detection of mass, so they can detect binding of low molecular weight compounds as easily as large proteins. The chemical surface of the biosensor can be derivatized for optimal attachment using much of the same chemistry as BIACORE chips. A single spectrometer reading can be performed in several milliseconds, allowing reaction kinetics to be monitored in real time.

In some embodiments, biosensors require that the protein of interest be immobilized on the biosensor surface. One skilled in the art will recognize that attachment conditions will vary depending on the biosensor used.

The SRU biosensor uses a polymer surface that is modified to contain carboxyl groups for surface attachment. Aside from the biosensor surface, the other major surface involved is on the lipoparticles.

The lipoparticles surface is similar to that of a cell, containing lipids, proteins, and carbohydrates, any of which can be readily used or modified to facilitate attachment.

In some embodiments, the screening of samples on a SRU biosensor can follow the following sequence: pre-blocking, blocking, application/binding of sample, and regeneration. For example, the biosensor can be created to include lipoparticles containing anthrax toxin receptors. In some embodiments, the biosensor can be prepared during the pre-blocking stage with PBS for 10 minutes. Blocking can be performed using 10% Serum in PBS for 5 minutes. Samples can be diluted 1:1 with PBS and can be applied to the biosensor at a rate of 5 ul/min for 10 minutes at pH 7.2. Regeneration of the biosensor can proceed with three 30 second applications of Sodium Carbonate at pH 9 with 0.5 molar NaCl. The sequence can then be repeated for the examination of another sample.

In some embodiments the array of lipoparticles comprises a lipoparticle that does not contain a protein of interest. The lipoparticle that does not comprise a protein of interest can be referred to as a control lipoparticle. The lipoparticle that does not comprise a protein of interest can also be referred to as a negative control lipoparticle. In some embodiments, the array of lipoparticles does not comprise a control lipoparticle. In some embodiments, the array of lipoparticles attached to a sensor surface comprises a position on the sensor surface that is "empty." As used herein, the term "empty" refers to a position on the sensor surface that does not contain a lipoparticle. In some embodiments the array of lipoparticles attached to a sensor surface comprises at least one location that contains a lipoparticle with a specific membrane protein. The specific membrane protein can be any membrane protein.

For example, the array of lipoparticles attached to a sensor surface comprises CCR5, CXCR4, DC-SIGN, DC-SIGNR, CFTR, CD44, mannose receptor MRC1, alpha dystroglycan, beta dystroglycan, the anthrax toxin receptor, and the like. In some embodiments, a single lipoparticle in the array of lipoparticles comprises one membrane protein, two, three, four, five, six, seven, eight, nine, ten, fifteen, twenty, thirty, forty, fifty, one hundred, or more than one hundred membrane proteins. The lipoparticles can comprise any membrane protein or protein that can be inserted into a lipoparticle.

The lipoparticles can also comprise proteins derived only from naturally occurring sources. The lipoparticles can be produced from a primary cell, an organ, a stem cell, a cell line, and the like. With such lipoparticles, the proteins are not exogenously added (i.e. they are normally produced by the source.) The organ can be any organ from an organism and includes, but not limited to, liver, kidney, brain, pancreas, intestine, skin, testes, ovaries, heart, lung, and the like.

In some embodiments, the lipoparticles are attached to the biosensor using one of the following three methods: Amine coupling: (Parameters of pH (5.5), ionic strength, coupling reagents (0.25 M EDC, 1.0 M NHS), and amine quenching (1 M ethanolamine, pH 8.5)); Avidin-Biotin attachment: Streptavidin can be amine coupled to the biosensor surface, and lipoparticles will be biotinylated by incorporation of phosphatidylcholine-biotin lipids or alternatively by chemical coupling of biotin moieties; or Lectin binding: A wheat germ agglutinin (WGA) surface will be created by covalently coupling WGA (Vector Laboratories) to the biosensor surface. WGA is a lectin that binds glycolipids on cell membranes and is routinely used for binding of membrane vesicles, and can bind lipoparticles directly.

In some embodiments, lipoparticles, viruses, or virus-like particles can be captured in similar ways. lipoparticles, viruses, or virus-like particles can also be captured to surfaces by mixing the particles in solution with a capture agent, such as WGA-biotin, and then flowing the particles over a suitable surface, such as avidin. Lipoparticles can also be captured using a membrane protein in the lipoparticle, such as a transmembrane-anchored avidin fusion protein or a fusion protein containing a His-tag, that allows attachment of the lipoparticle to a suitable surface such as biotin or Ni+2.

In some embodiments, the lipoparticles are attached as follows: Activate the surface carboxyl groups with a 1:1 mixture of 1M 1-ethyl-3-(3-dimethylaminopropyl)carbodiimide hydrochloride (EDC) and NHS for 8 minutes. Lower the flow rate to 1 µL/min and inject the lipoparticle solution mixed 1:1 with 0.1 M sodium acetate, pH 5.5). Inject manually for about 20 minutes until the desired level of attachment is achieved. Block with 1 M ethanolamine, pH 8.5 for 8 minutes.

Lipoparticles can also be attached to the Biacore chip. Attachment of lipoparticles using microfluidic flow-cell delivery has already been used within the BIACORE biosensor with success (Hoffman, et al. (2000), Proc. Natl. Acad. Sci. USA, 97:11215-11220). The microfluidic mechanism inherently keeps the sample uniform as it is delivered to the biosensor surface.

To attach lipoparticles to a BIACORE chip the following procedure can be followed. The BIACORE sensor surface uses a gold surface that is covalently modified with free carboxyl groups, and we have successfully used this surface (C1 and F1 BIACORE chips) for covalent attachment of lipoparticles via amine coupling. For amine coupling, the C1 biosensor chip surface can be activated with a 1:1 mixture of 0.25 M EDC and 1 M NHS. Lipoparticles that have been mixed 1:1 with 0.1 M NaOAc pH 5.5 can be injected for 15 min at 1 µl/min. Following attachment, the remaining surface carboxyl groups can be quenched with 1 M ethanolamine, pH 8.5.

In some embodiments, binding of conformation-dependent MAbs (Monoclonal antibodies) are used to ascertain successful attachment and retention of membrane protein conformation. A range of lipoparticles concentrations (0.1-10 µg) can be captured and compared. Lipoparticles without any membrane protein can serve as a standard negative control.

The sensor surface can also be modified to bind lipoparticles. In some embodiments the sensor surface is modified with a composition comprising poly-lysine, alkane modification (the covalent attachment of hydrophobic carbon chains), gamma-aminopropylsilane, histidine, protein A, lectin, avidin, streptavidin, acylation, $Ni^{++}$, and the like. The sensor surface can also be modified by any combination of compositions that will facilitate the binding of lipoparticles. In some embodiments the lectin is wheat germ agglutinin. In some embodiments the sensor surface is modified to preserve membrane protein structure. To preserve membrane protein structure the sensor surface can be modified with, but not limited to, trehalose, glycerol, sucrose, gelatin, gamma-amino-propylsilane, or a combination thereof.

As used herein, the term "alkane modification" refers to the covalent attachment of hydrophobic carbon chains.

In some embodiments, the lipoparticles are modified to facilitate their binding to the sensor surface. For example, if the sensor surface is coated with avidin the lipoparticles can be modified to be biotinylated so that the biotinylated bioparticles will bind to the avidin on the sensor surface. Alternatively, the lipoparticles can be coated with WGA-biotin which in turn can bind avidin or streptavidin surfaces. The lipoparticles can be modified with other agents (e.g. $Ni^{++}$) as well so long as the integrity of the lipoparticle remains intact.

Once coated onto a surface lipoparticles containing a membrane protein can be used, for example, to screen an array of antibodies. In some embodiments, the antibodies are allowed to bind to the lipoparticles and are then washed away. The binding of the antibodies can be detected by coating the entire slide with a fluorescent secondary antibody that recognizes the first antibody. The slide is washed and spots that have bound antibody are detected by visualizing fluorescent spots.

Methods of visualizing secondary antibodies are known to one of ordinary skill in the art.

In some embodiments, a library may be composed of antibodies, hybridoma supernatants, drug candidates, or peptides. In some embodiments, the library arrayed onto the Lipoparticles may also contain glycerol to prevent drying of the spots. In some embodiments, lipoparticles can be coated by covering the entire slide with a solution of lipoparticles in sucrose, allowing lipoparticles to attach for 1 hour, and then removing the lipoparticle solution. In some embodiments, the solution of sucrose comprises about 0.1%, about 0.2%, about 0.5%, about 1.0%, about 2.0%, about 3.0%, or about 5.0% sucrose. In some embodiments, the solution of sucrose comprises more than 0.1%, more than 0.5%, more than 1%, more than 2%, more than 3%, more than 4%, or more than 5% sucrose.

One skilled in the art will recognize that lipoparticles modified chemically (e.g. PEGylation, biotinylation, fluorescent labels) and genetically (elimination of retroviral protease to increase particle production) may be used in the creation of the biosensor. Furthermore, one skilled in the art will recognize that different methods for producing lipoparticles than herein disclosed may be employed for the creation of the bioparticles.

Although the array of lipoparticles can comprise proteins from one species, in some embodiments, the lipoparticles present in the array can comprise membrane proteins from more than one species. For example, an array of lipoparticles may contain 10 different lipoparticles, 5 lipoparticles may comprise a human protein, while the other 5 lipoparticles may comprise mouse proteins. The number of species represented by a lipoparticle is not limited. An array may comprise lipoparticles that each have proteins from a different species. Thus in some embodiments, an array of lipoparticles may comprises lipoparticles comprising proteins from one, two, three, four, five, six, seven, eight, nine, ten, or more than ten species.

In some embodiments, the array of lipoparticles comprises lipoparticles comprising proteins that are homologues from at least two species.

The present invention can be used for many applications. A non-exhaustive list of applications are described for example in Table 2. There are other numerous applications for which the present invention can be used for that are not disclosed herein and are readily apparent to those of ordinary skill in the art and are included in the present invention.

TABLE 2

Specific examples of applications for the Receptor Biosensor

| Class | Application |
|---|---|
| Drug Discovery | Refinement of lead compound specificity (lead optimization) |
| Drug Discovery | Identification of ligands to orphan receptors (ligand fishing) |
| Drug Discovery | Identification of receptors for orphan ligands (de-orphaning) |
| Drug Discovery | Identification of undesired binding reactions (toxicity correlates) |
| Biomedical Research | Proteomic network mapping |
| Biomedical Research | Basis for in silico modeling of biologically complex binding scenarios |
| Diagnostics | Dynamic monitoring of immune response during disease |
| Diagnostics | Detection of auto-antigen immune responses |
| Diagnostics | Detection of narcotics, pathogens, and biological warfare agents |

Another aspect of the present invention relates to methods of detecting a ligand binding to a lipoparticle. In some embodiments, the method comprises the steps of contacting a ligand with an array of lipoparticles attached to a sensor surface and detecting the binding of the ligand with the array of lipoparticles. In some embodiments, the method comprises the steps of contacting a ligand with an array of, lipoparticles, viruses, or virus-like particles attached to a sensor surface and detecting the binding of the ligand with the array of lipoparticles, viruses, or virus-like-particles. In some embodiments the ligand comprises a fluorescent tag, enzymatic tag, biotinylated tag, a radioactive tag, and the like. In some embodiments the method of detecting a ligand binding to a lipoparticle can be used to determine the affinity of a ligand to a membrane protein present in a lipoparticle. For example, an array of lipoparticles can comprise lipoparticles containing the membrane protein of interest as well as at least one lipoparticle without the membrane protein of interest or a location on the array that is empty. The ligand is contacted with the array of lipoparticles under conditions which enable the ligand to bind to the lipoparticle. Once the ligand binds to the lipoparticle the sensor surface measures the interaction from which the affinity of the ligand is determined. The interaction can also be used to determine the on-rate, the off-rate or the specificity of the ligand. For example, to determine the specificity of the ligand, the array of lipoparticles can comprise at least one lipoparticle comprising a membrane protein and a lipoparticle that does not comprises a membrane protein. In some embodiments, the array of lipoparticles can comprises at least one lipoparticle with a first membrane protein and at least one lipoparticle with a second membrane protein. In some embodiments, the array of lipoparticles comprises about 5, about 10, about 20, about 30, about 50, about 100 lipoparticles comprising different membrane proteins. It is not required that each lipoparticle comprise a different membrane protein.

In some embodiments, the present invention provides methods of detecting ligand binding partners comprising the steps of contacting a ligand with lipoparticles with test binding partners; and detecting binding of test binding partners with said lipoparticles. In some embodiments, the test binding partner comprises a fluorescent tag, enzymatic tag, biotinylated tag, paramagnetic tag, a radioactive tag, or a combination thereof. In some embodiments, the binding of the testing binding partner to the lipoparticle comprises scintillation proximity or filtration binding.

In some embodiments, determining the specificity of a ligand comprises comparing the binding of a ligand to a location on the array that contains a lipoparticle with a specific membrane protein to the binding of the ligand to a location on the array that contains a lipoparticle without any specific membrane protein (i.e. a different membrane protein) or to a location on the array that does not contain a lipoparticle.

When screening samples, ligands, and the like on a biosensor one of skill in the art can follow the following sequence: pre-blocking, blocking, application/binding of sample, and regeneration.

One skilled in the art will recognize that to optimize the system, a number of experimental conditions can be altered. Examples of conditions that can be altered include, but are not limited to, those disclosed in Table 3.

TABLE 3

Usage Conditions & Alternative

| Usage Conditions | Alternatives |
|---|---|
| Pre-blocking | None, BSA, Gelatin, Serum, Glucose |
| Blocking agent in buffer | None, BSA, Gelatin, Serum, Glucose |
| NaCl (mM) | 0, 50, 150 |
| Blocking time (min) | 0, 5, 10, 30 |
| Attachment flow rate (μl/min) | 2, 5, 10, 30 |
| Coupling pH | 4, 5, 6, 7 |
| Running buffer | PBS, HBS, DMEM |
| Dispersive agents | None, Pluronics, Gum arabic |
| Neutralization of charged lipids | None, Polybrene, DEAE-Dextran |
| Experimental flow rate (μl/min) | 15, 30, 60 |
| Particle concentration (mg/ml) | 0.05, 0.1, 0.2, 0.5, 1.0 |
| Regeneration conditions | low pH, high pH, chaotropic agents, salt |
| Control surface | no lipoparticles, no receptor, irrelevant receptor |

A biosensor using lipoparticles to detect interactions can also be generated using a BIACORE system. In some embodiments, conditions for using a BIACORE system are described, but not limited to, in Table 4.

TABLE 4

Conditions used with BiaCore System.

| Variable | Current Status |
|---|---|
| Coupling reagent | 0.25M EDC, 1M NHS, fresh preparation |
| Chip type | C1 > F1 > L1 > B1 |
| Coupling rates | Fast activation rate (10 μl/min), slow coupling rate (1 μl/min), fast quenching rate (10 μl/min) resulted in 2× rate of attachment and 3× attachment level |
| Lipoparticles | High purity and high receptor density are better. Concentration has small effect |
| Specificity | Demonstration of specificity using controls including irrelevant MAbs, Lipoparticles with irrelevant membrane proteins, blank flow cells |
| Buffer | HEPES ≥ Tris > Phosphate |
| Ionic strength | NaCl 50-150 mM, pH 6.0-7.0 |
| Additives | Stable to glycerol, sucrose, ethanol, DMSO, PEG |
| Blocking reagents | 1 mg/ml BSA |
| Sensitivity | Detection limit as low as 20 pM (3.2 ng/ml) with MAb |
| Orientation | a) Lipoparticles can be captured on the biosensor surface and MAbs flowed across (better quantization), and b) Lipoparticles can be flowed across a MAb surface (increased sensitivity) |
| Regeneration | Na$_2$CO$_3$, pH 9 + 0.5M NaCl, supports up to 200 cycles, baseline stability can be improved |
| Ligand size | 8 kDa natural ligand (SDF-1) can be detected |

One skilled in the art will recognize that these conditions can be modified to test for infectious agents, food-borne illnesses, water-borne illnesses and contaminants, and other disease causing agents not described herein, and are within the scope of the present invention. The array of lipoparticles attached to a biosensor can also be modified to incorporate any membrane protein of interest or protein that is associated with the membrane. Example of Water-borne illnesses and contaminants are listed in Table 5

TABLE 5

Water Contaminants

| Type of Water Contaminants: | Examples: |
|---|---|
| Coliform bacteria | Fecal Coliform and *E coli* |
| | Turbidity |
| | *Cryptosporidium* |
| | *Gairdia lamblia* |
| Inorganic Contaminants | Arsenic |
| | Fluoride |
| | Lead |
| Synthetic Organic Contaminants, including pesticides & herbicides | Dioxin |
| | Endothall |
| | PCBs |
| Volatile Organic Contaminants | Carbon Tetrachloride |
| | Toluene |
| Disinfectants | Chlorine |
| | Chloramine |
| Disinfecting Byproducts | Chlorite |
| | MTBE |

The present invention also relates to methods of detecting an infectious pathogen. In some embodiments a method of detecting an infectious pathogen comprises the steps of: a) contacting a sample with an array of lipoparticles attached to a sensor surface, wherein the array of lipoparticles comprises membrane proteins that interact with infectious pathogens; and b) detecting an interaction with said array of lipoparticles, wherein the detection of an interaction indicates the presence of an infectious pathogen.

In some embodiments, the creation of a biosensor to detect an interaction between a lipoparticle and a binding partner comprise: 1) selection of membrane proteins; 2) production of lipoparticles containing membrane proteins; 3) selection of biosensor surface and/or system; 4) attachment of lipoparticles to the biosensor surface; and 5) screening of samples.

In some embodiments, a sample can be contacted with an array of lipoparticles. The lipoparticles can comprise membrane proteins that interact with agents. These include receptors that interact with infectious pathogen proteins, toxins, and the like. The infectious pathogen can be any pathogen, including, but not limited to bacteria, viruses, and the like. In some embodiments the infectious pathogen to be detected is anthrax, plague, or Ebola. However, it is not necessary for the infectious agent to be known because the array of lipoparticles can comprise lipoparticles that comprise different membrane proteins that can interact with different infectious pathogens.

As used herein, the term "agent" can refer to a chemical, compound, or infectious pathogen that can cause sickness, disease, and/or death.

As used herein, the term "infectious pathogen" refers to a micro-organism (e.g. virus or bacteria) that can cause sickness, disease, and/or death. Examples of infectious pathogens include, but are not limited to, HIV, Ebola, plague, *E. Coli*, anthrax, West Nile Virus, smallpox, chickenpox, monkey pox, hanta virus, SARS, tuberculosis, whooping cough, cholera, and the like.

Other examples of infectious pathogens, including their proposed receptors, are provided in Table 6.

TABLE 6

Selected membrane proteins proven or proposed (in parentheses) to function as pathogen receptors.

| Membrane Protein | Proven (or proposed) pathogen Usage |
|---|---|
| Anthrax Toxin Receptor | Anthrax Toxin binding |
| Alpha and beta dystroglycan | Lassa Fever, LCMV hemorrhagic fever viruses |
| CD44 | Shigella |
| Mannose receptor (MRC1) | Ricin toxin |

TABLE 6-continued

Selected membrane proteins proven or proposed (in parentheses) to function as pathogen receptors.

| Membrane Protein | Proven (or proposed) pathogen Usage |
| --- | --- |
| CFTR | *Salmonella enterica* |
| CCR5, CXCR4 | HIV coreceptors, (smallpox, *yersinia pestis*) |
| DC-SIGN, DC-SIGNR | HIV, Ebola, Dengue, CMV, *Candida* |

The present invention also relates to detecting any agent that can cause sickness, disease, and/or death that may be present in a sample. These agents may be food-borne, water-borne, air-borne, present in fecal material, and the like. The agent may be an organic compound, a peptide, a protein, a micro-organism (e.g. virus or bacterium), and the like. It is not necessary that the agent be infectious (i.e. being capable of being transmitted from one organism to another). The compound can be identified as long as it is able to be bound by a protein or a membrane protein that is part of a lipoparticle that is attached to a sensor surface.

The present invention also relates to methods of determining the presence of a substance comprising the steps of: contacting a sample with an array of lipoparticles attached to a sensor surface, wherein the lipoparticles comprise membrane proteins that interact with the substance; and detecting an interaction with the array of lipoparticles, wherein the detection of the interaction indicates the presence of the substance.

An array of lipoparticles attached to a sensor surface can also be used to detect a substance that is derived from saliva, blood, serum, urine, semen, vaginal secretions, cell lysate, cell supernatant, tissue homogenate, food, water samples, and the like.

In some embodiments, an array of lipoparticles can be used to detect a substance from a swarm of virus, which is, in some embodiments, obtained from an infected individual.

The present invention also provides for the creation of an Infectious Disease Receptor Biosensor (IDRB) using lipoparticles, such that known membrane proteins having functions known to be involved with infectious disease will be incorporated into the array.

As used herein the term "Infectious Disease Receptor Biosensor" refers to a sensor surface that is used in conjunction with a biosensor machine and/or system to detect infectious pathogens.

Such a tool can have extensive applications for diagnostics and biomedical research. Using this tool, samples can be screened to detect molecules which interact with known infectious disease related membrane proteins. As more infectious disease related proteins are discovered they can be incorporated into the Receptor Biosensor.

In some embodiments, a use of the IDRB with human clinical samples is to detect pathogens, toxins, and proteins. Pathogens tested can include, but are not limited to, both viruses and bacteria. Viruses can include single species as well as swarms that may use multiple receptors. Both spiked control fluids and clinical samples from pathogen-infected patients can be tested.

A number of complex fluids (including serum, urine, and saliva) can be analyzed to detect and quantify the presence of infectious agents in these samples that bind to the membrane proteins represented on the cell surface biosensor. Samples spiked with known ligands and antibodies can be used as positive controls.

Such a focused receptor biosensor is useful for the generation of a kit designed for diagnostics where a sample is screened against known membrane proteins known to bind with soluble infectious agents.

The creation and screening of the IDRB will closely parallel the methods described for other biosensors described herein. First, lipoparticles containing known infectious disease related membrane proteins can be produced. Second, these lipoparticles can be attached to a biosensor surface. Finally, these biosensors can be screened using serum, urine, and saliva to determine the presence of infectious agents.

The present invention also provides for the creation of a Water Quality Receptor Biosensor (WQRB) using lipoparticles, such that known membrane proteins having functions known to be involved with contaminants to the water supply can be incorporated into the array.

As used herein the term "Water Quality Receptor Biosensor" refers to a sensor surface that is used in conjunction with a biosensor machine and/or system to detect water contaminants.

Such a tool can have extensive applications for diagnostics and biomedical research. Using this tool, samples can be screened to detect molecules that interact with known water contaminant related membrane proteins. As more water quality related membrane proteins are discovered they can be incorporated into the Water Quality Receptor Biosensor. Examples of water contaminants can be found Table 5, but any water contaminant can be included.

The creation and screening of the WQRB will closely parallel the methods described for biosensors described herein. First, lipoparticles can be produced containing known membrane proteins having functions known to be involved with contaminants to the water supply. Second, these lipoparticles can be attached to a biosensor surface. Finally, these biosensors can be screened using water samples to determine the presence of contaminants. The result of this can be a tool to aid in the rapid testing of multiple water samples for a large number of potential contaminants. One skilled in the art would also recognize that a similar system can also be used for detection of contaminants or components of other liquids, beverages, foods, chemicals, or aqueous solutions.

The present invention also relates to methods of identifying an inhibitor of a substance comprising the steps of: contacting a substance and a compound with an array of lipoparticles attached to a sensor surface, wherein said substance can bind to said array of lipoparticles in the absence of the compound; and detecting an interaction of said substance with said array, wherein if an interaction is detected, then the compound does not inhibit the binding and if an interaction is not detected then the compound inhibits the binding of the substance with the lipoparticle.

Compounds that can be tested as inhibitors include, but are not limited to, organic compounds, peptides, proteins, pharmaceuticals, nucleic acids, —e.g. RNA, DNA, oligonucleotides, double-stranded RNA, and the like.

The present invention also relates to methods of identifying a binding partner for a substance comprising the steps of: a) contacting a substance with an array of lipoparticles attached to a sensor surface; b) detecting an interaction of the substance with the array; and c) identifying the binding partner. In some embodiments, the binding partner is a membrane protein that can bind to the substance. In some embodiments, a substance is contacted with an array of lipoparticles where the composition of each lipoparticle is known. In some embodiments the composition of the lipoparticles is unknown, but the protein of interest can be determined through known cloning and sequencing techniques. After contacting the substance with the array of lipoparticles, an interaction is detected by the sensor surface at a particular position(s). The lipoparticles are identified and the binding partner present in the lipoparticle is identified as the binding partner of the substance. The substance can be any substance which can bind to a lipoparticle or a membrane protein present in the lipoparticle. Examples include, but are not limited to an organic compound, chemical, peptide, protein, antibody, virus, bacteria, toxin, multiple proteins (i.e. more than one), a pharmaceutical composition, a monoclonal antibody, a chemokine, a cytokine, a secreted protein, a neurotransmitter, and the like.

The present invention also relates to methods of determining an interaction map of a substance comprising the steps of: a) contacting at least one substance with an array of lipoparticles attached to a sensor surface; b) measuring binding of said at least one substance with said array of lipoparticles; c) determining which lipoparticles bind with at least one substance; and d) creating said interaction map based upon said binding.

As used herein, the term "interaction map" refers to the identification of interactions that a particular substance makes with an array of lipoparticles. A substance is any substance that can interact with an array of lipoparticles attached to a sensor surface, such as, but not limited to, an organic compound, chemical, peptide, protein, antibody, virus, bacteria, toxin, multiple proteins (i.e. more than one), a pharmaceutical composition, a monoclonal antibody, a chemokine, a cytokine, a secreted protein, a neurotransmitter, and the like. A substance or a group of substances may interact with more than one membrane protein and therefore with more than one lipoparticle present in an array of lipoparticles. The "interaction map" would be a compilation of all the interactions that a substance or a group of substances make. The interaction map may list only the positions on the array that the substances interacts with, or in some embodiments, it may list the proteins that are present at the interaction sites in the lipoparticles.

Interaction maps can be used for many purposes including, without limitation, metabolism, toxicity, patient health, disease progression, clinical outcome, absorption, and the like. For example, serum may be obtained from a patient at different time points during the progression of a disease. The serum can be contacted with an array of lipoparticles attached to a sensor surface. An interaction map can be created from each time point and the changes that are seen during the disease progression can be used to better treat the patient or to better understand the disease and/or disease progression.

Interaction maps can also be used to understand toxicity of a drug. A drug can be contacted with an array of lipoparticles attached to a sensor surface and an interaction map can be created. If that drug is known to be toxic, (i.e. have unwanted side effects), the interactions can be listed as potentially being predictive of a drug's toxicity. A novel drug can then be tested against an array of lipoparticles attached to a sensor surface to create an interaction map. If the interaction map of the novel drug is similar to the drug with the unwanted side effects, one of ordinary skill in the art could predict that the novel drug would also have the unwanted side effects. The interaction maps can also be used in a similar way to map a patient's clinical outcome and patient health.

As is the case for all the sensor surfaces described herein, the sensor surface can comprise a biosensor or a microfluidics device.

An interaction map can also be created for more than one substance.

The present invention also relates to methods for spotting lipoparticles, pseudotypes, or viruses in an array format onto a solid surface without allowing the liquid to completely desiccate. In some embodiments, the spotting comprises including in the spotting medium trehalose, glycerol, sucrose, collagen, or gelatin. In some embodiments, the lipoparticles are dried or lyophilized.

The present invention also relates to methods of identifying a ligand for, for example, a membrane protein, comprising the steps of: a) contacting a composition containing a potential ligand with an array of lipoparticles attached to a sensor surface; b) isolating said ligand; and c) determining identity of said ligand. An array of lipoparticles attached to a sensor surface can also identify a ligand for the lipoparticle. For example, a membrane protein can be identified that is thought to interact with another substance, which can be any substance such as, but not limited to, an organic compound, chemical, peptide, protein, antibody, virus, bacteria, toxin, multiple proteins (i.e. more than one), a pharmaceutical composition, a monoclonal antibody, a chemokine, a cytokine, a secreted protein, a neurotransmitter, and the like. An array of lipoparticles comprising the protein of interest is contacted with at least one ligand or a mixture containing potentially multiple ligands. A ligand's binding is detected by the sensor surface and the ligand can then be isolated from the mixture by known techniques. The ligand can be isolated and identified by liquid or gas chromatography, mass spectrometry, antibody detection (i.e. Western Blot, ELISA), northern blot, PCR, NMR, x-ray crystallography, and the like. The ligand may be part of a library whose identity is already known and what is being identified is the interaction, or the ligand may be unknown and part of a complex mixture. It should be noted that biosensors are now routinely being used in conjunction with mass spectrometry to identify new ligands in eluted material (Nedelkov, et al. (2001), Biosensors & Bioelectronics, 16:1071-1078, Nedelkov, et al. (2001), Proteomics, 1:1441-1446, Williams, et al. (2000), Trends in Biotechnology, 18:45-48), however this has not been done with lipoparticles. One skilled in the art will recognize that future applications involving orphan receptors, de novo ligand design (below), and other applications may employ mass spectrometry.

In some embodiments the ligand is identified from saliva, blood, serum, urine, semen, vaginal secretions, cell lysate, cell supernatant, tissue homogenate, food, water samples, and the like, or a combination thereof.

In some embodiments, the present invention also provides methods of identifying a binding partner of a membrane protein comprising contacting a lipoparticle, virus, or virus-like particle comprising the membrane protein with a library. In some embodiments, the library comprises more than one, more than 10, more than 50, more than 100, more than 1,000, more than 5,000, more than 10,000, about 500, about 1,000, about 5,000, about 10,000 potential binding partners. In some embodiments, the method comprises detecting the binding of the binding partner to the membrane protein. In some embodiments, the library is a phage display library or ribosome display library. In some embodiments, the binding partner is a monoclonal antibody, a polyclonal antibody, an affinity-purified polyclonal antibody, a Fab fragment derived from a monoclonal antibody, an immunoglobulin-fusion protein, a single-chain Fv, an Fc-fusion protein, peptide, or polypeptide.

The present invention also relates to methods of ligand design comprising the steps of: a) contacting at least one ligand with a lipoparticle attached to a sensor surface; and b) identifying ligands that bind to said lipoparticle. In some embodiments, the methods further comprise modifying the ligand and repeating steps a and b modifying the ligand until a ligand is identified that binds to the lipoparticle to satisfy a user-defined criteria. In some embodiments, the lipoparticle to which the ligand binds comprises a membrane protein. In some embodiments, the user-defined criteria is a high binding constant.

Previous investigators have reported successfully using the BIACORE biosensor for phage screening, although not with membrane proteins or lipoparticles (Malmborg, et al. (1996), Journal of Immunological Methods, 198:51-57, Schatzlein, et al. (2001), J Control Release, 74:357-362). The lipoparticle biosensor has predicted advantages over traditional phage panning of wells or beads: 1) phage binding is monitored in real time to better control specific binding, 2) binding can be monitored on control flow cells simultaneously for monitoring of non-specific binding, 3) elution can be monitored in real-time so only the fractions binding most strongly and specifically to the correct flow-cells need be collected, and 4) even weak affinities can be detected with a biosensor so difficult receptor-ligand pairs still can be identified. Several high affinity, short sequences of proteins that bind CXCR4 have been identified by ourselves and others using techniques that did not involve lipoparticles (Crump, et al. (1997), EMBO J, 16:6996-7007, Doranz, et al. (1997), J. Exp. Med., 186:1395-1400, Doranz, et al. (1999), J. Virol., 73:2752-2761, Murakami, et al. (1997), J. Exp. Med., 186:1389-1393), suggesting that high affinity peptides can be identified when used with lipoparticles. It should be noted that this approach could also be used for a phage library displaying antibody (Fv) fragments, a popular commercial method for deriving human MAbs.

As used herein, the term "user-defined criteria" refers to a standard by which the iterative process is stopped. This could be, for example, how tight the binding of the ligand to the lipoparticle is. Any user-defined criteria, however, can be used. In some embodiments, the ligand that is being identified and/or modified is a peptide, a protein, an antibody, a nucleic acid, molecule, an oligonucleotide, —e.g., DNA, RNA, double-stranded RNA, and the like. In some embodiments, the ligand(s) are presented to the lipoparticles on a phage.

The present invention also relates to a composition of multiplexed biosensors designed to recreate the cell surface proteins of a cell. In some embodiments, the composition will be a biosensor chip that can contain thousands of individually addressable membrane proteins. In some embodiments, the surface of the array comprises all membrane proteins encoded by the human genome, and can detect binding of unlabeled molecules (drugs or proteins) in real-time, and can quantify binding to each receptor. Operationally, the end-user would simply insert a sample of interest, such as human sera. One skilled in the art will recognize that such a technology would allow the detection of interaction between any soluble protein with any integral membrane protein that the soluble protein would naturally bind to. This could include finding unknown receptors, ligands, or antibodies.

Kits

In some embodiments, the present invention relates to a disposable biosensor component that can be used to identify an infectious pathogen or other disease or sickness causing agent. In some embodiments the disposable biosensor component is used to detect or identify Ebola, anthrax, plague, smallpox, SARS caronavirus, West Nile Virus, and the like. In some embodiments, the disposable biosensor component will allow for screening of samples for infectious pathogens or disease or sickness causing agents that interact with membrane proteins on the biosensor.

Lipoparticles Comprising Ion Channels and Methods Using the Same

In the present invention, the lipoparticles comprise ion channels or transporter proteins and are used to measure function. When making lipoparticles, contaminants of unwanted proteins may also be included in the lipoparticle. In some embodiments, to avoid the contaminating proteins from having undesired effects on how one uses the lipoparticles, the lipoparticles can be contacted with contaminating protein inhibiting toxins and/or ionophores to inhibit the contaminating proteins. The contaminating protein inhibiting toxin and/or ionophore is selected so that it does not inhibit or affect the protein(s) that are desired to be present in the lipoparticle.

In some embodiments, a virus, lipoparticle, or virus-like particle can be used to measure ion channel or transporter protein function. For example, viruses such as influenza contain ion channels (e.g. M2) and the methods described herein can be used assess the function of virally encoded ion channels and transporter proteins in a virus or virus-like particle.

In some embodiments, the ion channel protein is a neurotransmitter receptor.

The lipoparticles of the present invention can also be modified such that the modified lipoparticle can be used to detect ion channel protein function or transporter protein function. The modifications can be any modification that results in a parameter that can be measured, quantified, visualized, and the like. Examples of modifications that can be made to lipoparticles include, but are not limited to, modifying the membrane lipid composition, modulating the fluorescent dye content of the lipoparticle (e.g. adding fluorescent dyes), modulating the water content of the lipoparticle, and modulating the ion content of the lipoparticle. In some embodiments, a change in the detectable agent can indicate an increase in protein function. In some embodiments, a change in the detectable agent indicates a decrease in protein function.

The fluorescent dyes can be used to monitor, visualize and/or measure protein function. For example, when an ion channel or transporter protein is activated, the dye can either flow into or out of the lipoparticle, which would indicate, in some embodiments, that proteins are functioning. Similarly, when an ion channel or transporter protein is activated, an ion or molecule can either flow into or out of the lipoparticle and interact with a dye either inside or outside or in the membrane of the lipoparticle, which would indicate, in some embodiments, that proteins are functioning. The amount of dye and the fluorescent signal that is generated can be used to determine the level of activity of the membrane protein.

The present invention also provides for methods to determine membrane protein function using a lipoparticle comprising the membrane protein. In some embodiments, the lipoparticles comprises an ion channel or transporter protein and a detectable agent. The detectable agent can be any agent that can be detected by any means. For example, the agent can be detected using fluorescence, ultra-violet light, or visual light. Examples of detectable agents include, without limitation, voltage-sensitive fluorescent dyes and ion-sensitive fluorescent dyes.

As used herein, the term "voltage-sensitive fluorescent dye" refers to a dye that fluoresces or changes its fluorescent properties in response to a change in voltage.

As used herein, the term "ion-sensitive fluorescent dye" refers to a dye that fluoresces or changes its fluorescent properties in response to a change in ion concentration.

Examples of ion-sensitive and voltage-sensitive fluorescent dyes include, but are not limited to, di-4-ANEPPS ($C_{28}H_{36}N_2O_3S$), di-8-ANEPPS, rhodamine 421, oxonol VI, JC-1, DiSC3(5), CC2-DMPE, DiSBAC2(3), DiSBAC4(3), VABSC-1, and the like (Molecular Probes, Inc.).

The choice of which detectable agent is used is not essential and depends on the use of the lipoparticle. A plethora of fluorescent dyes and probes exist for detecting the function of ion channels, ranging from ion-specific dyes to dyes that respond to changes in membrane potential (Molecular Probes Handbook (2002)). To choose a probe, defined criteria exist by which dyes may be chosen, these include but are not limited to: easy to incorporate into pre-formed lipoparticles (encapsulation not necessary); versatility in detecting the function of a range of ion channels ($K^+$, $Na^+$, $Cl^-$, $H^+$, $Ca^{+2}$); high signal-to-noise and sensitivity to voltage changes caused by ion channel gating; or ratiometric measurement of fluorescent wavelengths, which provides an internal standard for a more stable baseline independent of artifacts such as leakage and loading. Ratiometric measurements can increase signal:noise values over 10-fold by better discrimination between bound and unbound forms of the dye (Molecular Probes Handbook (2002), Montana, et al. (1989), Biochemistry, 28:4536-4539).

In some embodiments, membrane potential fluorescent dyes are used. Such dyes were first used in the early 1970s, many being identified during a systematic search by Cohen and Salzberg (Cohen, et al. (1978), Rev Physiol Biochem Pharmacol, 83:35-88). Fluorescent dyes of membrane potential are classified as either "slow" or "fast" dyes, based on their mechanism of action (Haugland (2003), (2002), Plasek, et al. (1996), J of Photochemistry and Photobiology, 33:101-124, Smith (1990), Biochim Biophys Acta, 1016:1-28). Fast-response dyes respond to a change in membrane potential with a change in their electronic structure (spatial rearrangement of valence electrons) and, consequently, their fluorescence properties. Their optical response is sufficiently fast to detect transient (millisecond) potential changes, but the magnitude of their fluorescence change is relatively small, approximately 2-10% per 100 mV. Slow-response dyes respond to a change in membrane potential with a transmembrane redistribution that is accompanied by a fluorescence change. Their optical response is slower than fast probes (seconds to minutes), but the magnitude of their fluorescence change is greater, up to 100% per 100 mV.

Of the more than two dozen different membrane potential dyes available, examples include, but are not limited to, the ANEPPS dyes, di-4-ANEPPS and di-8-ANEPPS, with di-4-ANEPPS being preferred. Both ANEPPS dyes have identical fluorophores, exhibit good photostability, low toxicity, and a fairly uniform 10% per 100 mV changes in fluorescence intensity (Molecular Probes Handbook (2002), Rohr, et al. (1994), Biophysical Journal, 67:1301-1315). Due to its longer alkyl chains, di-8-ANEPPS is better retained in the membrane, slightly more photostable, and less phototoxic, but also more difficult to work with. Both ANEPPS dyes are essentially nonfluorescent in aqueous solutions but have absorption/emission maxima of 467/631 nm when bound to lipid membranes. Di-4-ANEPPS can be incorporated into lipoparticles (see, for example, FIG. 9). Further, the ANEPPS dyes can be measured ratiometrically, responding to increases in membrane potential with a decrease in fluorescence excited at approximately 440 nm and an increase in fluorescence excited at 530 nm. Ratiometric measurements between +120 mV and −120 mV are linearly responsive to membrane potential using ANEPPS dyes.

A number of alternative dyes are also available that can measure membrane potential, ((2002), Plasek, et al. (1996), J of Photochemistry and Photobiology, 33:101-124, Smith (1990), Biochim Biophys Acta, 1016:1-28). These dyes include but are not limited to the following.

Oxonol VI. Lipophilic anionic dyes such as the oxonols can detect relatively large changes in membrane potential which occur over periods of several minutes. In addition to the traditional use of oxonol to detect absolute changes in fluorescence, a ratiometric method has been developed using a fluorescence resonance energy transfer mechanism based on reactivity between oxonol and fluorescently labeled lipids (Gonzalez, et al. (1995), Biophysical Journal, 69:1272-1280). This approach reportedly can sense fast potential changes with fluorescence changes that exceed 50% per 100 mV JC-1. JC-1 is a carbocyanine fluorescent dye that forms aggregates upon depolarization and can be measured ratiometrically. Aggregation within the confined membrane interior results in decreased fluorescence and maximal emission shifts from 527 nm to 590 nm. The dye has been used successfully in many experiments, but is noted by some to exhibit unacceptable variability.

DiSC3(5). For many years, DiSC3(5) was considered to be the dye of choice for membrane potential assays due its high sensitivity, 50-80% per 100 mV (the highest of all cyanine dyes). This high signal is unavoidably related to the dye's high accumulation in cells, and thus to its high toxicity, but the toxicity should not effect signal within lipoparticles. Depending on the environment of use, DiSC3(5) may be assayed ratiometrically, increasing signal-to-noise about 10-fold.

Rhodamine 421. RH 421 has yielded the most sensitive response recorded for a fast potentiometric probe, greater than 20% fluorescence change per 100 mV. The optimal excitation and emission from RH 421 is dependent on its environment.

The properties of some fluorescent dyes that can be used to measure membrane potential are listed in Table 7. Other detectable agents include, but are not limited to fluorescent probes (e.g. fluorescent proteins, fluorescent amino acids, or fluorescent lipids). In some embodiments, the detectable agents can be used to make a ratiometric measurement to determine the function of the membrane protein.

TABLE 7

Fluorescent dyes are listed. Dyes were selected from more than two dozen fluorescent dyes that are responsive to membrane potential (Molecular Probes Handbook (2002),, Rohr, et al. (1994), Biophysical Journal, 67: 1301-1315).

| Category | Dye | Ratiometric | Advantages/Disadvantages |
| --- | --- | --- | --- |
| Fast | Di-4-ANEPPS | yes | Fast response (msec)/ |
|  | Di-8-ANEPPS | yes | Low signal (10%/100 mV) |
|  | Rhodamine 421 | no |  |
| Slow | Oxonol VI | yes | Slow response (sec-min)/ |
|  | JC-1 | yes | High signal (100%/100 mV) |
|  | DiSC3(5) | yes | Slow dyes noted for variability of response |

As used herein the term "ratiometric measurement" refers to the ratio of at least two measurements that are used to create a ratio. For example, di-4-ANEPPS responds to an increase in membrane potential with a decrease in fluorescence excited at approximately 440 nm and an increase in fluorescence excited at 530 nm. By measuring the emission wavelength at 630 nm, the 440/630 response can be divided by the 530/630 response to produce a ratio measurement.

As with all methods described herein, a computer can be used to calculate and measure the detectable agent, and calculate and determine the ratiometric measurement, and the like.

When using fluorescent detectable agents, one can measure the function of the membrane protein by resonance energy transfer (FRET). Resonance energy transfer is well known to one of ordinary skill in the art. For example, two separate fluorescent species can interact and they generate a distinct and different fluorescent signal. The distinct signal can be used to determine the function of the membrane protein.

In some embodiments, the present invention provides for methods of identifying inhibitors or stimulators of proteins (e.g. GCPRs, ion channels, transporter proteins and the like) comprising measuring changes in detectable agents. A lipoparticle comprising a membrane protein (e.g. ion channel or transporter protein) and a detectable agent will generate a detectable signal when the protein is active or inactive. The lipoparticle can be contacted with a test compound and a change in the detectable signal indicates that the compound is either an inhibitor or a stimulator. The change in the detectable signal could be a complete inhibition of the detectable signal (e.g. the signal is no longer detectable) or the detectable signal may be reduced. In some embodiments, the detectable signal may increase. Examples of test compounds include but are not limited to, proteins, peptides, amino acids, organic molecules, antibodies, nucleic acids, inorganic compounds, and the like.

The present invention also provides for methods for identifying inhibitors of a known stimulator of a membrane proteins (e.g. GCPRs, ion channels, or transporter proteins) within a lipoparticle comprising contacting the lipoparticle with the stimulator and the potential inhibitor. In some embodiments, the potential inhibitor and stimulator are contacted concurrently. In some embodiments, the potential inhibitor is contacted with lipoparticle before or after the stimulator is contacted with the lipoparticle. This method can be used, for example, to test antagonists of known ligands of GCPRs, ion channels, and neurotransmitters. In some embodiments, instead of an inhibitor, an agonist is used to determine what effect the agonist has on the function of the membrane protein.

As used herein, the term "inhibitor" refers to a compound, peptide, or protein that inhibits the function of a protein. In some embodiments, the inhibitor is an antibody or fragment thereof.

Toxins are known to bind membrane proteins. Some toxins can only bind when the membrane protein is in a certain conformation or active state. Therefore, in some embodiments, the present invention provides methods of confirming membrane protein conformation by binding a toxin to a lipoparticle containing an ion channel or membrane protein comprising contacting the lipoparticle with the toxin. In some embodiments, the ability of the toxin to bind to the membrane protein indicates the structure or active state of the ion channel. The binding status of the toxin can also be used to determine that the membrane protein has properly folded and presented in the correct conformation on the surface of the lipoparticle. Therefore, this can be used in some embodiments as a quality control test to determine the structure and folding of a membrane protein in a lipoparticle.

The present invention also provides for methods of measuring membrane protein function comprising the steps of microinjecting lipoparticles to a location and measuring the function of the membrane protein. The location can be, for example, an intracellular compartment, an organelle (e.g. mitochondria), the cell surface, gap junctions, or a synapse. Once the lipoparticle is microinjected into its location, the lipoparticle can be used to detect membrane protein function. The lipoparticle can be used to detect the function of the membrane proteins within the lipoparticle and the lipoparticle can also be used to detect changes in the environment (e.g. ion concentration) of its surroundings. For example, if the ion concentration of the environment in which the lipoparticle has been injected into changes, a lipoparticle comprising an ion channel and a fluorescent dye can be used to detect this change. The change in ion concentration can, in some embodiments, open the ion channel allowing the signal generated by the fluorescent dye to increase, or in some embodiments, decrease thereby indicating a change in the location. The lipoparticle comprising an ion channel can be used to detect the change in ion concentration or membrane potential. As with all the methods described herein, in some embodiments, the measured function of the ion channel is the absolute level. This can involve calibrating the lipoparticles to a calibration standard. Examples of a calibration standard include, but are not limited to, ionophores. When used with known molar amounts of a specific ion (e.g. potassium), the ionophore allows the ion to permeabilize the membrane, as measured by a 100% signal. By knowing the ion concentration and using the Nernst equation, the 100% signal can be converted to millivolts of membrane potential. The signal measured experimentally can then be calibrated to absolute units (e.g. millivolts).

As used herein, the term "absolute level" refers to the quantity of a substance as measured in units that represent the level of the substance, independent of experimental measurement. Units of absolute levels can be in molar or millivolts. For example, the membrane potential of a typical living cell in absolute units is approximately −70 mV.

The present invention also provides for kits for assessing the function of an ion channel or transporter, wherein the kit comprises a lipoparticle comprising a desired membrane protein and a protocol for assaying function.

The present invention facilitates the detection of ion channel function within a nano-scale. The ability to sense ion channel function within a nano-scale sensor using lipoparticles has many applications, including, for example, microfluidic drug screening, and subcellular detection.

The benefits of microfluidics, in turn, include miniaturization, integration of multiple processes, automation, reduced labor cost, reduced reagent requirements, multiplexed detection, and higher speed. Cells, however, cannot be used within many microfluidic devices because of their size and environmental requirements for viability. At commercial use, lipoparticles can be used for high throughput testing of drug candidates for inhibition of ion channels using microfluidic devices. In the simplest case, an array of several hundred lipoparticles will be created using multi-well plates (e.g. 384-well). In more sophisticated applications, lipoparticles can be attached to sensors with microfluidic flow channels (e.g. BIACORE, CALIPER systems) that allow a continuous flow detection system. These systems are capable of detecting interactions with more than one target at a time (multiplexing), making screening even more efficient. Other devices that can be incorporated with lipoparticles to measure function or activity include, but are not limited to a Lab-on-a-Chip™, a 96-well plate, a 384-well plate, a 1536-well plate, a glass slide, a plastic slide, an optical fiber, a flow cytometer, a microscope, a fluorometer, a spectrometer, or a CCD camera.

Nanometer-sized sensors of ions and voltage can also be used to probe subcellular structures during physiological responses. For example, neurons can be monitored under conditions that they are activated. Moreover, the probes that can be constructed are not limited to sensing changes, but can be calibrated to detect absolute levels of ions and voltage, allowing local measurements of important, but inaccessible, structures.

The lipoparticles of the present invention can be readily tested to determine if the membrane protein is functional and detectable as described herein. There are a number of reasons that the membrane protein (e.g. ion channel or transporter protein) function cannot be detected. One such reason is that the interior is not large enough to allow for detection of functionality. Therefore, in some embodiments, at least two lipoparticles can be fused together to increase the interior volume of the lipoparticle. One can also increase the size of the lipoparticle by increasing the lipid concentration or by fusing it with a liposome. One of skill in the art would readily know how to fuse at least two particles together (see, for example, Sparacio et al., Virology. 2000 271:248-52 and Sparacio et al. Virology. 2002 Mar. 15; 294(2):305-11). In some embodiments, at least 3, at least 4, or at least 5 lipoparticles are fused together. In some embodiments, the fused lipoparticles are isolated and used based on their size, which can be done using methods such as, for example, fractionation, sedimentation, centrifugation, column chromatography, HPLC, FPLC, and the like. However, any method to isolate a lipoparticle of a particular size or determine the size of a lipoparticle can be used.

Antibody Production

Lipoparticles provide a novel mechanism for the presentation of antigens to the immune system, with unprecedented control over the antigen being presented.

In some embodiments, lipoparticles are used for the direct presentation of membrane proteins for antibody generation. Antibodies are now in use throughout the biotechnology industry as therapeutics, diagnostics, and R&D reagents, and are an inherent product of vaccination.

A lipoparticle allows the stable presentation of structurally intact membrane proteins within a particulate format that is suitable for antigen presentation because the structure of complex membrane proteins can be maintained using the lipoparticle. In some embodiments, the present invention provides for methods of using lipoparticles comprising a protein of interest as an antigenic composition for production of antibodies that specifically bind with the membrane protein.

As used herein, the phrase "protein of interest" refers to a protein for which antibody screening and/or antibody generation is desired. The protein can be any protein and can include, for example, intracellular proteins, membrane proteins (e.g. ion channels), receptors (e.g. G protein-coupled receptors), membrane proteins from infectious pathogens (e.g. membrane proteins from viruses), and the like. A "protein of interest" can also refer to a protein that is to be included or is included in a lipoparticle. In some embodiments, the "protein of interest" is a membrane protein.

In some embodiments, the antibodies produced can bind with the protein in its native structure, and thus the present invention provides methods for producing antibodies that can, for example, inhibit protein function by steric blocking and/or antibodies that can affect protein function by allosteric effect. The production of lipoparticles using viral vectors can allow lipoparticles to be produced for antibody purposes using non-human (e.g. mouse) cells for incorporation of human membrane proteins.

Examples of non-human cell types include, but are not limited to, mouse cells, goat cells, rabbit cells, sheep cells, donkey cells, quail cells, and the like. The advantage of using non-human cell types for the production of antibodies is that, if the lipoparticle produced from the non-human cell type is injected into an organism that is the same from which the non-human cell type was derived, the immune response generated by the organism should be specifically directed at the cellular protein of interest that is not native to the non-human cell type. This may enable the generation of antibodies that are more specific for the cellular protein of interest rather than the other components of the immunogen (e.g. the lipoparticle membrane and other proteins). Lipoparticles can also be produced from immortalized cell lines, stem cells, primary cells (e.g. limited life span), and hybridomas.

Therefore, in some embodiments, the present invention provides for immunogens comprising a lipoparticle, wherein the lipoparticle comprises a cellular protein of interest. In some embodiments, immunogens can be modified for a number of reasons, for example, to increase the immunogenicity of the lipoparticle. The modification can comprise modifying either the lipoparticle, the cellular protein of interest, or a combination thereof. The cellular protein of interest can be modified, for example, by modifying the amino acid sequence (e.g., to render the protein more immunogenic or antigenic).

Modifying the amino acid sequence of the cellular protein of interest can include nonsense mutations, missense mutations, conservative substitutions, non-conservative substitutions, deletions of one or more amino acids, insertions of one or more amino acids, and the like. The cellular protein of interest can also be modified by creating a chimeric protein containing a portion of the cellular protein of interest and a portion of another polypeptide. A chimeric protein can also be referred to as a "fusion protein." As used herein, the term "portion" refers to either the whole protein or a fragment of the entire protein. In some embodiments, the chimeric protein comprises a non-fluorescent protein and a fluorescent protein.

The modification of the cellular protein of interest can also affect the function of the protein. The modification can create a constitutively activated protein or an inactive protein. The activity of the protein need not be present in the lipoparticle, rather whether the modification affects the activity of the protein can also be determined in a cellular environment, in a test tube and the like.

Modifications can also include adding or removing targeting signals on the polypeptide to ensure that the cellular protein of interest is targeted to the membrane of the cell and is contained in the lipoparticle that is produced from the cell. See, U.S. Provisional Application Ser. No. 60/491,477.

Modifications to the lipoparticle to increase immunogenicity of the antigen can also comprise any modification known to those of skill in the art. These modifications can comprise, for example, a soluble protein bound to the cellular protein of interest in the lipoparticle. The soluble protein can be bound to the cellular protein of interest, for example, by cross-linking the soluble protein to the cellular protein. The soluble protein can also be tethered to the lipoparticle. The tether can be, for example, a fusion of a soluble protein and polyethylene glycol (PEG), a fusion of the soluble protein to a transmembrane protein, or a fusion of the soluble protein to a GPI anchor. For example, the soluble chemokine RANTES can be cross-linked or tethered to its cognate receptor CCR5. Other ligands could also work, for example MIP1alpha or MIP1beta. In addition, other receptors could work, such as, without limiting the number of receptors possible, CCR2, CCR3, or CXCR4.

As used herein, the term "soluble protein" refers to a protein that is soluble. In some embodiments the soluble protein is the protein of interest. In some embodiments, the soluble protein is a ligand or a binding partner of the protein of interest.

Lipoparticles engineered to contain both a receptor and a tethered ligand offer possibilities to immobilize the receptor in their engaged conformation. For example, the CCR5/MIP1α receptor-ligand system can be linked to the lipoparticle such that the CCR5 is incorporated into the membrane, retaining its secondary structure, and MIP1α is tethered to the distal end of a phospholipid-poly(ethylene glycol) (PL-PEG). This allows the lipoparticle to present the receptor bound to the ligand without the worry of diffusion of the ligand. Mabs could be generated against the activated receptor which may have a different conformation than the non-activated receptor. PL-PEG-Biotin may also be linked to the CCR5 expressing lipoparticle. Subsequent contact with a fusion protein made of avidin and MIP1α will essentially link the MIP1α to the membrane by the biotin avidin complex formation.

The creation of a fusion protein consisting of both the receptor and the ligand may serve as an alternative to tethering, incubating in ligand, or incubating in ligand and cross-linking. In this case a ligand will be "connected" to the extracellular portion of the receptor by expressing a fusion protein with the sequence of the ligand on the end of the sequence of the receptor. For example, the chemokine ligand RANTES can be expressed at the N-terminus of CCR5, its receptor. Different fusion proteins with peptide spacers can be constructed to allow the ligand enough room to a) adopt an appropriate conformation and b) interact and bind with the receptor.

The antibodies generated by tethering or cross-linking can, in some embodiments, specifically recognize receptors which are bound by their ligand. Such antibodies can be used, for example, to determine the state of a given receptor or tested for their ability to alter the stability of the receptor-ligand interaction. The antibody may cause a ligand to have a stronger interaction with the receptor and bind for a longer time resulting in more signaling. This has the potential for therapeutic use in cases where signaling through a particular receptor is insufficient. Furthermore, these antibodies, in some embodiments, can have the capacity to recognize a complex, providing a research tool for showing how and where the complex forms, diagnostic tools for seeing if the complex forms, and therapeutic tools for targeting the complex.

In some embodiments, the cellular protein of interest may be a protein that is a naturally expressed membrane protein from a specific cell or cell type. As used herein, the term "naturally expressed" refers to a protein that is expressed by the cell without the introduction of an exogenous polynucleotide encoding for a protein. Therefore, antibodies can be produced against naturally expressed proteins that can be captured by a lipoparticle when produced from that the cell containing the naturally expressed protein.

The immunogenic compositions can also further comprise at least one immunostimulatory component besides the lipoparticle comprising the cellular protein of interest. In some embodiments, the immunogenic and/or antigenic composition can comprising at least one, at least two, at least three, at least four, at least five, or at least 10 immunostimulatory components. As used herein, the term "immunostimulatory component" refers to a component that facilitates generation of an immune response. The immunostimulatory component can be, for example, DNA, RNA, oligonucleotide, adenovirus, an adjuvant, or another polypeptide. Adjuvants, however can alter the structure of cellular protein of interest contained in the lipoparticle and thus, in some embodiments, an adjuvant is used that does not destroy the structure of the cellular protein of interest.

As used herein the term "adjuvants" refers to compounds that are insoluble or undegradable substances that non-specifically enhance the immune response to an antigen by promoting nonspecific inflammation in order to recruit mononuclear phagocytes to the site of immunization. In some embodiments, adjuvants incorporate two components. The first component can form a deposit to protect the antigen from catabolism. Mineral oils or aluminum hydroxide precipitates are typically used, but liposomes and synthetic surfactants have also worked well (R Hunter, et al, (1981), J Immunology, 127:1244-50). The second component can be a nonspecific stimulant that activates antigen processing cells to secrete increased levels of lymphokines and cause a local inflammatory reaction. Heat-killed bacteria (*Bordetella pertussis* or *Mycobacterium tuberculosis*) or lipopolysaccharide are non-limiting examples of nonspecific stimulants.

The use of adjuvants can have a marked effect on the ability to elicit an immune response, but each adjuvant has unique characteristics that may or may not be useful for immunization with lipoparticles. Complete Freund's adjuvant, for example, has resulted in only linear epitope Mabs in prior experiments, suggesting that its composition is not conducive for retention of receptor conformation. Ribi adjuvant, on the other hand, has proven to be capable of maintaining the conformational structure of complex proteins during immune stimulation. Similarly, TiterMax (CytRx, Norcross, Ga.) is designed specifically to retain protein structure for use with Mab immunization, suggesting that it too would not denature protein conformation during immunization.

The immunostimulatory component can also comprise a chemokine or a cytokine, which can be used to enhance the immunogenicity of the lipoparticle. Examples of chemokines include, but are not limited to, RANTES, MIP1a, MIP1b, and the like. Examples of cytokine include, but are not limited to, IL-1, IL-2, IL-3, IL-4, IL-5, IL-6, IL-7, IL-8, IL-9, IL-10, IL-11, IL-12, GM-CSF and the like.

Membrane bound receptors may alter their extracellular epitopes when activated by their ligand and lipoparticles can be used to generate antibodies that identify epitopes specific to membrane proteins that are bound by their ligand. These epitopes can be, for example, the membrane protein, the ligand, a combination of both, or a new epitope on either that is exposed by conformational changes induced by ligand binding.

Intracellular proteins can also influence the extracellular structure of membrane proteins or receptors. For example, it is has been established that many GPCRs can bind agonists with high affinity when cytosolic G-proteins are simultaneously bound, but have only weak affinity for these same agonists when G-proteins are not bound. With GPCR crystal structures extremely difficult to obtain, modeling of the structural changes of GPCRs upon G-protein binding remains poorly defined. Antibodies that can detect such structural changes could be used to detect and measure active and non-active conformations of the desired receptor within cells, as well as help determine the intrinsic activity of GPCRs. Therefore, in some embodiments, antibodies can be generated against membrane proteins that can differentiate between a protein bound to a cytosolic protein or not bound to a cytosolic protein. Examples of GPCRs include, but are not limited to, ORF74, CXCR2, and β-adrenergic receptor. Therefore, in some embodiments, the immunogens of the present invention can also include one or more binding substances that bind to the cellular protein of interest. Examples of binding substances include, for example, a ligand, G-protein, a kinase, a phosphatase, an antibody, a peptide, small organic molecule, and the like. The binding substance can change the conformation of the receptor. In one way, by mere fact of binding a different structure has been created (the receptor+ligand vs. the receptor alone). Some antibodies recognize epitopes that are formed by both the receptor and ligand. The second is allosteric—the ligand binds and changes the shape of the receptor. There are antibodies that recognize such epitopes (e.g. the MAb 17b recognizes an epitope within HIV-1 gp120 that is exposed only after binding of the receptor CD4) (Hoffman, et al. (1999), Proc. Natl. Acad. Sci. USA, 96:6359-6364). In some embodiments at least one, at least two, at least three, at least four, at least 5, or at least ten binding substances can be used.

Mabs can be used to characterize the protein expression patterns of GPCRs in cells that have previously only been detectable functionally or through RNA expression analysis.

As used herein, the term "antibody" is meant to refer to complete, intact immunoglobulin molecules as well as fragments thereof including, without limitation, Fab fragments and $F(ab)_2$ fragments thereof, an immunoglobulin-fusion protein, a single-chain Fv, and an Fc-fusion protein. Complete, intact immunoglobulin molecules include, but are not limited to, polyclonal antibodies, monoclonal antibodies such as murine monoclonal antibodies, rabbit antibodies, goat antibodies, donkey antibodies, horse antibodies, chicken antibodies, human antibodies, chimeric antibodies and humanized antibodies. Antibodies that bind to an epitope on the cellular protein are also useful to isolate and purify that protein from both natural sources or recombinant expression systems using well known techniques such as affinity chromatography. Such antibodies are useful to detect the presence of such protein in a sample and to determine if cells are expressing the protein.

A number of important classes of both multi-spanning and single-spanning proteins form homo- or hetero-oligomers (i.e. multimers) in a lipid membrane, including ion channels, integrins, Tyr-kinases such as the EGF receptor, some GPCRs, Hepatitis C E1-E2, and HIV Envelope. Mabs that recognize multimeric complexes could be especially useful in identifying the importance of multimerization to signaling, subcellular locations in which multimers form, and the importance of multimerization for some diseases. The domains that mediate this oligomerization are often located within cytoplasmic or transmembrane regions. Other oligomerization domains are located extracellularly, often near the transmembrane domain, but are dependent on protein structures within the transmembrane or cytoplasmic domains. Lipoparticles can be useful for the presentation of such proteins since the proteins can be concentrated on the surface of the lipoparticle, hence stabilizing multimeric structures that might otherwise be short-lived or interact with low affinity.

Mabs can also have the additional ability to detect oligomers. Functional uses of these Mabs can include channel or receptor blocking, inhibition, and activation. Specifically, in the case of Kv1.3 (a potassium channel), the Mab can be used for immunosupression. Antibodies to DC-SIGN (Dendritic Cell-Specific, ICAM-3 Grabbing Non-integrin) can be used in the rhesus macaque model to determine if they impact sexual transmission of either SIV or SHIV animal models. Mabs to a ErbB2/ErbB4 heterodimer may help identify particularly aggressive forms of cancer, and help direct appropriate treatment.

Therefore, in some embodiments, the antibodies are specific to an epitope that is specific to the quaternary structure of a protein. The cellular protein of interest having the quaternary structure can be the result of a cellular protein or a membrane protein forming an oligomeric structure. In some embodiments, the oligomeric structure comprises a homo-oligomer. In some embodiments, the oligomeric structure comprises a hetero-oligomer. The oligomeric structure can be, for example, a dimer, a trimer, tetramer, or higher order oligomer. The higher order oligomer may comprise at least 5, at least 6, at least 7, at least 8, at least 9, or at least 10 members.

Antibodies can also be generated against less complex membrane bound proteins and single transmembrane proteins, where conformation may be less important. The antibodies directed against less complex membrane proteins, as well as the other antibodies discussed herein can be used for many applications including, but not limited to, Western blot analysis, immunocytochemistry, immunohistochemistry, signal blocking or inhibition, and activation of pathways. For example, a CD4 antibody could be used to crosslink CD4 and inhibit the immune response for organ transplantation or to model the clinical symptoms of AIDS. Monoclonal antibodies to Resistin could be administered to Type 2 diabetes patients to improve their blood sugar and insulin action.

The generation of antibodies and the protein structures of complete, intact antibodies, Fab fragments and $F(ab)_2$ fragments and the organization of the genetic sequences that encode such molecules are well known and are described, for example, in Harlow, E. and D. Lane (1988) ANTIBODIES: A Laboratory Manual, Cold Spring Harbor Laboratory, Cold Spring Harbor, N.Y. which is incorporated herein by reference. For example, to produce monoclonal antibodies the lipoparticle is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the cellular protein, the hybridoma that produces them is isolated and expanded in culture to produce a continuous supply of antibodies.

The present invention also provides methods of producing polyclonal antibodies and/or vaccinating against a membrane protein. Antibodies can be produced against membrane proteins by introducing lipoparticles containing the membrane protein into an animal to produce antibodies. The antibodies are then isolated by techniques well known to those of skill in the art and screened against the membrane protein to determine if the antibodies recognize the membrane protein. The antibodies can be screened against a recombinant form of the protein or be screened against samples that are known to contain the membrane protein. The antibodies can also be compared to other known antibodies that recognize the membrane protein to determine that the antibodies are recognizing the proper membrane protein. In some embodiments, the antibodies generated are specific for the membrane protein. As used herein, the term "specific for the membrane protein" refers to an antibody that recognizes one membrane protein and no other membrane protein.

The present invention can also be employed to generate antibodies against proteins which are difficult to express or which undergo post-translational modifications which require other genes present in the natural state.

Capture of naturally expressed membrane proteins can result in populations of membrane proteins that better represent native membrane protein structure. Some proteins are modified after translation, and this modification may depend on factors within the cell. For example, CCR5 is sulfated on Tyrosine 11 and this sulfation is known to alter its structure and make it more competent for interaction with HIV-1 Envelope proteins (Farzan, et al. (1999), Cell, 96:667-76). Similarly, CXCR4 is glycosylated, and if this glycosylation is removed, additional structures of CXCR4 are exposed (Chabot, et al. (2000), J Virol, 74:4404-13). Different cell types are known to have different conformations of the CXCR4 membrane protein. Other cell types can be induced (e.g. with hormones, growth factors, cytokines, or chemicals) to differentiate or change, often resulting in a change in the membrane proteins at the surface of the cell. Different cell types can also contain different transcriptional splice variants of the same gene. For example, CCR2 has two cell-type specific splice variants, CCR2a and CCR2b, which have differences in their C-terminus.

The generation of lipoparticles from natural cell sources can circumvent the difficulties that arise from using non-natural cell sources (e.g. no post-translational modifications). Post-translational modification and interaction with other proteins from the cells is insured by using the natural cells, which should increase the likelihood of generating an antibody against a proper epitope.

In some embodiments, antibodies can be generated that are specific to an individual cancer patient's tumor. Lipoparticles can be used to isolate the membrane proteins of tumors cells and present them for antibody production. This can be accomplished, for example, by taking a biopsy of a tumor and isolating cancerous cells. These cells can be grown in cell culture and an aliquot of the culture can be used to generate lipoparticles as described herein. Antibodies can then be produced against the membrane proteins of the tumor cells. The antibodies can then be screened against the cancer cells in culture and the effects on cell growth and death can be observed. In some embodiments, antibodies that trigger cell death can be used as a drug to treat the patient's tumors. Multiple iterations of this procedure can be performed to identify proteins that are often expressed and tumors can be classified by the membrane proteins that they are expressing. In some embodiments, this information can be used to improve the treatment of cancer. This procedure can also be modified to screen membrane proteins that are specific for other diseases. Diseased cells can be isolated and used to generate lipoparticles and antibodies as described herein. The antibodies can then be used as diagnostic tools to identify diseased cells and in some embodiments, the antibodies can be used to treat the disease if the antibodies are found to kill the diseased cells.

Antibodies can also be generated against membrane proteins using lipoparticles, viruses, or virus-like particles, and a phage library and/or ribosome display (see, for example Hoogenboom H R. "Overview of antibody phage-display technology and its applications." *Methods Mol Bio*. (2002); 178: 1-37; He, M. et al., Brief Funct Genomic Proteomic. (2002) July; 1(2):204-12; D, Pluckthun A, et al., *J Immunol Methods*. (2004) July; 290(1-2):51-67). In some embodiments, the libraries comprise a library of monoclonal antibody binding domains.

The particulate nature of lipoparticles makes them comparable to killed-virus vaccines currently used to successfully elicit immune responses (e.g. humoral and cellular). The ability to place non-viral molecules within such an immunogen allows lipoparticles to have direct application to both preventative and therapeutic vaccines.

Thus, the present invention provides methods of eliciting immune responses against membrane proteins. The lipoparticles can be introduced into an animal to elicit an immune response. Examples of animals or subjects from which immune responses can be elicited from include, for example, mice, rats, chickens, sheep, horses, goats, pigs, non-human primates, or humans.

In some embodiments, the use of lipoparticles as an immunogen will elicit a cytotoxic T-cell response as well as a humoral (antibody) response. Therefore, lipoparticles can be used in the preparation of vaccines to protect or treat a disease, disorder, or condition. The antibodies generated in response to using a lipoparticle as an immunogen can be used, for example, as therapeutics or as diagnostics (e.g. identification of proteins, disease states, and the like). The immune responses generated can treat or protect against, without limitation, cancer (e.g. breast cancer, prostate cancer, lung cancer, blood-borne cancer (e.g. multiple myeloma), bone cancer, leukemias, head and neck cancers, brain cancer, and the like), viral and bacterial infectious agents (e.g. HIV, HSV, HCV, Hepatitis A, Hepatitis B, coronaries, SARS, West Nile Virus, anthrax, vaccinia, and the like).

The present invention also provides antigenic compositions comprising lipoparticles with a cellular protein of interest (e.g. an exogenous protein or a naturally expressed protein) and a pharmaceutical acceptable carrier.

The immunogen can be prepared in dose form by well-known procedures. The immunogen can be administered, for example, parenterally (e.g. intravenous drip, subcutaneous, intraperitoneal or intramuscular injection, (e.g., by inhalation or insufflation, or intrathecal or intraventricular administration), topically (e.g. ophthalmic, vaginal, rectal, intranasal, transdermal), orally, intramuscularly, subcutaneously, pulmonary administration, or intranasally. For parenteral administration, such as intramuscular injection, the immunogen may be combined with a suitable carrier, for example, it may be administered in water, saline, or buffered vehicles with or without various adjuvants or immunostimulating agents such as aluminum hydroxide, aluminum phosphate, aluminum potassium sulfate, beryllium sulfate, silica, kaolin, carbon, water-in-oil emulsions, oil-in-water emulsions, muramyl dipeptide, bacterial endotoxin, lipid X, *Corynebacterium parvum, Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.). Compositions for parenteral, intravenous, intrathecal or intraventricular administration may include sterile aqueous solutions which can also contain buffers, diluents and other suitable additives and are preferably sterile and pyrogen free.

Formulations for topical administration may include transdermal patches, ointments, lotions, creams, gels, drops, suppositories, sprays, liquids and powders. Conventional pharmaceutical carriers; aqueous, powder or oily base; thickeners and the like can be used. Compositions for oral administration include powders or granules, suspensions or solutions in water or non-aqueous media, capsules, sachets or tablets. Thickeners, flavoring agents, diluents, emulsifiers, dispersing aids or binders may be desirable.

The proportion of immunogen and immunostimulating agent can be varied over a broad range so long as both are present in effective amounts. For example, aluminum hydroxide can be present in an amount of about 0.5% w/v of the vaccine mixture. On a per dose basis, the concentration of the immunogen can range from about 0.015 µg to about 1.5 mg per kilogram per body weight. A preferable dosage range is from about 1.5 µg/kg to about 0.043 mg/kg of body weight. A suitable dose size in humans is about 0.1-1 ml, preferably about 0.1 ml. Accordingly, a dose for intramuscular injection in humans, for example, would comprise 0.1 ml containing 1.5 µg/kg immunogen in admixture with 0.5% aluminum hydroxide.

The dosage administered can also vary and depend upon factors such as: pharmacodynamic characteristics; mode and route of administration; age, health, and weight of the recipient; nature and extent of symptoms; kind of concurrent treatment; and frequency of treatment. Usually, the dosage of an immunogenic composition can be about 1 to 3000 milligrams per 50 kilograms of body weight; preferably 10 to 1000 milligrams per 50 kilograms of body weight; more preferably 25 to 800 milligrams per 50 kilograms of body weight. In some embodiments, 8 to 800 milligrams administered to an individual per day in divided doses 1 to 6 times a day, or in sustained release form, is effective to obtain desired results. Formulation of therapeutic compositions and their subsequent administration is believed to be within the skill of those in the art.

The compositions according to the present invention can be administered as a single dose or in multiple doses. The compositions of the present invention can be administered either as individual therapeutic agents or in combination with other therapeutic agents. The treatments of the present invention may be combined with conventional therapies, which may be administered sequentially or simultaneously.

In the instance of vaccines, the vaccine can also be combined with other vaccines for other diseases to produce multivalent vaccines. It can also be combined with other medicaments such as antibiotics.

The present invention also provides pharmaceutical compositions that comprise the immunogens of the invention and pharmaceutically acceptable carriers or diluents. The compositions of the present invention may be formulated by one having ordinary skill in the art with compositions selected depending upon the chosen mode of administration. Suitable pharmaceutical carriers are described in Remington's Pharmaceutical Sciences, A. Osol, a standard reference text. In carrying out methods of the present invention, immunogenic and/or antigenic compositions of the present invention can be used alone or in combination with other diagnostic, therapeutic or additional agents. Such additional agents include excipients such as flavoring, coloring, stabilizing agents, thickening materials, osmotic agents and antibacterial agents. Such agents may enhance the lipoparticle use in vitro or in vivo, the stability of the composition during storage, or other properties important to achieving optimal effectiveness.

For parenteral administration, the immunogenic and/or antigenic compositions of the invention can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils can also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The compositions of the present invention may be administered by any means that enables the active agent to reach the site of action. Because lipoparticles may be subject to being digested when administered orally, parenteral administration, i.e., intravenous, subcutaneous, transdermal, intramuscular, can be used to optimize absorption. Intravenous administration may be accomplished with the aid of an infusion pump. The compositions of the present invention can be formulated as an emulsion. Alternatively, they can be formulated as aerosol medicaments for intranasal or inhalation administration. In some cases, topical administration can be desirable.

Depending upon the disease or disorder to be treated, the compositions of the present invention may be formulated and administered to most effectively to treat the disease or disorder. Modes of administration will be apparent to one skilled in the art in view of the present disclosure.

Incorporation of membrane-bound receptors and/or cellular proteins into lipoparticles avoids the complex issues associated with membrane protein solubilization, purification, and reconstitution. Once produced, lipoparticles are easy to purify, in addition to being quite stable. Thus, the use of lipoparticles allows the cell and/or viral machinery to do the work of reconstituting the protein of interest into a native, biological membrane. Importantly, the lipid membrane surrounding the lipoparticle is not significantly different from the membrane that surrounds the cell from which the lipoparticle was derived, thus the incorporated proteins are presented in a native lipid environment.

Advantages of using lipoparticles as compared to a commonly used alternative technique in which vesicles are prepared from membranes of cells expressing the desired receptor are listed in Table 8. Briefly, antigens prepared from cell membranes are heterogeneous, receptors may be misoriented, the antigens are impure, and are not concentrated. Vesicles containing antigens derived from cells also tend to be heterogeneous in size, not particularly stable, and can be contaminated with undesirable proteins. Table 8 compares the advantages of using lipoparticles to produce antigens over other methods (e.g. purifying recombinant proteins, peptide synthesis, transient cellular expression, and stable cell lines).

TABLE 8

Advantages of producing antigens using lipoparticles versus conventional methodologies for Mab development.

| Technologies and Advantages for Antibody Development to Complex Proteins | Lipoparticles | Traditional Methods of Producing Antigens | | | |
| --- | --- | --- | --- | --- | --- |
| | | Transient Cellular Expression | Stable Cell Lines | Proteins | Peptides |
| Stable Receptor Expression | X | | X | X | |
| Retention of Receptor Structure | X | X | X | | |
| Application to Toxic Proteins | X | X | | X | X |
| Use of Transient Protein Expression | X | X | | | |
| High Protein Expression | X | X | X | X | X |
| Protein Concentration | X | | | X | X |
| Rapid Purification | X | X | | | X |
| Enriched Proteins | X | | | X | X |

TABLE 8-continued

Advantages of producing antigens using lipoparticles versus conventional methodologies for Mab development.

| Technologies and Advantages for Antibody Development to Complex Proteins | Lipoparticles | Traditional Methods of Producing Antigens | | Proteins | Peptides |
|---|---|---|---|---|---|
| | | Transient Cellular Expression | Stable Cell Lines | | |
| Intracellular Receptors | X | | | X | X |
| Particulate Size (~100 nM) | X | | | | |

The present invention also provides for methods for treating a disease using the antibodies produced using the methods of the present invention. The antibodies can be used to treat, for example, cancer (e.g. breast cancer, cervical, lung cancer, ovarian cancer, bone cancer, leukemia, myelomas, melanomas, skin cancer, head and neck cancer, bladder cancer, liver cancer, pancreatic cancer, esophageal cancer, colon cancer, and the like), rheumatoid arthritis, osteo-arthritis, crohn's disease, viral infections (e.g. HIV, Hepatitis A, B, and C, Human Papilloma virus, West Nile Virus, SARS, Ebola, smallpox, influenza, common cold, viral meningitis, Epstein-Barr virus, herpes simplex virus, and the like), neurological diseases (e.g. Alzheimer's diseases, Parkinson's disease, and the like) multiple sclerosis, bacterial infections (e.g. *salmonella, E. coli*, anthrax, bacterial meningitis, botulism, *Bordetella pertussis, Streptococcus*), and the like. The antibodies can be administered as compositions as described for other compositions described herein.

Lipoparticles containing a Gag fusion protein can also be used as immunogens to elicit antibodies against the fusion protein. Lipoparticles will be produced in large quantities and will contain large amounts of the fusion protein in every lipoparticle, linked to the Gag structural protein. When injected into mice, the fusion protein can serve as a source of antigen for immune presentation.

The present invention provides for kits for eliciting an immune response against a membrane protein, wherein the kits comprises a lipoparticle comprising a cellular protein of interest and a protocol for immunization and/or instructional material.

While traditional protein transfection localizes exogenous protein into the target cell's cytoplasm or nucleus, membrane protein transfection localizes membrane proteins onto a target cell's plasma membrane. The present invention provides methods of transferring a membrane protein from the bilayer of a lipoparticle to a target cell's membrane bilayer. Transfection can be facilitated by fusion and/or endocytosis of a lipoparticle, which results in the transfer of the lipoparticle's membrane proteins to the target cell.

Membrane protein transfection extends the benefits of protein transfection to membrane proteins. In addition to allowing transfection of proteins inherently toxic to cells, membrane protein transfection techniques can be used on cells difficult to transfect with DNA. Additional obstacles that can be overcome using membrane protein transfection include, for example, proteins that are otherwise difficult to express on the plasma membrane, proteins that have difficulty trafficking to the plasma membrane, and proteins that do not fold correctly. Additionally, because the lipoparticle already contains the intact protein, post-translational and splicing modifications can be specifically controlled using lipoparticles for membrane protein transfection to specify the protein product that is contained within a cell.

Fusing lipid membranes is known to one of ordinary skill in the art. Therefore, any technique that can be used to fuse one lipid membrane with another lipid membrane can be used for membrane protein transfection using lipoparticles. Examples of methods and reagents that can be used to fuse two lipid bilayers include, but are not limited to, exposure to low pH, exposure to high calcium concentrations, calcium phosphate precipitate, PEG8000, DNA transfection reagents (e.g. lipofectamine and effectene), Peptide Transduction Domains (e.g. Chariot™, protein delivery reagent), sonication, viral fusion proteins such as VSV Envelope, detergents (e.g. .beta.-octylglucoside), alkanes, exposure to DEAE Dextran, centrifugation, and electroporation. Additional methods of lipid fusion and/or membrane permeabilization are indicated in the table below.

| Method of Plasma Membrane Breach |
|---|
| Chemical |
| ATP |
| Influx pinocytic cell-loading reagent (I-14402) |
| EDTA |
| Ca3(PO4)2 |
| DEAE-dextran |
| Alpha Toxin of *Staphylococcus aureus* |
| Transferrin polylysine |
| Vehicle |
| Red blood cell fusion |
| Vesicle and liposome fusion |
| Mechanical |
| Microinjection |
| Hypoosmotic shock |
| Osmotic lysis of pinosomes |
| Scrape loading |
| Agitation in cold |
| Sonication (mild) |
| High-velocity microprojectiles |
| Glass beads |
| Scratching to wound culture |
| Electrical |
| Electroporation |

Table 9 reproduced from Molecular Probes catalog. Table adapted from McNeil, P. L., in Fluorescence Microscopy of Living Cells in Culture, Part A.

To detect whether protein transfection has occurred using lipoparticles any method can be used. Examples of detection methods include, but are not limited to, calcium flux to detect GPCRs transfected into the cell, ion channel conductance to detect ion channels transfected into the cell, membrane fusion, lipid dye mixing, fluorescence quenching, and Western blot.

For example, lipid dye mixing can be used to monitor the fusion of the two lipid membranes. A lipoparticle comprising a membrane protein can be generated that incorporates a lipid dye. When the lipoparticle fuses with its target (e.g. another cell, viral particle, bacteria, lipoparticle, and the like) the dye will also enter and mix with the target. A change in the dye's fluorescence or intensity can be used to monitor the progress and completion of the protein being transfected into the target.

Western blot can also be used to monitor protein transfection. After fusing the lipoparticle with its target cell, the protein can be detected in the target by isolating the target cell (e.g. washing away unincorporated molecules) and performing a Western blot to detect the transfected protein. Similar to Western blot, immunofluorescence can also be used. The target can be contacted with either a labeled primary antibody that recognizes the transfected protein or through the use of a labeled secondary antibody. The labels can be any label that is detectable and can include, for example, FITC, Texas-Red, and the like. A radioactive label can also be used.

The present invention provides methods of transfecting a protein into a cell comprising contacting the cell with a lipoparticle comprising the protein. In some embodiments the lipoparticle comprises a viral protein component. In some embodiments the viral protein component comprises a viral structural protein. An example of a viral structural protein includes, but is not limited to, Gag. In some embodiments, the lipoparticle is integration incompetent, protease incompetent, reverse transcription incompetent, or combinations thereof.

Any protein can be transfected from a lipoparticle to a cell. The protein can be, for example, a membrane protein. Membrane proteins comprise a diverse group of proteins including, for example, G-protein coupled receptors, ion channels, receptors, tyrosine kinase receptors, and the like. In some embodiments, the membrane protein is the cystic fibrosis transmembrane regulator (CFTR).

The present invention also provides for methods for the transfer of a protein from a lipoparticle to a cell to correct or modulate a defect in the cell. In some embodiments, the protein modulates at least one property of the cell. The property of the cell can be, for example, but is not limited to, growth property, ion-conductance property, signaling property.

The present invention also provides for methods for the transfer of a protein from a lipoparticle to a cell to enhance the function of a cell. In some embodiments, the protein is not expressed within the target cell, or is expressed at low levels, and protein transfection of the membrane protein into the target cell leads to an enhancement of the properties of that cell. The property of the cell can be, for example, but is not limited to, growth property, ion-conductance property, signaling property.

Although, the protein that is transfected can be wild-type, the protein can also be modified. In some embodiments, the modification is a mutation, deletion, insertion, post-translational modification, chimeric modification, or combinations thereof.

The cell that the protein is transfected into can be any type of cell. Examples of cells that a protein can be transfected into include, but are not limited to, primary cells, stem cells, cancer cells, quiescent cells, terminally differentiated cells, and the like. In some embodiments, examples of cells also include, but are not limited to, 293T, 293, HeLa, Vero, BHK, CHO, NT-2, 3T3, QT6 cells, and the like. In some embodiments, the type of cell is a cell that cannot be transfected well with a nucleotide molecule (e.g. plasmid). As used herein, the term "cannot be transfected well" refers to a cell that when transfected with a nucleotide molecule does not provide an effective amount of a protein. An "effective amount of a protein" as used herein, refers to an amount that is determined to be necessary to perform a function in the cell. The function can be any function or use of the protein. For example, the function can be the ability to measure the expression of the protein or the function can be the ability of the protein to modulate a property of the cell. Other functions are also included within the scope of the present invention. As used herein, the term "cannot be transfected well" also refers to a low percentage of cells being transfected with a nucleotide molecule. As used herein, the term "low percentage of cells" refers to less than less than 50%, less than 40%, less than 30%, less than 20%, less than 10%, less than 5%, less than 4%, less than 3%, less than 2%, or less than 1% of cells being transfected with a nucleotide molecule. In some embodiments, the cell is taken from a subject and then transfected with a lipoparticle comprising a protein. In some embodiments, this is referred to as "ex vivo" transfection. Methods of isolating cells from a subject or individual are well known to those of skill in the art.

The present invention provides cells comprising a membrane protein that was transfected into the cell using lipoparticles of the present invention. In some embodiments, the cell comprises at least a portion of a lipoparticle's membrane.

The present invention also provides methods of treating a disease comprising administering a lipoparticle comprising a membrane protein. Examples of diseases include, but are not limited to cystic fibrosis and cancer. In some embodiments the lipoparticles are administered to an animal. In some embodiments, the animal is a human, a mouse, a rat, a dog, a cat, a horse, and the like.

The present invention also provides methods for administering lipoparticles comprising a protein and a pharmaceutically acceptable carrier. In some embodiments, the protein is a membrane protein.

The lipoparticle can be prepared in dose form by well-known procedures. The lipoparticle can be administered, for example, parenterally (e.g. intravenous drip, subcutaneous, intraperitoneal or intramuscular injection, (e.g., by inhalation or insufflation, or intrathecal or intraventricular administration), topically (e.g. ophthalmic, vaginal, rectal, intranasal, transdermal), orally, intramuscularly, subcutaneously, pulmonary administration, or intranasally. For parenteral administration, such as intramuscular injection, the lipoparticle may be combined with a suitable carrier, for example, it may be administered in water, saline, or buffered vehicles with or without various adjuvants or immunostimulating agents such as aluminum hydroxide, aluminum phosphate, aluminum potassium sulfate, beryllium sulfate, silica, kaolin, carbon, water-in-oil emulsions, oil-in-water emulsions, muramyl dipeptide, bacterial endotoxin, lipid X, *Corynebacterium parvum, Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.). Compositions for parenteral, intravenous, intrathecal or intraventricular administration may include sterile aqueous solutions which can also contain buffers, diluents and other suitable additives and are preferably sterile and pyrogen free.

Formulations for topical administration may include transdermal patches, ointments, lotions, creams, gels, drops, suppositories, sprays, liquids and powders. Conventional pharmaceutical carriers; aqueous, powder or oily base; thickeners and the like can be used. Compositions for oral administration include powders or granules, suspensions or solutions in water or non-aqueous media, capsules, sachets or tablets. Thickeners, flavoring agents, diluents, emulsifiers, dispersing aids or binders may be desirable.

On a per dose basis, the concentration of the lipoparticle can range from about 0.015 µg to about 1.5 mg per kilogram per body weight. A preferable dosage range is from about 1.5 µg/kg to about 0.043 mg/kg of body weight. A suitable dose size in humans is about 0.1-1 ml, or about 0.1 ml. Accordingly, a dose for intramuscular injection in humans, for example, would comprise 0.1 ml containing 1.5 µg/kg lipoparticle in admixture with 0.5% aluminum hydroxide. The dose of a lipoparticle can also be administered based on the number of lipoparticles per kilogram of body weight. In some embodiments, the dose is about 5 lipoparticles/kg, about 100 lipoparticles/kg, about 1000 lipoparticles/kg, about 10,000 lipoparticles/kg, about 100,000 or lipoparticles/kg, about 500,000 lipoparticles/kg, about $1\times10^6$ lipoparticles/kg, about $1\times10^7$ lipoparticles/kg, about $1\times10^8$ lipoparticles/kg, about $1\times10^9$ lipoparticles/kg, about $1\times10^{10}$ lipoparticles/kg, about $1\times10^{11}$ lipoparticles/kg, or about $1\times10^{12}$ or more lipoparticles/kg. In some embodiments more than 500,000 lipoparticles/kg are administered as a dose.

The dosage administered can also vary and depend upon factors such as: pharmacodynamic characteristics; mode and route of administration; age, health, and weight of the recipient; nature and extent of symptoms; kind of concurrent treatment; and frequency of treatment. Usually, the dosage of a lipoparticle composition can be about 1 to 3000 milligrams per 50 kilograms of body weight; preferably 10 to 1000 milligrams per 50 kilograms of body weight; more preferably 25 to 800 milligrams per 50 kilograms of body weight. In some embodiments, 8 to 800 milligrams administered to an individual per day in divided doses 1 to 6 times a day, or in sustained release form, is effective to obtain desired results. Formulation of therapeutic compositions and their subsequent administration is believed to be within the skill of those in the art.

The compositions according to the present invention can be administered as a single dose or in multiple doses. The compositions of the present invention can be administered either as individual therapeutic agents or in combination with other therapeutic agents. The treatments of the present invention may be combined with conventional therapies, which may be administered sequentially or simultaneously.

For parenteral administration, the lipoparticle compositions of the invention can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils can also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The compositions of the present invention may be administered by any means that enables the active agent to reach the site of action. Because lipoparticles may be subject to being digested when administered orally, parenteral administration, i.e., intravenous, subcutaneous, transdermal, intramuscular, can be used to optimize absorption. Intravenous administration may be accomplished with the aid of an infusion pump.

The compositions of the present invention can be formulated as an emulsion. Alternatively, they can be formulated as aerosol medicaments for intranasal or inhalation administration. In some cases, topical administration can be desirable.

Depending upon the disease or disorder to be treated, the compositions of the present invention may be formulated and administered to most effectively to treat the disease or disorder. Modes of administration will be apparent to one skilled in the art in view of the present disclosure.

Measurement of a Virus, Virus Like Particles, Lipoparticles and Other Uses

The ability to produce lipoparticles does not confer the ability to detect, visualize, count, or measure the lipoparticles. The present invention provides these abilities. In addition, the membrane proteins within the lipoparticles can be quantified, their density within each lipoparticle measured, and the purity of the lipoparticles determined. The methods disclosed herein are described in relation to lipoparticles, but can also be applied to naturally occurring or laboratory strains of viruses, viral particles, or virus-like-particles. Therefore, as used herein, the term "particle" refers to any particle comprising a phospholipid layer comprising a viral core protein and an additional protein, a virus, viral particle, virus-like-particle, or lipoparticle. In some embodiments, the additional protein is a membrane protein.

The present invention provides for particles comprising a fluorophore. In some embodiments the particle is a virus, a viral particle, virus-like-particle, or a lipoparticle. The fluorophore can be any compound or composition that fluoresces. In some embodiments, the fluorophore is a fluorescent protein or a fluorescent dye. The fluorescent protein can be a fusion protein that comprises a fluorescent protein and a non-fluorescent protein. Examples of fluorescent proteins include, but are not limited to, Green Fluorescent Protein (GFP), Yellow Fluorescent Protein (YFP), Blue Fluorescent Protein (BFP), Cyan Fluorescent Protein (CFP), DsRED, AsRED, AmCyan, HcRed, ZsGreen, ZsYellow, or variants thereof. In some embodiments, the fluorescent protein comprises a viral structural protein (e.g. Gag). The use of a composition comprising a lipoparticle and a fluorescent protein allows for the lipoparticles to be detected and/or quantified in ways that have not been done previously. Making lipoparticles with specific viral structural proteins and/or specific membrane proteins is described in U.S. Patent Application US 2002/0183247A1, U.S. Application Ser. No. 60/491,477, U.S. Application Ser. No. 60/491,633, U.S. Application Ser. No. 60/498,755, and U.S. Application Ser. No. 60/502,478. Additionally, membrane proteins can be transfected into other cells or particles as described herein and in U.S. Provisional Application 60/509,677, filed Oct. 7, 2003.

Fluorophores can also be incorporated into particles using fluorescent dyes. In some embodiments the fluorescent dye is a hydrophobic dye. A hydrophobic fluorescent dye is a dye that fluoresces more strongly in a non-aqueous environment. In some embodiments, the hydrophobic fluorescent dye does not appreciably fluoresce in an aqueous environment. In some embodiments, the hydrophobic fluorescent dye does not fluoresce in an aqueous environment. As used herein, the term "does not appreciably fluoresce in an aqueous environment" refers to the fluorescent property of a compound (e.g. dye). In some embodiments the fluorescence of a compound that does not appreciably fluoresce in an aqueous environment is about 10% less, about 20% less, about 30% less, about 40% less, about 50% less, about 60% less, about 70% less, about 80% less, about 90% less, about 91% less, about 92% less, about 93% less, about 94% less, about 95% less, about 96% less, about 97% less, about 98% less, about 99% less, or 100% less in an aqueous environment than it fluoresces in a non-aqueous environment. Examples of non-aqueous environments include, but are not limited to, a lipid bilayer, cell membrane, and the like. Fluorescent dyes can be incorporated into particles as described in U.S. Application Ser. No. 60/498,755. In some embodiments, dyes that fluoresce strongly in both aqueous and lipid environments, the dye can be separated from the lipoparticles prior to visualization, for example, by a gel filtration spin column.

Examples of dyes that bind and/or label lipids include, but are not limited to, Amphiphilic dyes; DiA; 4-Di-10-ASP; FASTDiA; FM 1-43; FM 4-64; FM 5-95; NBD; TMA-DPH; TMAP-DPH; ANS; MBDS; BADS; 4-amino-4'-benzamidostilbene-2,2'-disulfonic acid, disodium salt (MBDS); 1-anilinonaphthalene-8-sulfonic acid (1,8-ANS); 2-anilinonaphthalene-6-sulfonic acid (2,6-ANS); bis-ANS (4,4'-dianilino-1,1'-binaphthyl-5,5'-disulfonic acid, dipotassium salt), (E,E)-3,5-bis-(4-phenyl-1,3-butadienyl)-4,4-difluoro-4-bora-3a,4a-diaza-s-indacene (BODIPY® 665/676); 1,10-bis-(1-pyrene)decane; 1,3-bis-(1-pyrenyl)propane; Dapoxyl® sulfonic acid sodium salt; 4-(dicyanovinyl)julolidine (DCVJ); 6,8-difluoro-4-heptadecyl-7-hydroxycoumarin (C17DiFU); 4,4-difluoro-1,3,5,7,8-pentamethyl-4-bora-3a,4a-diaza-s-indacene (BODIPY® 493/503); 4,4-difluoro-1,3,5,7-tetramethyl-4-bora-3a,4a-diaza-s-indacene (BODIPY® 505/515) 4-dihexadecylamino-7-nitrobenz-2-oxa-1,3-diazole (NBD dihexadecylamine); 4-(N,N-dimethyl-N-tetradecylammonium)methyl-(7-hydroxycoumarin) chloride (U-6); 1,6-diphenyl-1,3,5-hexatriene (DPH); 5-dodecanoylaminofluorescein; 6-dodecanoyl-2-dimethylaminonaphthalene (laurdan); fluorescein octadecyl ester; 4-heptadecyl-7-hydroxycoumarin; 5-hexadecanoylaminofluorescein; 6-hexadecanoyl-2-(((2-(trimethylammonium)ethyl)methyl)amino) naphthalene chloride (patman); Nile red; Di-4-ANEPPS; Di-8-ANEPPS; 5-octadecanoylaminofluorescein; N-octadecyl-N'-(5-(fluoresceinyl))thiourea (F18); octadecyl rhodamine B chloride (R18); 3-(4-(6-phenyl)-1,3,5-hexatrienyl)phenylpropionic acid (DPH propionic acid); N-((4-(6-phenyl-1,3,5-hexatrienyl)phenyl)propyl)trimethylammonium p-toluenesulfonate (TMAP-DPH); N-phenyl-1-naphthylamine; 6-propionyl-2-dimethylaminonaphthalene (prodan); 1-pyrenebutanol; 1-pyrenenonanol; 1-pyrenesulfonic acid, sodium salt; 2-(p-toluidinyl)naphthalene-6-sulfonic acid, sodium salt (2,6-TNS); 1-(4-trimethylammoniumphenyl)-6-phenyl-1,3,5-hexatriene p-toluenesulfonate (TMA-DPH); diI; diS; diO; Oxonol VI; JC-1; DiSC3(5); DiSC3; CC2-DMPE; DiSBAC2(3); DiSBAC4(3); VABSC-1; Rhodamine 421; and the like.

The present invention also provides methods for detecting other sub-microscopic particles. Previously, it has been very difficult, time consuming, and expensive to detect and/or visualize such particles. Techniques that are expensive and laborious, such as electron microscopy (EM), have been previously used to detect and quantify particles. However, the present invention provides methods that are easier to use, less expensive, and less laborious. By using a composition comprising a particle and a fluorophore one can now easily detect and quantify the particles with methods that were thought to have not been practical or technically feasible.

In some embodiments the detection of a particle is done on the basis of the particle comprising a fluorophore (e.g. fluorescent dye or fluorescent protein). The detection can be done using any means that can measure fluorescence including, but not limited to, microscopy, flow cytometry, immunofluorescence, and the like. In some embodiments, the microscopy is performed with a microscope containing an epifluorescent light. In some embodiments, the microscopy is performed with a confocal microscope. In some embodiments, if the fluorescent is bright enough, it is contemplated that a fluorescent microscope may not be necessary to detect the fluorophore in the particles.

Being able to detect particles can allow the particles to be quantified or counted. The counting can be done by any means including, for example, using a hemocytometer and a microscope, flow cytometry, dynamic light scattering, static light scattering, quantitative light scattering, immunofluorescence, reflectance, absorbance, and the like. Being able to count particles can enable doses to be more easily and accurately calculated when administering a composition that contains particles to an animal or an individual. Counting particles can also be used to determine the concentration and/or purity of particles in a sample. Thus, the present invention provides methods for determining the concentration and/or purity of particles in a sample.

In some cases, the results of quantification are not returned in terms of absolute number of particles. For example, the particles can be counted by dynamic light scattering, static light scattering, quantitative light scattering, or reactivity with a fluorescent molecule, and the results from these assays are in units of light, intensity of light, or a similar measurement unit, not particle numbers. In some embodiments, the particles can be quantified by quantitative PCR or quantitative RT-PCR, by detection of Gag by Western blot or dot blot, or by detection of membrane phospholipids or cholesterol, resulting again in relative units of detection. The units of detection, however, can be readily converted to absolute particle numbers by correlating the results of such an assay with a standard curve using known quantities of lipoparticles, beads, DNA, Gag protein, or other standards of known quantity.

The purity of a lipoparticle preparation can be calculated by determining the number of particles in a sample and dividing that number by the total protein concentration of the sample. Determining the protein concentration of a sample is well known to those of skill in the art and can be done using any method. Some commercially available products that can be used include, but are not limited to, BCA assay kit (Pierce, Rockford, Ill.) and microBCA assay kit (Pierce, Rockford, Ill.), NanoOrange (Molecular Probes, Eugene, Oreg.). The protein concentration can be calculated in any units including, for example, ug/µl, ug/ml, mg/µl, mg/ml, mg/l, and the like. Therefore, in some embodiments the equation Purity of Particles=(Number of Particles per unit volume)/(Total Protein per unit volume)

can be used to determine the number of particles per unit weight (e.g. µg, mg, and the like). This can allow one to calibrate experiments and compositions more accurately as compared to other methods known in the art. In some embodiments the purity is determined by taking the number generated by the equation Purity of Particles=(Number of Particles per unit volume)/(Total Protein per unit volume) and dividing the purity of particles number by the theoretical weight of the lipoparticle or the theoretical protein weight of the particle. If this calculation is about 1 or equal to 1, the particles are said to be pure. If the number is greater than one, the particles are less pure. In some embodiments, if the number is greater than 1.1, greater than 1.2, greater than 1.3, greater, than 1.4, greater than 1.5, greater than 1.6, greater than 2.0 the particles are not pure.

In some embodiments, the quantifying the number of said membrane protein comprises purifying the membrane protein from the lipoparticles and determining the concentration of protein in the purified membrane protein sample. In some embodiments, the quantifying the number of the membrane protein comprises determining the number of ligand binding sites per mg protein in the sample. The quantifying the number can be done with a method comprises a Western blot, dot blot, or total protein stain SDS-PAGE. In some embodiments, a total protein stain SDS-PAGE comprises a Coomassie, Sypro, or silver stain.

In some embodiments, the total protein stain SDS-PAGE comprises calculating the percent of total protein represented by the membrane protein. In some embodiments, the Western blot, dot blot, or total protein stain SDS-PAGE comprises a protein standard.

As discussed above, when detecting and/or counting lipoparticles one can use flow cytometry. To overcome limitations in the resolution of flow cytometry, in some embodiments, the present invention provides compositions comprising particles and beads. In some embodiments, the particles are attached to the beads either through non-covalent or covalent interactions. The attachment can be through, for example, a biotin-avidin interaction, wheat germ agglutinin interaction, or a poly-lysine interaction, where the bead has one molecule or compound that interacts with a molecule or compound present on the particle. The number of particles that can be attached to a bead can be varied based on the conditions that the particles and the beads are contacted with one another. In some embodiments, the number of particles attached to each bead is 1, 2, 3, 4, 5, 6, 7, 8, 9, 10, 11, 12, 13, 14, 15, 16, 17, 18, 19, 20, or more. The conditions that can be varied include temperature, concentration of lipoparticles, concentration of the beads, and the like. The beads can be any type of bead made out of any material that is suitable for flow cytometry. The size of the beads can also be any size. In some embodiments the diameter of the bead is about 1 um, about 2 um, about 5 um, about 10 um, about 15 um, about 20 um, about 30 um, about 40 um, or more than 41 um. Once the particles are attached to beads, they can be counted using the flow cytometer. In some embodiments, the bead comprises a fluorophore or the particle comprises a fluorophore to enable detection by the flow cytometer.

Being able to count the number of particles can also allow one to determine the number of membrane proteins or a specific membrane protein that is present on the particle. A person of ordinary skill in the art can calculate the amount of a membrane protein within a sample using standard techniques known including, but not limited to, Western Blot, ELISA, and the like. When these techniques are used in conjunction with a standard (as described herein) the amount of a protein can be calculated in a sample. Then using the equation No. of Membrane Proteins per particle=(No. of Membrane Protein per μl of sample)/(No. of lipoparticles per μl of sample)

By using this equation one can determine the amount of a specific membrane protein per particle. This can be used to standardize doses of a composition, as well as monitor how well or how much of a membrane protein is incorporated into a particle during the production of the particle. In some embodiments, it is determined that there are at least 1, at least 5, at least 10, at least 20, at least 30, at least 40, at least 50, at least 100, at least 200, at least 1000, at least 10,000, or more specific membrane protein molecules per particle. In some embodiments there are about 1 to about 10,000, about 1 to about 1,000, about 1 to about 500, about 1 to about 200, about 1 to about 100, about 1 to about 50, about 5 to about 500 specific membrane protein molecules per particle. As used herein, the term "specific membrane protein" refers to a membrane protein that is being quantified. This does not refer to the total number of membrane proteins on or in the surface of a particle.

The present invention provides methods for determining the density of a membrane protein on the surface of a particle. The size of a particle can be determined using dynamic light scattering. Based on the size of the particle one can calculate the density of the membrane protein using the equation Surface Density of a Membrane Protein=(No. of Membrane Proteins per particle)/(Size per particle)

The equation will result in an answer with units of number of membrane particles per unit size which equals the surface density or probable distribution of the membrane protein on or in the particle.

Based on the ability to detect particles using fluorophores, the present invention further provides methods of detecting the binding of compounds to particles. In some embodiments the methods detect binding of compounds to lipoparticles. The compound can be any compound that is thought to bind to, or it is wanted to know if it binds to, the particles including, but not limited to, ligands, peptides, proteins, antibodies, organic chemical compounds (e.g. small molecular weight compounds), or inorganic chemical compounds. In some embodiments, the compound comprises a fluorophore or fluorescent label.

The compounds can be contacted with the particle to determine if the compound can bind to the particle. To determine if the compound can bind to the lipoparticle one can detect the binding through the fluorescence of bound compound when the compound comprises a fluorophore or fluorescent label. Detection methods include, but are not limited to, flow cytometry, immunofluorescence, sensors, microscopy, and the like. Sensors and using them with particles is described, for example, in U.S. Application No. 60/491,633. In some embodiments, the compound is immobilized on the sensor surface. In some embodiments, the particle is immobilized on the sensor surface.

The present invention also provides methods of identifying compounds that bind to the same site as that of a compound that is known to bind to a particle or to a site that prevents the compound known to bind to a particle by some other mechanism such as a steric hindrance or allosteric change in the particle. This can be detected using the ability to detect particles using the present invention. The method comprises contacting a first compound with a particle to which a second compound is already bound to or to which it is known that a second compound can bind to, but has not yet been contacted with the particle. In some embodiments, the first compound comprises a fluorophore. In some embodiments, the second compound comprises a fluorophore. In some embodiments, the first and second compounds comprise different fluorophores. One can detect if the second compound is prevented from binding to the particle by the change in fluorescence that would be observed. If only the second compound comprises a fluorophore, then a decrease in fluorescence once the first compound is brought in contact with the particle would indicate that the first compound prevents or inhibits the second compound from binding to the particle. If only the first compound comprises a fluorophore, then an increase in fluorescence would indicate that the second compound is inhibited or prevented from binding to the particle by the presence of the first particle. In some embodiments, the particle comprises a fluorophore and the fluorescence can indicate whether or not a compound is bound to the particle. In some embodiments, when the second compound is bound to the particle, the particle fluoresces, whereas when the first compound binds to the particle the particle does not fluoresce and vice versa. Therefore, the changes in fluorescence can be used to determine if the first compound inhibits or prevents the second compound from binding to the particle. The changes in fluorescence, either associated with the particle or the compound, can also be used to determine if the first compound can bind to the particle. Methods of measuring fluorescence are known to those of ordinary skill in the art.

The present invention also provides methods for detecting the structural integrity of a membrane protein on or in a particle. In some embodiments, the method comprises contacting the particle with an antibody that binds to the membrane protein and detecting the binding of the antibody to the particle. In some embodiments, the detection of the antibody being bound to the particle indicates that the structural integrity of the membrane protein is intact. "Structural integrity" as used herein refers to the proper folding and presentation of a membrane protein on or in the surface of a particle. In some embodiments it refers to the proper folding and expression on or in the surface of a lipoparticle.

The binding of an antibody to a membrane protein can indicate structural integrity because in some embodiments, the antibody is a conformationally dependent antibody. A "conformationally dependent antibody" refers to an antibody that only binds to a protein or membrane protein when the protein is properly folded and retains its correct structure. In some embodiments the antibody can recognize a conformationally active protein (e.g. activated receptor) or a conformationally inactive protein. Any method can be used to determine structural integrity, including Virus-Detection Elisa, Antibody-Detection Viral Elisa, a sensor, flow cytometry, and immunofluorescence staining. In some embodiments, centrifugation can be used to isolate the particles before or during the determination of the structural integrity process. In some embodiments, methods comprising Virus-Detection Elisa, Antibody-Detection Viral Elisa, or immunofluorescence further comprise a centrifugation step or spin down step. Centrifugation can be used in any method to facilitate the detection of the particles.

Detection of Antigens and/or Ligands Using a Lipoparticle

Lipoparticles can also be used here to construct pathogen, antibody, and ligand biosensors that utilize cellular single-transmembrane signaling machinery. By incorporating the necessary target-recognition elements (a single-transmembrane protein capable of independent or antibody-assisted binding of pathogens, ligands and antibodies) and reporter elements (e.g. fluorescent and/or luminescent proteins), one can use an assay for the detection of pathogen antigens, pathogen-specific antibodies, and receptor ligands. Uses of these assays include, but are not limited to, evaluating biological, food and environmental samples for the presence of infectious agents and contaminants for a range of purposes including bioterrorism screening, disease diagnosis, epidemiological surveys, food contamination assessment, and the like. The lipoparticles can also be used to detect a humoral immune response to an infectious agent of interest in potentially exposed subjects, to assess vaccination protocols or in the development of vaccines. Examples of these applications include, but are not limited to the detection of particular strains of Flaviviruses such as DEN or WNV in human blood, or in insect vectors, or detection of circulating antibodies directed against a particular strain of DEN prior to commencement of a vaccination program. With the appropriate recognition elements, the assay can also be used to detect the presence of non-pathogen 1-TM receptor ligands such as epidermal growth factor (EGF).

Accordingly, the present invention provides for lipoparticles comprising at least one fusion protein, wherein the fusion protein comprises at least one binding domain, at least one transmembrane domain, and at least one reporter domain.

As used herein, the term "binding domain" refers to a domain that is present in the fusion protein that is capable of binding to a ligand. The ligand can be a peptide, protein, fragment of a protein, a nucleic acid molecule (e.g. RNA or DNA), small molecule, hormone, antigen, pathogen (e.g. virus or bacteria), and the like. In some embodiments, the binding domain is an antibody binding domain. An antibody binding domain can come from any protein including, but not limited to Protein A, Protein G, Protein M, or Protein L. In some embodiments, the binding domain comprises a ligand-binding portion of a cellular membrane protein. As used herein, the term "antibody binding domain" refers to a domain that can bind an antibody.

In some embodiments, the fusion protein comprises a transmembrane domain that spans the lipid bilayer once, twice, three times, four times, five times, six times, or seven times. In some embodiments, the transmembrane domain comprises a membrane anchor. In some embodiments, the membrane anchor comprises about 3, about 4, about 5, about 6, about 7, about 8, about 9, or about 10 amino acid residues. In some embodiments, the membrane anchor comprises at least 3, at least 4, at least 5, at least 6, at least 7, at least 8, at least 9, or at least 10 amino acid residues. In some embodiments, the membrane anchor comprises a lipid or a lipid modification. In some embodiments, the membrane anchor comprises amino acid residues and a lipid or lipid modification. By "lipid modification" it is meant to refer to a protein that is modified by a lipid that allows the protein to be anchored to the membrane. In some embodiments, the lipid modification comprises a covalent attachment of a lipid to the protein. In some embodiments, the lipid modification is non-covalent (e.g. ionic bond, hydrogen bond, and the like). In some embodiments, the membrane anchor is glycosylphosphatidylinositol (GPI).

As used herein, the "reporter domain" refers to a domain in the fusion protein that can be used to generate a signal that can indicate binding to the binding domain of the fusion protein. The reporter domain can have any activity that can indicate binding. In some embodiments, the activity of the reporter domain comprises enzymatic activity or fluorescent activity. In some embodiments the reporter domain generates a signal that can be used in a calorimetric, bioluminescent, or chemiluminescent assay. In some embodiments, the reporter domain comprises a fluorescent protein. In some embodiments, the fluorescent protein is CFP, YFP, GFP, dsRED, or BFP. In some embodiments, the reporter domain comprises secreted alkaline phosphatase activity, luciferase, chloramphenicol acetyltransferase, β-glucuronidase or β-galactosidase activity. In some embodiments, the reporter domain is monomeric.

In some embodiments, the reporter domain is inactive unless it is in contact with a complementary inactive form. Non-limiting examples of such domains include the kinase domains of the EGF receptor (EGFR), the platelet-derived growth factor receptor (PDGFR), fibroblast growth factor receptors (FGFRs), the erythropoietin (EPO) receptor, and the growth hormone receptor. These kinase domains are inactive until they are phosphorylated during homodimerization, which is facilitated by the binding of ligand to the extracellular domain of the receptor.

In some embodiments, a lipoparticle comprises a first fusion protein and a second fusion protein, wherein each fusion protein comprises at least one binding domain, at least one transmembrane domain, and at least one reporter domain. In some embodiments, the first and second fusion proteins comprise two different reporter domains. In some embodiments, the first and second fusion proteins comprise the same or different binding domains, transmembrane domains, reporter domains, and combinations thereof.

In some embodiments, the reporter domains are capable of FRET or BRET. Examples of domains that are capable of FRET or BRET include, but are not limited to, CFP, YFP, and the like. Accordingly, in some embodiments, the first reporter domain comprises CFP and the second reporter domain comprises YFP or vice versa.

In some embodiments, the first and second fusion proteins comprise an antibody binding domain and comprise one or more antibody-like molecules. As used herein the term "antibody-like molecule" refers to a molecule that is an antibody or a fragment of an antibody. In some embodiments, an antibody-like molecule comprises a monoclonal antibody, a polyclonal antibody, an affinity-purified polyclonal antibody, a Fab fragment derived from a monoclonal antibody, an immunoglobulin-fusion protein, a single chain Fv, an Fc-fusion protein, or combinations thereof.

In some embodiments, a fusion protein comprises two different antibody-like molecules that each recognize different epitopes on the same protein. In some embodiments, a fusion protein comprises two different antibody-like molecules that each recognize different epitopes on different proteins.

In some embodiments, a lipoparticle comprises a first fusion protein comprising an antibody binding domain and a second fusion protein comprising a ligand-binding portion of a cellular membrane protein.

In some embodiments, the binding domain of a first and/or second fusion protein recognizes different epitopes on the same protein or recognizes different epitopes on different proteins.

The present invention also provides for sensors comprising a lipoparticle comprising at least one fusion protein, wherein the sensor is capable of detecting the signaling activity of a cellular membrane protein. In some embodiments, the signal is detectable in the absence of a living cell.

"Living cell" refers to any cell that is capable of cell division or contains a nucleus. A "living cell" also refers to a cell that has active metabolic machinery (e.g. mitochondria). In some embodiments, the cellular membrane protein is a seven transmembrane protein or a single transmembrane domain. In some embodiments, the cellular membrane protein is a GPCR.

The lipoparticle comprising the fusion proteins can be used to detect the presence of an antigen. Accordingly, the present invention provides methods of detecting the presence of an antigen comprising contacting the antigen with at least one lipoparticle and detecting the signal from said lipoparticle. In some embodiments, the lipoparticle comprises at least one fusion protein comprising at least one binding domain, at least one transmembrane domain, and at least one reporter domain. Lipoparticles can be constructed with binding domains that are specific for different antigens which would allow the lipoparticles to be used to differentiate between antigens. Lipoparticles can also be constructed that contain one or more fusion proteins, wherein each fusion protein comprises a different binding domain with a different reporter domain. For example, a lipoparticle can comprise a first and second fusion protein, wherein the first fusion protein has a binding domain for an epitope of Dengue Virus (DEN) E protein linked to a reporter domain comprising CFP and the second fusion protein comprises a binding domain to a different epitope of DEN E protein linked to a reporter domain comprising YFP. Therefore, when an antigen is contacted with a lipoparticle comprising the first and second fusion proteins, the detection of CFP and YFP FRET activity will indicate the presence or absence of DEN. In some embodiments, the antigen is contacted with a group of lipoparticles, wherein the group of lipoparticles comprises different fusion proteins comprising different binding domains linked to different reporter domains. A "group of lipoparticles" comprises more than one lipoparticle. In some embodiments, a "group of lipoparticles" comprises at least two, at least three, at least four, at least five, at least six, at least seven, at least eight, at least nine, at least ten, at least twenty, at least thirty, or at least fifty lipoparticles comprising different fusion proteins. In some embodiments, a "group of lipoparticles" comprises two, three, four, five, six, seven, eight, nine, ten, twenty, thirty, or fifty lipoparticles comprising different fusion proteins. In some embodiments, the lipoparticles are an array of lipoparticles.

As used herein the term "binding domain linked to a reporter domain" refers to an association between the binding domain and the reporter domain in the fusion protein. This linkage can occur directly by fusing the binding domain to the reporter domain or can be done indirectly through an intervening sequence such as, for example, a transmembrane domain. A "different binding domain linked to a different reporter domain" refers to binding domains that bind to either different antigens or different epitopes and that each binding domain is linked to a different reporter domain. In some embodiments, as a non-limiting example, if there is a first and a second fusion protein, wherein the first has a binding domain specific for HIV and the second has a binding domain for WNV, the first fusion protein will have a reporter domain that is different from the second fusion protein so that the activities can be differentiated and thus, the antigens can also be differentiated from one another based on the activity of the reporter domain.

As used herein, "antigen" refers to a composition comprising at least one pathogen protein, at least one whole-pathogen organism, at least one secreted cellular peptide, at least one immobilized protein, at least one tissue section, at least one cell, at least one ligand, at least one small molecule, at least one hormone, or at least one antibody. In some embodiments, that pathogen protein is a pathogenic protein or peptide from an agent selected from: picomavirus family, calcivirus family, togavirus family, flariviridue family, hepatitis C virus, coronavirus family, rhabdovirus family, filoviridue family, paramyxovirus family, orthomyxovirus family, bungvirus family, arenavirus family, reovirus family, retrovirus family, papovavirus family adenovirus family, parovirus family, herpesvirus family, poxvirus family, hepadnavirus family, hepatitis delta virus, pathogenic gram posititive cocci, pathogenic gram-negative cocci, pathogenic enteric gram-negative bacilli, pathogenic anaerobic bacteria rickettsia, mycoplasms, Chlamydia, pathogenic protozoans, and pathogenic helminthes. In some embodiments, the antigen is a pathogenic protein or peptide from an agent causing a disease selected from HIV-1 infection, HIV-2 infection, SIV infection, Hepatitis C, Hepatitis B, HPV infection, HSV infection, HTLV infection, HCMV infection, WNV infection, Dengue Virus infection, spirochete *B. bugdorferi*, rabies, gastroenteritis, foot and mouth, dengue, yellow fever, encephalitis, common cold, bronchitis, encephalymylitis, haemorrhagic fever, mumps, new Castle disease, canine distemper, Rift Valley fever, Nairobi sheep disease, Lassa Fever, Colorado Tick fever, Lebombo, equine encephalosis, blue tongue, smallpox, anthrax, and cowpox. In some embodiments, the antigen is a composition that comprises more than one antigen, a group of antigens, or an array of antigens. In some embodiments, the composition comprises one, two, three, four, five, six, seven, eight, nine, ten antigens. In some embodiments, the composition comprises at least two, at least three, at least four, at least five, at least six, at least seven, at least eight, at least nine, at least ten different antigens.

In some embodiments, the presence of an antigen is detected by fluorescence, resonance energy transfer, luminescence, or total internal reflectance fluorescence. Detection can be done with any device including, but not limited to a microfluidic device, a flow cell, a Lab-on-a-Chip, a microplate with wells, a 96-well plate, a 384-well plate, a 1536-well plate, a glass slide, a plastic slide, an optical fiber, a prism, a flow cytometer, a microscope, a fluorometer, a spectrometer, or a CCD camera.

In some embodiments, the method detects an infectious agent, a receptor's ligands, or a pathogen-specific antibody. The methods can also be used for pathogen screening, disease diagnosis, drug screening, epidemiological surveys, or food contamination assessment.

In some embodiments, the method further comprises contacting at least one lipoparticle with a control antigen and generating a signal in response to the control antigen relative to another antigen that is unknown or needs to be characterized. If the signal generated or detected are the same, this would indicate that the unknown antigen is the same as the control. If the signal generated or detected by the control and unknown antigen are different, this would indicate that the two antigens are not the same. Therefore, this method can be used to identify or confirm an antigen as being similar or different to a control (e.g. known) antigen. This can be use, for example, to rule out pathogenic agents as the cause of a disease, disorder, epidemic, or contamination. This can also be used in conjunction with an array or group of control antigens so that more than one antigen or pathogen can be ruled out or in at a time, which would be important in saving time to identify the cause of a disease, disorder, epidemic, or contamination.

In some embodiments, the present invention provides devices comprising at least one lipoparticle that can be used to identify the presence or identity of an antigen. In some embodiments, the device comprises a fluorometer, which can be, for example, a portable fluorometer weighing under 50 pounds, under 20 pounds, under 5 pounds, or under 2 pounds.

The present invention also provides other uses of lipoparticles. Lipoparticles can be used for the development of nanometer scale biological probes, known as LipoProbes. In some embodiments, LipoProbes use lipoparticle structure as a vehicle for the assembly of a targeting and/or reporter combination. In some embodiments, a LipoProbe comprises a lipoparticle, which comprises surface targeting molecules (e.g. membrane-bound antibodies or antibody-fragments), and/or reporting molecules (e.g. fluorescent proteins fused to the Gag protein). In some embodiments, the lipoparticle enables the assembly of multiple targeting and reporting systems individually or in combination. These can be coupled to the lipoparticle surface, incorporated within the lipid or protein components of the membrane, linked to structural proteins such as Gag, and encapsulated in soluble form within the lipoparticle membrane-bound cavity. In addition, lipoparticles can incorporate molecular constructs to facilitate LipoProbe handling, and to modify targeting, sensing and reporting functions (such as channels for ion sensitivity or biotin tags for manipulation), as well as effector molecules capable of perturbing micro-environmental systems (e.g. enzymes). LipoProbes are suitable for a vast range of applications, including monitoring protein-protein interactions such as ligand binding, structural mapping, cell signaling, detection of micro-environmental conditions such as pH or ion concentration, and tracking lipid interactions such as during viral-host fusion. LipoProbes can exploit a variety of detection techniques, including innate fluorescence and luminescence, enzyme-mediated detection, FRET, polarization, and TIRF, and can be monitored using a diverse array of detection modalities including microscopy, micro-plate, cuvettes, and flow cytometry. They are suitable for use with a range of target formats (e.g. in vitro, ex vivo, or in vivo). LipoProbes have utility in a variety of health and biological science fields, including lead compound identification for drug discovery, pharmaceutical development, diagnostics and preventive medicine, cell biology, virology and proteomics. In addition, LipoProbes can provide valuable adjunct functions in research and development programs, including protein production and purification (e.g. for structural studies), isolation of ligands and drugs, monoclonal antibody production, hybridoma screening, and epitope mapping.

The flexibility of LipoProbes lies in the variety of methods by which lipoparticles can be modified to include active molecules. Lipoparticles can be endowed with a variety of interactive targeting, reporting, and effector functions by modifying the structure and composition of membrane lipids, membrane proteins, core proteins, and by altering the biochemical characteristics of the lipoparticle interior.

Lipoparticle Modifications: Creating LipoProbes
Modification of the Lipoparticle Surface Lipoparticles can be modified by coupling them to molecules or complex structures via reactive groups exposed on the lipoparticle surface. Lipoparticle membranes are derived from cells, and so incorporate proteins and carbohydrates that either naturally, or can be chemically modified to, possess reactive molecular groups, such as amines, carboxyl groups, carbonyls, and sulfhydryl groups. These groups can be recognized and acted upon directly by binding proteins. For example, lectins, such as concavalin A (ConA), wheat germ agglutinin (WGA), and legume lectins, bind oligosaccharide groups (e.g. galactose, acetyl-D-glucosaminyl, acetylgalactosaminyl, mannopyranosyl, and galactopyranosyl residues) commonly contained in glycoproteins, proteoglycans, and glycolipids. These lectins can, in turn, also be modified, such as biotinylated WGA lectin. Cholera toxin subunits (A and B) bind galactosyl moieties. Lipid moieties, such as fatty acids may also be directly targeted by binding proteins, such as I-FABP, a rat intestinal fatty-acid binding protein. Reactive groups may also be chemically modified by cross-linking agents, such as amine-reactive imidoesters and N-hydroxysuccinimide (NHS)-esters, sulfhydryl-reactive maleimides, pyridyl disulfides and haloacetyls, carbonyl-reactive hydrazides, or carboxyl-reactive carbodiimides. Such binding proteins and cross-linking agents are commonly conjugated to functional molecular species. These methods can be used to link functional molecules, such as fluorescent or non-fluorescent reporters, enzymes, binding and targeting proteins (e.g. antibodies), and complex structures such as beads or other solid substrates, magnetic particles, gold particles and radioactive substances to lipoparticle surfaces. These modifications can confer unique interactive properties on lipoparticles that enable localization to targets or substrates, visual detection (e.g. fluorescence), and detection by MRI, electron microscopy, radiography, or PET.

The lipoparticle can be modified to accommodate any of these interactions, such as its use as a probe on cells. Modifications can include treatment with a protease such as proteinase K or trypsin, a glycosidase such as EndoF or EndoH, or mixing with a blocking reagent such as BSA, serum, PEI, Pluronics, an RGD-containing peptide, or polylysine. In some embodiments, the lipoparticle comprises a membrane protein resistant to such treatments, for example a ZZ-TM fusion protein engineered to lack any trypsin cleavage sites.

In some embodiments, the virus, virus-like particle, or lipoparticle comprises at least one of a radioactive molecule, a magnetic substance, a paramagnetic substance, a biotinylated molecule, an avidin-like molecule, gold, or combinations thereof and optionally a fluorophore.

Modification of the Lipids within the Lipoparticle Membrane

The lipid composition of cell membranes is an important determinant of such properties as fluidity, permeability, and electrical potential. Alterations in the nature and quantity of membrane lipids can influence the formation of specialized micro-structures (e.g. microvilli) and membrane protein functions. The lipid composition of lipoparticles can be influenced by depletion of specific lipid constituents (such as cholesterol or sphingolipids), by addition of lipid moieties (e.g. insertion of amphiphilic molecules such as phospholipids and other glycerol-derived components), and by modification of the chemical and structural nature of naturally incorporated lipids (e.g. modification of the saturation state of acyl chains, stabilization using lipid fixatives such as osmium tetroxide). Modification of membrane lipids present in the lipoparticle structure can be achieved during lipoparticle production by inducing metabolic alterations in producer cells, or post-production by chemical treatment of lipoparticles. Lipolytic enzymes (e.g. phospho- or galactolipases, acyl hydrolases), mild detergents (e.g. polyethylene glycol, and lubrols such as Lubrol W), and lipid-complex forming agents (e.g. cyclodextrins) can be used to selectively or non-specifically deplete lipids from lipoparticle membranes. The specific lipid composition of lipoparticle membranes can be altered by liposome-mediated lipid enrichment, or by treatment with fatty acids and fatty-acid analogs (e.g. pyrenes, undecanoic acid, parinaric acid) or phospholipids (e.g. phosphoinositides, phsophocholines, phosphoethanolamines). A variety of other lipid analogs and lipophilic molecules, such as sphingolipids, steroids, triacylglycerols, octadecyl rhodamine, lipophilic fluoresceins, coumarins, dialkylcarbocyanine probes, and dialkylaminostyryl probes, could similarly be incorporated directly into the lipid bilayer of the lipoparticle membrane. These lipid molecules may possess chemical modifications of acyl chains or other molecular groups, or may be conjugated to molecular groups or complex structures, conferring the capacity for target interaction (e.g. biotin, avidin, antibodies, enzymes), reporter functions (e.g. fluorescent and/or luminescent dyes such as Nile Red, Rhodamine 421, di-4-ANEPPS, Oxonol VI, DiSC3(5), diI, di-BAC4), other effector or detector functions (e.g. leukotrienes, prostaglandins, eicosanoids, thromboxanes), or for altered lipoparticle longevity or tissue processing (e.g. PEG).

Additional changes in the lipid composition of the lipoparticle can also be introduced. For example, purified lipids (e.g. PE) can be added to purified lipoparticles and allowed to partition into the lipoparticle. Similarly, cholesterol can be depleted from the lipoparticle by using MDBC, which soaks up cholesterol from cell membranes. In addition, lipids can be cross-linked to toughen the lipid bilayer of the lipoparticle.

Modification of the Proteins within the Lipoparticle Membrane

Lipoparticles can incorporate a variety of membrane proteins, including receptors, ion channels, and transporters, in their native, functionally-active forms. However, it is also possible to produce lipoparticles containing structurally-modified versions of membrane proteins. Plasmids containing sequences for two or more proteins can be used to generate lipoparticles incorporating membrane proteins fused to a variety of other functional proteins. These fusion partners can confer target interaction properties (e.g. enzymes, antibody-binding proteins), reporter properties (e.g. fluorescent proteins such as GFP, YFP, CFP and dsRed; enzymes such as luciferase, alkaline phosphatase, horseradish peroxidase, beta-galactosidase, and other oxidases, kinases and proteases). Membrane proteins can also be modified post-lipoparticle production. Fixation of complex biological structures, such as cells and tissues, with aldehyde solutions such as formaldehyde, paraformaldehyde, and glutaraldehyde results in the formation of methylene bridges between protein nitrogen atoms. The cross-linking preserves protein structural integrity, and forms an insoluble matrix that traps carbohydrates and lipids without altering their chemical compositions. Fixation of lipoparticle protein constituents in this way can alter their longevity and behavior in a number of applications such as immunoprobing.

Modification of the Lipoparticle Core Proteins

Normal retroviruses express a core polyprotein consisting of a main structural component, Gag, fused to enzymatic proteins, Pol. However, Gag is the one retroviral protein necessary, and sufficient, for lipoparticle production. The Pol polyprotein sequence can be substituted with a variety of alternative genes, including those for fluorescent reporter proteins such as GFP, YFP, BFP, CFP, DsRED, AsRED, AmCyan, HcRed, ZsGreen, ZsYellow or variants thereof (Bennett, et al. (1991), J Virol, 65:272-80, McDonald, et al. (2002), J. Cell Biol., 159: McDonald, et al. (2003), Science, 300:1295-7, Weldon, et al. (1990), J Virol, 64:4169-79), and non-fluorescent proteins (e.g. esterases, proteases, kinases, alkaline phosphatase, peroxidase, beta-lactamase, luciferase). Approximately 1,000-2,000 Gag proteins form the structural core of each lipoparticle (Knipe, et al. (2001)), so proteins fused to Gag are highly represented. They can confer reporter functions (e.g. fluorescent proteins), protein manipulation functions (e.g. HA epitope tags), or other modifying functions (e.g. enzymes) to lipoparticles. Additionally, Gag can act as a protein production scaffold for the large-scale production and purification of partner proteins for structural studies.

The Gag fusion protein may also comprise a fusion between Gag and the binding portions of an antibody, for example a single-chain region Fv. The specificity of the antibody can be used to link the Gag fusion protein with other proteins during lipoparticle production, which can be used in the purification of the other protein.

In some embodiments, more than one enzyme is incorporated into a lipoparticle simultaneously. In some embodiments, the more than one enzymes could act synergistically on a substrate that requires both of their activities. Thus, lipoparticles can act as a reaction center, providing all enzymes necessary for a certain reaction. If provided with a substrate and/or cofactors, entire enzymatic activities can be recapitulated.

Modification of the Biochemical Characteristics of the Lipoparticle Interior

Although the biochemical features of retroviruses are poorly understood, the characteristics of their membrane-limited space bear some resemblance to that of the host-cells from which they were derived. It is possible to alter these features in lipoparticles in order to confer specific sets of functional properties. The enrichment or depletion of specific ions (e.g. $Ca^{++}$, $K^+$, $Na^+$, $Mg^{++}$, and the like), and the inclusion of small molecules (e.g. nucleic acids such as ATP and GTP and their analogs), of proteins (e.g. enzymes, nucleic acid binding proteins), of dyes and reporters (e.g. water soluble fluorescent molecules), or of complex structures (e.g. quantum dots) within the lipoparticle structure are possible. The lipoparticle membrane, although generally considered impermeable, will allow the equilibration of small species such as ions or small nucleic acid binding molecules (e.g. YOYO-1) across it over time, allowing adjustment of lipoparticle ion concentration by treatment in appropriate buffers. Some water-soluble molecules can be allowed to cross lipid membranes by acetoxymethyl esterification (e.g. AM-PBFI, calcein-AM, Fura-2-AM, SNARF-1-AM, AM-SBFI, DAF-FM), after which they are trapped within the membrane-delineated space by enzymatic removal of ester groups. Larger molecules and structures that cannot cross lipid membranes, and are not amenable to chemical modification such as esterification (e.g. quantum dots, Phen-Green, lucigenin, OPA, radioactive particles, paramagnetic beads, Raman probes (DSBB), gold particles) can be loaded into lipoparticles using temporary poration or permeabilization of the lipoparticle structure. Temporary poration or permeabilization can be achieved by such treatments as electroporation, exposure to chemicals or proteins (e.g. streptolysin-O, aerolysin, maltoporin, P2X7, melittin), mechanical stress (e.g. sonication, vortex mixing), and the like. Permanent poration of lipoparticle membranes could also be performed in order to allow interaction of trapped molecules (such as reporters) with small molecules in the microenvironment. Any other method of temporary poration or permeabilization can also be used.

Caged Reporters

Caged molecules are not active until stimulated in a defined manner, (e.g. by exposure to UV light). Such molecules can be loaded into lipoparticles to confer specific activation characteristics to the lipoparticle probe. Caged molecules include caged versions of nucleotides and phosphatases (e.g. ATP, ADP, cAMP, cGMP, GTP, GTP-gammaS, GDP, IP3, H+(pH), PO4, ADP-ribose), ion scavengers (e.g. EGTA, EDTA, Diazo-2, thapsigargin, terbium), neurotransmitters (e.g. carbachol, GABA, NMDA, L-glutamic acid), fluorescein, fluorescent IP3, nucleotides (e.g. GTP-gammaS), amino acids, L-glutamic acid, carbachol, gamma-aminobutyric acid, NMDA, O-GABA, and the like.

Lipophilic Fluorophores

Fluorophores can also be incorporated into lipoparticles using fluorescent dyes. In some embodiments the fluorescent dye is a hydrophobic dye. A hydrophobic fluorescent dye is a dye that fluoresces more strongly in a non-aqueous environment. In some embodiments, the hydrophobic fluorescent dye does not appreciably fluoresce in an aqueous environment. In some embodiments, the hydrophobic fluorescent dye does not fluoresce in an aqueous environment. As used herein, the term "does not appreciably fluoresce in an aqueous environment" refers to the fluorescent property of a compound (e.g. dye). In some embodiments the fluorescence of a compound that does not appreciably fluoresce in an aqueous environment is about 10% less, about 20% less, about 30% less, about 40% less, about 50% less, about 60% less, about 70% less, about 80% less, about 90% less, about 91% less, about 92% less, about 93% less, about 94% less, about 95% less, about 96% less, about 97% less, about 98% less, about 99% less, or 100% less in an aqueous environment than it fluoresces in a non-aqueous environment. Examples of non-aqueous environments include, but are not limited, a lipid bilayer, cell membrane, and the like. Fluorescent dyes can be incorporated into particles as described in U.S. Application Ser. No. 60/498,755. In some embodiments, dyes that fluoresce strongly in both aqueous and lipid environments, the unincorporated dye is separated from the lipoparticles prior to visualization, for example, by a gel filtration spin column.

Examples of dyes that bind and/or label lipids include, but are not limited to, Amphiphilic dyes; DiA; 4-Di-10-ASP; FASTDiA; FM 1-43; FM 4-64; FM 5-95; NBD; TMA-DPH; TMAP-DPH; ANS; MBDS; BADS; 4-amino-4'-benzamidostilbene-2,2'-disulfonic acid, disodium salt (MBDS); 1-anilinonaphthalene-8-sulfonic acid (1,8-ANS); 2-anilinonaphthalene-6-sulfonic acid (2,6-ANS); bis-ANS (4,4'-dianilino-1,1'-binaphthyl-5,5'-disulfonic acid, dipotassium salt), (E,E)-3,5-bis-(4-phenyl-1,3-butadienyl)-4,4-difluoro-4-bora-3a,4a-diaza-s-indacene (BODIPY® 665/676); 1,10-bis-(1-pyrene)decane; 1,3-bis-(1-pyrenyl)propane; Dapoxyl® sulfonic acid sodium salt; 4-(dicyanovinyl)julolidine (DCVJ); 6,8-difluoro-4-heptadecyl-7-hydroxycoumarin (C17DiFU); 4,4-difluoro-1,3,5,7,8-pentamethyl-4-bora-3a, 4a-diaza-s-indacene (BODIPY® 493/503); 4,4-difluoro-1,3, 5,7-tetramethyl-4-bora-3a,4a-diaza-s-indacene (BODIPY® 505/515) 4-dihexadecylamino-7-nitrobenz-2-oxa-1,3-diazole (NBD dihexadecylamine); 4-(N,N-dimethyl-N-tetradecylammonium)methyl-(7-hydroxycoumarin) chloride (U-6); 1,6-diphenyl-1,3,5-hexatriene (DPH); 5-dodecanoylaminofluorescein; 6-dodecanoyl-2-dimethylaminonaphthalene (laurdan); fluorescein octadecyl ester; 4-heptadecyl-7-hydroxycoumarin; 5-hexadecanoylaminofluorescein; 6-hexadecanoyl-2-(((2-(trimethylammonium)ethyl)methyl)amino) naphthalene chloride (patman); Nile red; Di-4-ANEPPS; Di-8-ANEPPS; 5-octadecanoylaminofluorescein; N-octadecyl-N'-(5-(fluoresceinyl))thiourea (F18); octadecyl rhodamine B chloride (R18); 3-(4-(6-phenyl)-1,3,5-hexatrienyl)phenylpropionic acid (DPH propionic acid); N-((4-(6-phenyl-1,3,5-hexatrienyl)phenyl)propyl)trimethylammonium p-toluenesulfonate (TMAP-DPH); N-phenyl-1-naphthylamine; 6-propionyl-2-dimethylaminonaphthalene (prodan); 1-pyrenebutanol; 1-pyrenenonanol; 1-pyrenesulfonic acid, sodium salt; 2-(p-toluidinyl)naphthalene-6-sulfonic acid, sodium salt (2,6-TNS); 1-(4-trimethylammoniumphenyl)-6-phenyl-1,3,5-hexatriene p-toluenesulfonate (TMA-DPH); diI; diS; diO; Oxonol VI; JC-1; DiSC3(5); Rhodamine 421; and the like.

LipoProbe Function and Applications

In some embodiments, these probes described herein can be used to map cell and tissue structures both in vitro and in vivo, as well as to detect single or multiple cell signaling events. Modifying molecules can also be incorporated into the LipoProbe to alter its targeting, biophysical properties, and sensitivity. Table 10 outlines some of the embodiments of the LipoProbe and some of their applications.

TABLE 10

Examples of potential LipoProbe components and their applications.

| | Applications |
|---|---|
| Proteins | |
| ZZ-TM | This transmembrane anchored protein can bind the Fc portion of user-specified antibodies, enabling targeted localization of labeled LipoProbes. |
| CXCR4, CD4, DC-SIGN, Fas, TNFR | These membrane proteins bind cognate ligands, such as the chemokine SDF-1 (CXCR4), Fas Ligand, TNF, and HIV Envelope (CD4, CXCR4, DC-SIGN), enabling interactions among membrane proteins in their native, lipid-anchored form to be detected. Extracellular proteins such as integrins, TNF receptor family members, and immunoadhesins, are of special interest because they involve interactions between membrane proteins on opposing lipid surfaces. |
| Protein Kinase C (PKC), beta-site APP-cleaving enzyme (BACE) | Both soluble (PKC) and membrane-bound (BACE) enzymes can be incorporated into the LipoProbe and used as effectors on their natural targets (RXXS/T phosphorylation motifs and amyloid-beta precursor protein (APP), respectively). |
| Reporters | |
| BFP, CFP, GFP, YFP, dsRed | Fluorescent proteins can be used as simple fluorescent tags, to detect specific conditions (e.g. pH-sensitive GFP), or for detecting binding interactions (e.g. FRET). |
| di-4-ANEPPS, di-BAC4, Oxonol VI | Lipophilic molecules readily incorporate into the lipid membrane of LipoProbes. Many respond to environmental conditions (pH, membrane potential) during phagocytosis or in cellular structures (e.g. synapses). |
| Fura-2, Indo-1, quantum dots | Hundreds of soluble reporters (some in AM-ester form) can be incorporated that are responsive to changes in ion concentration or that exhibit incomparable fluorescence and longevity, creating probes of Ca++ and methods of tracking the destinations of infectious viruses (quantum dots). |
| $^3$H, $^{35}$S, paramagnetic beads, gold nanospheres | Radioactive tracers and substances that can change electromagnetic properties can be incorporated into LipoProbes for diagnostic imaging techniques such as MRI and PET |
| Modifications | |
| TRPV1, TRAP6, CFTR, Shaker-K | The incorporation of ion channels that open in response to specific stimuli (e.g. Ca$^{++}$-channel TRPV1 opens in response to heat) and gate select ions allows the LipoProbe to act as a sensor of these stimuli and to link incorporated reporters to the ion changes (e.g. Ca$^{++}$ responsive Fura-2). |
| Biotin-PE, PEG-PE | Partitioning of functionalized lipids into the LipoProbe can allow targeting (biotin) or enhanced longevity (PEG) |

Numerous alternative reporter proteins and dyes can be incorporated into LipoProbes using the methods tested here, including, but not limited to: Visual reporters (e.g. beta-lactamase, beta-galactosidase, HRP, alkaline phosphatase, luciferase); Catalytic enzymes (e.g. kinases, phosphatases, proteases, oxidases); Fluorescent proteins e.g. (GFP, BFP, CFP, YFP, dsRED, numerous variants); Lipophilic dyes (e.g. Nile Red, Rhodamine 421, Oxonol VI, DiSC3(5), diI); Water-soluble probes (e.g. Phen-Green (heavy metals), lucigenin (Cl$^-$), OPA (cyanide)); AM-ester conjugates (SNARF-1 (pH), Fura-2 (Ca$^{++}$), SBFI (Na$^+$), DAF-FM (NO)); Non-visual reporters (e.g. radioactivity, paramagnetic beads, Raman probes (DSNB), gold).

Many of these alternative reporters can improve LipoProbe sensitivity (e.g. luminescent proteins, FRET pairs, Raman assays), extend LipoProbe applications (PET, MRI), and/or improve the functional capabilities of LipoProbes (e.g. by sensing environmental conditions such as membrane potential, pH, and heavy metals). Because many second-generation detection techniques rely on the simultaneous activity of multiple reporters, LipoProbes allow incorporation of reporters by multiple independent methods, any of which can be combined.

In some embodiments, the lipoparticle combines individual reporters into an integrated detection system. The reporters are not only in close proximity within the lipoparticle, but can be linked so that their activation must occur sequentially. Reporters that can be incorporated into the lipoparticle include small molecules, proteins, ion channels, and quantum dots. Unlike liposomes reconstituted with detergent-solubilized ion channels, lipoparticles can be used to incorporate a wide variety of ion channels without the requirement for detergent solubilization. In addition, soluble protein reporters are incorporated as structural elements of the lipoparticle, ensuring high copy number and ease of production.

The reporters within a lipoparticle can be chosen to respond to the same or different signals. In some embodiments, the lipoparticles responds to about 2, about 3, about 4, about 5, about 6, about 7, about 8, about 9, or about 10 different signals. In some embodiments, the lipoparticle responds to least 2, at least 3, at least 4, at least 5, at least 6, at least 7, at least 8, at least 9, at least 10, at least 10 different signals. In some embodiments, the lipoparticles respond to only 1 signal. In some embodiments, the lipoparticles responds to about 1-100, about 1-50, about 1-40, about 1-30, about 1-20, about 1-10, about 1-5, about 2-10, about 2-5 signals. Thus, the lipoparticle Sensor can have the capability to monitor multiple points along a signal transduction pathway. When a lipoparticle detects the same stimulus, multiple reporters can provide increased sensitivity of detection over a greater range and increased detection specificity. When they detect different stimuli, multiple reporters can provide the ability to monitor multiple events within a signal transduction pathway. The reporters can also be designed to simultaneously detect different events from multiple signaling pathways, allowing complex cellular responses to be monitored. The use of a combinatorial detection system is especially important in cells where low signal-to-noise ratios and interference by background cellular pathways are a significant concern in the detection of real signals. The lipoparticle makes this sensing system possible by confining sensors to a nanometer-sized probe, which, by modifying the lipoparticle with specific external antibodies or proteins, can be targeted to defined subcellular locations.

Selective modifications can be introduced to the lipoparticle to enable it to be used in more harsh environments such as in cells, in animals, and with detergents. Modifications include PEGylation, polymerization of lipids, fixation of lipids, fixation of proteins, enzymatic digestion of exterior proteins, enzymatic removal of exterior carbohydrates, and pre-incubation with molecules that block non-specific binding.

Because the lipoparticle is based on a virus structure, the LipoProbe also has direct application to the study of viruses. The ability to incorporate more robust probes into viruses (e.g. quantum dots) and probes with more meaningful signals (e.g. pH- or membrane potential-sensitive dyes) could allow a number of new insights into viral infection processes.

The lipoparticle Sensor is a sensing system, combining existing reporters within a nanometer-scale vehicle with unique sensing properties. In some embodiments, cells microinjected with the lipoparticle Sensor can be monitored for both fluorescence and luminescence in real-time using microscopic imaging. Cells can be monitored while stimulating with 1) heat (heating to 43° C. activates TRPV1) and 2) the GPCR agonist TRAP-6 (initiates $Ca^{++}$ flux within the cell by stimulating the thrombin receptor PAR-1). When the cells are stimulated with heat, the $Ca^{++}$-ion channel on the lipoparticle Sensor is activated and allows the passage of $Ca^{++}$-ions into the lipoparticle. In some embodiments, the ion channel is activated and $Ca^{++}$ flows into the lipoparticle and activates the $Ca^{++}$-ion reporters, which can be detected by changes in fluorescence and luminescence. A simultaneous change in both reporters permits a high degree of confidence in the signal.

Target Interaction and LipoProbe Localization

Among the lipoparticle modifications that confer utility as probes are those that enable interaction with specified targets, for target recognition and detection, and/or for directing LipoProbes to specific locations. Target interactive-components can include molecules and complex structures (e.g. biotin, avidin, streptavidin, WGA beads, enzymes) linked covalently or otherwise to the lipoparticle surface, or conjugated to modified lipid molecules within the lipoparticle membrane. Functional membrane-associated proteins, either native, or modified, such as receptors (e.g. CXCR4, CCR5), antibody binding proteins (ProA, ProL, ProG), enzymes (e.g. protein kinase C, beta-site APP-cleaving enzyme), and ion channels (e.g. TRPV1, CFTR, Shaker) can be incorporated directly into the lipoparticle membrane. Active proteins (e.g. carboxylases) can be fused to membrane proteins or to viral structural proteins, while organic chemicals (e.g. ion chelators, active small molecules such as nucleic acid binding compounds, pH-sensitive molecules, oxygen-reactive species) can be incorporated within the lipoparticle interior. Target-interacting components can enable LipoProbes to interact with receptor ligands, with antibodies, with specific antigenic epitopes, with specific lipids or carbohydrates, with ions (e.g. $H^+, K^+, Na^+, Ca^{++}, Mg^{++}$), with reactive molecules in solution (e.g. reactive oxygen species), or with immobilizing substrates (e.g. coated or surface-reactive beads or solid substrates).

Methods for Visualizing and Detecting Lipoprobes and their Interactions

Lipoparticles can be modified to enable them to be visualized or detected by emission of fluorescence and luminescence, visible light, radioactivity, or other electromagnetic emissions. These reporters can be linked to the lipoparticle surface or incorporated into the lipid membrane (e.g. fluorescent beads, fluorescent lipid molecules, lipid-soluble dyes), fused to or otherwise attached to integral membrane proteins (e.g. CXCR4-GFP), fused or otherwise attached to structural proteins (e.g. Gag/luciferase, Gag/GFP), or loaded in soluble form into the lipoparticle interior (e.g. AM-ester dyes, nucleic acid binding molecules such as SYBR green, DAPI, and YOYO-1). Such reporters can be constitutively active (e.g. GFP, fluorescein, ALEXA), can require some interaction with targets or co-factors for detection (e.g. luciferase, FRET pairs, polarization reporters), or can require some user-defined intervention (e.g. exposure to ultraviolet light) to enable reporting activity. These so-called 'caged' reporters include caged versions of nucleotides and phosphatases (ATP, ADP, cAMP, cGMP, GTP, GTP-gammaS, GDP, $IP_3$, $H^+$ (pH), PO4, ADP-ribose), ion scavengers (EGTA, EDTA, Diazo-2, thapsigargin, terbium), neurotransmitters (carbachol, GABA, NMDA, L-glutamic acid), fluorescein, fluorescent IP3, nucleotides (GTP-gammaS), amino acids, L-glutamic acid, carbachol, gamma-aminobutyric acid, NMDA, O-GABA. LipoProbes incorporating reporters can be detectable using a variety of detection and assay platforms including, but not limited to conventional or confocal fluorescent microscopy, conventional fluorometry (microtiter plate or cuvette), fluorescent emission polarity shift detection, flow cytometry, and TIRF.

Application-Driven Modification Combinations

LipoProbes can be used for a variety of applications, defined by the specific combination of incorporated modifications. The LipoProbe is not a reporter in itself, but rather a sensing system, combining existing target interaction and reporter components, along with ancillary modifications that facilitate, modify, or enhance target interaction and reporting functions.

Binding Assays

Based on the ability to detect particles using fluorophores, the present invention provides methods of detecting the binding of compounds to particles. In some embodiments the methods involve detection of the binding of compounds to lipoparticles. The compound can be any compound that is thought to bind to, or it is being tested to determine if it binds to, the particles including, but not limited to, ligands, peptides, proteins, antibodies, organic chemical compounds (e.g. small molecular weight compounds), or inorganic chemical compounds. In some embodiments, the compound comprises a fluorophore or fluorescent label.

The compounds can be contacted with the particle to determine if the compound can bind to the particle. To determine if the compound can bind to the lipoparticle one can detect the binding through the fluorescence of bound compound when the compound comprises a fluorophore or fluorescent label. Detection methods include, but are not limited to, flow cytometry, immunofluorescence, sensors, microscopy, and the like. Sensors and using them with particles is described herein and, for example, in U.S. Application No. 60/491,633. In some embodiments, the compound is immobilized on the sensor surface. In some embodiments, the particle is immobilized on the sensor surface.

The present invention also provides methods of identifying compounds that bind to the same site as that of a compound that is known to bind to a particle or to a site that prevents the compound known to bind to a particle by some other mechanism such as steric hindrance or an allosteric change in the particle. This can be detected using the ability to detect particles using the present invention. In some embodiments, the method comprises contacting a first compound with a particle to which a second compound is already bound to or to which it is known that a second compound can bind to, but has not yet been contacted with the particle. In some embodiments, the first compound comprises a fluorophore. In some embodiments, the second compound comprises a fluorophore. In some embodiments, the first and second compounds comprise different fluorophores. One can detect if the second compound is prevented from binding to the particle by the change in fluorescence that is observed. If only the second compound comprises a fluorophore, then a decrease in fluorescence once the first compound is brought into contact with the particle would indicate that the first compound prevents or inhibits the second compound from binding to the particle. If only the first compound comprises a fluorophore, then an increase in fluorescence would indicate that the second compound is inhibited or prevented from binding to the particle by the presence of the first particle. In some embodiments, the particle comprises a fluorophore and the fluorescence can indicate whether or not a compound is bound to the particle. In some embodiments, when the second compound is bound to the particle, the particle fluoresces, whereas when the first compound binds to the particle the particle does not fluoresce and vice versa. Therefore, the changes in fluorescence can be used to determine if the first compound inhibits or prevents the second compound from binding to the particle. The changes in fluorescence, either associated with the particle or the compound, can also be used to determine if the first compound can bind to the particle. Methods of measuring fluorescence are known to those of ordinary skill in the art.

Detection of Protein-Protein Interactions

In some embodiments, the Lipoprobe can also be used to discover and characterize protein-protein interactions, using techniques such as far western, flow cytometry, and immunostaining. For example, lipoprobes carrying one membrane protein can be used to test binding to cells expressing other membrane proteins. Membrane protein pairs can include ICAM/LFA, Fas-FasLigand, class I/class II/CD4/CD8/T cell receptor combinations, or Notch and Delta, and the like.

In some embodiments, orphan membrane proteins can be used to search for pairing ligands. A lipoparticle comprising an orphan membrane protein is screened against a sample comprising molecules that may bind to the orphan membrane protein. In some embodiments, the sample is a library of ligands, tissue homogenate, cells, and the like. A ligand that can bind to the orphan protein can be identified by a change in fluorescence of the lipoparticle or detectable change in the lipoparticle that would indicate that a molecule has bound to the orphan membrane protein.

Flow Cytometry

Another means of detecting the structural integrity of membrane proteins contained in lipoparticles is flow cytometry. Because flow cytometry measures individual events, flow cytometry can be used to quantify the number of lipoparticles in a given sample. If a fluorescent marker to the membrane protein is used, flow cytometry can be used to quantify the number of membrane proteins in a given sample. The lipoparticles to be quantified can be made fluorescent using a Gag-GFP fusion protein, a lipid dye, a receptor-GFP fusion protein, a secondary antibody bound to the lipoparticle, or any other method of staining a lipoparticle. By using a control (200 nm latex beads) containing a known number of antibody binding sites, the number of receptors per lipoparticle can also be determined.

In some embodiments, the lipoparticles are attached to beads before flow cytometry. The beads may be larger in size (e.g. 10 µm) in order to better accommodate a flow cytometer detector. In one embodiment, the beads are fluorescently labeled. In another example, the lipoparticles are biotinylated and the beads are coated with streptavidin to facilitate linkage. In another example, the beads are coated with the lectin Wheat Germ Agglutinin (WGA).

Reactive Oxygen Detection

A wide variety of active substances can be delivered to specific locations by incorporation into targetable LipoProbes. Reactive oxygen species, with short (nano- to microsecond) lifespans or limited diffusion capabilities, such as singlet oxygen or hydroxyl radicals, can be delivered with nanoscale precision. Reactive oxygen and nitric oxide species react with a wide range of molecules, including NADH, dopa, ascorbic acid, histamine, tyrosine, tryptophan, cysteine, glutathione, nucleic acids, cholesterol, and unsaturated fatty acids, and can be difficult to distinguish in whole cells. By compartmentalizing them and/or agents for their detection within LipoProbes, specificity of delivery, interaction, and detection can be increased considerably.

Nucleic Acid Detection

The lipoparticle may also be incubated with a nucleic acid probe that is complementary to a nucleic acid sequence in the particle. In such case, the probe may be fluorescently or radioactively labeled. Hybridization of the probe with the lipoparticle and detection by, for example, fluorescent microscopy, would be indicative of the nucleic acid sequence existing in the nucleic acid occurring in the particle. Such methods may be useful for diagnostics. Nucleic acid probes can also be used to identify a specific type of virus. In some embodiments, a nucleic acid sequence is added to a sample containing a virus that will fluoresce if the nucleic acid molecule is able to hybridize to the virus. If a sequence that is specific to a virus or family of viruses is used these methods can used to identify the presence and/or type of virus or virus family in a sample. Accordingly, the present invention can be used for diagnostics of viruses in a sample. Additional components which interact with nucleic acids, such as the destabilizing enzyme RecBCD, could also be incorporated into lipoparticles. Nucleic acid-specific dyes used in conjunction with LipoProbes could have application, among other things, in diagnostics, and in viral classification. Staining of nucleic acid sequences could occur in conjunction with or separately from in situ amplification of viral RNA sequences.

DEFINITIONS

Certain terminology is used herein as follows.

The articles "a" and "an" are used herein to refer to one or to more than one (i.e., to at least one) of the grammatical object of the article. By way of example, "an element" means one element or more than one element.

The term "about", as used herein when referring to a measurable value is meant to encompass variations of ±20% or ±10%, ±5%, ±1%, or ±0.1% from the specified amount, as such variations are appropriate to perform a disclosed method or otherwise carry out the present invention.

The term "adenoviral vector" refers to an adenovirus comprising DNA that is not normally found in an adenovirus. An "adenoviral vector" can also be referred to as a chimeric adenovirus.

As used herein, a prefix to the term "lipoparticle" designates a specific membrane protein or other specific modification made to that lipoparticle. For example, "CXCR4-lipoparticle" is defined as a lipoparticle comprising the seven-transmembrane receptor CXCR4; "Gag/GFP-lipoparticle" is defined as a lipoparticle comprising a Gag/GFP fusion protein; "Gag/GFP-CCR5-lipoparticle" refers to a lipoparticle comprising a Gag/GFP fusion protein and the transmembrane receptor CCR5.

A "null-lipoparticle" is defined as a lipoparticle vehicle containing no specific membrane proteins. As used herein, "no specific membrane protein" means that a user has not specified a particular membrane protein to be incorporated into the lipoparticle. "Null-lipoarticles" can still comprise membrane proteins that naturally occur on the surface of the cell from which the lipoparticle was produced.

As used herein, the term "LipoProbe" refers to a lipoparticle bearing one or more targeting components and/or one or more signaling components.

As used herein, the term "targeting component" refers to a molecule comprising one or more target (molecular) recognition domains, and one or more domains which link it to the lipoparticle.

As used herein, the term "recognition domain" refers to a subunit of the targeting component which specifically binds to a target molecule.

As used herein, the term "signaling component" refers to a reporter which allows an event to be detected or monitored.

As used herein, the term "modifying component" refers to a unit of the LipoProbe, such as an ion channel, that does not in itself possess specific targeting or reporting characteristics, but which modulates the targeting and/or reporting ability of the LipoProbe by conferring specific sensitivities.

As used herein, the term "multimodal detection system" refers to the simultaneous detection or correlation of one or more reporters.

"Virus," as the term is used herein, refers to a particle comprising a complete viral genome and the proteins encoded by that genome in their native state.

By the term "applicator" as the term is used herein, refers to any device including, but not limited to, a hypodermic syringe, a pipette, and the like, for attaching a lipoparticle and/or composition of the invention to a surface, including a sensor surface. Further, the applicator can be used to contact a ligand and/or a test compound with a lipoparticle.

The term "exogenous protein" as used herein, refers to a protein that is not normally expressed in a cell. An exogenous protein is often, though not exclusively expressed in a cell from a plasmid, a virus, a vector, and the like.

The term "overexpressed" as used herein, refers to a level of protein expression that is greater than what is measured in a standard cell line. In some embodiments, a protein is overexpressed at least two times, at least three times, at least five times, at least 10 times, at least 100 times the level of standard cell line. The standard cell line can be any cell line that expresses the protein of interest. Examples of standard cells lines are mammalian cells, mouse cells, human cells such as, but no limited to HeLa cells, 293 cells, primary cells, stem cells, and the like.

The term, "cellular protein" is used to refer to a protein normally encoded by the cell and not viral DNA. However, the term also applies to a protein expressed by a recombinant virus wherein a cellular nucleic acid encoding the protein has been inserted into the genome of the recombinant virus for expression therefrom. Furthermore, the term also applies when the protein is provided to a virus or a virus vector in the form of a protein or a peptide.

The term "cellular virus receptor" refers to a membrane protein which is cognate to a viral envelope protein. When displayed on the surface of a cell, the cellular virus receptor is capable of binding a cognate envelope protein and, in some cases, mediating fusion of two lipid bilayers.

The term "cell" refers to any type of living cell. Cells of both unicellular and multicellular organisms are included. Examples of cells include, but are not limited to, human cells, animal cells, mammalian cells, avian cells, stem cells, primary cells, hybridoma cells, vertebrate cells, invertebrate cells, insect cells, and the like. As used herein, the term "primary cells" refers to cells that are taken from tissues of an organism and are not immortal. Cells can also be immortalized cells, cancer cells, and the like, and cells that have been immortalized. To immortalize a cell is well known to those of skill in the art.

The term "virus-infected cell" refers to a cell which has been infected by a virus which comprises a viral protein including, but not limited to, a viral structural protein in its outer membrane.

The term "producer cell" refers to a cell in which a lipoparticle can be generated.

As used herein, the term "primary cell" refers to a cell that is derived from a particular tissue and has a limited number of cell divisions before undergoing senescence. Examples of primary cells include, but are not limited to, keritinocytes, neurons, and the like.

As used herein, the term "cell line" refers to a cell line that is able to undergo an unlimited number of cell divisions. A "cell line" can also be referred to as an immortalized cell line.

As used herein, the term "hybridoma" refers to a type of cell that is both immortal and capable of producing antibodies. In some embodiments, a hybridoma produces monoclonal antibodies that are of the type IgG, IgA, IgM, and the like.

As used herein, the term "induced cell" refers to a cell that has been treated with an inducing compound that affects the cell's protein expression, gene expression, differentiation status, shape, morphology, viability, and the like. An induced cell can also be referred to as a "modified cell", a "selected cell," a "treated cell," and the like. In some embodiments an induced cell is contacted with hormones, chemokines, neurotransmitters, and the like.

As used herein, the term "organelle targeting sequence" refers to a peptide sequence that when fused with a second peptide sequence directs the second peptide sequence to a particular organelle. In some embodiments, an organelle targeting sequence targets a protein to the endoplasmic reticulum or the golgi apparatus.

As used herein, the term "gated" refers to a membrane protein whose opening and closing is governed by external conditions such as bound proteins or chemicals (e.g. neurotransmitters or hormones), membrane potentials, mechanical means (e.g., vibration or pressure), light, and the like.

As used herein, the term "non-gated" refers to a membrane protein whose channel is always open.

As used herein, the term "ionophore" refers to a compound that facilitates transmission of an ion across a lipid barrier by combining with the ion or by increasing the permeability of the barrier to it.

As used herein, the term "inactivation gate" refers to the part of an ion channel that when closed prevents the channel from reopening even under conditions that would normally open the channel. The channel can open once the inactivation gate opens. For example, an ion channel is opened by a change in membrane potential. After a period of time, the inactivation gate closes and prevents the channel from opening again until the inactivation gate opens. This is sometimes referred to as the "refractory" period.

As used herein, the term "contaminating protein inhibiting toxin" and "contaminating protein inhibiting ionophore" refers to either a toxin or an ionophore that inhibits the activity of a contaminating membrane protein (e.g. ion channel). "Contaminating protein" refers to a membrane protein whose presence is undesirable. The contaminating protein does not have to be identified before a contaminating protein inhibiting toxin or ionophore is used. The "contaminating protein inhibiting toxin" and "contaminating protein inhibiting ionophore" does not inhibit or interfere with the membrane proteins that are desired.

As used herein, the term "membrane potential" refers to an electrical potential difference between the intra- and extracellular aqueous phases of a cell separated by the cell membrane.

As used herein, the term "culturing" refers to the growing, incubating, or propagating of a cell. Examples of culturing include, but are not limited to, growing, incubating, or propagating cells in suspension, in spinner flasks, in roller bottles, or in a bioreactor.

The term "virus producer cell" refers to a cell in which a virus is produced. Examples of virus producing cells includes cells that produce adenoviruses, which include but are not limited to chimeric adenoviruses.

The term "replication competent" refers to a virus or lipoparticle that is able to infect or enter into a cell and then replicate and produce new viral particles or lipoparticles. In some embodiments, a replication competent particle comprises the entire viral genome.

The term "infectious" as used herein, refers to a virus or particle that is capable of both entering a cell and then producing progeny which are capable of leaving the cell and infecting another cell.

As used herein, a "non-infectious" particle refers to a particle that is not capable of producing progeny and leaving a cell, but may still be able to enter into the cell.

The term "fusion competent" refers to a viral particle or lipoparticle that is able to enter a cell. In some embodiments, a lipoparticle can be fusion competent without being replication competent.

The term "integration competent" refers to a lipoparticle that comprises an integrase protein and/or gene that encodes for an integrase.

The term "reverse transcription competent" refers to a lipoparticle comprising a reverse transcriptase protein and/or gene that encodes for a reverse transcriptase.

The term "protease competent" refers to a lipoparticle comprising a functional protease gene and/or protein and is capable of cleaving the gag protein.

As used herein, an "instructional material" includes a publication, a recording, a diagram, or any other medium of expression which can be used to communicate the usefulness of the lipoparticle and/or composition of the invention in the kit for assessing protein binding, identifying ligands for a membrane protein, identifying a compound that affects a ligand binding with its cognate membrane receptor protein, and the like, as more fully recited elsewhere herein. Optionally, or alternately, the instructional material may describe one or more methods of using a lipoparticle of the invention. The instructional material of the kit of the invention may, for example, be affixed to a container which contains the lipoparticle and/or composition of the invention or be shipped together with a container which contains the lipoparticle and/or composition. Alternatively, the instructional material may be shipped separately from the container with the intention that the instructional material and the compound be used cooperatively by the recipient.

As used herein, the term "transfection" refers to the uptake, incorporation, and expression of recombinant DNA by a cell. Methods of transfection include, but are not limited to chemical transfection, lipid-mediated transfection, electroporation, viral infection, and the like. Transfection can also be referred to as "transduction" and the like.

The term "host cell" means a cell that is susceptible to infection by a virus.

The term "protein" refers to peptides and polypeptides.

The term "fragment" in reference to a protein refers to a peptide or polypeptide comprising at least a portion of a protein. In some embodiments, a fragment comprises at least 5, at least 10, at least 15, at least 20, at least 25, at least 30, at least 40, at least 50, at least 75, or at least 100 contiguous amino acids of a protein. In some embodiments, a fragment comprises about 5 to about 100, about 5 to about 50, or about 5 to about 25 contiguous amino acids of a protein.

The term "competent portion of the genome of a virus" or "competent portion" refers to the portion of the genome of the virus which, when expressed in a cell, results in formation of at least one lipoparticle. In some embodiments a competent portion of a genome comprises gag or gag protein.

The term "antiviral agent" refers to a composition of matter which, when delivered to a cell, is capable of preventing replication of a virus in the cell, preventing infection of the cell by a virus, or reversing a physiological effect of infection of the cell by a virus. Antiviral agents are well known and described in the literature. By way of example, AZT (zidovudine, Retrovir® Glaxo Wellcome Inc., Research Triangle Park, N.C.) is an antiviral agent which is believed to prevent replication of HIV in human cells.

The term "cytotoxic compound" refers to a composition of matter which, when provided to a cell, is capable of killing the cell.

The term "library" refers to a plurality of nucleic-acid-containing vectors. Said vectors may comprise plasmids, viruses, or other components capable of propagating the nucleic acid. The term "library" may also refer to a large library of chemical or biological compounds that are not capable of propagation within a vector. The term "library" can also refer to a phage library or a ribosome display library.

As used herein the term "low-molecular weight organic compound" refers to compounds having a molecular weight less than 3,000. A "low-molecular weight organic compound" can also refer to a compound having a molecular weight less than 1,000.

The term "membrane protein" includes proteins that span the lipid membrane surrounding a cell, so part of the protein is inside the cell and part of the protein is outside the cell. "Membrane protein" can also include proteins that span a lipid bilayer that is not part of a cell. "Membrane protein" also refers to a membrane spanning protein, a multiple membrane spanning protein, an intracellular membrane protein, an extracellular membrane protein, an organelle membrane protein, and the like. "Membrane protein" also refers to a protein that is attached or linked to a membrane, but does not span the membrane. A "membrane protein" can also be referred to as a "transmembrane protein".

The term "membrane protein" can also refer to a protein which is expressed within the lipid bilayer cell surface membrane of a cell. In the case of a cellular membrane protein, said protein is encoded by the cell and, at least under certain conditions, is associated with the outer surface of the membrane of the cell. In the case of non-cellular membrane proteins, the proteins may be derived from a source other than the cell expressing the protein, such as a virus, bacteria, yeast, or pathogen. A membrane protein may be a full-length protein, as encoded by a normal cell, or may be a fragment thereof. In some embodiments, the membrane protein is monomeric or multimeric.

A "membrane spanning protein," as the term is used herein, refers to a polypeptide that spans the cell membrane at least once. That is, the peptide is typically present in a cell membrane where it spans the lipid bilayer at least once.

As used herein, the term "1-TM" refers to a membrane protein that spans a membrane once. Examples of proteins that can be referred to as "1-TM" include, but are not limited to, CD4, Tva, EGFR, and the like.

"A multiple membrane spanning protein," as the term is used herein, is a polypeptide that spans the cell membrane at least twice. That is, the peptide is typically present in a cell membrane where it spans the lipid bilayer at least twice. A multiple membrane spanning protein also refers to peptide that spans the lipid bilayer at least three times, at least four times, at least five times, at least six times, at least seven times, at least eight times, at least nine times, or at least ten times. A multiple membrane spanning protein also refers to peptide that spans the lipid bilayer three times, four times, five times, six times, seven times, eight times, nine times, or ten times.

"An intracellular membrane protein," as the term is used herein refers to a protein that is located inside the cell and is associated with the plasma membrane but does not span it. Examples of intracellular membrane proteins include, but are not limited to farnesylated proteins, lipid modified proteins, such as Ras, Src, kinases that associate with lipids, such as Protein Kinase C, and PI3-Kinase, and any other protein that is associated with intracellular side of the plasma membrane. An intracellular membrane protein can also refer to a membrane protein located on a membrane within the cell, such as, for example, in the endoplasmic reticulum, golgi, nucleus, mitochondria, and the like.

As used herein "associated with the plasma membrane" refers to a protein that is either covalently attached to the plasma membrane, but does not span it, or a protein that interacts through other bonding forces, such as polar and ionic bonds, with a molecule that is a part of the plasma membrane.

"Extracellular membrane protein," as the term is used herein refers to a protein that is located outside the cell and is associated with the plasma membrane, but does not span the plasma membrane.

As used herein, "an organelle membrane protein" refers to a protein that is either associated with an organelle membrane or spans the membrane of an organelle. Examples of organelle membranes include, but not limited to, golgi membranes and endoplasmic reticulum membranes.

"Exogenous protein" as the term is used herein refers to a protein not normally found in a specific cell type. For example, a human protein that is introduced into a mouse cell.

As used herein, the term "retention signal" refers to a signal that causes a compound to be retained at a specific location within the cell. In some embodiments the signal is a peptide or polypeptide. In some embodiments the retention signal retains a protein to the endoplasmic reticulum, nucleus, or golgi apparatus.

The term "non-human animal model of a human disease or disorder" refers to a non-human animal which has been rendered susceptible to infection by a human pathogenic virus and which, when so infected, exhibits a physiological condition which is analogous to a symptom exhibited by a human infected with the same virus. The term also means a non-human animal which is susceptible to infection by a non-human pathogenic enveloped virus. When the non-human animal is infected with the non-human pathogenic enveloped virus, the animal exhibits a pathology which is similar to the pathology of a human infected with the corresponding human pathogenic enveloped virus. By way of example, certain known species of monkeys are susceptible to infection by SIV, giving rise to a disease which is similar to that in humans infected with HIV.

The term "pharmaceutically-acceptable carrier" refers to a chemical compound or composition with which a lipoparticle of the invention may be combined for administering to an animal, which in some embodiments is a human. Suitable carriers are described in the most recent edition of *Remington's Pharmaceutical Sciences*, A. Osol, a standard reference text in this field, which is incorporated herein by reference in its entirety. Preferred examples of such carriers or diluents include, but are not limited to, water, saline, Ringer's solution, dextrose solution, and 5% human serum albumin.

The term 'biosensor' refers to an analytical instrument containing a biological sensing element in combination with a convenient readout.

The term 'biosensor chip' refers to the surface of a biosensor on which a test sample is placed in order to detect its biological, chemical, or physical properties.

The term "ligand" refers to a substance (chemical or protein) that binds to (matches) a protein. In biosensor applications, the ligand refers to the molecule attached to the biochip.

The term "ligand," as used herein, encompasses any protein or compound that can bind with a protein present in a lipoparticle. The ligand encompasses a protein or non-protein compound that can bind with a protein present in a lipoparticle. The term "ligand" can also be referred to as a "binding partner." In some embodiments, a "binding partner" can also be a monoclonal antibody, a polyclonal antibody, an affinity-purified polyclonal antibody, a Fab fragment derived from a monoclonal antibody, an immunoglobulin-fusion protein, a single-chain Fv, an Fc-fusion protein, peptide, polypeptide, and the like.

As used herein, the term "test ligand" refers to a ligand that is tested to determine if it binds to a lipoparticle comprising a protein. "Test ligand" can also refer to a ligand that is tested to determine if it inhibits the binding of another ligand to a lipoparticle comprising a protein.

As used herein, the term "test sample" refers to a sample that comprises a ligand, test ligand, and the like. Examples of test samples include, but are not limited to, blood, saliva, serum, cell lysate, organ lysate, tissue homogenate, animal secretions, vaginal secretions, feces, cell culture medium, and the like. In some embodiments, the test sample is diluted or concentrated, or dissolved with another solvent.

The term "receptor" refers to a protein, often a membrane protein, which binds to a ligand of biological significance and transmits the information so that it can influence cellular behavior.

A "chimeric virus" is a virus that includes nucleic acid sequences from two different viruses—a primary virus and a secondary virus. The term "chimeric virus" is used to refer to the packaged chimeric virus particle, while the term "chimeric viral genome" refers to the nucleic acid sequence that is packaged into the chimeric virus. The chimeric virus is capable of transducing a producer host cell and directing production of a secondary virus. The components of the chimeric viral genome include, but are not limited to, the following: (1) primary virus nucleic acid sequences that allow packaging into a primary virus particle, e.g., packaging signals; (2) optionally, secondary virus genes that encode proteins for packaging the genome of a secondary virus; (3) optionally, a secondary virus genome; (4) optionally, an expression cassette with a heterologous gene operably linked to a promoter, typically part of the secondary virus genome. The chimeric viral genome is typically packaged into a chimeric virus using packaging cells that complement the primary virus nucleic acid sequences. The chimeric virus can be replication deficient. An example of a chimeric virus includes, but is not limited to, an adenovirus that also has in its genome DNA for a retroviral gag gene.

The term "pseudotype" refers to an enveloped virus that does not comprise its natural or native envelope protein, which has been replaced by the envelope protein of another virus or another strain of the same virus.

The term "enveloped virus" refers to a virus comprising an envelope protein and a lipid bilayer.

The term "non-enveloped virus" refers to a virus that does not comprise an envelope protein or a lipid bilayer.

As used herein, the term "antigenic composition" refers to composition that binds to antibodies. The antigenic composition can be, but does not necessarily need to be, immunogenic. In some embodiments, an antigenic composition can comprise an antibody.

As used herein, the term "immunogenic" refers to a compound or composition that is able to generate an immune response including the generation of antibodies.

As used herein, the term "generate an immune response" includes humoral and cellular responses.

As used herein, the term "hybridoma" refers to a type of cell that is both immortal and capable of producing antibodies. In some embodiments, a hybridoma produces monoclonal antibodies that are of the type IgG, IgA, IgM, and the like.

As used herein, the term "induced cell" refers to a cell that has been treated with an inducing compound that affects the cell's protein expression, gene expression, differentiation status, shape, morphology, viability, and the like. An induced cell can also be referred to as a "modified cell", a "selected cell," a "treated cell," and the like.

As used herein, the term "quaternary structure" refers to the way the subunits fit together. In some embodiments, "quaternary structure" refers to the way polypeptide subunits fit together or form oligomers. In some embodiments the quaternary structure is a homo-oligomer. In some embodiments the quaternary structure is a hetero-oligomer. In some embodiments the quaternary structure comprises a dimer, a trimer, a tetramer, and higher-order oligomers.

As used herein, the term "growth property" refers to the division of a cell. Examples of defects in growth properties include, but are not limited to, hyperplasia, neoplasia, metaplasia, cancer, and the like. Examples of cancer, include, but are not limited to breast cancer, colon cancer, lung cancer, skin cancer, brain cancer, leukemia, multiple myeloma, cervical cancer, uterine cancer, ovarian cancer, prostate cancer, head and neck cancer, bladder cancer, pancreatic cancer, liver cancer, and the like.

As used herein, the term "ion-conductance property" refers to a cell's ability to modulate the ion conductance or the ion concentration of the cell. In some embodiments, a defect in ion-conductance is due to a defect in an ion channel protein.

As used herein, the term "signaling property" refers to the cells ability to transmit signals throughout the cell. In some embodiments, the signaling property refers to a signal that originates from a membrane protein and is transmitted inside the cell, the nucleus, or other cytoplasmic compartment (e.g. mitochondria, golgi apparatus, and the like).

As used herein, the term "mutation" refers to a protein that has at least one amino acid mutated or changed to another amino acid residue.

As used herein, the term "deletion" refers to a protein that has at least one amino acid residue removed as compared to the wild-type sequence. In some embodiments at least 2, at least 5, at least 10, at least 20, at least 50, at least 100 amino acid residues are removed. The residues that are removed can also be contiguous.

As used herein, the term "insertion" refers to a protein that has at least one amino acid residue inserted into the wild-type sequence. In some embodiments at least 2, at least 5, at least 10, at least 20, at least 50, at least 100 amino acid residues are inserted. In some embodiments about 1, about 2, about 5, about 10, about 20, about 50, about 100, or about 150 amino acid residues are inserted. In some embodiments about 1 to about 100, about 1 to about 50, about 1 to about 30, about 1 to about 10, about 5 to about 10 amino acid residues are inserted. The residues that are inserted can also be contiguous.

As used herein, the term "post-translational modification" refers to a modification of protein that occurs after it is translated from mRNA. Examples of post-translation modification include, but are not limited to, phosphorylation, dephosphorlyation, sulfation, desulfation, glycosylation, or deglycosylation chimeric modification.

As used herein, the term "chimeric modification" refers to joining fragments of two proteins to form a chimeric protein. A chimeric protein can also be referred to as a "fusion protein." An example of a chimeric protein includes, but is not limited to, a protein that comprises green fluorescent protein (GFP) and a fragment of another protein. In some embodiments, a fusion protein comprises a linker, a fluorescent protein, a fluorescent peptide, a protease cleavage sequence, a viral protein (e.g. Gag), and the like. In some embodiments, the fusion protein is a Gag-fusion protein. In some embodiments a fusion protein is a Gag-G-protein fusion protein.

As used herein the phrase "a portion of a lipoparticle's membrane" refers to the lipids and other proteins present in or on the surface of a lipoparticle. A portion of a lipoparticle's membrane is either the entire membrane of the lipoparticle or less than the entire membrane of the lipoparticle.

The "standard cell line" can be any cell line that expresses the protein of interest. Examples of standard cells lines are mammalian cells, mouse cells, human cells such as, but not limited to, HeLa cells, 293 cells, primary cells, stem cells, and the like. In some embodiments, the standard cell line expresses the protein of interest. In some embodiments, the standard cell line does not express the protein of interest or the protein of interest cannot be detected.

As used herein, the term "fluorophore" refers to a compound or composition that fluoresces. In some embodiments, a fluorophore is a dye or a protein.

As used herein, the term "labeling" refers to incorporating a fluorophore into a particle or bead. "Labeling" also refers to contacting a particle with a labeled bead.

As used herein, the term "viral particle" refers to complete virions (viruses), as well as related viral particles, but not single or isolated viral proteins or particles containing a single viral protein. Examples of viral particles include, but are not limited to capsids, core particles, virions depleted of one or more envelope proteins, virion envelopes without the nuclear capsid core, virion envelope fragments and defective or incomplete virions. In some embodiments, viral particles are retroviral particles.

As used herein, the term "Z domain" refers to any Fc-binding domain. In some embodiments, the Z domain is the Fc-binding domain of Staphylococcal Protein A, Protein G, or Protein M.

As used herein the term "B1 domain" refers to any Fab-binding domain. In some embodiments, the B1 domain is the Fab-binding domain of Peptostreptococcal Protein L.

As used herein the term "target sequence" refers to an oligonucleotide sequence to which another oligonucleotide sequence is able to hybridize to under varying conditions. In some embodiments, the hybridization is under stringent conditions. In some embodiments, the target sequence is about 8, about 10, about 20, about 30, about 40, about 50, about 60, about 0, about 80, about 90, about 100, about 200, about 300, about 400, about 500, about 1,000, about 8 to about 1,000, about 8 to about 50, about 8 to about 30, about 25 to about 100, about 10 to about 100, about 100 to about 1,000, about 100 to about 500 nucleotides in length. In some embodiments, the "target sequence" is specific for a family of viruses or is specific for a specific pathogen or a family of pathogens. In some embodiments, the target sequence is unique to a specific strain of a virus.

In some embodiments a microfluidic device is narrower than about 1,000 microns, about 100 microns, about 10 microns, or about 1 micron.

The present invention also provides methods of hybridizing an oligonucleotide to a target sequence in a lipoparticle, virus, or virus-like particle. In some embodiments, the method comprises contacting a oligonucleotide with a lipoparticle, virus, or virus-like particle comprising the target sequence under conditions that permit hybridization of said oligonucleotide to said target sequence. This method can be used to detect a specific virus, lipoparticle, virus-like particle, a virus family, or a type of pathogen.

EXAMPLES

The invention is now described with reference to the following examples. These examples are provided for the purpose of illustration only and the invention should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

Example 1

Lipoparticle Production Using Core Viral Proteins and Membrane Proteins

Murine leukemia virus (MLV)-based lipoparticles were produced by calcium phosphate-mediated transfection of 293T cells in 150-cm2 tissue culture plates with a plasmid encoding a desired receptor and the pCGP plasmid which encodes the MLV gag and pol genes, as performed previously (Hoffman, et al. (2000), Proc. Natl. Acad. Sci. USA, 97:11215-11220). For purposes of optimization, a model GPCR, the chemokine receptor CCR5, was used. The chemokine receptor CXCR4 was also used on occasion. After incubation of cells in transfectant overnight, fresh media supplemented with 10 mM n-butyric acid was added to increase protein expression. 48 h post-transfection, supernatant was harvested, and cell debris was removed by filtering through a 0.45 um filter. The supernatant was pelleted for 60 min in an SW28 rotor at 28,000 RPM through 20% sucrose in PBS, and resuspended overnight in 100 μl PBS. A second ultracentrifugation step through 20% sucrose in PBS was performed, and the pellet was resuspended in approximately 100 μl of 10 mM Hepes, pH 7.0. The lipoparticles were either stored at 4° C. or aliquoted and frozen at −80° C.

Using 6-well dishes, both the total amount of DNA used (data not shown), and the ratio of receptor to virus core plasmid were systematically varied. Plasmids encoding CCR5 and MLV structural proteins were co-transfected into 293T cells at ratios ranging from 1:3 to 3:1. Samples were harvested at day 2 and assayed for MLV Gag by ELISA (A405) and CCR5 by dot blot (quantitated by densitometry, in Arbitrary Units). A receptor:gag plasmid ratio of 3:1 produced particles with the highest density of membrane protein.

We also varied the length of time that transfection reagent was applied to cells (4, 6, or 24 hours, data not shown), the time of particle harvest (1-5 days, with media changes or cumulative, data not shown), and the concentration of sodium butyrate applied to cells. Addition of sodium butyrate (NaB) boosts protein expression by enhancing promoter activity, but can also result in cellular toxicity. The results indicate that transfection conditions can make a significant difference not only on total particle production, but also on the density of membrane protein in the particles as measured by the CCR5: Gag protein ratio (data not shown). Expression of CCR5 was slightly delayed relative to MLV Gag, causing earlier harvests to possess less receptor. NaB enhanced both particle production and receptor density per particle, causing an overall increase in total particle production but an even greater increase in CCR5 incorporation.

The results from small-scale experiments were used as a starting point for continued optimization at a larger scale. The final protocol included transfection of 293T cells by $CaPO_4$ precipitation in 150 mm dishes, addition of sodium butyrate 24 hours post-transfection, and harvesting supernatant on days 2 and 3.2% fetal bovine serum, rather than 10%, was used during production. We also tested the level of receptor per virion (CCR5:Gag protein ratio) in the presence and absence of NaB and at 37° C. and 32° C. As before, NaB had the effect of increasing the levels of membrane protein per virion over time. Reducing the growth temperature to 32° C. heightened this effect significantly, most likely due to slower production of MLV virions but continued production of CCR5 (data not shown).

To achieve high purification, particles must be separated from soluble proteins, cell debris, and membrane blebs released by cells. Previous protocols loaded supernatant directly into ultracentrifuge rotors, a direct but unscaleable methodology. To address this issue, we adopted an alternative purification scheme that is better suited for large-scale production and that is used in the viral vaccine production industry. Briefly, cell debris was removed by low speed centrifugation, and supernatant was clarified by filtration through a 0.45 μm filter (Step 1, Table below). Supernatant was concentrated using tangential flow filtration (TFF) with a 300,000 MW pore size (Step 2). Viral particles in the concentrated supernatant were then either exchanged with buffer using TFF (Step 3a), directly pelleted through a 20% sucrose cushion (Step 3b), or both (Step 4). Our final results (26-fold purification from supernatant), Table 11, compare to results reported for purified HIV (84-fold purification from supernatant) (Prior, et al. (1995), BioPharm, 25-35).

TABLE 11

| Stage | Purification Stage | Start Volume (ml) | Final Volume (ml) | [Protein] (mg/ml) | Gag (A405) | Gag:Protein Ratio | Fold Concentrate | Relative Purity |
| --- | --- | --- | --- | --- | --- | --- | --- | --- |
| 1 | Unpurified | 350 | 350 | 0.89 | 2.91 | 3.27 | 1.0 | 1.00 |
| 2 | Tangential Flow Filt. | 350 | 100 | 2.14 | 9.51 | 4.44 | 3.5 | 1.36 |
| 3a | TFF buffer exchange | 175 | 14 | 1.33 | 8.95 | 6.73 | 13 | 2.06 |
| 3b | Sucrose cushion | 175 | 4.5 | 0.45 | 32.17 | 71.5 | 39 | 21.9 |
| 4 | TFF + Sucrose | 125 | 2.0 | 0.32 | 27.74 | 86.7 | 63 | 26.5 |

A405 values are multiplied by 10 to adjust for the 10-fold dilution used for measurement
Start Volume indicates the adjusted initial volume after aliquots and sample divisions have been accounted for The experiments described above identify conditions needed to optimally produce lipoparticles that contain the GPCR CCR5. To test the generalization of our methodology to include additional membrane proteins, lipoparticles were prepared by co-transfecting MLV gag/pol (pCGP plasmid) with the receptors indicated (in various eukaryotic expression vectors), harvesting supernatant two days later, removing cell debris by low speed centrifugation, and dot-blotting for the membrane protein or tags on the protein. Negative controls (media with 10% fetal bovine serum, and cells transfected with MLV gag/pol plus pcDNA3 vector) did not demonstrate any reactivity. Multiple antibodies were required to detect all membrane proteins, so levels of incorporation cannot be directly compared. The results shown are from the same exposure of strip blots. All samples were also assayed for the production of MLV structural proteins by ELISA (data not shown). We were able to detect the membrane proteins CD4, CCR5, IL5Ralpha, DC-SIGN (a type II membrane protein), Shaker (an potassium ion channel), CXCR4, BACE, and Presinilin-1. All proteins appeared to be specifically incorporated into lipoparticles.

Several controls are worth noting. Sample 'CCR5 (no MLV)' included CCR5 plasmid but no MLV gag/pol, and the lack of signal rules out artifacts such as membrane blebs. HA-CXCR4 and CXCR4-HA possess the same HA tag but on the N-terminus and C-terminus, respectively, indicating that the tag does not interfere with incorporation into lipoparticles. IL5Ralpha-GFP is a single-TM protein with a 27 kDa cytoplasmic GFP fusion, and the signal indicates that proteins with large cytoplasmic tails can be incorporated into lipoparticles (data not shown).

Example 2

Production of a Lipoparticle Containing a Human Membrane Protein from a Non-Human Cell Seven cell types were tested (FIG. 1) for the ability to support lipoparticle production. Lipoparticles were prepared as described in above. We also tested dog CF2TH cells (not shown). Since lipoparticle production is a function of the number of cells transfected as well as the health of those cells after transfection, we also tested multiple transfection modalities. Although nearly all cells could be efficiently transfected by at least one technique (FIG. 1B), few produced lipoparticles efficiently (FIG. 1A), likely reflecting a species-specific block in lipoparticle assembly. Murine 3T3 cells (native host for MLV) would likely produce more particles upon transfection optimization. Nevertheless, we identified two cell types, quail QT6 cells and feline CCC cells, that could support moderate amounts of particle production.

Example 3

Production of a Lipoparticle Using a Gag-Fusion Protein

Lipoparticles containing a cellular membrane protein and Gag do not require separate proteins to be produced. In some instances, the membrane protein and Gag can be fused together to form one protein. The membrane protein targets the Gag molecule to the plasma membrane where Gag is able to facilitate the formation of lipoparticles. For example, Gag can be fused to the C-terminus (cytoplasmic) of the single-transmembrane protein CD4. When transfected into 293 cells, this fusion protein will direct the formation of lipoparticles that contain a Gag core and CD4 on its exterior. In some embodiments, this fusion protein will be constructed using a GPCR and Gag. In some instances, the Gag fusion protein will be co-transduced into a cell with Gag (unfused) in order to facilitate lipoparticle production.

Example 4

Incorporation of Intracellular Proteins

Traditional methods for drug screening have focused on membrane proteins which are present on the extracellular membrane. However, ninety-five percent of a cell's membrane structures are located within the cell itself, on organelles such as the mitochondria, golgi, endoplasmic reticulum, and nucleus (Lewin, 1994). Yet direct access to the regulatory proteins on these structures is rarely available because most have localization sequences that prevent them from reaching the cell membrane. Many of these proteins regulate metabolic activities, translocation, transcription, and translation processes that are fundamental to cell biology and disease pathways yet are difficult to study.

Like other viral envelope proteins, Hepatitis C(HCV) envelope glycoproteins E1 and E2 are promising targets for vaccine development. However, E1 and E2 are especially difficult to target with standard immunization protocols because they form a heterodimer through noncovalent interactions and are primarily expressed intracellularly on the membrane of the endoplasmic reticulum (ER), where HCV capsids are enveloped (9). When expressed in other locations, E1-E2 does not appear to form functional or structurally intact heterodimers. Thus, cell-based immunogens are not a viable option for HCV immunization, and HCV virus itself is difficult to grow in large quantities. To form lipoparticles with E1-E2 complexes, the ER-retention sequences on the cytoplasmic tails of E1 and E2 will be removed, allowing the proteins to reach the cell surface and be incorporated into lipoparticles.

In addition to the Golgi and ER, other intracellular organelles also contain membrane proteins of interest and are targeted using known retention signals. For example, peroxisomes are organelles which participate in the breakdown of fatty acids. In humans, proteins are targeted to the peroxisomes by one of two proteins. Peroxisome signal type 1 (PTS1) accounts for 95% of the targeting of proteins to the peroxisome. Peroxisomal signal type 2 (PTS2) is a second peroxisome signal. Similarly, mitochondrial proteins are targeted to the mitochondria using a signal sequence which is recognized by a chaperone protein called mitochondrial targeting signals (MTS). The mitochondria has two membranes, the outer membrane and the inner membrane. The outer membrane is very permeable due to a protein called porin. The inner membrane is not permeable due to a protein called cardiolipin. There are two transport mechanisms which function to actively move proteins through these membranes. One skilled in the art would recognize that either PTS1, PTS2, or a mitochondrial signal sequence could be deleted or replaced to retarget peroxisome membrane proteins to the cell surface for incorporation into lipoparticles.

An alternative method for generating lipoparticles containing intracellular membrane proteins is to relocalize retroviral Gag so that it buds from an intracellular location. HIV-1 particle formation normally takes place on the plasma membrane. However, mutations of the matrix domain of HIV-1 Gag have been shown to retarget the budding to the Golgi or post-Golgi vesicles (Ono, Orenstein, and Freed 2000). One can produce lipoparticles using HIV-1 Gag containing these mutations in order to capture Golgi membrane proteins from cells onto the surface of lipoparticles.

An alternative method for generating lipoparticles containing intracellular membrane proteins is to use another type of enveloped virus that naturally buds from an intracellular location. For example, the structural proteins of Hepatitis C (without the E1 and E2 envelope proteins of HCV) can be used to incorporate ER membrane proteins into the HCV virion.

Example 5

Use of a Single Chimeric Vector Adenovirus-Gag Vector to Make Lipoparticles

Murine leukemia virus (MLV)-based lipoparticles are produced using an Adenovirus expressing the structural proteins of a retrovirus. An Adenovirus vector that expresses the MLV gag gene is constructed. Recombinant Adenovirus vectors can be produced using well described recombination techniques (Ausubel, et al. (2001), Current Protocols in Molecular Biology). Once the Adenovirus-Gag vector is constructed, it is used to infect HeLa cells at a multiplicity of infection of 10 to ensure expression of Gag in every cell. One hour post-infection, the cells are transfected with a plasmid expressing the CCR5 protein from a eukaryotic promoter (pcDNA3-CCR5). Media is changed after 16 hours and cells are allowed to express the receptor and Gag proteins over the next 2-4 days at 37° C. Supernatant from these cells is harvested every 8 hours, and lipoparticles from the supernatant are purified as described in Example 1.

Example 6

Production Using Two or More Viral Vectors

Murine leukemia virus (MLV)-based lipoparticles were produced using an Adenovirus expressing the structural proteins of a retrovirus. An Adenovirus vector that expresses the MLV gag gene, in this case fused to a GFP protein, was constructed using Invitrogen's Gateway ViraPower™ Adenoviral Expression System. Briefly, the Gag-GFP gene was cloned into an 'Entry' vector that contains lambda integrase recombination sites that allow the target to be easily recombined into a variety of other 'Destination' vectors, in this case an adenovirus recombination plasmid. The adenovirus destination plasmid was transfected into HEK-293 cells, and cultured until recombinant adenovirus emerged. Recombinant adenovirus was checked by Western blot for Gag expression using anti-Gag rabbit sera. Separately, another Gag-GFP recombination Adenovirus was constructed using pCMV-LINK vector recombination with purified Adenovirus DNA, as instructed (Current Protocols in Human Genetics, 1995). Recombinant Adenovirus vectors can also be produced using other well described techniques or kits (Ausubel, et al. (2001), Current Protocols in Molecular Biology). Once the Adenovirus-Gag vector was constructed, it was used to infect 293T, BHK, HeLa, and NIH-3T3 cells at a multiplicity of infection of 10-500. Simultaneously, an Adenovirus expressing the membrane protein CCR5, produced using pCMV-LINK, was also used for infection of the same cells. Media was changed after 16 hours and cells were allowed to express the receptor and Gag proteins over the next 4 days at 37° C. Supernatant from these cells were harvested every 8 hours. One skilled in the art would recognize that similar viral expression systems could also be constructed using other viral vectors, including baculovirus, vaccinia, semliki forest virus, sindbis virus, or other alphaviruses, and expression in appropriate cell types.

Example 7

Production Using Vaccinia Virus

Recombinant vaccinia vectors will be produced by cloning MLV Gag and CXCR4 into the plasmid pSC60. Flanking the gene in this vector are recombination sites that allow the gene to be recombined into a wild type vaccinia virus (WR) when plasmid and virus are introduced into the same cell. The recombination event results in loss of the thymidine kinase gene within the virus, from which the virus can be selected (BrdU resistance). Once recombined, the recombinant virus is very stable and can be grown to high titers because the virus is replication competent. Once expanded, the vaccinia will be used for the production of lipoparticles. Lipoparticles and cells expressing lipoparticles will be characterized by Western blot for Gag expression using anti-Gag rabbit sera and for CXCR4 expression using an anti-epitope (V5) antibody. Although vaccinia can kill infected cells within 2-3 days, this length of time can be prolonged by addition of chemicals that inhibit vaccinia replication (AraC and rifampicin).

Example 8

Production Using Vaccinia Virus Encoded T7-Polymerase

Murine leukemia virus (MLV)-based lipoparticles are produced using an infection-transfection system utilizing vaccinia-expressed T7-polymerase. HEK-293T cells are transfected with a plasmid expressing the CCR5 protein from a T7 promoter. The T7 promoter is not normally active in eukaryotic cells, but can be turned on by expression of the T7 polymerase protein within the same cell. Three hours post-transfection, the same cells are infected with a vaccinia expressing the T7 polymerase (vTF1.1, MVA-T7-polymerase, or vTF7-3). Media is changed after 16 hours and cells are allowed to express the receptor and Gag proteins over the next 1-4 days at 37° C. Supernatant from these cells is harvested every 8 hours, and lipoparticles from the supernatant are purified as described in Example 1.

Example 9

Production Using Semliki Forest Virus

To create replication-competent SFV replicons, we will construct a plasmid containing an SFV replicon that is expressed from a CMV promoter and results in the production of SFV RNAs capable of replication in the cytoplasm of transduced cells. The precise 3' terminus of the SFV replicon RNA will be generated by ribozyme-mediated cleavage, a strategy used for similar constructs (West Nile Virus, Dengue virus, and SFV replicons) using the identical ribozyme (Khromykh, et al. (1998), J Virol, 72:5967-77, Khromykh, et al. (1997), J Virol, 71:1497-505, Pang, et al. (2001), BMC Microbiol, 1:18, Shi, et al. (2002), Virology, 296:219-33, Varnavski, et al. (1999), Virology, 255:366-75). SFV vectors expressing MLV gag and CXCR4 will be constructed. To produce SFV viral vectors, HEK-293T cells will be co-transfected with the plasmid encoding the SFV replicon and plasmids encoding the structural genes of SFV (capsid, E1 and E2/3). SFV will be harvested in the supernatant of these cells and stored frozen until used for infection of BHK cells to initiate lipoparticle production. BHK cells infected by recombinant SFV vectors will be characterized by Western blot for Gag expression using anti-Gag rabbit sera and for CXCR4 expression using an anti-epitope (V5) antibody.

Example 10

Capture of Naturally Expressed Membrane Proteins on the Cell Surface

The previous examples have focused on generating lipoparticles containing specific membrane proteins deliberately engineered into the lipoparticle. Lipoparticles can also be produced according to the invention from cells which contain native membrane proteins of interest (e.g. primary cells, stem cells, cell lines with interesting properties or receptors). Lipoparticles are produced using an Ad-Gag vector to deliver the structural protein of MLV. In the present example, however, no membrane protein will be exogenously introduced—the membrane protein will be expressed naturally from the cells chosen for production. This will allow us to capture naturally expressed membrane proteins from desired cell types.

Neural stem cells are cells which have the ability to self-renew, and can divide to produce all the cell types of the nervous system. One difficulty in neural stem cell biology has been the identification of these cells. The protein Nestin has been proposed to be a marker of these cells, yet Nestin is also expressed in other cell types such as astrocytes. At best, a sub-population of Nestin positive cells can act as neural stem cells. Similar problems exist with other neural stem cell markers, such as Musashi.

In order to generate lipoparticles from neural stem cells, flow cytometry is used to obtain a population of Nestin positive cells from primary culture. Lipoparticles from the Nestin positive cell membranes are then produced by infecting Nestin positive cells with an adenovirus that expresses MLV Gag. As the Gag drives budding from the cells, lipoparticles are formed containing the membrane proteins of the Nestin positive cells.

Example 11

Identification of an Infectious Pathogen

A biosensor chip is created with 95 lipoparticles in positions 1-95 and an empty position at position 96. The 95 lipoparticles each have a different membrane protein that bind to a different infectious agent. Among the 95 are membrane proteins directed against Ebola, anthrax, cholera, plague, *E. Coli*., chicken pox, HIV, HSV, *salmonella* receptor, Hepatitis A, Hepatitis B, Hepatitis C, and Influenza, including the membrane proteins CCR5, CXCR4, CD-SIGN, CD-SIGNR, CFTR, CD44 (*shigella* receptor), mannose receptor MRC1 (ricin toxin), alpha dystroglycan and beta dystroglycan (Lassa Fever and LCMV receptors), MCAT-1 (murine leukemia virus) and the anthrax toxin receptor. The lipoparticles are attached to the biosensor. A serum sample is screened against the array of lipoparticles. The biosensor indicates that the individual is infected with anthrax.

Additional membrane proteins, including all membrane proteins known to be receptors for pathogens and toxins, can be included.

Example 12

Using the Lipoparticle Biosensor to Identify Orphan Receptors, Orphan Ligands and Drug Targets Bacterial and viral pathogens enter their host cells (and eventually kill or weaken them) using a cellular receptor. Many of these receptors have been identified, but many have not. A lipoparticle biosensor is used to identify membrane proteins that interact with known pathogens. For example it is unknown how the SARS virus interacts with the cell surface to infect the cell. Screening a lipoparticle biosensor comprising the membrane proteins of a cell with a sample containing SARS virus will enable the identification of the membrane proteins which it interacts with. This screening will take place similar to the screening of the infectious agents in Example 11. Knowledge of these membrane proteins may better direct the development of therapeutics to combat SARS infection.

One skilled in the art would recognize that any virus, bacteria, toxin, etc., with an unknown cell receptor can be screened to discover unknown binding partners on the cell membrane. This will prove useful for the identification of infectious pathogens because less than 25% of them are linked to identified receptors. Similarly, one skilled in the art will recognize that the lipoparticle biosensor can be used to identify the target of a drug, protein, or peptide with an unknown surface protein interaction. Conversely, where known membrane proteins exist on the CSRB, soluble partners could be sought by washing large numbers of samples over the array.

Biosensors are capable of detecting ligands in complex mixtures at concentrations well below their $K_D$, and ligand binding can be monitored in real time, permitting accumulation of ligand during continuous flow across the surface. As such, a promising application for the lipoparticle biosensor is the identification of ligands in complex mixtures, often for "orphan" receptors that do not have known ligands ("ligand fishing") (Nedelkov, et al. (2001), Biosensors & Bioelectronics, 16:1071-1078, Nedelkov, et al. (2002), Proteomics, 2:441-446, Williams (2000), Current Opinion in Biotechnology, 11:42-46). Ligand fishing is performed on supernatant from the FC36.12 cell line to search for 13-chemokines. Cell supernatant fractions derived from the FC36.12 CD8+ T cell line were used in 1995 to identify the chemokines RANTES, MIP1α, and MIP1β as inhibitory factors of HIV (Cocchi, et al. (1995), Science, 270:1811-1815). Supernatant is flowed across a lipoparticle biosensor containing CCR5, and binding to CCR5 is monitored in real time. To verify that binding is due to β chemokines, non-competitive antibodies against the β-chemokines are flowed across to detect their presence on the lipoparticle biosensor. Alternatively, ligand is eluted (removed) from the chip using a regeneration solution (high salt, low pH, or high pH buffer) and assayed by Western blot. Additional controls can include non-specific lipoparticles, supernatant from other cell types, and inhibition of binding with blocking agents (CCR5 inhibitors, MAbs). In some embodiments, concentrated supernatants are used.

Example 13

Using the Lipoparticle Biosensor for De Novo Ligand Design

A large number of membrane proteins remain orphan receptors, without identified natural ligands. Other membrane proteins, such as CXCR4, are linked to identified ligands, but the ligands have undesirable characteristics (low affinity, low specificity, labile, highly charged). In such cases, de novo design of a better ligand, often starting with random peptides, is highly desirable. Even for proteins with well functioning ligands, de novo ligand design using peptides is often the first step in the process of rationally designing small molecule inhibitors.

A phage library displaying random 7-mer peptides is used to pan a CXCR4-biosensor chip to perform de novo ligand design. The "Ph.D. Phage Library" (New England BioLabs) contains over $2 \times 10^9$ independent clones, each carrying a random 7-mer peptide that in sum represents every possible permutation of seven amino acids. Phage are flowed over the lipoparticle biosensor surface, washed, and then eluted in successively more stringent (lower pH) elutions to collect pools of increasingly selective peptides. The pools with highest affinity for the target are amplified and re-screened to select phage with the highest affinity (or avidity in this case) for the target receptor. Approximately twenty high-affinity phage from each stage of screening are sequenced to determine any consensus sequence. One skilled in the art would recognize that phage panning could also be conducted using whole virus or virus-like particles.

Example 14

Using the Lipoparticle Biosensor to Generate Protein Interaction Maps

The lipoparticle biosensor is used to quantify the reactivity of a secreted protein with the complete set of membrane proteins that it is capable of binding to. Similar interaction maps have been deciphered for the yeast proteome and for subsets of human cytoplasmic networks, but not for membrane proteins. Biosensors are capable of detecting affinities of interaction from sub-picomolar to micromolar, enabling the complete range of reactivities to be characterized. The chemokines MIP1α, MIP1β, and RANTES are assayed on the cell surface biosensor to determine the complement of receptors to which they bind and the kinetics of interaction with each membrane protein. This screening of the lipoparticle biosensor will take place as described herein.

Example 15

Using the Lipoparticle Biosensor to Determine the Toxicity of Reactivity of a Drug Lead drug candidates are tested on the lipoparticle biosensor for binding to membrane proteins that could cause unwanted biological effects (a component of standard toxicity testing). Currently, only closely related targets are tested, and side effects that could have been avoided are often identified late in drug development. This screening of lead drug candidates will take place similar to as described herein. Briefly, each drug candidate is diluted and washed over the lipoparticle biosensor. The receptor biosensor will detect where the drug candidate interacts with a membrane protein. Particular attention will be paid to interactions with membrane proteins on the array which are known to be linked to negative drug side effects.

Known drugs can also be screened on the lipoparticle biosensor to determine if they interact with other receptors. For example, samples containing Cimetidine (Tagamet™) are screened on the lipoparticle biosensor. Cimetidine is known to interact with the Histamine H2 G-protein coupled receptor, which plays a role in ulcers. It is not known, however, how strongly Cimetidine interacts with many other membrane proteins, a question that can be answered using the lipoparticle biosensor. For example, the ability of drug such as Cimetidine to bind selectively to the Histamine H2 GPCR and not the Histamine H1 or H3 GPCRs is a strong determinant of effectiveness and side-effects. This screening of the lipoparticle biosensor will take place as described in Example 11.

Example 16

Using Lipoparticle Biosensor to Generate a Profile of Compounds Sharing a Measurable Characteristic The CSRB will be used to develop a profile of compounds sharing any measurable characteristic. Measurable characteristics could include, but are not limited to, toxicity, efficacy, solubility, absorption profiles, or the ability to cross the blood-brain barrier. The lipoparticle biosensor is able to identify similarities in the binding to cell surface proteins of compounds which share characteristics. Conversely, the lipoparticle biosensor can identify differences in binding of compounds which have different characteristics.

For example, a battery of compounds which have been determined to be non-toxic (or "safe") are screened against the lipoparticle biosensor. Each of these safe compounds (known drugs with non-toxic profiles) is screened on the lipoparticle biosensor with techniques similar to the screening described in Example 11. Membrane proteins on the lipoparticle biosensor which interact with all of the safe compounds will be considered "hits" and will constitute a positive profile of a safe compound. Conversely, membrane proteins on the lipoparticle biosensor which interact weakly or rarely with the safe compounds will be considered "misses." A similar screen using toxic compounds will generate "hits" and "misses" for toxicity. By combining the safe "hits" (membrane proteins that are bound by compounds with good safety profiles) with the toxic "misses" (membrane proteins that are bound by compounds with poor safety profiles) a profile of safe membrane proteins are generated. Such information is then used to predict the characteristics of other compounds.

One skilled in the art will recognize that a similar system of "hits" and "misses" could be used to generate profiles of any group of compounds which share a similar measurable characteristic. Compounds which elicit similar side effects, beneficial outcomes, or drug interactions could be screened with the lipoparticle biosensor to determine a profile of that characteristic.

Example 17

Using the Lipoparticle Biosensor to Pre-Screen for Non-Toxic Molecules and Compile the "Safe Candidate" Library Chemical libraries are available from commercial sources for assay validation. The library is chosen to contain known receptor agonists and antagonists, non-specific analogs within the same chemical family, and other non-specific compounds. This library is used to screen the cell surface biosensor for "lead compounds" in a trial drug screen. Drug candidates matching the profile of a safe drug (binding to membrane proteins on the lipoparticle biosensor (see Example 16) which have been associated with known safe drugs) are added to a Safe Candidate library. The Safe Candidate library will serve as a basis for traditional drug discovery with the advantage being that the candidates are pre-screened to match a profile for non-toxicity.

In this way a large library can be built even before specific targets are linked to specific diseases or phenotypes. For example, a biotechnology company may discover that a new gene (X) is involved in cancer. Rather than screen for small molecule compounds or antibodies which may turn out to be toxic, the company could screen the Safe Candidate Library, with higher confidence that any drug identified will be not toxic. In this manner, the early stages of drug development can be hastened and better molecules for human application (e.g. toxicity, bioavailability) can enter drug discovery.

One skilled in the art will recognize that candidate libraries can be constructed such that many characteristics of candidate compounds can be predicted based on profiles of known drugs. Ideally, a library of candidate molecules which fit the profile of non-toxic, cheap, easily delivered drugs will be generated.

Example 18

Using the Lipoparticle Biosensor to Identify the Interactions of Membrane Proteins with Candidate Compounds Because the lipoparticle biosensor can express all membrane proteins, small molecules can be screened against these proteins to identify reactions. In this manner, purified monoclonal antibodies and small-molecules (e.g. organic drugs) can be identified that target proteins of specific structures or phenotypes of defined function, even without knowing the precise target of interest.

A random, purified monoclonal antibody from a defined hybridoma clone is used to screen the lipoparticle biosensor. The same could be done for a chemically pure small-molecule. The protein that the antibody reacts with can then be defined. Monoclonal antibodies should react specifically with only one protein. This may be useful if antibodies (or small molecules) have effects of interest, but their targets are not known. Moreover, if a random antibody or chemical binds to a small number of targets on the array (ideally a single target), then the specificity of that antibody or chemical is defined. Screening a large number of purified monoclonal antibodies or chemically pure small-molecules will enable the development of a library of antibodies/chemicals that have already been pre-screened for the specificity desired. Moreover, if these antibodies or chemicals are also pre-screened for their toxicity, bioavailability, etc., a library of compounds will arise that has known specificity and that are pre-screened to be better compounds for drug development—i.e. a library of lead compounds to defined targets. Targets of complex nature (e.g. membrane receptors, glycosylated proteins) are particularly amenable to the array. One skilled in the art will recognize that any protein, compound, antibody, or natural or synthetic drug could be screened using the lipoparticle biosensor in this manor.

Example 19

Using the Lipoparticle Biosensor to Investigate Changes in Membrane Protein Ligands During Disease Progression or in Different Disease States The multiplexed nature of the lipoparticle biosensor enables not just single binding events to be measured, but patterns of reactivity. Like gene chips, where every feature of the array may not be completely known, correlates of reactivity can be as predictive (or more) of disease than understanding single pathways of interaction. Complex samples, such as serum, urine, and saliva from individuals with a variety of disorders, are run over the cell surface biosensor to correlate patterns of reactivity with the individual's health. The application of these samples will proceed as described in Example 11. Multifactorial causes of disease can be identified even if multiple new ligands combine to cause a physiological effect. The serum of an individual will be tested throughout the course of a viral or bacterial infection to correlate cytokine immune response with disease pathogenesis and drug treatment. A lipoparticle biosensor can measure and quantitate dynamic changes of chemokines, hormones, and biologically active peptides simultaneously.

In this way a profile of the disease will be generated similar to the generation of a profile of a drug candidate described above. For example, blood samples taken from an HSV2 patient during the latent phase of the disease may bind to a different, yet predictable, set of membrane proteins than samples taken during the active phase. This information will serve multiple purposes. First, it will help to define disease state based on measurements other than clinical assessment, and second and more importantly, it will identify membrane proteins correlated to changes in the disease. These membrane proteins are potentially important research targets for understanding the underlying disease state and for the potential development of novel treatments.

Example 20

Using the Lipoparticle Biosensor to Investigate Differences in Membrane Proteins Expressed in Different Samples of Primary Tissue/Cell Types/Organs The lipoparticle biosensor will be used in this example to generate a profile of different sources of ligands. Specific cell types, tissues or organs are obtained, lysed to liberate the proteins, and screened using the lipoparticle biosensor. In this way, all of the membrane proteins interacting with proteins from a specific sample are identified, and differences between sources will be obtained.

Two kinds of tumor samples are obtained, malignant and benign. These tumors are lysed by mechanical homogenization and the soluble proteins isolated by eliminating the membranes using centrifugation. The malignant tumor samples are examined using the lipoparticle biosensor using a similar protocol to the one described in Example 11. In this manor the cell membrane receptors that bind to the soluble proteins in the malignant tumor will be identified. Likewise, the benign tumor sample will be examined using the lipoparticle biosensor. Differences in receptor binding will be evident by comparing the samples.

Example 21

Receptor Biosensors Designed to Represent Two or More Different Populations

Lipoparticles are generated from various cell types, tissues, or organs. An organ-specific receptor biosensor is constructed by making lipoparticles from all of the human organs and arraying them onto a biosensor. Lipoparticles are generated as described above, except the cell source will be primary tissue which is not expressing membrane proteins other than those found naturally on the cells. Candidate libraries could be screened for candidates that interact with a specific organ but not with others. Similar receptor biosensors could be constructed to investigate specific binding in tissues or specific cell types. Such a biosensor could also be constructed to look at differences between tumor kinds, healthy vs. diseased organs or tissues, or differences before and after stimulation of a region using a chemical or other stimulus. One skilled in the art will recognize that any population with distinct differences in membrane proteins could be compared in this way.

Example 22

Receptor Biosensors Designed to Represent Two or More Species

Receptor biosensors are designed such that the lipoparticles containing membrane proteins from human and bacteria are included on the same biosensor. The lipoparticles will be produced as described above with the exception being that the membrane proteins expressed on the cell surface are bacteria. The human receptor lipoparticles will comprise proteins only found in humans. Such a receptor biosensor is screened with a library of potential antibiotics to find candidates which interact with bacterial membrane proteins but do not interact with human membrane proteins.

It is evident to one skilled in the art that other lipoparticle biosensors containing two or more samples from different sources of lipoparticles could be constructed to distinguish differential candidate interactions.

Example 23

Portable In-Field Diagnostics

A lipoparticle biosensor surface is used to create in-field use devices for detecting samples interactions with membrane proteins. This tool comprises a receptor biosensor surface including relevant proteins, a portable biosensor, and a microprocessor to interpret the data and provide real time readout.

Versions of this tool will be designed using a lipoparticle biosensor, which can test for infectious agents, water quality, food quality, and the like.

The samples analyzed by the lipoparticle biosensor kits can originate from many sources, including but not limited to biological fluids taken from an organism, liquid samples from nature, man made liquid samples, aerosols, or dissolved biologic or man-made solids from various sources. Size and weight of the receptor biosensor are not essential to the invention, however the preferred size will be a biosensor that can be carried in one hand, weighing not more than fifty pounds, more preferably not more than ten pounds, and more preferably not more than one pound.

Example 24

Lyophilization of Lipoparticles

To test their stability, lipoparticles starting in 10 mM Hepes 7.0, 30 mM NaCl were suspended in increasing amounts of sucrose, trehalose, or glycerol, and lyophilized overnight. The lyophilized mixture was resuspended in water to their original starting particle count of 20 E+6 per ul, based on the pre-lyophilization counts. Once resuspended, the lipoparticles were tested for retention of membrane protein structure by VELISA using a CXCR4-specific conformation-dependent monoclonal antibody. The results demonstrated that the addition of sucrose, trehalose, or glycerol allowed the retention of membrane protein structure during lyophilization, as seen by the continued binding of CXCR4 to the MAb 447.08 (FIG. 4A). The results also demonstrate that the lipoparticles lose their native structure without such additives, as demonstrated by the lack of binding of lipoparticles lyophilized without additive (0%). Controls included in the same experiment indicated the additives alone did not produce these effects (FIG. 4B).

The lipoparticles were also tested for size and purity after lyophilization by dynamic light scattering, showing a monomodal 200 nm peak when lyophilization occurred in the presence of sucrose, similar to the type of peak seen with unlyophilized lipoparticles (FIG. 5). Without sucrose, the lipoparticles showed spurious peaks at higher sizes, suggesting aggregation or destruction of the lipoparticles. A similar experiment was also conducted by drying the lipoparticles at room temperature and testing for the retention of CXCR4 structure by biosensor analysis. These lipoparticle also retained CXCR4 structure. One skilled in the art would recognize that other drying techniques and other additives such as glucose could also be used.

Example 25

Attachment to Biosensor Surfaces

Lipoparticles were immobilized to a BIACORE C1 chip through two non-covalent attachment methods. In the first, 400 RU of WGA (wheat germ agglutinin, 1.0 mg/ml in Hepes pH 7.0, 100 mM NaCl) was covalently attached via amine coupling to the C1 chip in flow cell 4. 6000 RU of NeutrAvidin (Pierce, 1.0 mg/ml in Hepes pH 7.0, 100 mM NaCl) was immobilized in flow cell 2 by the same reaction. Both proteins were diluted to 0.5 mg/ml immediately prior to injection in 10 mM pH 4.5 acetate buffer. Injections were performed at 20 .mu.l/min and were proceeded by 7 minute injections of 5× (1M and 0.25M) EDC/NHS solutions, and proceeded by quenching of the activated carboxylates with a 7 minute injection of 1M ethanolamine.

Figure 6:
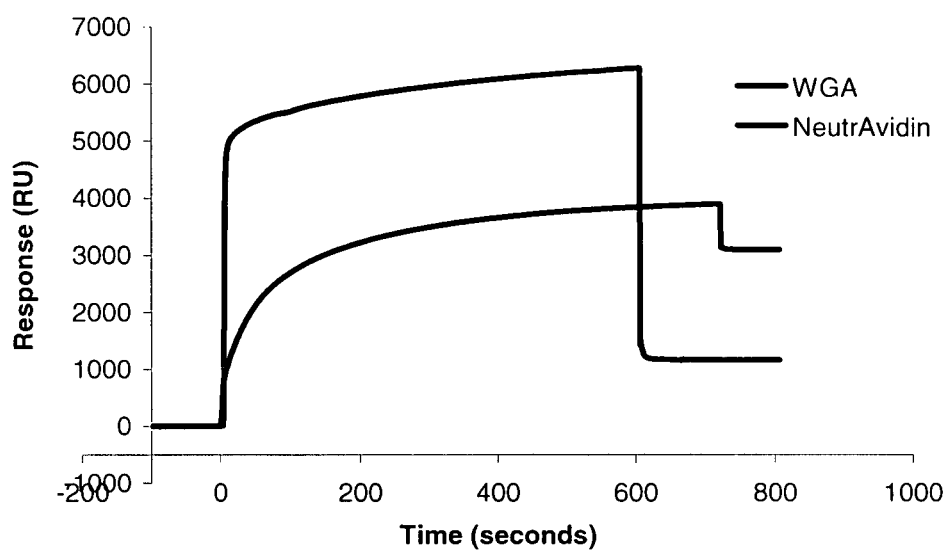
FIG. 6. Lipoparticles were attached to a C1 biosensor chip via WGA attachment or via NeutrAvidin attachment, as indicated. NeutrAvidin attached lipopaticles were first biotinylated.

Lipoparticles were then injected at a flow rate of 5 $1$/min. Lipoparticles diluted to 30 million particles per microliter in Hepes pH 7.0, 100 mM NaCl were injected over the attached WGA in flow cell 4 for 720 seconds, resulting in approximately 3000 RU of immobilized particles (FIG. 6).

Biotinylated lipoparticles were prepared with Sulfo-NHS-LC-biotin, performed for one hour in pH 8.0 PBS buffer with an excess of reagent relative to total protein content of 1000 to 1. The chemically biotinylated particles were in 10 mM Hepes, pH 7.0 100 mM NaCl, and were purified after biotinylation by column chromatography on anionic exchange resin, and further purified by high speed centrifugation and buffer exchange. Chemically biotinylated particles, determined to be 10 million particles per microliter, were injected over flow cell 2 containing attached neutravidin at a rate of 5 microliters/minute for 10 minutes, resulting in approximately 1100 RU attachment (FIG. 6).

One skilled in the art would recognize that lipoparticles, viruses, or virus-like particles could be captured in similar ways. Lipoparticles, viruses, or virus-like particles could also be captured to surfaces by mixing the particles in solution with a capture agent, such as WGA-biotin, and then flowing the particles over a suitable surface, such as avidin. Lipoparticles could also be captured using a membrane protein in the lipoparticle, such as a transmembrane-anchored avidin fusion protein or a fusion protein containing a His-tag, that allows attachment of the lipoparticle to a suitable surface such as biotin or $Ni^{+2}$.

Example 26

Attachment to a Hydrophobic Biosensor Surface

Figure 7:
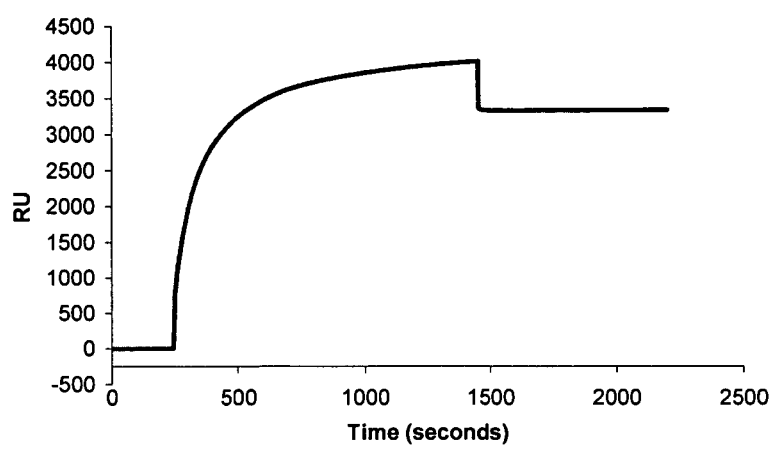
FIG. 7. An E1 chip was constructed and lipoparticles were attached to it via hydrophobic interactions.

An "E1" chip was created by incubation of gold chip (BIACORE Au Sia kit, cleaned by rinsing with 100% ethanol) in 0.1 mM DSPE-PEG(2000)-PDP (90/10, v/v EtOH, $diH_2O$), a gold (Au) reactive PEG molecule functionalized with lipid tail groups that acts as attachment points for lipoparticles. The surface was rinsed in 100% EtOH, followed by $diH_2O$, dried with pressurized air, and assembled into a BIACORE chip cartridge as per kit directions. The chip was prepped with three injections of 0.2% deoxycholate prior to injection of lipoparticles. Lipoparticles (diluted with Hepes pH 7.0, 100 mM NaCl to a final concentration of 30 million/ul) were injected for 10 minutes at 5 ul/min, resulting in approximately 3200 RU of binding (FIG. 7).

Example 27

Making Lipoparticle Biosensors Based on Lipoparticles Arrayed on Slides

The spotting of lipoparticles onto slides offers the fastest method for large-scale multiplexing of lipoparticles on a biosensor. Biosensor surfaces are currently being developed as chips for arrays, in addition to more traditional 96- and 384-wells. The ability to array lipoparticles on a biosensor chip would enable the detection of thousands of membrane protein interactions simultaneously. When large sets of binding interactions are measured simultaneously, patterns of binding can be indicative of disease and health profiles. Lipoparticles can be disrupted by harsh conditions and the proteins within them are dependent on the integrity of the lipid membrane for retention of structure. Dehydration while arraying may cause a significant loss of functional activity.

Two procedures are used in the spotting of lipoparticles onto a glass slide. First, one can use a surface chemistry (gamma-aminopropylsilane, GAPS) that has been reported to stabilize membrane proteins within lipid environments on the surface of slides (Fang, et al. (2002), J Am Chem Soc, 124: 2394-2395). This chemistry was used by this group to attach membrane vesicles to glass slides, and the membrane proteins were demonstrated to adhere, withstand extensive washing, and maintain their ability to bind ligands. Second, one can include preservatives to the lipoparticles preparation that can stabilize membrane structures even under extreme conditions. For Example, the simple carbohydrate trehalose (naturally found in insects and plants to help them withstand harsh conditions) has proven to stabilize viruses, proteins, and lipids under conditions including lyophilization, dehydration, and heating (Bieganski, et al. (1998), Biotechnol Prog, 14:615-620, Paiva, et al. (1996), Biotechnol Annu Rev, 2:293-314). Other additives (glycerol, sucrose, gelatin) have also been used as preservatives.

One skilled in the art will recognize that while the preferred use of lipoparticles linked to a glass slide will be screening by biosensor, it is also possible to screen the slide by labeling the probes. The glass slide biosensor will be hybridized with marked probes. The probes consist of any sample to be tested for interaction with membrane proteins which have been labeled using fluorescent molecules such as Cy3 or Cy5, radioactive molecules, enzyme-linked molecules, or biotinylated molecules. Labeled slides can be read using a variety of methods depending on the labeling technique, including using computerized readers currently produced to read microarrays. One skilled in the art would recognize that such probes can consist of a fluorescent, enzymatic, biotinylated, or radioactive tag.

Example 28

Lipoparticles and Biosensors to Detect Multi-Protein Complexes

The propensity of multiple proteins to form larger complexes is a fundamental attribute of pathways going to, from, and within a cell (also sometimes termed "proteomics"). Protein interaction maps have been constructed using the biosensor (Nedelkov, et al. (2001), Biosensors & Bioelectronics, 16:1071-1078, Nedelkov, et al. (2001), Proteomics, 1:1441-1446) and other techniques, but such maps are difficult to construct for membrane proteins. Lipoparticles containing the chemokine receptor CXCR4 (or CCR5) are attached to a biosensor chip. A complex of HIV gp120 and sCD4 (soluble versions of each that lack transmembrane domains) are bound to the CXCR4 molecule, as previously performed (Hoffman, et al. (2000), Proc. Natl. Acad. Sci. USA, 97:11215-11220). Non-blocking antibodies to gp120 and sCD4 are then sequentially introduced. Next, secondary antibodies against the primary antibodies (e.g. anti-rabbit, anti-mouse) are sequentially introduced. Finally, antibodies targeted to tags on the secondary antibodies (horseradish peroxidase, alkaline phosphatase) are introduced. The detection of these proteins indicates that multi-protein complexes can be detected.

Example 29

Lipoparticles and Biosensors for Antibody Characterization

One of many applications for the lipoparticle-biosensor is the characterization of antibodies directed to membrane proteins. There are many sources of large panels of candidate therapeutic monoclonal antibodies against membrane protein targets that need to be characterized for kinetics and specificity. Traditional methods of analysis for membrane proteins (competitive radioligand binding or ELISA) are often not sufficient to derive the information (on-rate, off-rate, affinity, specificity) that they desire in an efficient manner. For example, a panel of 10-20 CXCR4 and CCR5 antibodies were previously isolated and characterized (Baribaud, et al. (2001), J. Virol., 75:8957-8967, Lee, et al. (1999), J. Biol. Chem., 274:9617-9626). The lipoparticle biosensor is to be used to measure each antibody's on-rate, off-rate, affinity, and specificity. For each antibody, these measurements can be gathered in a single experiment. Monovalent Fab fragments of each MAb are used to ensure accurate analysis of kinetic data.

In another embodiment, the lipoparticle biosensor comprises lipoparticles that express membrane-bound antibodies. Lipoparticles are prepared that contain membrane-bound antibodies. The antibody can be a whole antibody or a fragment of an antibody such as a Fab fragment, an immunoglobulin-fusion protein, a single-chain Fv, an Fc-fusion protein, or combinations thereof. Each antibody can be specific for a known or unknown epitope or target proteins. The lipoparticles are spotted in an array on the lipoparticle biosensor. The array is screened against proteins of interest in order to identify which, if any, of the antibodies on the array bind the protein of interest. The ligand used to bind the array of lipoparticles can be an antibody, protein, peptide, drug, or another lipoparticle. In another embodiment, the array is prepared using lipoparticles expressing T-cell receptors.

Example 30

Lipoparticles and Biosensors May be Used to Track the Quality of an Immunization or to Detect Antibodies Against Particular Infections Blood samples are taken at various stages after an immunization. The antigen which is the target of the immunization is included on the lipoparticles. The addition of boosters will depend on the binding to that antigen on the biosensor. Upon measuring low binding, a booster is administered to the individual or animal. Upon measuring high binding, no booster is administered.

This technology is similarly used to determine if a patient has been exposed to infections. Lipoparticles on the array contain antigens recognizable to antibodies circulating in the blood of the patients. Epitopes for diseases such as influenza virus, respiratory syncytial virus, HSV1, HSV2, varicella zoster, Epstine Bar Virus, HHV8, or different kinds of HPV are included on the array. One skilled in the art will recognize that any protein that is potentially recognized by antibodies generated against a disease can be included. In some embodiments, this lipoparticle biosensor is used for diagnosis of infections, giving the physician the ability to screen for hundreds of potential infections simultaneously.

Example 31

Kinetic Analysis of MAbs Directed to Membrane Proteins

As a result of optimization, we can reproducibly attach lipoparticles to a BIACORE biosensor chip, detect the binding of unlabeled molecules as small as 8 kDa (the chemokine SDF-1), and can detect with a sensitivity down to 20 pM (with MAbs). Importantly, we are able to detect binding of the HIV-1 Envelope protein gp120 to one of its receptors (CXCR4) and we are able to detect binding of whole virus (lipoparticles containing receptors) to the biosensor chip surface conjugated with a MAb. One of the highlights of this optimization has been the enablement of the first kinetic analysis of MAbs against membrane proteins (FIG. 3B), a major application of the BIACORE biosensor that was previously limited to non-membrane protein targets. In this example, nine different monoclonal antibodies against GPCRs were characterized for their on-rate, off-rate, and affinity.

Example 32

Creation of Sensory Biosensor

This Example involves the creation of a lipoparticle biosensor, such that known membrane proteins having functions known or suspected to be involved in the senses of smell and taste are incorporated into the array. The receptors that mediate the senses of taste and smell fall into the category of membrane proteins, primarily G-protein coupled receptors and ion channels. Such a tool will have extensive applications for diagnostics, biodefense, food quality, water safety, and narcotics detection. A lipoparticle biosensor is constructed that contains all known membrane proteins involved in the senses of taste and smell, with each receptor being incorporated into a lipoparticle and the lipoparticle biosensor being composed of many such lipoparticles. As related membrane proteins are discovered, they will also be incorporated into the lipoparticle biosensor.

The creation and screening of the Sensory Biosensor will closely parallel the methods described in Example 11. First, lipoparticles are produced containing known membrane proteins having functions known to be involved with taste and smell. Second, these lipoparticles are attached to a biosensor surface. Finally, this lipoparticle biosensor will be screened using samples to determine the presence of constituent molecules that stimulate specific taste and smell receptors. The result of this Example will be a tool to aid in the rapid testing of multiple samples for a large number of potential stimulants. One skilled in the art would also recognize that a similar system could also be used for detection of contaminants or components of other liquids, gases, beverages, foods, chemicals, perfumes, cosmetics, alcoholic beverages, narcotics, or aqueous solutions.

Example 33

Effect of Additives on Antibody Binding to Lipoparticles

The effects of additives on the binding of antibodies to a membrane protein in a lipoparticle were measured. 10,000 RUs of the CXCR4 monoclonal antibody 12G5 were amine-coupled to the surface of a CM5 chip (available from BIACORE, Piscataway, N.J.) (Flow Cell 2, Fc2). Fc1 contained 10,000 RUs of mouse IgG. The data were reference subtracted using the signal from the mouse IgG surface. Additives were mixed with lipoparticles just before their injection across the biosensor surface. The large spikes were due to changes in refractive index between running buffer and sample solution magnified by the increased viscosity of additives. BSA was not used in these experiments. The additives had different effects on the binding of the antibody to lipoparticles containing CXCR4 on their surface (data not shown).

Example 34

Detection Ability of Antibody Binding to Lipoparticles

To determine the ability of the biosensor to detect antibody binding to the lipoparticles, different concentrations of antibody were screened against a biosensor surface comprising attached lipoparticles containing CXCR4. Lipoparticles containing CXCR4 were coupled to the surface of a BIACORE biosensor C1 chip. Monoclonal antibody concentrations down to 20 picomolar were detected (FIG. 3A). A plot of 'apparent' $k_{on}$ v $k_{off}$ for nine different (bivalent) monoclonal antibodies against CXCR4 and CCR5 was created (FIG. 3B). Each kinetic data point is derived from a dilution series of the monoclonal antibody binding to attached lipoparticles. Points falling on the same diagonal line have the same $K_D$. Each binding series fit a bivalent model, and $K_D$ was calculated using the ratio of $k_{off}$ to $k_{on}$.

Example 35

Incorporation of an Ion Channel

Figure 8:
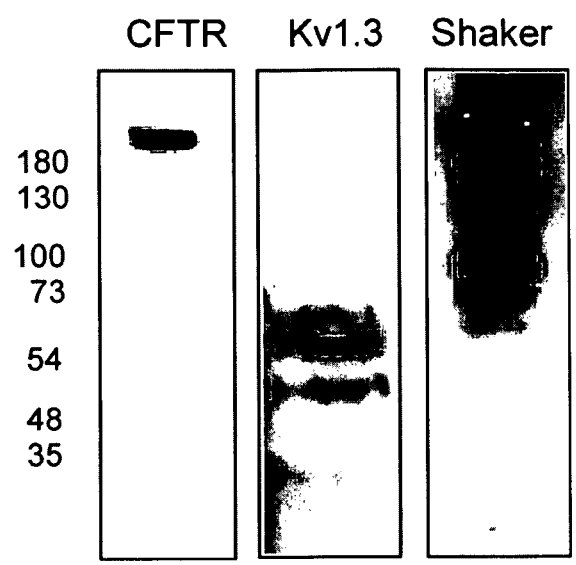
FIG. 8. Incorporation of ion channels. Incorporation of the ion channels CFTR, Kv1.3, and Shaker into three different preparations of lipoparticles. Ion channels were detected by Western blot using epitope tags on the ion channels (V5 tag on CFTR and Kv1.3, and FLAG tag on Shaker).

Membrane potential is generated and maintained by concentration gradients of charged ions, as regulated by selective ion channels and transporters. Potassium ion (K+) channels have been particularly well studied due to their primary importance in excitable cells (see (Deutsch (2002), Annu Rev Physiol, 64:19-46, Ford, et al. (2002), Prog Drug Res, 58:133-168)). A number of toxins are known to bind specifically to K-channels, a bacterial K-channel has been crystallized, and a variety of K-channels with various regulatory features have been defined and characterized. *Drosophila* Shaker (GenBank Accession Number M17211, GI: 157063) is a voltage-regulated (opens upon depolarization) K-channel that serves as a prototype ion channel herein due to its extensive characterization. Lipoparticles containing Shaker, as well as two other ion channels (Kv1.3 and CFTR) (FIG. 8) were produced as described herein by co-transfecting 293 cells with plasmids encoding MLV Gag and the ion channel under the control of CMV promoters.

Example 36

Detection of Membrane Potential

Like many ion channels, Shaker is a complex membrane protein, containing six transmembrane domains and forming tetramers in the membrane (Deutsch (2002), Annu Rev Physiol, 64:19-46). The structural integrity of its active and non-active conformations is confirmed by ligand binding and functional assays. Even if the ion channel does conduct ions, it is possible that it may conduct for too brief a period to be detected (e.g. through inactivation or ion depletion). To allow for this possibility, we will be using an inactivation-gate removed variant of Shaker. Various methods for detection are described herein to detect even brief changes in membrane potential (e.g. substrate injection, fast response probes).

The purity and concentration of membrane protein can be important in determining sensitivity and signal-to-noise. For ion channels, in which a hundred channels can be responsible for an entire cell signal, membrane protein density may not be a critical parameter. To test this, lipoparticles are prepared with high, medium, and low amounts of Shaker (on a relative basis) by varying the amount of DNA ranging from 5-40 µg per 10 cm dish used to prepare the lipoparticles. These preparations are then tested to determine signal-to-noise and sensitivity to correlate functional response with protein density.

Figure 9:
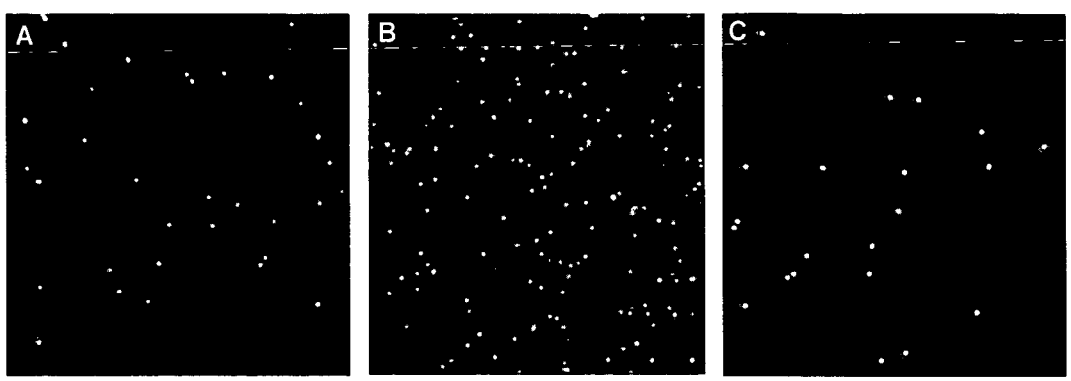
FIG. 9. Fluorescence microscopy of GFP or di-4-ANEPPS labeled Lipoparticles. A. Lipoparticles containing the fusion protein CXCR4-GFP were imaged by fluorescence microscopy. B. DI-4 ANEPPS was added to lipoparticles to visualize them. C. 0.2 micron YG Fluoresbrite beads (Polysciences, Inc.) were imaged at the same magnification as the other two panels for comparison.

The lipoparticles were then loaded with the dye. Unlike water-soluble dyes, membrane potential probes are lipophilic, simplifying the incorporation and use of the dye with lipoparticles. As previously used (Montana, et al. (1989), Biochemistry, 28:4536-4539, Rohr, et al. (1994), Biophysical Journal, 67:1301-1315, Venema, et al. (1993), Biochim Biophys Acta, 1146:87-96), the membrane potential probe di-4-ANEPPS was obtained as a powder, resuspended in ethanol, and added to an aqueous solution containing lipoparticles to a final concentration of 5 µM. The dye partitions into membranes nearly instantaneously, as shown in FIG. 9.

One skilled in the art would also recognize that additional changes in the composition of the lipoparticle could be introduced in order to facilitate ion channel measurement. Such changes can include changing the internal ion concentration, changing the membrane lipids, modulating fluorescent dye content, or modulating water content. For example, lipoparticles can be soaked in high potassium buffer for several days in order to equilibrate the internal content of the lipoparticles with the ion concentration of the outside buffer. Similarly, purified lipids can be added to suspensions of lipoparticles where the lipids will partition into the lipoparticle membrane. One skilled in the art would also recognize that membrane enveloped viruses, such as influenza, could also be loaded with a membrane potential dye as described herein.

Example 37

Testing for Ion Channel Function

Experimental use of labeled lipoparticles containing functional K-channels follows well-established protocols (Montana, et al. (1989), Biochemistry, 28:4536-4539, Rohr, et al. (1994), Biophysical Journal, 67:1301-1315, Venema, et al. (1993), Biochim Biophys Acta, 1146:87-96). Shaker lipoparticles are purified and resuspended in low K-buffer (1 mM KCl in 10 mM Hepes, plus sucrose to maintain osmolarity). Lipoparticles are aliquoted into 96-well plates just before use (100 µg/ml final concentration in 100 µl), and inhibitory toxins are incubated with the ion channels for 30 min. Assuming that the lipoparticle has an internal K+ concentration less than 150 mM and that its lipid membrane is intact and impermeable to K+, addition of high K-buffer (150 mM KCl in 10 mM Hepes buffer) will initiate depolarization. If no ion channel is present, membrane potential will be maintained as long as lipoparticles remain intact (half life of several hours at 37° C.), and thus no further fluorescence change will be observed. If a functional voltage-regulated K-channel is present, the ion channel will open in response to depolarization and a change in fluorescence of di-4-ANEPPS will occur.

96-well format fluorometry detectors are used. The most useful detectors permit ratiometric detection of two emitted or excited wavelengths. An example detector is Wallac Victor® fluorescence detector. Due to the low internal volume of lipoparticles, transmembrane electrochemical gradients are expected to reach equilibrium rapidly and with very small ion concentration changes. In order to capture even fleeting signals generated milliseconds after addition, an automated injector is used to add high-K buffer to samples. Lipoparticles containing high and low quantities of ion channels for increased stability of signal are also tested.

Failure to detect a specific signal can be categorized in two ways: no signal or non-specific signals. In the first case, lack of a signal is measured as the same fluorescence before and after addition of high-K buffer, as compared to control lipoparticles lacking the ion channel of interest. Primary causes may be lack of correct protein conformation, rapid equilibration of potassium across the membrane, or low sensitivity of detection. In the second case, a non-specific signal is measured as an increase in fluorescence in both experimental and control lipoparticles. Primary causes may be contaminating ion channels in the lipoparticles or leakiness of the lipoparticle membrane. These issues are addressed with the use of contaminating protein inhibiting toxins and impermeable ion substitutes, production from other cell types, control of buffer ionic strength, and, if necessary, direct measurement of the leakiness of the viral membrane. Because the absolute value (in mV) of membrane potential can be measured (see calibration with valinomycin, below), no membrane potential fluorescence (0 mV) can be distinguished from non-specific high membrane potential fluorescence.

The level of fluorescence detected from membrane potential dyes or fluorescent probes is calibrated to measure the absolute value of electrical membrane potential in mV. Absolute measurements are important as an internal control, for comparison of inhibitors, toxins, and new ion channels, and for comparison to others' results using different detection systems. The most widely used calibration procedure is based on membrane potential clamping to a potassium equilibrium diffusion potential. Saturating amounts (1 μM) of valinomycin is added to cells at gradients of potassium solution from 0-150 mM. A calibration curve is plotted to correlate fluorescence to membrane potential, as calculated from the Nernst equation. One skilled in the art would also recognize that membrane enveloped viruses, such as influenza, could also be tested for ion channel function as described herein.

Example 38

Ligand Binding

A prerequisite for ion channel function within lipoparticles is the correct conformation of the ion channel. Table 12 lists some toxins and the ion channels to which they bind. Toxins that bind to Shaker have been well characterized for their ability to bind under defined conditions and in defined conformational states; in many cases, binding can distinguish active vs. non-active conformations.

TABLE 12

Inhibitors of K-channels

| Toxin | Binding/Blocking Conditions |
|---|---|
| Charybdotoxin | Blocks Kv1.3 and Shaker |
| | Binds strongly (10 pM) to closed K-channels (−70 mV) |
| | Ca inhibits binding |
| | Low ionic strength, high pH (8.5) enhances binding |
| Alpha-Dendrotoxin | Blocks Kv1.3 and Shaker |
| | Binds strongly under low ionic strength conditions |
| | Binds very weakly under high ionic strength conditions |
| Agitoxin-2 | Blocks Kv1.3 and Shaker |
| Margatoxin | Blocks Kv1.3, not Shaker |
| Iberiotoxin | Blocks Ca-activated K-channels, not Kv1.3 or Shaker |

Charybdotoxin (CHTX), a 37 amino acid (4.3 kDa) peptide purified from scorpion venom can be used as one method to demonstrate that the Shaker channel is conformationally intact within lipoparticles. CHTX is a highly specific, potent, and impermeant blocker of both Shaker and Kv1.3, and is resistant to functional degradation under in vitro culture conditions. Ionic conditions strongly influence the ability of CHTX to bind and block (see table above) and can serve as additional specificity controls. Other controls can include, for example, identical lipoparticles that contain an unrelated receptor or no receptor. CHTX and additional toxins of known specificity (dendrotoxin, iberiotoxin, margatoxin, and others as necessary) can be used within the following binding experiments:

Biosensor Binding. Lipoparticles containing Shaker are covalently bound to BIACORE biosensor chips and used to detect direct binding of ligands to the membrane protein.

Direct Binding. Labeled toxins (radioactive or fluorescent) are used to assess direct interaction with the Shaker ion channel. Direct binding of labeled toxins can be readily performed using a filtration assay with minor modifications, similar to experiments we have performed previously (Baik, et al. (1999), Virology, 259:267-273, Deutsch, et al. (1991), J. Biol. Chem., 266:3668-3674, Doranz, et al. (1999), J. Virol., 73:10346-10358, Doranz, et al. (1999), J. Virol., 73:2752-2761). In cases where labeled toxins are not available, unlabeled toxins are used to competitively inhibit binding of a labeled toxin.

Example 39

Detection within Microfluidic Devices

The ability to present structurally intact, functional ion channels within a 100 nm particle allows more advanced technologies to be used for drug discovery against them. Lipoparticles are used within several microfluidic devices to test their compatibility for the detection of functional response. Multiplexed microfluidic devices with the capability of detecting hundreds to thousands of samples simultaneously will be preferred.

Detection of ion channel activity is performed on a Caliper 250 workstation. $2 \times 10^7$ lipoparticles are loaded into wells of a LabChip™. The lipoparticles are labeled by loading membrane potential indicators into a well of the LabChip and the Caliper 250 mediates mixing and integration of dyes into the lipoparticle membrane. Various buffers containing PBS alone, and PBS containing agonists/antagonists as described herein are utilized to determine specificity and activity of the ion channels. The agonists/antagonists are titered to determine a dose response curve for each molecule. The Caliper 250 performs screening of the samples by mixing small volumes of lipoparticles (>50 ul) with the various buffer solutions and detecting changes in fluorescence associated with a change in membrane potential eluded to by changes in fluorescence of indicators of membrane potential integrated into the lipoparticles as described above. Ligands and toxins used for experimentation include but are not limited to those described above. In addition, antagonists and toxins with known activity such as those identified herein can be used as a control for ion channel blocking. Thereafter, high throughput screening applications are established to observe the effects of various compounds on ion channel activation and thus membrane potential changes. One skilled in the art would recognize that additional detection devices, including microfluidic devices, flow cytometry, a 96-well plate, a 384-well plate, a 1536-well plate, a glass slide, a plastic slide, an optical fiber, a flow cytometer, a microscope, a fluorometer, a spectrometer, or a CCD camera could also be used.

Example 40

Subcellular Detection

Lipoparticles are used as nanometer-sized sensors of ions and voltage to probe the synaptic junctions and intracellular compartments of, for example, living neurons. Fluorescent measurements are taken using a microscope in both resting cells (absolute levels of ions or membrane potential) and in cells responding to stimuli (relative changes). As a model system, primary neurons or N-tera 2 (NT2, Stratagene Cloning Systems) cells are used, which can be differentiated into neuron like cells that contain all of the physical properties of neurons and can be grown in culture. Lipoparticles are labeled with membrane potential dye as described in Example 35. The lipoparticles are microinjected either into or onto the NT2 cells or neurons. The cells or neurons are activated using electric charge to artificially depolarize the membrane thus causing activation. Alternatively, the NT2 differentiated neurons are activated by addition of 100 µM γ-aminobutyric acid (GABA) or N-methyl D-aspartate (NMDA). Both of these neurotransmitters have been shown to cause membrane depolarization in neurons using patch clamp techniques. Activation of the NT2 cells causes changes in membrane potential and ion concentration in areas around the cell that is detected using lipoparticles containing reactive fluorescent dye. Organelles such as mitochondria can also be monitored by targeting lipoparticles to the mitochondria. In addition, membrane potential is observed near the site of neurotransmitter release, using fluorescent lipoparticles responsive to membrane potential to determine how membrane potential affects vesicle fusion events.

Example 41

Cell Based Detection

Nanometer-sized sensors of ions and voltage are used to probe membrane potential of various cells upon activation. Lipoparticles containing membrane potential dyes are attached to membranes of Jurkat T-cells (ATCC) and primary T-cells isolated from normal human volunteers. The T-cells are activated using antibodies targeted against CD3, a member of the T cell receptor complex that induces cell activation. In addition, SDF-1alpha, a ligand for CXCR4, is also used to observe cellular activation states upon stimulation of CXCR4, thus mimicking some aspects of HIV infection. Observation is performed using fluorescence microscopy to verify expected changes in lipoparticle fluorescence. Subsequently, microfluidic devices such as those described herein will be utilized for HTS of inhibitors of activation.

Example 42

Amino Acid Transporters and Microfluidic Devices

Lipoparticles are used to monitor the ability of amino acid transporters to move amino acids across a membrane. Specifically, MCAT-1 is incorporated into a lipoparticle(s). Microfluidic devices described herein are employed to detect transporter activity. MCAT-1 containing lipoparticles are loaded into a well of a LabChip. In another well, tetramethylrhodamine (TR) is loaded and subsequently mixed with the lipoparticles whereby the TR is loaded into the lipoparticle. Fluorescein (FL) tagged amino acids are added into wells of the LabChip for eventual mixing with lipoparticles. In addition, MCAT-1 agonists and antagonists are loaded into wells of the LabChip. The Caliper 250 mediates mixing of the lipoparticles with the TR. Once the TR has entered the lipoparticle, they are mixed with either control buffer or buffer containing an agonist or antagonist of MCAT-1. Once this process is finished, the lipoparticles are exposed to the FL tagged amino acids. The ability of MCAT-1 to mediate transport of the amino acids into the lipoparticle is evaluated by measuring the resonance energy transfer (RET) between the FL-amino acids and the TR in the lipoparticle. RET is a very sensitive technique to measure interaction between participating fluorophores. Therefore, minute changes in RET determines the efficiency of transport across the lipoparticle membrane. Different pairs of fluorophores capable of participating in RET can also be used to determine presence of amino acids that have been transported.

Example 43

Amino Acid Transporters

Lipoparticles are used to monitor the ability of amino acid transporters to move amino acids across a membrane. MCAT-1 is incorporated into lipoparticles. MCAT-1 containing lipoparticles are placed in an eppendorff tube. Radioactive amino acids are added into tubes with the lipoparticles. A buffer containing cofactors necessary for MCAT-1 activity (e.g. ATP) is also added. The lipoparticles are incubated with the radioactive amino acids for 1 hour and then separated from free amino acids by spinning the lipoparticles through a sucrose cushion. The ability of MCAT-1 to mediate transport of the amino acids into the lipoparticle is evaluated by measuring the radioactivity remaining in the lipoparticles. Lipoparticles without MCAT-1 will serve as negative controls. On skilled in the art would also recognize that other types of detection could also be used, such as the incorporation of fluorescent amino acids.

Example 44

Fluorescent Dye Incorporation into Lipoparticles

Lipoparticles containing the fusion protein CXCR4-GFP were generated by methods described herein. The lipoparticles were imaged by fluorescence microscopy to visualize the expression of the protein and to visualize the lipoparticles. FIG. 9A demonstrates the signal generated by CXCR4-GFP. To determine if a fluorescent dye is capable of being incorporated into a lipoparticle DI-4 ANEPPS was added to the lipoparticles. As discussed above, the dye does not fluoresce unless it is incorporated into lipids. FIG. 9B demonstrates that the lipoparticles can be visualized after adding DI-4 ANEPPS, thereby indicating that the dye has been incorporated into the lipoparticle. For comparison, 0.2 micron YG Fluoresbrite beads (Polysciences, Inc.) were imaged at the same magnification as the other two panels (FIG. 9C).

Example 45

Using a Lipoparticle to Generate an Immune Response in a Mouse

Lipoparticles were used to generate polyclonal antibodies against the GPCR chemokine membrane proteins CCR5 and CXCR4. CCR5 and CXCR4 are chemokine receptors that are also used by HIV as a cellular receptor (Berger, et al. (1999), Annu. Rev. Immunol., 17:657-700). The chemokine receptors CCR5 and CXCR4 have been well studied and have been shown to be involved in HIV infection, hematopoiesis, breast cancer metastasis, stem cell migration, neuronal development, and rheumatoid arthritis. In order to better understand their structure and function, both of these receptors have previously been incorporated into lipoparticles (Endres, et al. (1997), Science, 278:1462-1464, Hoffman, et al. (2000), Proc. Natl. Acad. Sci. USA, 97:11215-11220).

The production of lipoparticles containing CCR5 and CXCR4 has been previously described (Hoffman, et al. (2000), Proc. Natl. Acad. Sci. USA, 97:11215-11220). Briefly, 293T cells were transfected overnight with 120 µg of plasmid expressing the receptor CCR5 or CXCR4 and 30 μg of pCGP (encoding for MLV-gag/pol under the control of the CMV-promoter). The following morning, the medium was replaced with fresh media supplemented with 10 mM sodium butyrate (an up-regulator of the CMV-promoter). Supernatants were harvested after approximately 2 days. Lipoparticles were purified by filtration of supernatants through a 0.45 μm filter and ultracentrifugation through a 20% sucrose cushion. To detect incorporated proteins, particles were analyzed by Western blot using an anti-MLV-gag antibody to detect the primary structural protein of the virus and anti-receptor antibodies to detect the receptor of interest or a tag on the receptor. For the purposes of the present experiments, lipoparticles were produced using human HEK-293 cells. HEK-293 cells are a human embryonic kidney cell line. Lipoparticles can also be produced in murine 3T3 cells or retroviral packaging cells (e.g. PA317 cells) that constitutively produce MLV virus in order to produce an antigen using cells syngeneic to the immunized host.

Two mice were immunized for each receptor (4 mice total). Each mouse was immunized with approximately 100-200 μl of sample at a concentration of 0.5 mg/ml by injecting mice intraperitoneally and then boosting three times at days 14, 21, and 49 each with 50-100 μl additional lipoparticles at the same concentration. The dosage was based on total viral particle protein. No adjuvant was used in initial experiments in order to retain the complete structure of the lipoparticles and membrane proteins.

Figure 10:
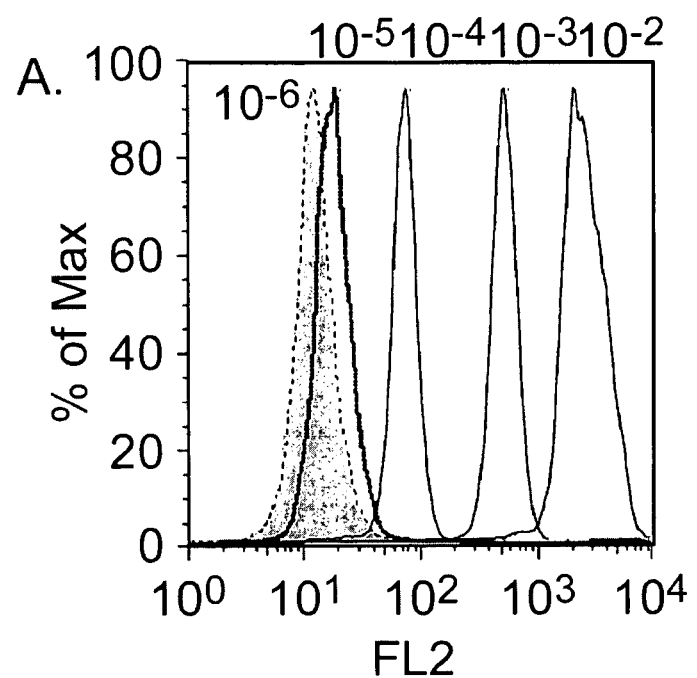
FIG. 10. Reactivity of mice sera against native cell surface proteins demonstrates reactivity specific for the parental cell line. A. Serum diluted from 1:100 to 1:1,000,000 was used to stain parental HEK-293 cells. This mouse was immunized with 125 ug of CXCR4 lipoparticles. The shaded curve indicates pre-immune sera (indistinguishable from the $10^{-6}$ dilution, dashed line) B. Serum (1:100) derived from a mouse immunized with 300 ug CCR5 lipoparticles was used to stain different cell types (NIH-3T3, quail QT6, Hamster CHO, or human HEK-293 cells, which express little or no endogenous CCR5 or CXCR4). The same Prebleed (shaded curve) and Test bleed (open curve) sera were tested against all cell types. Each flow cytometry curve was generated using 30,000 cells stained with mouse serum and PE-coupled secondary antibody. Cells were fixed in 200 ul paraformaldehyde prior to flow cytometry.
Figure 10:
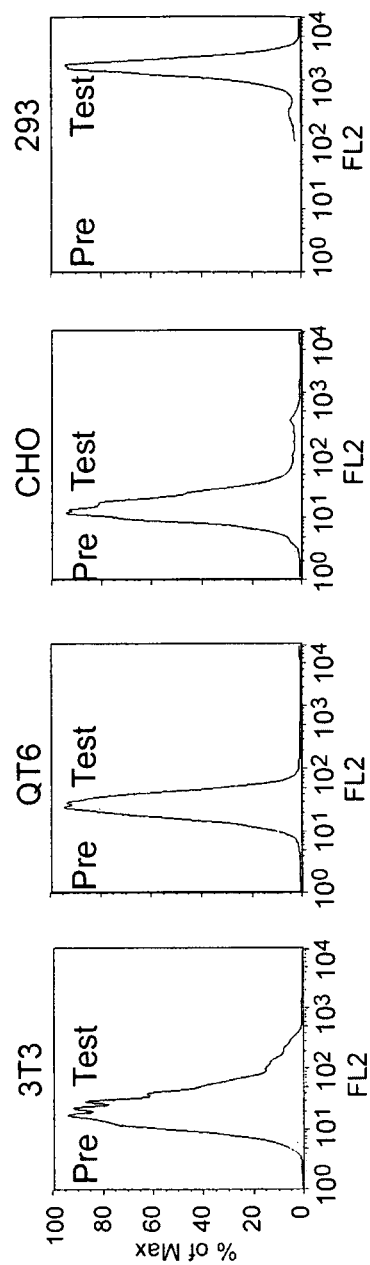
Figure 11:
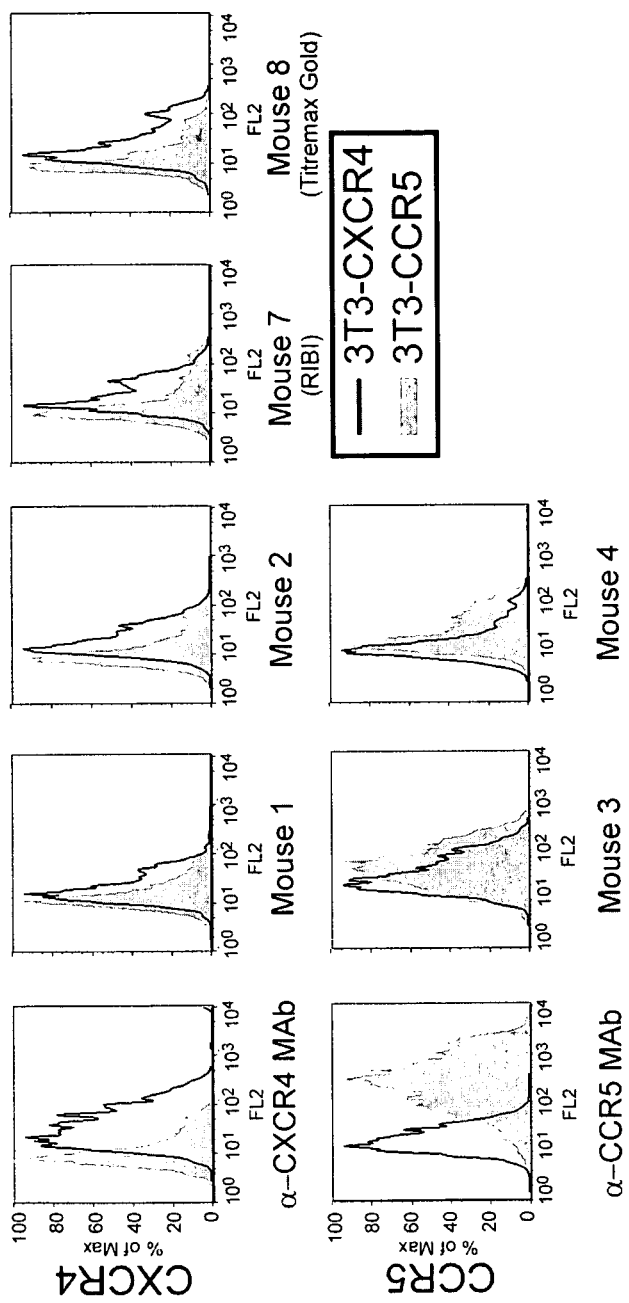
FIG. 11. Lipoparticles induce a sera response against CXCR4 and CCR5. Sera (1:100) from mice injected with lipoparticles containing CXCR4 (top panel) or CCR5 (bottom panel) were tested by flow cytometry for reactivity against the membrane proteins using NIH-3T3 stable cell lines expressing either CXCR4 (line) or CCR5 (shaded). The lipoparticles resulted in detectable and specific antibody responses. The two left-most panels show the response of control antibodies against CXCR4 (447.08) and CCR5 (45523).
Figure 12:
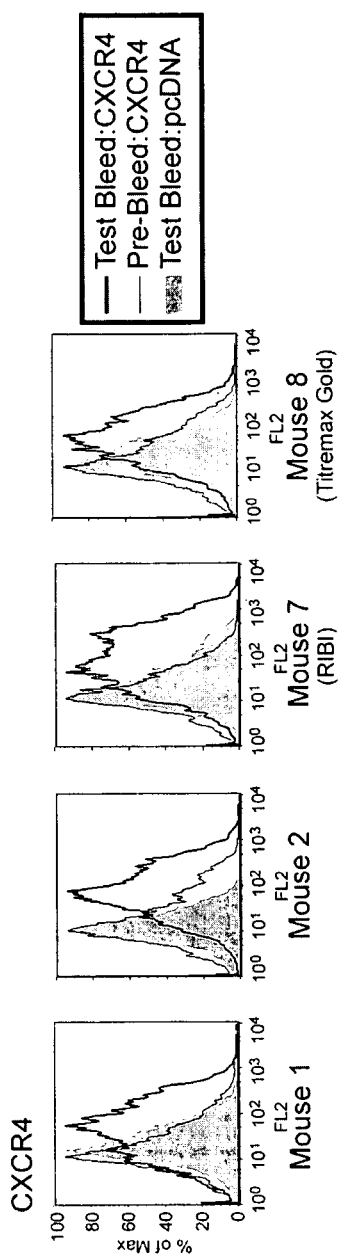
FIG. 12. Effect of adjuvants on immune response. Tests were conducted to ascertain the effect of two adjuvants, RIBI and Titremax Gold, on the immune response to membrane proteins within lipoparticles. Baby Hamster Kidney (BHK) cells were transiently transfected with CXCR4 or pcDNA3 vector (no membrane protein) using Lipofectamine 2000 with approximately 60% transfection efficiency (not shown). Cells were then stained with test bleed or pre-bleed sera (1:100) from each mouse and tested by flow cytometry. Results suggest that mice immunized with CXCR4 lipoparticles produced antibodies against CXCR4.

The sera from each mouse was collected by retro-orbital bleed and screened by flow cytometry and western blot. Sera from lipoparticle-immunized mice were first analyzed by flow cytometry to identify their reactivity against parental HEK-293 cells. Flow cytometry results demonstrated that a strong immune response was generated against the surface molecules of the parental HEK-293 cell. As little as a 1:100,000 dilution of mouse serum was sufficient to stain the surface of 293 cells (FIG. 10A). Testing of cell types not involved in the immunization indicated little or no cross-reactivity (FIG. 10B), indicating that the response was specific to molecules from the 293 cell-derived lipoparticle surface. Flow cytometry analysis of sera from lipoparticle-inoculated mice also revealed that antibodies were generated against the membrane protein of interest (FIGS. 11 and 12).

Figure 13:
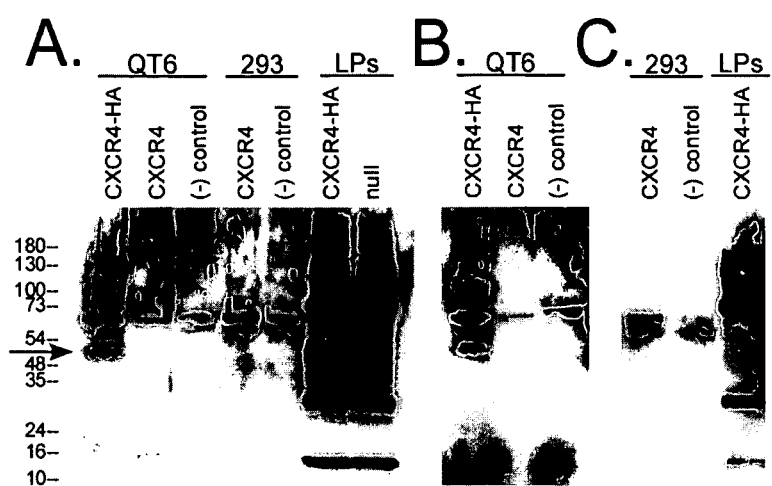
FIG. 13. Western blot analysis of sera from mice. Sera from mouse #2 (A) and mouse #1 (B) (both immunized with CXCR4-HA lipoparticles) reacted with the HA epitope tag, but did not detect untagged CXCR4. Arrow indicates the 50 kDa CXCR4-HA band. A dimer of CXCR4-HA is detected in B. A 60 kDa background band is seen in all cell lysates. Negative control cells are untransfected and do not express CXCR4 or CCR5. C. A lighter exposure of a serum reacting with the lipoparticle (LPs) Gag protein is shown. The Gag protein is cleaved by the viral protease into several subfragments.
Figure 14:
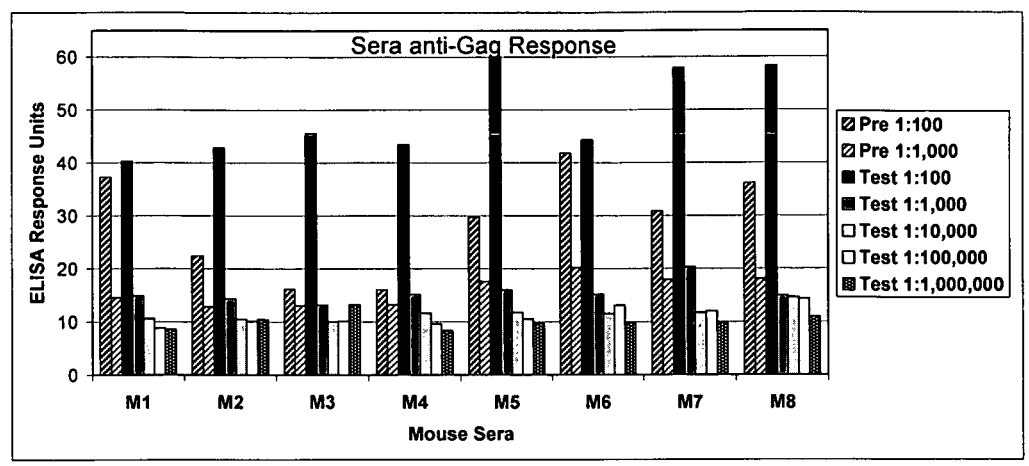
FIG. 14. Response of mice sera to Gag. The response of mice sera to Gag, the structural protein of lipoparticles, was tested using an ELISA assay. Null lipoparticles (without membrane proteins) lysed in Triton X-100 were used as a source of Gag and captured to wells of an ELISA plate. Both pre-bleed and test bleed sera were tested for reactivity against Gag. All mice test sera exhibited a response to Gag. 5 of 8 pre-bleed sera also exhibited a response to Gag. Since lipoparticle Gag is from Murine Leukemia Virus (MLV), these results may be explained if mice were previously infected by naturally occurring MLV, which is quite common. By ELISA and western blot, mice sera exhibited no significant reactivity against 293 cell lysate (not shown).

Western blot is an alternative method of analyzing a sera response. However, detection is limited to linear (non-conformational) epitopes because the proteins are denatured during analysis. Western blot analysis of sera from lipoparticle-immunized mice showed little reactivity with 293 cell lysate or other (QT6 cell) lysates (FIG. 13). ELISA results against Triton-disrupted 293, NIH-3T3, CHO, and QT6 cell lysates were similarly non-reactive with mice sera (data not shown). The lack of response to 293 cell lysates suggests that antibodies against undesired intracellular proteins from producer cells were not generated. However, western blot (FIG. 13) and ELISA (FIG. 14) did reveal a large response against the Gag structural protein of the lipoparticle. The antibody response to Gag does not interfere with hybridoma screening because cells do not naturally express Gag.

In some of the lipoparticle inoculations, CXCR4 with a C-terminal HA tag (CXCR4-HA) was used. The resulting sera demonstrated a clear reactivity with the HA-tagged protein (FIG. 4) but not with the untagged protein, indicating that sufficient CXCR4-HA protein was present in the lipoparticle preparations to generate antibodies against it.

Polyclonal antibodies directed against CCR5 and CXCR4 are thus generated. Standard CCR5 and CXCR4 polyclonal antibodies are used for inhibition of HIV infectivity, blocking of chemokine binding and signaling, localization of receptors during intracellular trafficking, detection of expression in cells and tissues, and blocking of HIV gp120 binding.

Example 46

Generation of Monoclonal Antibodies Using an Antigenic Composition Comprising a Lipoparticle The production of lipoparticles is discussed herein and the immunization protocol for the generation of polyclonal antibodies as described above is followed.

The sera from each mouse is screened for antibody production. Flow cytometry can be used to determine reactive sera. Stably transfected cell lines expressing CCR5 or CXCR4 are used for detection. Alternatively, sera can be screened against cells expressing either CCR5 or CXCR4 in a cell-ELISA format (CELISA) as described herein. The spleens from the mice giving the strongest response are harvested, and the B cells therefrom are fused with murine myeloma cells to form hybridomas following standard protocols (Harlow, E. and D. Lane. *Antibodies: A laboratory manual*. Cold Spring Harbour Laboratory Press. 1988).

The resulting hybridomas are screened and those exhibiting antibody production are diluted to achieve single-cell isolation and grown to produce enough supernatant for screening antibodies. Hybridoma supernatants are screened using CELISA as the first test to detect native cellular expression of the receptor on human cells. Briefly, stably transfected cells expressing either CCR5 or CXCR4 are adhered to an ELISA plate and incubated with supernatant from each hybridoma at a 1:5 dilution. Binding is detected with GAM antibody. To verify reactivity, Mabs are screened using untransfected cells as a negative control.

In some embodiments, where stable cells are not available for the cellular protein of interest, a number of alternate screening mechanisms are employed on an as-needed basis. First, transiently transfected cells are employed because cells can be prepared with minimal effort and for which prolonged expression is not necessary. This can be particularly useful if the protein of interest is toxic. Second, inducible cell lines can be prepared that express the receptor of interest under an inducible promoter. Third, the hybridomas are screened against lipoparticles themselves. In particular, sera from mice immunized with lipoparticles are screened against lipoparticles containing the same protein. Finally, cells can be permeabilized to allow access to intracellular epitopes.

The hybridomas having reactive supernatants are then expanded in number and are typed for immunoglobulin class. The antibodies can be produced in milligram quantities by injecting the hybridomas in mice intraperitoneally and harvesting the ascites fluid.

Similar to as was performed above, Western blotting is used to determine if Mabs are directed to linear epitopes of receptors. Lysates of cells expressing CCR5 or CXCR4 are run on SDS-PAGE under denaturing conditions, transferred to PVDF membranes, cut into strips, and reacted with Mabs. Antibodies to linear epitopes of CCR5, Mabs to epitope tags on CCR5 and CXCR4, and mouse and rabbit seras previously made against CCR5 and CXCR4 serve as positive controls. Reactivity of a Mab to a receptor by Western blot is indicative of recognition of a non-conformational, linear epitope within the receptor. Previous Mabs directed to linear epitopes against CCR5 (e.g. Mabs CTC5 and CTC8) are all directed to the first thirteen amino acids of the receptor (distal N-terminus), and were all produced by immunization with cells expressing CCR5 in the presence of Freund's adjuvant (Lee, et al. (1999), J. Biol. Chem., 274:9617-9626). Previously, only one Mab to a linear epitope of CXCR4 (4G10) has been isolated, and that Mab was produced using an N-terminal peptide.

Flow cytometry is used to complement CELISA in determining which Mabs are best for detecting antigen on the cell surface. Stably transfected cell lines expressing CCR5 or CXCR4 are used for detection. Different conformations of CCR5 and CXCR4 can be expressed on different cell lines, and many Mabs, such as 12G5 against CXCR4, are capable of recognizing only a subset of these conformations (Baribaud, et al. (2001), J. Virol., 75:8957-8967, McKnight, et al. (1997), J. Virol., 71:1692-1696). Therefore, cell lines that express CCR5 or CXCR4 endogenously (e.g. PM1 cells and HeLa cells, respectively) are tested against select Mabs for reactivity within different cellular contexts.

The structure and function of over one hundred CCR5 and CXCR4 mutations has previously been characterized, including CCR5 N-terminal truncations, CCR5-CCR2 receptor chimeras, CCR5 mutations that individually change each extracellular charged amino acid to Alanine, CXCR4-CXCR2 chimeras, and CXCR4 point mutations (Blanpain, et al. (1999), J. Biol. Chem., 274:34719-34727, Doranz, et al. (1997), J. Virol., 71:6305-6314, Doranz, et al. (1999), J. Virol., 73:2752-2761, Edinger, et al. (1997), Proc. Natl. Acad. Sci. USA, 94:4005-4010, Lu, et al. (1997), Proc. Natl. Acad. Sci. USA, 94:6426-6431, Rucker, et al. (1996), Cell, 87:437-446). These genetic panels are used to characterize the antigenic structure of the Mabs that are isolated using lipoparticle immunizations. In particular, receptor chimeras are used to quickly and accurately identify CCR5 and CXCR4 domains that are involved in Mab binding.

CELISA using transiently transfected cells facilitates the rapid screening of large numbers of Mabs against a large number of mutations or conformations of a protein in a 96-well format. Flow cytometry can be used to test some Mabs for reactivity against select mutations or conformations of a protein, for example, to identify the epitope that the antibody recognizes. Quantitative flow cytometry, which can determine the affinity of a Mab for a receptor using quantitative standards, can also be employed to distinguish antigenic reactivity from affinity.

Example 47

Epitope Mapping

Epitopes of several dozen Mabs against CCR5 and CXCR4 that have been produced using various immunization protocols have been previously mapped (Baribaud, et al. (2001), J. Virol., 75:8957-8967, Lee, et al. (1999), J. Biol. Chem., 274: 9617-9626). Each of these antibodies can be compared to antibodies produced using lipoparticles. These antibodies were mapped using the same panels of CCR5 and CXCR4 mutants identified above, so competition with lipoparticle-derived Mabs provides a confirmation of epitope reactivity.

Competition assays are used to determine the Mabs that have unique or overlapping epitopes with the Mabs currently available. These assays are done by CELISA in 96-well format for high throughput mapping using biotinylated Mabs. Cells expressing either CCR5 or CXCR4 are incubated with a Mab produced according to the present invention, and then a biotinylated Mab that has been previously characterized is used to bind to the same cells. The inability of a biotinylated Mab to bind would suggest that the test Mab was bound to the same or an overlapping epitope used by the biotinylated Mab.

Panels of CCR5 and CXCR4 Mabs were previously tested in functional assays to determine their ability to block ligand binding and virus infection (Baribaud, et al. (2001), J. Virol., 75:8957-8967, Lee, et al. (1999), J. Biol. Chem., 274:9617-9626). Specifically, the ability of these panels to block binding of radiolabeled chemokines ($^{125}$I-labeled RANTES and MIP-1α against CCR5, and SDF against CXCR4), binding of radiolabeled HIV gp120 ($^{125}$I-labeled JRFL and CM235 against CCR5, and HXB against CXCR4), signaling of chemokines (chemotaxis assays using SDF and CXCR4-containing cells) and entry of HIV virus (JRFL, ADA, and BaL against CCR5, HXB against CXCR4) was assessed. Standard CCR5 and CXCR4 Mabs are utilized for mapping of receptor structures, inhibition of HIV infectivity, blocking of chemokine binding and signaling, localization of receptors during intracellular trafficking, detection of expression in cells and tissues, and blocking of HIV gp120 binding. Mabs generated according to the present invention allow similar questions to be addressed for different membrane proteins.

Example 48

Making Mabs Against a Multimeric Membrane Protein

For Mab production against a complex single-TM protein, the single-spanning membrane protein DC-SIGN is used. DC-SIGN has been characterized extensively. DC-SIGN is a type II integral membrane protein that is expressed at high levels on dendritic cells (DCs) and that functions as a homotetramer. A related receptor, DC-SIGNR, is expressed on endothelial cells in the liver, lymph node sinuses, placenta, and intestine. DC-SIGN binds to both ICAM-2 and ICAM-3, and in so doing mediates interactions between dendritic cells and endothelial cells and T-cells, respectively. In addition, HIV and SIV bind with high affinity to DC-SIGN, and this binding event appears to account in large measure for the ability of DCs to efficiently mediate infection of T-cells. It has been proposed that HIV-DC-SIGN interactions may also play a role in sexual transmission of virus. After crossing the epithelium, HIV encounters immature, DC-SIGN positive DCs in the submucosa. If HIV binds to these cells, it is believed to be transported to regional lymph nodes as a consequence of normal DC trafficking, thus delivering infectious virus to the major site of HIV replication in vivo. To test this model, antibodies to DC-SIGN are generated that potently inhibit virus binding to DC-SIGN. Such antibodies can be used in the rhesus macaque model to determine if they impact sexual transmission of either SIV or SHIV in this animal model (SHIVs are SIV particles that bear an HIV envelope protein).

Mabs to DC-SIGN are generated as described herein. Briefly, lipoparticles containing DC-SIGN are produced and used to immunize mice. The sera is screened for reactivity and hybridomas established for antibody production.

Example 49

Making Mabs Against an Ion Channel Protein

Kv1.3 is a well-studied type of potassium channel (K-channel) that actively transports potassium ions across the cell membrane. Kv1.3 is expressed in T-cells, and inactivation of this channel results in the suppression of T-cell activation. A specific inhibitor of Kv1.3 would be useful as a therapeutic immunosuppressant. Kv1.3 spans the lipid bilayer six times and functions as a tetramer in the membrane. Kv1.3 is highly conserved and the majority of the protein is buried in the lipid bilayer (Doyle, et al. (1998), Science, 280:69-77), explaining why only a handful of Mabs have ever been elicited to any K-channel and those few Mabs have been generated using peptides and fusion proteins.

Mabs to Kv1.3 are generated as described herein. Lipoparticles containing Kv1.3 are produced and used to immunize mice. The sera is screened for reactivity and hybridomas established for antibody production.

The ability of Kv1.3 to form homotetramers has been well-studied, and mutations in T1, its tetramer-formation domain, eliminate its ability to tetramerize (Doyle, et al. (1998), Science, 280:69-77, Lu, et al. (2001), Biochemistry, 40:10934-46). By producing cells which express either wild-type Kv1.3 or the mutant non-oligomerizing form of Kv1.3, the Mabs with reactivity against the monomer and the tetramer can be produced. Mabs that have proven reactive against tetramers of the K-channel (the primary screen) are screened against cells that express monomeric Kv1.3. Mabs that react with tetrameric but not monomeric Kv1.3 are assumed to recognize epitopes in Kv1.3 that are formed when the protein oligomerizes. Such Mabs would be highly valuable in determining, among other questions, when during the synthesis of Kv1.3 within the cell does oligomerization and functional activation occur.

Example 50

Making Mabs Against ErbB2 and ErbB4

Members of the Epidermal Growth Factor (EGF) family of receptors are single transmembrane Tyr kinase proteins that operate as homo-dimers or heterodimers. Members of this family have been implicated in tumor growth, and the combination of receptors expressed within a tumor has been shown to have an effect on the severity of the tumor. For example, in medulloblastomas, the expression of ErbB2 and ErbB4 has a worse prognosis for the child than if the tumor only expressed one of these receptors. This raises the possibility that the heterodimer of the receptors is forming in the more deadly tumors (see, for example, Gilbertson R J, Perry R H, Kelly P J, Pearson A D, Lunec J. (1997), "Prognostic significance of HER2 and HER4 co-expression in childhood medulloblastoma." Cancer Research August 1; 57(15):3272-80).

By expressing different combinations of Erb receptors in lipoparticles, the generation of Mabs specific to a certain combination of subunits is possible. Screening the Mabs is accomplished using CELISA with cells that express either a single Erb receptor subunit forming homodimeric receptors or with cells expressing known combinations of receptor subunits which will form heterodimers. A Mab for a specific combination will bind to cells expressing that combination but not to cells expressing only one type of subunit or a different combination of receptor subunits.

Mabs that can distinguish between the heterodimer and the homodimers of these receptors are useful to clinically test the combinations of these receptors in tumors, and possibly help direct specific therapies.

Example 51

Making Mabs Against a Constitutively Active Receptor

Monoclonal antibodies are generated against mutant constitutively active receptors following a procedure that is similar to examples herein. Cysteine substitutions in the extracellular regions of the ErbB4 receptor result in a constitutively active form of the receptor. Lipoparticles containing this mutant are used to generate Mabs against the active form of the receptor.

Example 52

Using Lipoparticles to Generate Antibodies Against Proteins where Conformation is Less Important Lipoparticle are used as an antigen delivery tool for single membrane spanning proteins or tethered soluble proteins.

Proteins that span the membrane once (CD4, Neuropilin, and Plexin-2) can also be embedded within lipoparticles (Hoffman, et al. (2000), Proc. Natl. Acad. Sci. USA, 97:11215-11220). However, single-TM proteins are less dependent on a lipid membrane for their conformation; many can simply be truncated just before their transmembrane domain in order to create a soluble form of the protein that often retains the same extracellular structure as the intact protein.

Polyclonal and monoclonal antibodies to the single transmembrane protein CD4 are generated as described in Examples 1 and 2. Briefly, cells over-expressing CD4 are used to produce lipoparticles containing CD4. These particles are used to immunize mice. The sera is screened for reactivity and either polyclonal antibodies will be collected or hybridomas established for monoclonal antibody production. The antibodies generated will be screened as described herein.

The CD4 antibodies generated are compared to other available antibodies in a variety of tests including binding, cross-reactivity, and efficacy in inhibiting an immune response.

Example 53

Making an Antibody Against a Non-Membrane Protein

Another application for the lipoparticle is to link soluble proteins to the membrane of the lipoparticle in order to generate a Mab. Resistin is a soluble protein derived from adipocytes. In mice, Resistin has been demonstrated to cause insulin resistance and glucose intolerance, symptoms which are stereotypic of Non-Insulin-Dependant Diabetes Mellitus (NIDDM, or Type 2 diabetes). The administration of anti-resistin antibodies have been demonstrated to improve blood sugar and insulin action in obese mice. Generation of a variety of human Mabs to Resistin may help patients of Type 2 diabetes.

Resistin is tethered to the lipoparticle in several ways. First, Resistin is linked to phospholipids-poly(ethylene glycol) (PL-PEG) (Wong et al. Science, 1997, 275:820-822; L1 and Kao Biomacromolecules. 2003 July-August; 4(4):1055-67). Incubation of Resistin-PL-PEG with lipoparticles results in coating of the lipoparticles with Resistin extending from the membrane.

Alternatively, a fusion protein of a transmembrane domain (the transmembrane domain of CD4) and Resistin is expressed in a 293 cell line. Lipoparticles are produced from these cells which have Resistin on the exterior of the membrane. Additionally, Resistin can be linked to a GPI anchor and expressed on cells for lipoparticle production.

The Resistin-linked lipoparticles are injected into mice as described herein. Polyclonal and monoclonal antibodies to Resistin-linked lipoparticles are generated as described in examples herein. Briefly, lipoparticles containing linked-Resistin are produced and used to immunize mice. The sera is screened for reactivity and either polyclonal antibodies will be collected or hybridomas established for monoclonal antibody production.

Example 54

Using Lipoparticles to Make Specific Antibodies to Activated Receptors

CCR5 is incorporated into lipoparticles as described herein for other membrane proteins. Lipoparticles containing CCR5 are incubated with MIP1α (ligand to CCR5) resulting in the binding of the ligand to the receptor. Unique epitopes formed by the bound receptor are present.

As described herein, the lipoparticle with the bound receptor-ligand complex is used to generate an immune response in mice. This is accomplished by using the lipoparticles directly after incubation and relying on the interaction between the receptor and the ligand to be maintained during the immunization.

Alternatively, after incubation with the ligand, the lipoparticle/receptor/ligand complex is cross-linked in order to covalently bind the receptor to the ligand. Determination of the cross-linker is dependent on the specific functional groups and can be determined empirically. A water-soluble membrane impermeable cross-linker is used because the interaction between the ligand and the receptor is outside the membrane. This technique results in a stronger bond between the receptor and ligand. Initially, 5-10 mM EGS (ethylene glycol bis[succinimidylsuccinate]) is combined with the ligand and the receptor lipoparticle for 30 minutes at 37° C. The cross-linked lipoparticle/receptor/ligand complex is kept on ice until injected into the animal for antibody production.

CELISA, as described herein, is used to screen seras, with the additional step of screening the antibodies against cells expressing the bound receptor-ligand complex. Antibodies specific to bound receptor should be positive in the presence of MIP1α but negative in cells which have the receptor but have not had ligand presented.

Alternatively, MIP1α is linked to PL-PEG as described in Wong et al (1997) Science 275, 820-823. MIP1α-PL-PEG is incubated with lipoparticles containing CCR5. During this incubation the PL-PEG molecule incorporates into the lipid membrane of the lipoparticle. With the MIP1α tethered to the lipoparticle, the interaction between the ligand and receptor is likely and diffusion of the ligand away from the receptor is unlikely. Antibodies are generated against the lipoparticles as described above. CELISA is performed with the additional step of adding MIP1α to one group of cells to be screened against. Antibodies specific to bound receptor are positive in the presence of MIP1α but negative in cells which have not had ligand presented. Antibodies can further be screened against "bathed" lipoparticles that have been pre-incubated with ligand from the above example.

Example 55

Generation of Antibodies Against Lipoparticles Containing Membrane Proteins Produced from Natural Cell Sources Antibodies are generated against naturally occurring membrane proteins. Lipoparticles will be produced as described above and using an Ad-Gag vector to deliver the structural protein of MLV as described in U.S. Provisional No. 60/491, 477, however, no membrane protein is exogenously introduced—the membrane protein is expressed naturally from the cells chosen for production. This allows the capture of naturally expressed membrane proteins from desired cell types.

Neural stem cells are cells which have the ability to self-renew, and can divide to produce all the cell types of the nervous system. One difficulty in neural stem cell biology has been the identification of these cells. The protein Nestin has been proposed to be a marker of these cells, yet Nestin is also expressed in other cell types such as astrocytes. At best, a sub-population of Nestin positive cells can act as neural stem cells. Similar problems exist with other neural stem cell markers, such as Musashi.

In order to generate lipoparticles from neural stem cells, flow cytometry is used to obtain a population of Nestin positive cells from primary culture. Lipoparticles from the Nestin positive cell membranes are produced by infecting with a semliki forest virus vector that expresses MLV Gag. As the Gag drives budding from the cells, lipoparticles are formed containing the membrane proteins of the Nestin positive cells.

It can also be useful to generate antibodies which recognize subpopulations within this group. Mabs are produced which recognize the proteins of the Nestin lipoparticles. These Mabs are screened against cultures of Nestin positive cells. Mabs which identify subpopulations within these cultures are identified. These antibodies can then be used to further employ flow cytometry analysis and subdivide the population.

Example 56

Using Lipoparticles to Generate Mabs Against Receptor Variants

Antibodies to HHV8 ORF74 are generated. ORF74 is incorporated into lipoparticles for immunization. Cells expressing the activated (wild type) conformation of the receptor are used to screen the Mabs that result from this immunization. Positively reacting Mabs are characterized for their ability to recognize active vs. non-active conformations of the receptors by screening Mabs for reactivity against cells expressing non-active forms of the receptor (G-protein coupling can be destroyed in nearly any GPCR by changing the conserved Asp-Arg-Tyr (DRY) motif in the second intracellular loop). Mabs that recognize the active form of the receptor but fail to recognize the non-active form of the receptor are assumed to have extracellular epitopes that are induced to form upon intracellular G-protein coupling.

To differentiate conformational changes induced by the mutations from conformational changes induced by G-protein coupling, wild type ORF74 is chemically uncoupled from G-proteins (inhibitors such as pertussis toxin and cholera toxin can uncouple many GPCRs, and analogs of GTP, such as GTP-gamma-S, can also lock GPCRs in a coupled or uncoupled state). In addition, Mabs are screened against additional independent mutations (e.g. DRY-box mutants (Doranz, et al. (1997), J. Virol., 71:6305-6314, Doranz, et al. (1999), J. Virol., 73:2752-2761),) that fail to signal. As an alternative screening procedure, Mabs to inactive conformations of receptors are produced by immunizing with lipoparticles expressing non-active forms of GPCRs, screening for reactivity against the same, and then counter-screening for Mab reactivity with constitutively activated forms of the receptor.

Example 57

Generation of Antibodies for Specific Epitopes

The Mabs produced in the examples described herein have been directed against entire receptor structures such as the extracellular region of CXCR4. In some cases, however, antibodies that react with all epitopes of the receptor are not desired. For example, of many Mabs targeted to CXCR4, only one has ever been isolated that targets the amino terminus of the receptor. That Mab was raised against a peptide sequence of the amino terminus, is not conformationally sensitive, does not block chemokine binding or signaling, does not block HIV infection, and has only weak affinity (Baribaud, et al. (2001), J. Virol., 75:8957-8967). The amino terminus of CXCR4 has been shown by several groups to play an integral role in chemokine interaction and HIV fusion. In addition, no Mabs to the third extracellular loop of CXCR4 have yet been identified. Such Mabs could be useful as western blotting reagents, for detecting structural changes in the receptors, for blocking HIV and chemokine interactions, and for screening compounds to these molecules that target specific domains of the receptor. Traditional methods of Mab production, however, may never elicit such Mabs.

Therefore, Mabs targeting epitopes of CXCR4 are generated using mutations to target epitope reactivity. Specifically, CXCR4-CXCR2 chimeras are used in which each domain is substituted individually or in combination with the equivalent domain of the other receptor (Baribaud, et al. (2001), J. Virol., 75:8957-8967, Doranz, et al. (1999), J. Virol., 73:2752-2761, Lu, et al. (1997), Proc. Natl. Acad. Sci. USA, 94:6426-6431). A chimera that contains the amino-terminus of CXCR4 but the extracellular loops of CXCR2 (a chimera termed 4222) has been previously created (Doranz, et al. (1999), J. Virol., 73:2752-2761). An equivalent panel with CCR5-CCR2 chimeras can also be used. To screen for CCR5 or CCR2 epitope-reactive antibodies.

Such chimeras are used to produce Mabs against specific domains of desired receptors. For example, lipoparticles are produced containing the chimeric receptor 4222 and these lipoparticles are used for immunization. The resulting Mabs are screened against wild type CXCR4, and positive clones will be counter-screened against the background parental receptor, CXCR2. Mabs that are raised against 4222 and recognize CXCR4 but do not recognize CXCR2 are presumed to be directed to the amino terminus of CXCR4. Mabs that react with both receptors are likely to recognize conserved structures within this chemokine receptor family. Additional point mutations of CXCR4 can be used to map the exact residues of reactivity within CXCR4.

Example 58

Improvement of Antibody Elicitation Using Different Methods of Production and Immunization To determine optimal conditions to generate antibodies and elicit immune responses, various conditions are modified. A wider range of doses for initial immunization and subsequent boosts, the use of adjuvant, and the route of immunization is explored. Results from these experiments enable one to base future immunizations on protocols that have been well characterized, rather than the hit-or-miss approach to generating useful Mabs to complex receptors that is often taken. The experiments are summarized in Table 13.

TABLE 13

Summary of varied conditions

| Group | Prime | Boost | Route | Adjuvant |
|---|---|---|---|---|
| 1 | 100 µg | 3 × 50 ug | IP | Ribi |
| 2 | 250 µg | 3 × 100 ug | IP | Ribi |
| 3 | 100 µg | 3 × 50 ug | Footpad | Ribi |
| 4 | 100 µg | 3 × 50 ug | IP | TiterMax |
| 5 | 100 µg | 3 × 50 ug | IP | None |

Two mice are used for each group above, and the co-receptor CCR5 is used as the prototype receptor in these experiments. In most cases hybridomas are not made; sera reactivity (titered dilutions) is adequate to determine the quantitative increase in reactivity using different immunization protocols. In the case of adjuvant, a fundamental difference in the type of Mab produced (e.g. linear or non-linear epitope) is determined by competition of sera with CCR5 Mabs of known reactivity, and by Western analysis of denatured protein as described in Example 45.

Intraperitoneal (IP) injection, intravenous (IV) immunization, subcutaneous (SC), and footpad injections (FP) have all been used successfully for the isolation of Mabs to complex receptors. In order to compare these routes of immunization, mice are injected with lipoparticles IP and FP, the two routes that have worked best in the past. Sera from these mice are compared for quantitative reactivity by titering the seras and comparing to a standard for relative reactivity.

The number of lipoparticles can also be tested. Based on calculations comparing lipoparticles to cellular immunogens, it is estimated that 80-160 µg of virus particles will provide approximately the same amount of receptor antigen as $10^7$ cells (assuming $10^6$ copies of receptor per cell, $10^7$ cells would contain $10^{13}$ receptors). Lipoparticles are estimated to carry 50-100 receptors/particle, and the MW of a retrovirus is approximately $4 \times 10^8$ g/mol. So 80-160 µg of retrovirus is required to deliver $10^{13}$ receptors. This range of dosage is consistent with expectations based on prior experience and comparison to viral vaccines (above). Because Lipoparticles are expected to deliver a higher quality antigen (purified or concentrated and retaining structural integrity) in a better format for processing (particulate), a 100 µg lipoparticle prime is used and subsequently three 50 µg boosts (250 µg total) are used. A higher dosage of antigen is also used (550 µg total) in order to assess improved responsiveness with increased dosages. Specifically, one group of mice receives 250 µg of lipoparticles in prime immunization and 100 µg in each of three boosts. The responsiveness of the sera of mice is tested for reactivity to determine the increase in responsiveness gained with this protocol. A second series of increased dosage (1 mg total) is employed if experimental results indicate that further improvements could be gained.

The use of adjuvants is also tested. For these experiments, three different conditions—no adjuvant, Ribi adjuvant, and TiterMax adjuvant—are used to enhance the immune response to lipoparticles. Particles containing 100 µg CCR5 are mixed with an equal volume of emulsified adjuvant for the priming immunization. The first boost also contains adjuvant, but subsequent boosts are administered without adjuvant. Seras are screened, as above, to determine the level of reactivity increase under each condition. Seras are screened for blocking of Mabs to determine the epitope response of each condition and to ensure that no condition is producing Mabs only to linear epitopes.

Example 58

Generation of a Neutralizing Humoral Immune Response Using a Lipoparticle as a Vaccine The preceding examples have demonstrated that lipoparticles present antigens for antibody production in a variety of ways, and that these antibodies are useful for a variety of applications. In this example lipoparticles are used for vaccination.

Open reading frame 74 (ORF74) is a constitutively active seven transmembrane (7TM) receptor stimulated by angiogenic chemokines, and inhibited by angiostatic chemokines. ORF74 is encoded by human herpesvirus 8 (HHV8). Expression of ORF74 has been linked to development of rapidly growing, metastasizing, highly vascularized, tumors. One model for the elimination of these tumors would be to generate an immune response against cells expressing ORF74.

Since ORF74 is a 7TM receptor, and the protein relies on a lipid bilayer to maintain its structure, it is unlikely that vaccination with just the protein would elicit the proper immune response. Killed or attenuated HHV8 virus vaccination is not sufficient because the virus does not express the protein on its own membrane. The use of lipoparticles for vaccination offers the unique opportunity to present the ORF74 receptor in its transmembrane form and to use a particle similar in size and composition to a virus.

Successful vaccination against ORF74 would prevent the formation of tumors and prevent cancers developed from this pathway, by eliminating cells which express this receptor (i.e. cells infected by HHV8 since only HHV8 encodes this receptor).

Similarly, HER2 (human epidermal growth factor receptor 2) is a receptor found to be over expressed in 25% to 30% of breast cancer patients. This over expression increases cell growth and division, making the cancer more aggressive than types not expressing HER2. Herceptin is a Mab which is used as a drug to block HER2. Vaccination against HER2 may serve a similar purpose—to slow the cancer, with the exception being that the body would generate its own immune response, effectively immunizing the patient against breast cancer.

Lipoparticles comprising either HER2 or ORF74 are administered to an animal at a dosage of 100 ug of lipoparticles per 20 g of animal by injecting intraperitoneal. Boosters of 100 ug lipoparticles per 20 g animal are administered at 2 weeks and 4 weeks after the initial inoculation. Antibodies from the animal are monitored by FACS to measure the immune response against ORF74 and HER2. Additional booster injections may be made to increase the titer of antibodies in the sera if desired. The animal is then challenged (e.g. with a tumor or with HHV8) in order to determine the protection given by the vaccination.

Example 59

Using a Lipoparticle and an Immunostimulating Component to Improve an Immune Response Lipoparticles are used in conjunction with other immunomodulators, which will serve to optimize the potency and longevity of the immune response. The lipoparticle itself is also improved to increase the humoral immune response.

Recent evidence suggests that using multiple vaccine vehicles to present a common antigen in a sequenced prime-boost protocol may serve to better induce a humoral immune response. The secondary immunogen can be added in several ways including 1) as a protein co-injection, 2) in cells expressing the protein, 3) as a killed or attenuated virus, or 4) by several genetic techniques whereby the DNA in introduced to the antigen presenting cells (APCs) via plasmid DNA vehicles or a variety of viral vectors. For the case of an integral membrane protein which is not present on a normal virus, any of these techniques except the killed or attenuated virus (#3) could be employed.

For example, lipoparticles containing ORF74 are co-injected with plasmid DNA (e.g. pcDNA3 expressing ORF74 under a CMV promoter) vehicles or a variety of viral vectors (e.g. a recombinant adenovirus expressing ORF74 under a CMV promoter) to increase the immune response. Alternatively, a lipoparticle comprising ORF74 is coadministered with IL-2. IL2 normally serves to signal CD4+ immune cells to divide. IL2 administration is already in use clinically for some cancer patients and it is being tested for use in AIDS patients. It is the CD4+ cells which die during an HIV infection and IL2 administration has been used to boost these cells to maintain an immune response. In the case of vaccines, IL2 co-administration may increase the number of CD4+ cells beyond the normal amount and improve the immune response to the immunogen being presented by the lipoparticle. IL2 use has been demonstrated to improve the immune response from a peptide vaccination.

Example 60

Making Antibodies Using Lipoparticles and Macrophages

Lipoparticles can also be modified to mimic the effects of membrane proteins and antigens which are present in the cells of the immune system. Co-injection of this type of particle may serve to boost individual steps of the immune response and improve the overall response.

A lipoparticle which has on its surface an antigen bound to MHC class 1 may mimic the effects of a macrophage which is presenting an antigen, and stimulate a cytotoxic T-cell to activate. To generate this lipoparticle, macrophages are harvested from a mouse that has been immunized with a desired immunogen. Once the macrophages begin to present the antigen, lipoparticles are generated from the macrophages following the methods described herein and in U.S. Patent Application US 2002/0183247A1, U.S. Ser. No. 60/491,477, filed Jul. 30, 2003, and U.S. Ser. No. 60/491,633, filed Jul. 30, 2003. These particles should contain all the membrane proteins of the macrophage and can then be used as a vaccine. Lipoparticles can also be engineered to express MHC class I membrane protein. Alternatively, lipoparticles can be engineered that express the antigen and MHC class II. Lipoparticles can alternatively be bathed in MHC proteins to elicit binding prior to immunization. This complex may bind to an activated helper T-cell, stimulating the transformation of the relevant B cell into an antibody-secreting plasma cell.

The experiments for this example will proceed as in described herein with the addition of secondary immunogens or modifications to the Lipoparticle.

Example 61

Use of Libraries to Isolate Monoclonal Antibodies

Previous examples have relied upon an organism, such as a mouse or human, to generate antibodies against an injected lipoparticle. In this example a library of human Monoclonal antibodies is expressed in Phage or using Ribosome display and screened using lipoparticles expressing a protein of interest. In this manner, a monoclonal antibody to the protein of interest will be isolated ex vivo. This avoids the problems of an antigen not being immunogenic or of an immune response directed to the Gag protein of the lipoparticle. Phage libraries have been generated by others to express human antibody fragments, and can contain >$10^7$ unique antibodies. The combination of this library and lipoparticles will provide a powerful tool for rapid antibody isolation.

lipoparticles containing CCR5 are constructed and bound to high binding ELISA plate wells by incubating particles in Hepes Buffered Saline (HBS, 10 mM Hepes pH 7.5, 150 mM NaCl) buffer for 2 hours. The unbound lipoparticles are washed away with three washes of HBS. Non-specific binding sites are blocked using HBS containing 3% BSA. A commercial phage library of human Mab is incubated with the lipoparticles. Unbound phage are washed away by washing wells three times with HBS. Bound phage are eluted by washing with 100 mM triethylamine, pH 11. The eluted phage are neutralized in 1M Tris-HCl, pH 7.4. The resulting phage are amplified in bacteria. The procedure above can be repeated three times to isolate phage that are specific to the membrane protein of interest. Isolation of a plaque of phage results in the identification of a single Mab which binds to CCR5. One skilled in the art would recognize that phage panning could also be conducted using whole virus or virus-like particles.

Alternatively, a method that avoids the use of bacteria and phage but accomplishes similar results is the use of ribosome display. This is similar to using a phage library but instead the antibodies to be screened are attached to a polysome, as described in He M, and Taussig M. Briefings in functional genomics and proteomics. Vol 1. no 2. 204-212. July 2002. Once isolated, the mRNA in the polysome is amplified for the identification of the antibody.

Example 62

Transfection of CCR5 into 293T Cells Using a Lipoparticle

This experiment involves the transfection of the CCR5 chemokine receptor present in the membrane bilayer of CCR5 lipoparticles into the target plasma membrane of 293T cells. The transfection of CCR5 can be verified using a Calcium Flux assay. A flux in the intracellular calcium of levels of the transfected target cell is expected when stimulated with the agonist CCR5 ligand MIP1-α.

Approximately $3 \times 10^6$ 293T cells are cultured in a 60 mm plate. 20 μl of the Pro-Ject™ reagent (Pierce Biotechnology, Inc., Rockford, Ill.), which is obtained as a thin film of powder on a tube that is then dissolved by adding 250 ul methanol and is pipetted to the bottom of an Eppendorf™ tube and dried after allowing 1-2 hours for evaporation. In a separate tube, 4 μl of CCR5 lipoparticles ($6.5 \times 10^7$ particles/μl), prepared as previously described (Hoffman, et al. (2000), Proc. Natl. Acad. Sci. USA, 97:11215-11220), is diluted in 250 μl Hepes Buffered Saline (HBS). The lipoparticle/HBS mixture is added to the Eppendorf tube containing the dried Pro-Ject™ reagent and is mixed by pipetting up and down. The lipoparticle/Pro-Ject™ mixture is vortexed for three seconds and incubated 3-5 minutes at room temperature. 2.2 ml Optimem™ is added to the lipoparticle/Pro-Ject™ mixture. The existing 293T media is aspirated and replaced with 2.5 ml of the lipoparticle/Pro-Ject™/Optimem mixture and subsequently incubated for 4 hours at 37° C.

To commence the calcium flux assay, 25 μl of Fura-2AM (1 mM in DMSO) is added to 10 ml 10% FBS DMEM for a final concentration of 2.5 μM. The existing 293T media is replaced with 2.5 ml of 2.5 μM Fura-2AM/media mixture. The cells are then incubated for 1 hour at 37° C. After incubation, the cells are washed with PBS and incubated for 5 minutes in PBS to lift the cells. The cells are then centrifuged for 5 minutes and resuspended in 1 mM Ca/Mg PBS with 2% FBS at $2 \times 10^6$ cells/ml.

$3 \times 10^6$ cells (1.5 ml) are used per Ca Flux reaction. A 5 μl MIP1-α (0.1 μg/μl) injection is used to challenge the 293T target cells and detect a Ca Flux, as previously described (Doranz, et al. (1999), J. Virol., 73:2752-2761), by placing cells in a 4.5 ml cuvette, stirring at low speed, and injecting reagents at desired times.

Since the 293T cell line does not endogenously express CCR5 on the plasma membrane, the transfection of CCR5 into the target 293T cell membrane bilayer can enable the cell to respond to an external MIP1-α ligand challenge. Intracellular calcium levels can increase five- to seven-fold from basal state when the cell is challenged with MIP1-α. When loaded with Fura-2AM, the cell can fluoresce during this flux and allow proper detection of CCR5 transfection.

Example 63

Detection of Fusing Cells Using a Lipoparticle

This experiment involves the detection of two cells fusing, which can be used to detect the interaction of a membrane protein with its ligand, which can also be a membrane protein. The CCR5 chemokine receptor, present in the membrane bilayer of CCR5 lipoparticles, is used to transfect the target plasma membrane of quail QT6 cells. The transfection of CCR5 can be verified using a cell fusion assay with a luciferase reporter, as previously described (Doranz, et al. (1996), Cell, 85:1149-1158). Additionally, the confirmation of a protein interaction can also be confirmed when the resulting interaction causes the cells to fuse together. Briefly, HeLa cells are prepared as effector cells and QT6 cells are prepared as target cells. A fusion event between effector cells and target cells, as detected by luciferase activity, indicates the transfection of CCR5 into target QT6 cells.

For effector cell preparation, $2 \times 10^5$ (a 24-well well) HeLa cells are cultured and prepared for vaccinia infection. Vaccinia viruses vTF7-3 (expresses T7-polymerase) and vBD3 (expresses HIV-1 Envelope protein 89.6) are used to infect HeLa cells at a Multiplicity of Infection (MOI) of 10 each. Vaccinia strains are prepared by incubating virus with 1 volume of 0.25 mg/ml trypsin for 30 minutes while vortexing every 5-10 minutes. Once thawed and trypsinized, the virus is added to the effector cells and incubated for 2 hours in half volume at 37° C. After two hours of infection, the culture media is replaced with 10% FBS media containing rifampicin (1× final concentration) and allowed to incubate overnight at 32° C. When ready for use, Effector cells are washed with PBS, centrifuged for 5 minutes, and resuspended at $2 \times 10^6$ cells/ml in 10% FBS media containing AraC and rifampicin.

For target cell preparation, $2 \times 10^5$ QT6 target cells are transfected by calcium phosphate. Precipitate is prepared by combining 17.5 μl sterile water, 2.5 2M $CaCl_2$, 0.5 μl CD4-PT4 plasmid (1.385 μg/μl), 0.7 μl T7-luciferase plasmid (0.9 μg/μl), and 0.7 μl PHF-GFP plasmid (0.94 μg/μl). Plasmids can be prepared as previously described (Doranz, et al. (1996), Cell, 85:1149-1158). The plasmid mixture was subsequently added to 20 μl 2×HBS while vortexing to ensure adequate mixing and precipitate formation. The precipitate is subsequently incubated for 15 minutes at room temperature and then added to existing QT6 media. QT6 cells are incubated with the calcium phosphate precipitate for 4-6 hours. Cell media is subsequently replaced with 10% FBS DMEM, and cells are incubated overnight at 37 C.

To begin the CCR5 transfection process, 2.5 µl of the Pro-Ject™ reagent dissolved in methanol is pipetted to bottom of an Eppendorf tube and incubated for 1-2 hours to permit methanol evaporation. In a separate tube, 4 µl of CCR5 lipoparticles ($6.5 \times 10^7$ particles/µl and prepared as described herein) are diluted in 10 µl Hepes Buffered Saline (HBS). Once combined, the lipoparticle/HBS mixture is added to the tube containing dried Pro-Ject™ reagent and thoroughly mixed by pipetting up and down. The lipoparticle/Pro-Ject™ mixture is briefly vortexed and incubated for 3 to 5 minutes at room temperature. After the brief incubation, Optimem serum-free media is added to the lipoparticle/Pro-Ject™ for a final volume of 250 µl. Existing QT6 media is replaced with lipoparticle/Pro-Ject™ mixture and incubated for 4 hours at 37° C.

To initiate the fusion event, 100 µl of effector HeLa cells ($2 \times 10^5$ cells) are added to $2 \times 10^5$ target QT6 cells and incubated for 8 hours at 37 C. After incubation, cell lysate is prepared by adding 200 µl of PBS with 1% Triton X-100 and incubating at room temperature for one minute. Luciferase activity is measured by adding 50 µl of cell lysate to a 96-well plate with 50 µl Luciferase substrate (Promega) per well. Luciferase activity is detected using an ML3000 luminometer.

The QT6 cell line does not endogenously express CCR5 on the plasma membrane. The transfection of CCR5 into the target QT6 plasma membrane bilayer can enable the HeLa effector cells expressing the 89.6 HIV-1 envelope protein to fuse with the QT6 target cells expressing both CD4 and CCR5. The fusion event permits the effector's T7-polymerase to transcribe the T7-driven luciferase construct present in the target cells. Successful transfection of CCR5 can allow a fusion event between the effector and target cells with commensurate detection of luciferase activity.

Example 64

Transfection of Membrane Proteins Toxic to a Cell

The ion channel Kv1.3 can be toxic when over-expressed in some cell types. Nevertheless, Kv1.3 is a membrane protein of considerable interest. Kv1.3 can be incorporated into lipoparticles using the protocols described in US 2002/0183247A1, U.S. Application Ser. No. 60/491,477, U.S. Application Ser. No. 60/491,633, and U.S. Provisional Ser. No. 60/498,755, filed Aug. 29, 2003. Alternative cell types can be used for production of lipoparticles in which Kv1.3 is less toxic. Kv1.3 can then be transfected into an NT2 differentiated neuron, or another cell type, using the membrane protein transfection protocol described above. Membrane transfection enables mutagenic study by circumventing potential complications of DNA transfection.

Example 65

Transfection of a Mutant Membrane Protein

Mutagenesis of chemokine receptor CCR5 provides an effective way to study its interaction with HIV-1 and chemokines. However, CCR5 cannot always be introduced into desired cell types, such as differentiated macrophages that lack endogenous CCR5 (CCR5-delta32 homozygotes). The introduction of mutant forms of CCR5 would enable the study of the protein and its functional properties within an important cell type. Mutants of CCR5 can be incorporated into lipoparticles using the protocols described US 2002/0183247A1, U.S. Application Ser. No. 60/491,477, and U.S. Application Ser. No. 60/491,633. Point mutations, chimeras, and truncation of CCR5, such as previously described (Doranz, et al. (1997), J. Virol., 71:6305-6314, Rucker, et al. (1996), Cell, 87:437-446), can be made. CCR5 mutants are then transfected into primary macrophages. Some of the macrophages can lack endogenous CCR5, or another cell type, using the membrane protein transfection protocol described in Example 62. Once within the cell, the transfected protein can be used to study signaling pathways within this cell.

Example 66

Transfection of a Membrane Protein with Altered Post-Translational Modifications Post-translational modifications of the chemokine receptor CCR5 are important in regulating its location and signaling properties within a cell. However, post-translational modifications of CCR5 cannot always be introduced as desired. The control of post-translational variants of CCR5 would enable the study of the protein and its functional properties. CCR5 can be incorporated into lipoparticles as described herein. To control the post-translational state of CCR5, lipoparticles are biochemically manipulated to introduce or eliminate post-translational modifications. The lipoparticle is treated with endoglycosidase F to remove N-linked carbohydrates. For other extracellular modifications, lipoparticles are treated with chemicals, enzymes, or reagents in order to modify N-linked carbohydrates, O-linked carbohydrates, or sulfated residues. The lipoparticle are made to contain a phosphatase to remove any phosphorylation sites added to CCR5. For other intracellular modifications, the lipoparticle interior is made to contain chemicals, enzymes, or reagents that can function as kinases, phosphatases, or intracellular binding partners. The post-translationally modified CCR5 protein is then transfected into a 3T3 cell, or another cell type, using the membrane protein transfection protocol described in Example 62. Once within the cell, the modified protein can be used to study signaling pathways within this cell.

Example 67

Membrane Protein Transfection for Delivery of a Poorly Expressed Membrane Protein Some membrane proteins are not efficiently transcribed, translated, or processed within a cell, resulting in poor surface expression. In other cases, the membrane protein is quickly internalized, degraded, or inactivated, also resulting in poor surface expression. Membrane protein transfection can overcome these obstacles by delivering high levels of the membrane protein directly to the surface of a desired cell. The chemokine receptor CCR3, for example, is often poorly expressed on the cell surface. CCR3 is incorporated into lipoparticles using the protocols described in US 2002/0183247A1, U.S. Application Ser. No. 60/491,477, and U.S. Application Ser. No. 60/491,633. CCR3 is transfected into 293 cells, or another cell type, using the membrane protein transfection protocol described herein. Once within the cell, the protein is used to study signaling pathways within this cell.

Example 68

Membrane Protein Transfection for Delivery of a Therapeutic Membrane Protein The Cystic Fibrosis Transmembrane Regulator (CFTR) membrane protein is a chloride channel that, when defective, is responsible for causing Cystic Fibrosis. Studies suggest that effective treatment of Cystic Fibrosis could be achieved by administering the CFTR gene via gene therapy. However, gene therapy techniques, in which the DNA encoding a protein is delivered to a target cell for therapeutic purposes, face many challenges. The method disclosed herein, as described, for example, in Example 62 provides an alternative means of delivering the membrane protein and providing an effective treatment to the disease. CFTR has been incorporated into lipoparticles, using techniques previously described (Hoffman, et al. (2000), Proc. Natl. Acad. Sci. USA, 97:11215-11220)). The lipoparticles are prepared as a pharmaceutical carrier or diluent. The lipoparticles are administered to the individual. The delivery of the CFTR protein to effected tissue (e.g. lung) lacking a functional CFTR protein, using methods disclosed below, can ameliorate the disease. The cells that the membrane protein is to be transfected into are targeted. Method of targeting cells in vivo are well know in the art, including, but are not limited, using an antibody, using a specific receptor on the surface of cell, and the like.

Example 69

Membrane Protein Transfection for Targeting of Stem Cells In Vivo

A current limitation of stem cell therapies is the inability to localize therapeutic stem cells to the appropriate target tissue. The chemokine receptor CXCR4 is known to help regulate migration of hematopoietic stem cells in vivo (Lee, et al. (1998), Stem Cells, 16:79-88, Peled, et al. (1999), Science, 283:845-848). Membrane transfection of CXCR4 onto the stem cell plasma membrane would aid in the targeting of the stem cell to the appropriate tissue type. CXCR4 lipoparticles are prepared according to the methods described in US 2002/0183247A1, U.S. Application Ser. No. 60/491,477, and U.S. Application Ser. No. 60/491,633 and transfected into stem cells ex vivo (i.e. in a tissue culture dish before being reintroduced into a patient) according to examples herein. The stem cells are then administered to a patient using methods known to those of ordinary skill in the art (Hui (2002), Technol Cancer Res Treat, 1:373-84).

Example 70

Membrane Protein Transfection in a Terminally Differentiated Cell

DNA transfection of many cell types requires cell division in order to efficiently express the DNA of interest. Transfection using a viral delivery vehicle also usually requires a dividing cell in order to efficiently express the DNA in the viral vector. The introduction of membrane proteins using membrane protein transfection with lipoparticles, however, has no such requirements. Many cell types, such as differentiated cells and quiescent cells, are not efficiently transfected using DNA transfection or viral delivery vehicles. Ectopic introduction of membrane proteins via membrane protein transfection provides a suitable alternative to study protein interactions in said cells. Lipoparticles comprising CCR5 are fused with the terminally differentiated neuronal cell line N-tera 2 according to the methods described herein. The transfected cell line is used to study the function of CCR5 in a non-dividing cell. One of ordinary skill in the art would recognize that other cells in a quiescent state could also be transfected in such a manner.

Example 71

Imaging and Quantifying Lipoparticles

To visualize and quantify lipoparticle concentration we have used a fluorescent molecule that partitions into lipid environments and becomes fluorescent only when in a lipid environment. The membrane potential probe di-4-ANEPPS was obtained (Molecular Probes) as a powder, resuspended in 50% ethanol and 50% DMSO, and 1 μl was added to 100 μl of a 1:100 dilution of lipoparticles in 0.22 um filtered HBS. Unlike water-soluble dyes, di-4-ANEPPS is lipophilic, simplifying the incorporation and use of the dye with lipoparticles. The dye partitioned into membranes nearly instantaneously and dye that does not partition into the membrane is non-fluorescent. The particles were then placed onto a hemocytometer under a cover slip. The hemocytometer was placed on the stage of a fluorescence microscope and the lipoparticles were counted using an oil-immersion 100× lens (Nikon) under red epifluorescent illumination. The lipoparticles could be imaged under epifluorescent illumination as small coronas of fluorescent light, with each corona representing a single lipoparticle (data not shown). This number was mathematically extrapolated to lipoparticles per μl of solution by multiplying the number of fluorescent lipoparticles within a defined region of the hemocytometer by the volume of the hemocytometer that that region represents. The formula for this calculation was: ((Average #Lipoparticles per area visualized)*(1/0.0025 area visualized)*(0.1 μl per area visualized)*(Dilution of Lipoparticles)).

One skilled in the art would recognize that other lipophilic dyes could also be used to observe lipoparticles. In fact, any other dye that has lipophilic properties could be used for the same purpose. Many lipophilic dyes do not fluoresce or fluoresce only weakly in an aqueous environment, meaning that the dye need not be separated from the lipoparticle in order to visualize the lipoparticle. di-4-ANEPPS, diI, diBAC4, and Nile Red have been used to detect lipoparticles.

Example 72

Incorporation of Fluorescent Reporter Proteins into Lipoparticles

In order to detect and quantify lipoparticles in a more efficient and reproducible manner, we created a Gag protein with an Enhanced Green Fluorescent Protein (GFP) fused to the C-terminus of Gag. GFP was cloned using PCR to fuse the GFP protein to the C-terminus (amino acid 533) of Gag (nucleocapsid protein). When the construct is transfected into cells, a Gag-GFP fusion protein is produced and drives the budding of retroviral particles. We have used this construct to produce lipoparticles that, when visualized with a 100× lens under epifluorescent illumination, are readily visible (data not shown).

Lipoparticles containing receptors fused to a fluorescent reporter molecule (CXCR4-GFP and CCR5-GFP) were also produced. Both membrane proteins are G-protein coupled receptors with GFP fused to the C-terminus (intracellular) of the GPCR. Both of these lipoparticles were produced and used for imaging and quantification using microscope visualization.

Example 73

Protein Concentration of Lipoparticles

The overall protein concentration of the lipoparticle preparation was determined using a BCA assay kit (Pierce) and comparing to a known quantity of purified lipoparticles. 5 µl of lipoparticles were placed into a well of a microplate. 200 µl of BCA working reagent was added to each well, mixed on a shaker for 30 sec and incubated at 37° C. for one hour. The plate was cooled to room temperature and the absorbance at 562 nm was measured using an absorbance detector to determine protein concentration of each well of the microplate. When the experiment was conducted with protein standards of known concentration, the protein concentration of the lipoparticle preparation could be determined (Table 14). Alternative protein concentration kits have also been used, including microBCA and NanoOrange (data not shown).

TABLE 14

Protein Concentration of lipoparticle preparation

| Sample | Abs @ 570 nm - Blank Abs @ 570 nm | Conc. (µg/ml) | Conc. (mg/ml) |
|---|---|---|---|
| INT-0037A | 1.241 | 829 | 0.829 |
| INT-0038A | 0.49 | 292 | 0.292 |

Example 74

Dynamic Light Scattering

The size and purity of a lipoparticle preparation was determined using Dynamic Light Scattering (DLS). To determine the size distribution of the lipoparticles in a purified population of lipoparticles, approximately 2 ng of purified lipoparticles were suspended in 35 µl of Hepes Buffered Saline (HBS) in a microcuvette. The sample was placed in a Proterion DynaPro Dynamic Light Scatter machine and counts were measured. The data was analyzed by displaying the counted population on a histogram to determine the size distribution on the X-axis and the intensity of measurement on the Y-axis (FIG. 15). DLS is a measurement of both lipoparticle size (diameter) and lipoparticle purity (breadth of peak and number of peaks). A pure population is represented by a relatively narrow peak on the histogram whereas a less-pure preparation results in numerous peaks or a very broad peak. Polydispersity is a measure of the breadth of a DLS peak, and a value of <20% is generally considered a homogeneous peak. The size of the lipoparticle was determined to be 207.4 nm in diameter with a polydispersity of 18.1%. 200 nm beads (diameter as specified by the manufacturer) were used as a control (bottom panel) and measured 235.9 nm in diameter with a polydispersity of 8.3%.

Example 75

Quantification of Lipoparticles

In order to quantify the number of lipoparticles in a sample, we used three methods: fluorescent imaging, dynamic light scattering, and spectroscopy correlation. To validate the accuracy of these methods we first tested 200 nm synthetic fluorescent beads (YG Fluorbrite beads, Polysciences) using these three methods. The beads were imaged and counted by microscopy using a 100× lens and epifluorescent illumination in a calibrated hemocytometer. The beads were also subjected to dynamic light scattering using a Proterion DynaPro instrument. Finally, the beads were placed in a cuvette in a Perkin-Elmer LS50B fluorometer and light scatter was measured with an excitation of 540 nm, an emission of 570 nm. On skilled in the art would recognize that other wavelengths could also be used to measure light scatter, and that the wavelength will be a function of the size of the suspended material being measured. All methods were then plotted against the bead concentration as given by the manufacturer and measured during production by weight (FIG. 15C). All measurements were proportional to each other and to the published bead count, with some variation due to dilution accuracy.

We then used the same techniques to measure the concentration of lipoparticles in a given sample. The lipoparticles tested contained the Gag-GFP fusion protein, thus enabling easy visualization. The lipoparticles were imaged and counted by microscopy using a 100× lens and epifluorescent illumination in a calibrated hemocytometer. The lipoparticles were also subjected to dynamic light scattering using a Proterion DynaPro instrument. 200 nm Fluoresbrite beads were also included in this experiment for comparison. The results demonstrated that the measurements were directly correlated over a large concentration range. Furthermore, the intensity of DLS could be used to predict the concentration of lipoparticles (particles/ul) using a simple equation (FIG. 15D).

Example 76

Quantification of Receptors Using Western Blot

The number of receptors per lipoparticle is a measurement that can be used in determining the efficacy of membrane protein incorporation into the lipoparticles. Western blot is one technique that can be used to quantify the amount of specific membrane protein present in a sample. 10E9 lipoparticles containing two V5 epitope tagged GPCRs (CCR5 and CXCR4) were run on a 12% acrylamide SDS-PAGE gel. Predetermined amounts (30, 100, and 300 ng) of a control protein (GFP-V5) were run in separate lanes of the gel. The control protein consists of purified and quantified green fluorescent protein (GFP) that contains the same V5 epitope tag. The gel was transferred to PVDF and the membrane was incubated with an antibody against the V5 epitope tag. Finally, a secondary antibody conjugated to horseradish peroxidase (HRP) was used to detect the primary antibody. A chemiluminescent reagent (Pierce FemtoSignal) was added and the blot was visualized using an AlphaInnotech Fluorchem 8900 (FIG. 15E). Quantification with AlphaInnotech AlphaEase software allowed quantification of the amount of V5 tag detected in the lipoparticle lane and comparison to the standards containing the same V5 tag of known quantity in the other lanes.

One skilled in the art would recognize that any epitope tag could be used to achieve similar quantification results. One skilled in the art would recognize that other proteins, including Gag, could also be quantified in a similar manner. SDS-PAGE and Western blot also allowed visualization of the quality of the receptor (e.g. degraded, full-length, glycosylated, dimers, etc.). The standard protein contains a known quantity (µg) of protein, which could then be converted to moles and #molecules. By using these standards, the estimated number of µg, moles, and molecules of receptor protein was determined in the lipoparticle sample. 10 picomoles of CXCR4 and 4.9 picomoles of CCR5 were incorporated in 10E9 particles.

Example 77

Quantification of Receptors Using Sypro Staining

Lipoparticles containing the GPCR CXCR4 were purified using Ni+2 beads as follows: $1.8\times10^{11}$ particles (2.4 mL of 0.33 mg/mL total protein) were lysed in an imidazole lysis buffer solution comprised of 20 mM Tris pH 7.5, 150 mM NaCl, 1% Triton X-100, 20% glycerol and 20 mM imidazole (final concentrations are after mixing with the particle solution, final volume was 4 mL). The solution was vortexed and then incubated at 4° C. with rocking for 20 minutes. 25 uL of Ni-NTA His-Bind Superflow beads (Qiagen) were added and the solution incubated with rocking overnight at 4° C. The beads were pelleted by gentle centrifugation in a tabletop centrifuge (5 minutes at 2,000 RPM), resuspended in 100 uL of the lysis buffer, and transferred to an eppendorf tube. The wash step was repeated and the beads were washed with increasing concentrations of imidazole in the lysis buffer from 20-100 mM imidazole (2×100 uL wash for 20, 50, 75 and 100 mM imidazole buffers). CXCR4 was eluted from the beads with lysis buffer containing 250 mM imidazole in two 100 uL fractions. Residually bound lipoparticles were eluted with lysis buffer containing 500 mM imidazole in two 100 uL fractions.

Samples from the purification were run on SDS-PAGE (4-20% acrylamide gradient) and the gel stained using Sypro Orange (Molecular Probes). 30 uL of the following samples from the purification were run: starting material (unpurified lysed lipoparticles), flow through, 20 mM imidazole wash, elution fractions from 50-500 mM imidazole (FIG. 15F). In addition, a similar but separate SDS-PAGE gel was run, stained with Sypro Orange, and quantified. 30 uL of the following samples from the purification were run on this second gel: starting material (unpurified lysed lipoparticles), 250 mM imidazole elute fractions 1 and 2 (100 uL total volume each), 500 mM imidazole elute fractions 1 and 2 (100 uL total volume each). In addition 30, 100 and 200 ng samples of purified hPRR2 (Geraghty et al Science. 1998 Jun. 5; 280(5369):1618-20) were run as standards.

To calculate the total amount of CXCR4 in the preparation, the hPRR2 bands (background subtracted) were quantified using AlphEaseFC (Alpha Innotech) and the data plotted for a standard curve. The CXCR4 band in each of the elution fraction lanes was quantified and the values used to calculate the amount of protein in each band. The total amount of CXCR4 in the preparation was back-calculated from these values. To calculate the percent of total protein of CXCR4, the entire lane of the starting material was quantified using AlphaEaseFC as above. The CXCR4 band in that lane was quantified and the percent of total calculated. One skilled in the art would also recognize that the amount of protein in the purified CXCR4 sample could also be quantified by a total protein concentration analysis such as a BCA assay.

Example 78

Quantification of Receptors Using Dot Blot

A dot blot was performed to quantify the amount of receptor in a lipoparticle sample. Dilutions of a purified protein standard, a GFP protein containing a V5 epitope tag, were included on the same dot blot. Dilutions of two sample lipoparticle preparations containing two receptors, CXCR3 and CD4, with the same V5 tag were also included. The samples were blotted through a 96-well manifold onto nitrocellulose and then probed with an anti-V5 antibody. The dot blot was imaged using an Alpha Innotech Fluorchem and spots were quantified and compared. A calibration curve was constructed from the standard protein curve and curves were also constructed from the lipoparticle samples with unknown receptor quantity (FIG. 15G). Using the calibration curve, we were able to estimate the amount of CXCR3 and CD4 in these two lipoparticle preps on a ug/ul basis.

Example 79

Quantification of Receptors Using Ligand Binding

Radioligand binding curves were performed to detect ligand binding to lipoparticles and to estimate the concentration and receptors. Radiolabeled SDF-1α (Perkin-Elmer) was used to bind lipoparticles containing the CXCR4 membrane protein. Lipoparticles were resuspended in a total of 100 ul of Hepes++ Binding Buffer (50 mM Hepes 7.4, 5 mM $MgCl_2$, 1 mM $CaCl_2$, 100 mM NaCl, and 2% BSA) together with 0.1 nM radioligand. Increasing amounts of cold ligand (Peprotech) were also included where indicated. The mixture was incubated 1 h at room temperature and then filtered through Whatman GF/C filters soaked in 0.2% polyethyleneimine (PEI). Filters were counted in a Wallac gamma counter. The results indicated that CXCR4 on the lipoparticles was structurally intact and capable of binding ligand (FIG. 15H). The results also demonstrated a very high concentration of CXCR4 in the preparation, 230.2 pmol/mg. A titration curve using increasing amounts of lipoparticles also indicated very high concentrations of CXCR4, with an EC50 of 0.15 ug (FIG. 15I). These numbers were used to calculate the total amount of receptor per unit volume and per unit lipoparticle.

Example 80

Detection of Membrane Protein Structural Integrity Using Virus-Detection ELISA

To determine the structural integrity of membrane proteins incorporated into Lipoparticles, we have utilized a technique, termed Virus-Detection ELISA, (VELISA), that allows quantification of the structural integrity of a membrane protein within the lipoparticle. VELISA is a modified enzyme linked immunosorbant assay (ELISA). VELISA has been performed on both purified and unpurified lipoparticles. Lipoparticles containing either CCR5 or CXCR4 were used in a VELISA assay by binding lipoparticles to ELISA wells coated with antibodies against either CXCR4 or CCR5. Briefly, 0.75 µg of a primary monoclonal antibody was adsorbed to each well of a high-binding ELISA plate. The wells were incubated overnight, washed with HBS and blocked using 3% BSA in HBS. Next, 0.5 µg of purified lipoparticles were added to each well, and the plates were centrifuged for 1 hour at 3,000 rpm to sediment lipoparticles to the bottom of the wells. The wells were washed three times with HBS. Subsequently, 200 µl of 1% sodium dodecyl sulfate (SDS) was added to each well and incubated at room temperature for 10-60 minutes, followed by vigorous mixing. 100 µl of lipoparticle lysate was transferred to a dot-blot apparatus for detection of Gag protein using anti-Gag rabbit sera and anti-rabbit secondary antibody conjugated to horseradish peroxidase. The Gag protein is a structural protein that can be detected in order to quantify the amount of lipoparticles bound during VELISA assay. Specific binding of the lipoparticle during the VELISA assay is mediated solely by the interaction of a membrane protein with an antibody that recognizes that membrane protein (FIG. 16). Detection of Gag indicates that the membrane protein was embedded in the lipoparticle formed by the Gag protein. Control lipoparticles and antibodies are used to indicate specificity. A similar VELISA assay was performed in the presence of various additives to test the effect of each additive on the membrane protein-antibody interaction. CXCR4-containing lipoparticles were bound to an anti-CXCR4 MAb (447.12) or a non-specific anti-CCR5 MAb (45523) in the presence or absence of various additives (ethanol, DMSO, glycerol, sucrose, trehalose, Pluronics, polyethylene glycol, phosphate buffered saline, tris buffered saline, or Triton X-100). In this case, ELISA, rather than a dot blot, was used to detect Gag after specific binding by binding the lysate to a new ELISA plate and detecting bound protein using a rabbit anti-Gag sera. Results demonstrate that most additives had little or no effect on binding (FIG. 16B). Additives such as detergent, however, completely destroyed lipoparticle structure and binding, as expected.

Example 81

Detection Membrane Protein Structural Integrity Using Antibody-Detection Viral ELISA To determine the structural integrity of membrane proteins incorporated into lipoparticles we have utilized another technique, termed Antibody-Detection Viral ELISA (AVELISA) that allows quantification of the structural integrity of a membrane protein within the lipoparticle. AVELISA is a modified enzyme linked immunosorbant assay (ELISA). Lipoparticles containing either CCR5 or CXCR4 were used in a AVELISA assay by binding lipoparticles directly to ELISA wells and then detecting bound lipoparticles using antibodies specific for CXCR4 (12G5 and 447.08) or CCR5 (CTC8). Briefly, 0.75 µg of purified lipoparticles were adsorbed to each well of a high-binding ELISA plate. The plates were centrifuged for 1 hour at 3,000 rpm to sediment particles to the bottom of the wells. The wells were washed with HBS and blocked using 3% BSA. Next, 0.5 µg of membrane protein-specific primary antibody was added to each well, and the plate was incubated for 2 h at room temperature. The wells were washed three times with HBS, and an HRP-conjugated secondary antibody was added to detect the primary antibody bound to the membrane protein. The secondary antibody was allowed to incubate for 30-60 min and then washed three times with HBS. The HRP was then detected with a chemiluminescent substrate for HRP (Pierce FemtoSignal reagent) in order to quantify the amount of antibody bound specifically to each membrane protein (data not shown). Control lipoparticles and antibodies are used in both configurations to indicate specificity.

Example 82

Detection of Membrane Protein Structural Integrity Using Sensor Detection

In the present method, detection is accomplished in one of two configurations. In the first, a lipoparticle is attached to the sensor surface and a conformation-specific antibody is flowed across the surface. Specific binding of the antibody to the membrane protein in the lipoparticle is indicative of the structural integrity of the membrane protein. In the second configuration, the conformation-specific antibody is attached to the sensor surface directly. Lipoparticles are then flowed across the antibody surface and specific binding is detected when the membrane protein in the lipoparticle binds to the specific antibody. Control lipoparticles and antibodies are used in both configurations to indicate specificity. This assay is indicative of the structural integrity of the membrane protein within the lipoparticle and is used as a test to insure membrane protein integrity within lipoparticles.

Example 83

Detection of Membrane Protein Structural Integrity Using Flow Cytometry

Another means of detecting the structural integrity of membrane proteins contained in lipoparticles is flow cytometry. $1 \times 10^9$ purified lipoparticles are labeled with a conformation-specific fluorescein-conjugated antibody (12G5) directed at the protein of interest (CXCR4). Control lipoparticles are prepared using no integral protein or control proteins. In addition, control antibodies are used to confirm specificity. The samples are analyzed on a FACScan flow cytometry measurement device. Data are analyzed using CellQuest software. Comparing samples and control samples (no antibody, lipoparticles with no protein of interest) allows the structural integrity of membrane proteins on lipoparticles to be determined. By using a control (200 nm latex beads) containing a known number of antibody binding sites, the number of receptors per lipoparticle can also be determined.

Because flow cytometry measures individual events, flow cytometry can also be used to quantify the number of lipoparticles in a given sample. The lipoparticles to be quantified can be made fluorescent using a Gag-GFP fusion protein, a lipid dye, a receptor-GFP fusion protein, a secondary antibody bound to the lipoparticle, or any other method of staining a lipoparticle.

Lipoparticles can be attached to beads to facilitate detection by flow cytometry. The beads may be larger in size (e.g. 10 µm) in order to better accommodate a flow cytometer detector. In one embodiment, the beads are fluorescently labeled. In another example, the lipoparticles are biotinylated and the beads are coated with streptavidin to facilitate linkage. In another example, the beads are coated with the lectin Wheat Germ Agglutinin (WGA).

Example 84

Detection of Membrane Protein Structural Integrity Using Immunofluorescence

Another means of detecting the structural integrity of membrane proteins contained in lipoparticles is by labeling the lipoparticles with fluorescently-conjugated antibodies or ligands and visualizing the lipoparticles. Lipoparticles and viruses have generally been thought to be too small to stain and visualize in such a manner, but we disclose methods herein to accomplish such staining. Briefly, $5 \times 10^6$ CXCR4 or CCR5 lipoparticles were incubated with 50 ng of primary antibody in a total volume of 10 µl HBS. Primary antibodies consist of specific and non-specific antibodies (12G5 against CXCR4, 2D7 against CCR5). After 30 minutes at room temperature, 90 µl of HBS was added to the lipoparticles and the mixture was spun in an Eppendorf 5415c microfuge at 14,000 rpm for 30 minutes at 4° C. The supernatant was removed and 10 µl of Cy3-anti mouse secondary antibody, diluted 1:400 in HBS, was added. After 30 minutes at room temperature, 90 μl of HBS was added and the mixture was spun for 30 minutes as before. The supernatant was removed and the pellet was resuspended in 10 μl of HBS and visualized using an epifluorescent microscope. Lipoparticles were stained with antibodies specific to the receptor within the lipoparticles, but not with antibodies that did not react with receptors within the lipoparticles (data not shown). Alternative methods of detection, such as flow cytometry, could also have been used.

Example 85

Detection of a Lipoparticle

Figure 17:
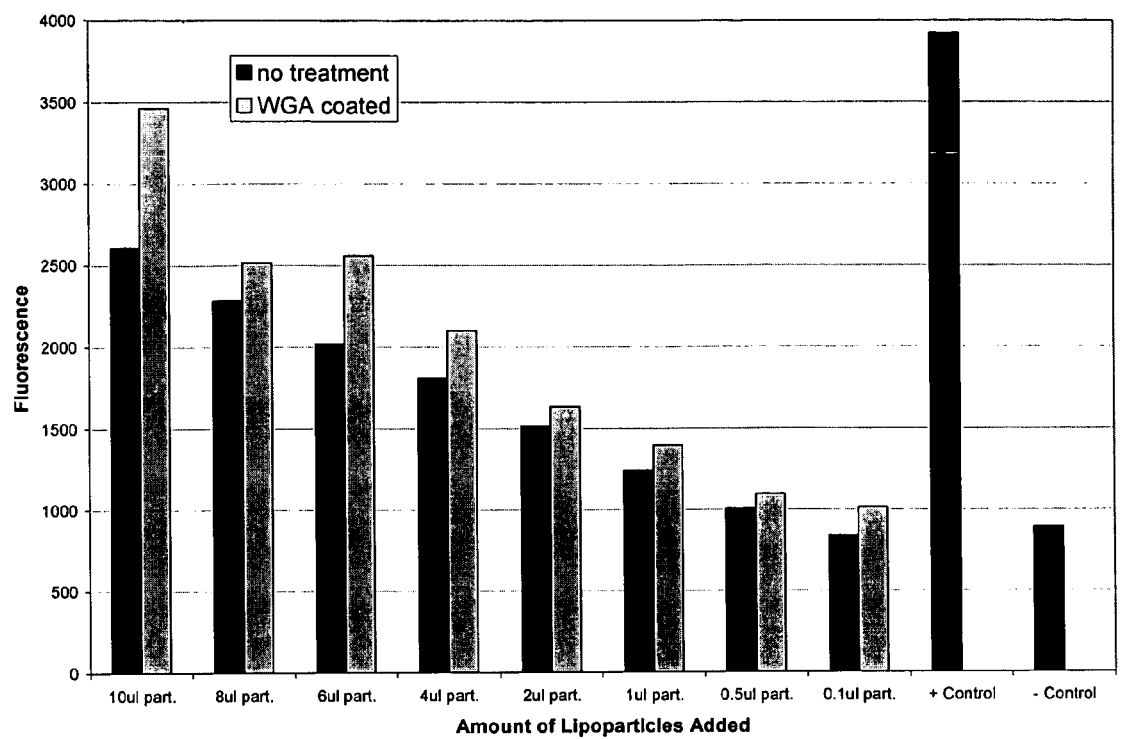
FIG. 17. Quantification of lipoparticles using a hydrophobic fluorophore. The indicated amounts of lipoparticles were quantified using the hydrophobic dye di-4-ANEPPS, which fluoresces only when in a lipid environment. Lipoparticles were bound to WGA-coated or non-coated ELISA wells with equivalent results. Fluorescence in each well was measured using a microplate fluorometer. The positive control represents lipoparticles added directly to the well with di-4-ANEPPS, and the negative control represents buffer alone (no lipoparticles).
Figure 18:
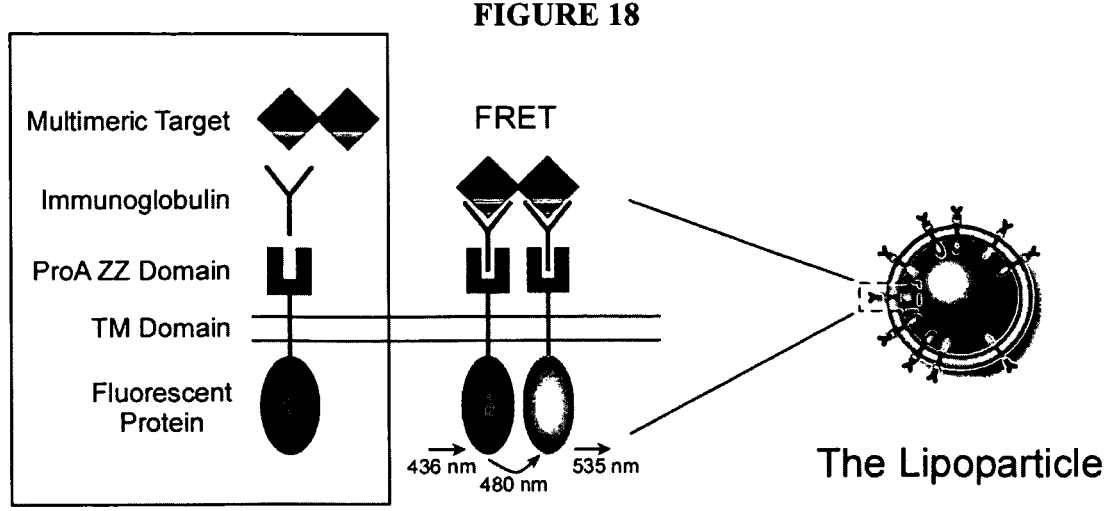
FIG. 18. Elements of a lipoparticle-based biosensor are shown schematically. Following binding of a multimeric target, the lipoparticle-incorporated sensors will cross-link. Sensor cross-linking will bring complementary fluorescent proteins (CFP and YFP) into close proximity, allowing the transfer of resonant energy (FRET), and the emission of a signal that can be measured as an increase of fluorescence.

To quantify lipoparticle concentration we have used a fluorescent molecule that partitions into lipid environments and becomes fluorescent only when in a lipid environment. The membrane potential probe di-4-ANEPPS was obtained (Molecular Probes) as a powder, and resuspended in 50% ethanol and 50% DMSO. A dilution of lipoparticles (0.1 ul to 10 ul of purified lipoparticles, each in a total volume of 50 ul HBS) was placed into separate wells of a clear 96-well plate. Wells were either coated with WGA or left uncoated. Lipoparticles were spun for 1 h at room temperature to adhere lipoparticles to the plate. The wells were then washed with HBS and 50 ul of di-4-ANEPPS (diluted 1:100 in HBS) was added to each well. The fluorescence in each well was measured using a microplate fluorometer (FIG. 17). Similar measurements were taken for purified lipoparticle preparations without adhesion to the microplate (Table 15). Unlike water-soluble dyes, di-4-ANEPPS is lipophilic, simplifying the incorporation and use of the dye with lipoparticles. The dye partitioned into membranes and dye that does not partition into the membrane is non-fluorescent. Therefore, fluorescence was measured only when lipoparticles were present, and the amount of fluorescence was proportional to the quantity of lipoparticles present. One skilled in the art would recognize that other lipophilic dyes could also be used to quantify lipoparticles. In fact, any other dye that has lipophilic properties could be used for the same purpose. Many lipophilic dyes do not fluoresce or fluoresce only weakly in an aqueous environment, meaning that the dye need not be separated from the lipoparticle in order to quantify the lipoparticle.

TABLE 15

| Lipoparticle Lot# | Fluorescence |
| --- | --- |
| 35A | 2,432 |
| 34A | 726 |
| 003-01-0005A | 456 |
| 32B | 828 |
| 003-01-0005C | 826 |
| 33A | 1,529 |
| 99A | 857 |
| 001-00-0002B | 1,014 |
| 006-01-0003A | 3,554 |
| 002-00-0006A | 230 |
| 006-00-0003A | 879 |
| 002-07-0001B | 1,138 |

Example 86

Determination of Receptor Purity and Concentration

The methods described in the examples above yield quantitative information about the number and purity of lipoparticles, as well as the number and purity of membrane proteins within the lipoparticles. Each of these assays alone is valuable, but when used in combination, they are additionally informative. For example, we have used the formula X=(#Lipoparticles per μl)/(Total Protein Concentration) as an estimate of the purity of the lipoparticle preparation. The number of lipoparticles was derived from imaging and the Total Protein Concentration was derived from BCA assay. The resulting calculation (Lipoparticles per ug total protein) is indicative of the purity of the lipoparticle preparation (Table 16). The higher the value the greater the purity of the preparation. A lower number may be indicative of contamination of the lipoparticle preparation with other proteins (e.g. serum or BSA).

TABLE 16

Lipoparticle purity and concentration.

| Lot # | Receptor | Particles/μl (×E6) | Protein [ ] (ug/μl) | Particles/ug (×E6) |
| --- | --- | --- | --- | --- |
| 1 | CXCR4 | 7 | 0.40 | 18 |
| 2 | CXCR4 | 50 | 0.43 | 116 |

Similarly, we have used the formula X=(# Receptors per μl)/(#Lipoparticles per μl) as an estimate of the density of receptors within the lipoparticles. The number of lipoparticles was derived from imaging and the concentration of receptors (in units of #molecules) was derived from Western quantitation. The resulting calculation (Receptors per Lipoparticle) is indicative of the density of receptors within the lipoparticle preparation. The formula calculates an average number of receptors per average lipoparticle, and individual lipoparticles may deviate from this mean. The higher the value, the greater the density of the receptor within the preparation. A lower number may be indicative of low incorporation of receptor into the lipoparticles (e.g. low receptor expression, poor incorporation, etc.).

One skilled in the art would recognize that these calculations are valuable not only for measuring lipoparticles, but also for measuring any particle (e.g. retrovirus, enveloped virus, virus, virus fragment, or virus derivative).

Example 87

Incorporation of Gαi into Lipoparticles by Fusion to Gag

A fusion protein comprising a G protein and Gαi was created by fusing the Gα$_{i2}$ isotype G protein to the Gag protein, at residue 1955 of Gag, using standard cloning methodology (see, for example, *Molecular Cloning: A Laboratory Manual* 3$^{rd}$ ed., Sambrook et al. Cold Spring Harbor Laboratory). Lipoparticles containing the Gag-G protein fusion and the GPCR CXCR3 were created by standard techniques. The presence of G protein fusion proteins within producer cells and lipoparticles was verified by Western blot using anti-G protein antibodies and anti-Gag antibodies (FIG. 19).

Example 88

Incorporation of G Proteins into Lipoparticles by Fusion to Gag

A fusion protein comprising a G protein and Gag is created. The fusion protein may also contain an amino acid linker, which allows adequate mobility of the G protein component for its interaction with incorporated GPCRs. The Gag-G protein fusion protein is created by fusing the $G\alpha_z$ isotype G protein to the Gag protein, at residue 1955 of Gag. Fusion proteins are created using standard cloning methodology (see, for example, *Molecular Cloning: A Laboratory Manual* $3^{rd}$ *ed.*, Sambrook et al. Cold Spring Harbor Laboratory) and in one embodiment incorporates a poly-alanine (15 residue) linker between the fused protein elements. Lipoparticles containing the Gag-G protein fusion and the GPCR CXCR4 are created by standard techniques. The presence of G protein fusion proteins within producer cells and lipoparticles is verified by Western blot using anti-G protein antibodies and anti-Gag antibodies.

The ability of the G protein to interact with the GPCR is tested by immunoprecipitation as follows: Lipoparticle membranes are disrupted using 1.0% CHAPSO, and GPCRs are immunoprecipitated using an antibody recognizing an N-terminal HA epitope tag on the GPCR. Co-precipitation of G proteins with the GPCRs, as detected by Western blot, is indicative of coupling. Interaction of the GPCR and G protein may also be confirmed by chemical cross-linking as follows: When added to mixtures, the cross-linking agent EGS (Pierce) covalently couples molecules that are in contact with each other (within 16 Å). The irreversible covalent coupling achieved by this method would result in a shift in the molecular weight of the GPCR and co-localization of G protein as detected by Western blot, indicating their functional association (proximity without specific interaction at this distance is atypical). Controls for both of these experiments may include pertussis toxin inhibition of GPCR-G protein coupling, and non-GPCR membrane proteins with the same HA epitope tag that do not interact with G proteins (e.g. CD4). One skilled in the art would recognize that incorporation of additional or alternative G protein isotypes, such as $G\alpha_i$, $G\alpha_s$, $G\alpha_q$, and $G\alpha_{12}$, into lipoparticles can also be performed using this or similar techniques.

Example 89

Incorporation of G Proteins into Lipoparticles by Fusion to GPCRs

The $G\alpha_z$ protein isotype is fused to the GPCR CXCR4 at the membrane protein's C-terminus. The GPCR-G protein fusion protein is incorporated into lipoparticles using techniques previously described herein. A linker and/or a protease cleavage site may be included, as desired, to provide adequate spacing of the fusion proteins to allow interaction. The presence of GPCR-G protein fusion proteins within producer cells and lipoparticles is verified by Western blot using anti-G protein antibodies and anti-CXCR4 antibodies. One skilled in the art would recognize that additional or alternative G protein isotypes and additional or alternative GPCRs could be fused and incorporated into lipoparticles in a similar manner.

Example 90

Incorporation of G Proteins into Lipoparticles by Fusion to an Inert Membrane Protein Anchor The $G\alpha_z$ protein isotype is fused to the C-terminus (cytoplasmic) of the single transmembrane protein CD4. Alternatively, a fusion protein containing a truncated version of CD4 with a shorter C-terminus could also be constructed. The CD4-G protein fusion protein is incorporated into lipoparticles using techniques described herein. A linker and/or a protease cleavage site may be included, as desired, to provide adequate spacing of the fusion proteins to allow interaction. The presence of CD4-G protein fusion proteins within producer cells and lipoparticles is verified by Western blot using anti-G protein antibodies and anti-CD4 antibodies. One skilled in the art would recognize that additional or alternative G protein isotypes and additional or alternative membrane proteins could be fused and incorporated into lipoparticles in a similar manner.

Example 91

Incorporation of G Proteins into Lipoparticles Using Transient Poration

Lipoparticles incorporating the GPCR CXCR4 are produced by standard techniques. Lipoparticles are transiently permeabilized using electroporation. Electroporation causes pores to open in lipid membranes, allowing entry of soluble, extracellular molecules. The pores reseal within milliseconds, leaving the particle intact. Lipoparticles are suspended in a highly concentrated solution of purified $G\alpha_z$ and electroporated using five 1,000 V pulses of 10 msec duration each. One skilled in the art would recognize that alternative electroporation conditions may also be employed, including the use of between one and twenty pulses of voltage between 100 and 2,000 V, each of 1 to 1,000 msec duration. Unincorporated G protein is removed by passing lipoparticles through a sucrose cushion. The presence of G proteins within lipoparticles is verified by Western blot using anti-G protein antibodies. One skilled in the art would recognize that additional or alternative G protein isotypes may be incorporated and that additional or alternative transient or permanent permeabilization techniques may be employed. Alternative permeabilization techniques include adding excess ATP, EDTA, Ca++, $Ca_3(PO_4)_2$, DEAE-dextran, polyethylene-glycol, I-14402 (a cell-loading reagent), *S. aureus* alpha-toxin, melittin, or streptolysin-O. Alternatively, lipoparticles can be permeabilized by agitation, vortexing, or sonication.

Example 92

Incorporation of G Proteins into Lipoparticles Using G Protein Over-Expression

Lipoparticles incorporating the GPCR CXCR4 are produced by standard techniques. During production the cells are cotransfected with a plasmid that expresses the G protein Gz. Over-expression of Gz during GPCR incorporation into lipoparticles increases the likelihood of G protein incorporation with the GPCR. The presence of G proteins within lipoparticles is verified by Western blot using anti-G protein antibodies. One skilled in the art would recognize that additional or alternative G protein isotypes could be incorporated.

Example 93

Incorporation of Fluorescent GPCR Fusion Proteins into Lipoparticles and Detection of Ligand-Mediated Activation of GPCRs Cyan fluorescent-protein (CFP) is fused to the third intracellular loop of the transmembrane domain, and yellow fluorescent protein (YFP) fused to the cytoplasmic tail of the GPCR CXCR4. Upon ligand binding, GPCR conformational changes bring the intracellular cytoplasmic tail of the GPCR within close proximity of the transmembrane domain loops, allowing fluorescence resonant energy transfer (FRET) from the donor protein label to the acceptor, which subsequently emits a detectable signal, as previously demonstrated for other GPCRs (Vilardaga, et al. (2003), Nat Biotechnol, 21:807-12). Fusion proteins are created using standard cloning methodology, and incorporated into lipoparticles using standard techniques. The presence of the fusion protein within producer cells and lipoparticles is verified by Western blot using anti-CXCR4 antibodies. G proteins and GTP are incorporated into the lipoparticles as described herein.

To test its function, the labeled lipoparticles (approximately 1 vg) are stimulated with the CXCR4 agonist SDF-1 (60 nM). Ligand mediated activation of CXCR4 results in a conformational change in the GPCR, causing the emission of a detectable fluorescent signal from the CFP-YFP FRET pair. Co-treatment of lipoparticles with a CXCR4 antagonist, such as the antibody 12G5, will inhibit this fluorescent signal. Lipoparticles lacking CXCR4 (null Lipoparticles) fail to exhibit any change in fluorescence. Fluorescence is measured in real-time, beginning prior to addition of SDF-1, using a Perkin Elmer LS-50B fluorometer. A 2 ml cuvette and 750 ul volume will be used, but other formats, such as a microplate, could also be used. One skilled in the art would recognize that additional or alternative GPCRs and fluorescent or luminescent proteins (e.g. FRET or BRET pairs) could also be fused and incorporated into lipoparticles in a similar manner.

Example 94

Detection of GPCR-G Protein Activation and Signaling by Incorporation of Fluorescently-Labelled GTP-γS into Lipoparticles FL-GTP-γS is available in non-hydrolysable formats that bind irreversibly to G proteins, and in which the fluorescent signal is approximately 90% quenched in the free, but not bound moiety. FL-GTP-γS containing a variety of fluorophores are available (for example, the MANT or BODIPY fluorophores available from Molecular Probes). MANT is used in this experiment, but BODIPY, or other fluorescent or bioluminescent reporters could also be used. FL-GTP-γS will be loaded by electroporation into pre-formed lipoparticles containing the GPCR CXCR4 and a G protein, incorporated as described herein. lipoparticles are suspended in a concentrated solution of purified FL-GTP-γS, and electroporated using five 1,000 V pulses of 10 msec each. One skilled in the art would recognize that alternative electroporation conditions may also be employed, and that alternative methods for incorporation of FL-GTP-γS could also be used. These include, but are not limited to, transient poration using mild sonication, or permanent poration using peptides such as melittin. Unincorporated FL-GTP-γS is removed using a G50 spin column, and incorporated fluorescence is detected using a Perkin-Elmer LS-50B fluorometer. Controls will include lipoparticles that have not been electroporated.

To test their functional integrity, the labeled lipoparticles are stimulated with the CXCR4 agonist SDF-1. Stimulation of CXCR4 will cause Gα to irreversibly bind FL-GTP-γS, allowing the MANT fluorophore to emit a detectable fluorescent signal. Fluorescence emission is not altered in null-lipoparticles, or in lipoparticles treated with a CXCR4 antagonist such as the antibody 12G5. Fluorescence is measured in real-time, beginning prior to addition of SDF-1, using a Perkin Elmer LS-50B fluorometer. One skilled in the art would recognize that alternative guanine-nucleotides could be incorporated into lipoparticles in a similar manner, including MANT-GTP, MANT-GMPPNP, BODIPY-FL-GTP, BODIPY-R6G-GTP, BODIPY-TR-GTP, BODIPY FL GMPPNP, BODIPY FL GTP-γ-S thioester, TNP-GTP (2'-(or 3'-)O-(trinitrophenyl)guanosine 5'-triphosphate), BzBzGTP (2'-(or 3'-)O-(4-benzoylbenzoyl)guanosine 5'-triphosphate), S-(DMNPE-caged) GTP-γ-S, or Europium-GTPγ S. One skilled in the art would also recognize that the lipoparticles within this example could be modified prior to stimulation with agonist to permit signaling components to interact. Such modification could include, but is not limited to, disruption by sonication, vortexing, or detergent; or poration using melittin, Streptolysin-O, polyethylene glycol, high amounts of calcium, or low amounts of alkanes.

Example 95

Incorporation of Fluorescently-Labeled G Proteins into Lipoparticles

YFP is fused to the carboxy-terminus of Gα$_z$, and CFP fused to the carboxy terminus of Gβγ. Fusion proteins are created using standard cloning methodology. Lipoparticles containing the GPCR CXCR4 are constructed. The fusion proteins are incorporated into these lipoparticles as described herein. The presence of fusion proteins in producer cells and lipoparticles is verified by Western blot using anti-G protein antibodies. One skilled in the art would recognize that additional or alternative GPCRs, G proteins, and fluorescent protein labels could similarly be incorporated. To test their function, the labeled lipoparticles are exposed to the CXCR4 agonist SDF-1. Ligand binding by CXCR4 will stimulate dissociation of the heterotrimeric G protein complex, causing a reduction in the fluorescent emission from the CFP-YFP FRET pair. Fluorescently excited G-protein tryptophan residues could act as an alternative donor for excitation of the FRET acceptor. Fluorescence emission is not altered in null-lipoparticles, or in lipoparticles treated with a CXCR4 antagonist such as the antibody 12G5. Fluorescence is measured in real-time, beginning prior to the addition of SDF-1, using a Perkin Elmer LS-50B fluorometer.

Example 96

Incorporation of Fluorescently-Labeled G Proteins and GPCRs into Lipoparticles

YFP is fused to the carboxy-terminus of Gα$_z$, and CFP fused to the C-terminus of CXCR4. Fusion proteins are created using standard cloning methodology. Lipoparticles containing the CXCR4 fusion are constructed using standard techniques. G protein fusions are incorporated into these lipoparticles using one, or a combination of the methods outlined in previous Examples. The presence of fusion proteins in lipoparticles are verified by Western blot using anti-G protein and anti-GPCR antibodies. One skilled in the art would recognize that additional or alternative GPCRs, G proteins, and fluorescent protein labels could similarly be incorporated. To test their function, the labeled lipoparticles are exposed to the CXCR4 agonist SDF-1. Ligand binding by CXCR4 stimulates dissociation of the G protein from the GPCR, causing a reduction of fluorescence from the CFP-YFP FRET pair. Fluorescence emission is not altered in null-lipoparticles, or in lipoparticles treated with a CXCR4 antagonist such as the antibody 12G5. Fluorescence is measured in real-time, beginning prior to the addition of SDF-1, using a Perkin Elmer LS-50B fluorometer.

Example 97

Incorporation of a Membrane Potential Sensor

Lipoparticles containing CXCR4, Gα$_z$, and GTP are constructed. Lipoparticles are suspended in a concentrated solution of the fluorescent dye di-4-ANEPPS which diffuses preferentially into the lipid bilayer of cell membranes, and is incorporated into the Lipoparticles. Examples of alternative voltage-sensitive fluorescent dyes include, but are not limited to, di-4-ANEPPS($C_{28}H_{36}N_2O_3S$), di-8-ANEPPS, rhodamine 421, oxonol VI, JC-1, DiSC3(5), and the like (Molecular Probes, Inc.). The ANEPPS dyes can be measured ratiometrically, responding to increases in membrane potential with a decrease in fluorescence excited at approximately 440 nm and an increase in fluorescence excited at 530 nm. The presence of CXCR4 and $G\alpha_z$ in lipoparticles is verified by Western blot using anti-G protein and anti-GPCR antibodies. One skilled in the art would recognize that alternative GPCRs, G proteins, membrane potential-responsive fluorescent probes, or pH-responsive probes could also be used. To test their function, these lipoparticles are exposed to the CXCR4 agonist SDF-1. Ligand binding by CXCR4 results in a change in the structural conformation of the receptor associated with G-protein dissociation. This results in a change in the electrical potential across the lipoparticle membrane, causing a detectable signal emission from the ANEPPS probe. Fluorescence emission is not altered in null-lipoparticles, or in lipoparticles treated with a CXCR4 antagonist such as the antibody 12G5. Fluorescence is measured in real-time, beginning prior to the addition of SDF-1, using a Perkin Elmer LS-50B fluorometer.

Example 98

Incorporation of a Signaling Intermediate Ion Channel

Lipoparticles are constructed by standard techniques to contain CXCR4, $G\alpha_z$, GTP, and the ion channel. The ion channel may be an inwardly-rectifying potassium channels (GIRK) such as Kir3.x. The fluorescent dye di-4-ANEPPS is loaded into this lipoparticle as previously described. Di-4-ANEPPS fluoresces in a lipid environment and its fluorescence spectrum changes in response to fluctuations in membrane potential. The presence of CXCR4 and $G\alpha_z$ in lipoparticles is verified by Western blot using anti-G protein and anti-GPCR antibodies. One skilled in the art would recognize that alternative GPCRs, G proteins, and membrane potential-responsive fluorescent probes could also be used. To test their function, the labeled lipoparticles are exposed to the CXCR4 agonist SDF-1. Stimulation of CXCR4 causes dissociation of the G protein from CXCR4 and activation of the ion channel. The resultant movement of ions causes an alteration to the lipoparticle membrane potential, leading to a change in the fluorescence of the di-4-ANEPPS. Fluorescence emission is not altered in null-lipoparticles or in lipoparticles treated with a CXCR4 antagonist, such as the antibody 12G5. Fluorescence is measured in real-time before and after adding SDF-1 using a Perkin Elmer LS-50B fluorometer.

Example 99

Comparison of Ligand Affinity for GPCR with and without Incorporated G Proteins

Radioligand binding curves are performed to detect ligand binding to lipoparticles and to estimate the affinity of their interaction. In some cases, the affinity of ligand binding is affected by whether the GPCR is coupled or uncoupled from G proteins. The affinity change is a result of the GPCR exterior assuming different structural conformations in the presence and absence of G proteins. To measure this phenomenon in lipoparticles, CXCR3 lipoparticles are prepared with and without incorporated G protein. Radiolabeled I-TAC (Perkin-Elmer) is used to bind lipoparticles containing the CXCR3 membrane protein. Lipoparticles are resuspended in a total of 100 ul of Hepes++ Binding Buffer (50 mM Hepes 7.4, 5 mM $MgCl_2$, 1 mM $CaCl_2$, 150 mM NaCl, and 0.5% BSA) together with 0.1 nM radioligand. Increasing amounts of cold ligand (Peprotech) are also included. The mixture is incubated 1 h at room temperature and then filtered through Whatman GF/C filters soaked in 0.2% polyethyleneimine (PEI). Filters are counted in a Wallac gamma counter. The results are plotted as a competition curve to determine the affinity of the ligand for the receptor in its coupled versus uncoupled state.

Example 100

Incorporation of an Antibody-Anchoring ZZ-TM Fusion Sensor/Reporter Protein into Lipoparticles A 1-TM sensor/reporter is a fusion protein (ZZ-TM) comprising the following contiguous domains (from amino- to carboxy-termini): two Staphylococcal protein A Z-domains, the transmembrane domain of PDGFR, and a fluorescent protein (either the fluorescent donor CFP or the fluorescent acceptor YFP). When expressed within the membrane of a lipoparticle, the exterior Z-domains of the ZZ-TM fusion are capable of 'capturing' antibody by binding the constant (Fc) domains, and expressing it in the correct orientation for target recognition and binding. The internal fluorescent protein domains of the sensor/reporter will undergo FRET if acceptor and donor pairs are brought into close proximity by ZZ-TM clustering and cross-linking following target binding. One skilled in the art would recognize that the proteins could also be designed to undergo BRET.

The ZZ coding sequence is excised from pEZZ18 (codon optimized for expression within human cells, Amersham), and ligated into the cloning site of pDisplay (Invitrogen), a plasmid designed to facilitate expression of soluble molecules on the cell surface by fusing them to a minimal PDGFR transmembrane domain, a leader sequence (for surface expression), and epitope tags (for detection). The sequence for monomeric CFP or YFP is included at the 3'-end of the coding sequence for ZZ-TM using standard cloning techniques. Lipoparticles containing paired fusion proteins are produced in HEK-293 cells using methods previously described. Lipoparticles simultaneously contain both fluorescent protein fusion proteins (ZZ-TM-CFP and ZZ-TM-YFP) in order for FRET to occur. The presence of the fusion protein in producer cells and in lipoparticles is verified by Western blot using Fab fragment primary antibodies and anti-light chain secondary antibodies. Between 1 and 100 of each ZZ-TM pair are incorporated into each lipoparticle.

One skilled in the art would recognize that additional methods of incorporating functional membrane proteins into the lipoparticle are also possible, including avidin-biotin linkage, amine coupling, genetic fusion of Fv fragments onto reporters, or incorporation of naturally expressed BCRs.

Example 101

Use of ZZ-TM Lipoparticles and a Monoclonal Antibody for Pathogen Detection

Lipoparticles containing the ZZ-TM sensor/reporter fusion protein are created as described above. In order to make the ZZ-TM fusion proteins target-specific, a monoclonal antibody specific for DEN is 'captured' on the ZZ-TM sensor/reporter protein following lipoparticle production. Solutions of anti-DEN E-protein antibody (containing from 1 pg to 1 µg of antibody) are added to aliquots of ZZ-TM lipoparticles (containing 1 µg of protein) in Hepes buffered saline (HBS). After 30 minutes at 25° C., unbound antibody is removed by passing the lipoparticle suspensions through sucrose cushions. One skilled in the art would recognize that the ZZ-TM sensor reporter is capable of binding polyclonal or monoclonal antibodies singly or in combination, and that the target-specificity of the ZZ-TM fusion can be modified by replacing the 'captured' antibody with one with alternative epitope-recognition characteristics. Antibody-primed ZZ-TM lipoparticles are placed into stirred cuvettes in 1 ml HBS, and from 1 pg to 1 µg (protein) of DEN monomeric E protein, dimeric E protein, or non-infectious virions expressing E protein is added. Fluorescence is recorded in real-time using a Perkin-Elmer LS-50B fluorometer (excitation 436 nm, ratiometric emission at 480 and 535 nm). Baseline fluorescence is determined using ZZ-TM lipoparticles without MAb, and using lipoparticles not expressing the ZZ-TM sensor/reporter. Heat-destroyed antigen, WNV E proteins, and ZZ-TM linked to irrelevant antibodies are used as negative controls. Anti-mouse secondary antibodies are used as positive controls (will cross-link the captured primary antibodies). One skilled in the art would recognize that the basic pathogen detection assay could be applied to any infectious agent by changing the specificity of the captured recognition antibody, and that alternative detection formats or technologies (e.g. a microfluidic device, a flow cell, a Lab-on-a-Chip, a 96-well plate, a 384-well plate, a 1536-well plate, a glass slide, a plastic slide, an optical fiber, a flow cytometer, a microscope, a fluorometer, a spectrometer, or a CCD camera) could also be used.

Example 102

Use of ZZ-TM Lipoparticles and Combination Monoclonal Antibodies for Pathogen Detection An assay which utilizes multiple independent sensing and/or reporting mechanisms has a higher degree of fidelity and confidence than one relying upon a single target-recognition element. The goal of this experiment is to use ZZ-TM lipoparticles bearing multiple pathogen-specific MAbs to detect the presence of pathogen in samples. The use of two MAbs able to recognize different epitopes on the same antigen molecule increases the specificity of the pathogen detection assay when compared with using a single MAb. Lipoparticles containing the ZZ-TM sensor/reporter fusion protein are created as described herein. ZZ-TM lipoparticles are made target specific by adding two monoclonal antibodies with specificities to separate epitopes on the same protein. The HIV Envelope protein gp120 from strain IIIB is used, and MAbs include D47 and b12, which recognize different (non-competitive) epitopes on the same protein (V3 loop and CD4-binding site, respectively). Briefly, solutions of each monoclonal antibody (from 1 pg to 1 µg) are simultaneously added to aliquots of ZZ-TM lipoparticles (containing 1 µg of protein) in HBS. Unbound antibody is removed by passing lipoparticles through sucrose cushions. The basic pathogen detection assay described above is performed. Briefly, monomeric, oligomeric, or virion-expressed HIV Envelope protein is added to aliquots of antibody-primed ZZ-TM lipoparticles in stirred cuvettes and fluorescence is measured in real-time. One skilled in the art would recognize that the basic pathogen detection assay could be applied to any infectious agent or other antigen simply by changing the specificity of the captured recognition antibody. The MAbs may recognize epitopes on the same protein or on different proteins, so long as simultaneous recognition of both is sufficient to cross-link the ZZ-TM sensor protein.

Example 103

Use of ZZ-TM Lipoparticles and Polyclonal Antibodies for Pathogen Detection

The use of a polyclonal antibody increases the recognition diversity of the pathogen detection assay compared with using a single MAb. Lipoparticles containing the ZZ-TM sensor/reporter fusion protein are created as described above. ZZ-TM lipoparticles are made target specific by adding an anti-DEN polyclonal antibody, as described herein. Briefly, solutions of antibody (from 1 pg to 1 µg) are added to aliquots of ZZ-TM lipoparticles (containing 1 µg of protein) in HBS, and unbound antibody subsequently removed by passing lipoparticles through sucrose cushions. The basic pathogen detection assay described above is performed. Briefly, monomeric, dimeric, or virion-expressed DEN E protein is added to aliquots of antibody-primed ZZ-TM lipoparticles in stirred cuvettes and fluorescence is measured in real-time. One skilled in the art would recognize that the basic pathogen detection assay could be applied to any infectious agent or other antigen simply by changing the specificity of the captured recognition antibody. Affinity chromatography could be used to concentrate antigen-specific subsets of the polyclonal preparation.

Example 104

Use of ZZ-TM Lipoparticles and Antigen-IgG Fusions for Antibody Detection

Lipoparticles containing the ZZ-TM sensor/reporter fusion protein are created. ZZ-TM lipoparticles are made target specific by adding a DEN E protein-IgG fusion protein. This protein is created using standard cloning techniques by fusing the Fc portion of rabbit immunoglobulin G to the receptor binding domain (domain III) of the DEN E protein (courtesy of Dr. Ted Pierson). Because it contains an Fc domain, the protein can be bound by protein A (and the ZZ-TM sensor/reporter) in a manner similar to that for standard antibody molecules. Solutions of DEN E-IgG (containing from 1 pg to 1 µg of protein) are added to aliquots of ZZ-TM lipoparticles (containing 1 µg of protein) in HBS. After 30 minutes at 25° C., unbound E-IgG is removed by passing the lipoparticle suspensions through sucrose cushions. Primed ZZ-TM lipoparticles are placed into stirred cuvettes in 1 ml HBS, and from 1 pg to 1 µg (protein) of target antibody (anti-DEN E-protein) is added. Fluorescence is recorded in real-time using a Perkin-Elmer LS-50B fluorometer (excitation 436 nm, ratiometric emission at 480 and 535 nm). Baseline fluorescence is determined using ZZ-TM lipoparticles without captured E-IgG and/or using lipoparticles not expressing the ZZ-TM sensor/reporter. Heat-destroyed antibody, irrelevant IgG-protein fusions, and/or irrelevant antibodies in place of the target antibody are used as negative controls. One skilled in the art would recognize that the basic antibody detection assay could be applied to any target antibody simply by changing the epitope nature of the captured antigen-IgG.

Example 105

Incorporation of an Antibody Fab Fragment-Anchoring B1-TM Fusion Sensor/Reporter Protein into Lipoparticles The goal of this experiment is to incorporate a 1-TM protein into lipoparticles, capable of target recognition (e.g. pathogen, antibody, or ligand binding), of clustering and cross-linking upon target binding, and of reporting target binding/cross-linking (e.g. by participation in FRET). The 1-TM sensor/reporter is a fusion protein (B1-TM) comprising the following contiguous domains (from amino- to carboxy-termini): an immunoglobulin light-chain-binding domain (B1) of *Peptostreptococcus magnus* Protein L, the transmembrane domain of PDGFR, and a fluorescent protein (CFP or YFP). When expressed in lipoparticles, the external B1-domain is capable of 'capturing' target-specific Fab fragments, and presenting them in the correct orientation for target recognition and binding. The fluorescent protein domains undergo FRET if acceptor and donor pairs are brought into close proximity following B1-TM clustering and cross-linking upon antigen binding. One skilled in the art would recognize that alternative 1-TM backbones (e.g. CD4, Tva, EGFR), and alternative fluorescent proteins could also be used to create the B1-TM sensor/reporter. The B1-TM sensor/reporter fusion protein and lipoparticles containing it are created using standard molecular cloning techniques, as described for the production of the ZZ-TM lipoparticles. The B1-TM protein provides a sensor with a different target-binding stoichiometry than the ZZ-TM protein because B1 binds monomeric Fab fragments, whereas each Z domain binds dimeric antibodies. The presence of the fusion protein in producer cells and in lipoparticles is verified by Western blot.

Example 106

Use of B1-TM Lipoparticles and Fab Fragments for Pathogen Detection

The goal of this experiment is to use B1-TM lipoparticles bearing Fab fragments to detect the presence of pathogen in samples. Lipoparticles containing the B1-TM sensor/reporter fusion protein will be created as described above. B1-TM lipoparticles are made target specific by adding an anti-DEN Fab fragment in a manner similar to that described above. Briefly, Fab solutions (from 0.25 pg to 0.25 μg) are added to aliquots of B1-TM lipoparticles (containing 1 μg of protein) in HBS, and unbound Fab fragments are subsequently removed by passing lipoparticles through sucrose cushions. The basic pathogen detection assay described above is performed. Briefly, monomeric, dimeric, or virion-expressed DEN E protein is added to aliquots of Fab-primed B1-TM lipoparticles in stirred cuvettes and fluorescence measured in real-time. One skilled in the art would recognize that any Fab fragment could be incorporated into the sensor/reporter, and that the basic pathogen detection assay could be applied to any infectious agent or other antigen simply by changing the specificity of the captured recognition Fab fragment.

Example 107

Incorporation of a 1-TM Fusion Sensor/Reporter Protein into Lipoparticles, and its Use to Detect Receptor Ligands The goal of this experiment is to incorporate into lipoparticles a 1-TM receptor capable of target recognition, ligand-dependent clustering, and reporting of ligand binding. These lipoparticles are used for assay detection of ligands in samples. The 1-TM receptor comprises the epidermal growth factor receptor (EGFR) fused at its intracytoplasmic domain to a fluorescent protein (YFP or CFP). EGFR exists as a monomer when unliganded, but clusters and cross-links following binding by its cognate ligand, EGF. A plasmid containing the entire coding sequence for EGFR fused at its carboxy-terminus to YFP or CFP is created by standard cloning techniques. The fluorescent protein domains undergo FRET when both are incorporated into the same lipoparticle and acceptor and donor pairs are brought into close proximity by 1-TM receptor clustering and cross-linking following ligand binding. One skilled in the art would recognize that alternative 1-TM receptors, or alternative fluorescent or luminescent protein domains could also be incorporated into lipoparticles. Lipoparticles containing the 1-TM fusion sensor/reporter are produced by standard procedures as described herein. The presence of the fusion protein in producer cells and in lipoparticles is verified by Western blot.

For ligand detection, aliquots of 1-TM lipoparticles (containing 1 μg of protein) are placed into stirred cuvettes, and 1 pg to 1 μg of target ligand (dimeric EGF) in 1 ml HBS is added. Fluorescence is recorded in real-time using a Perkin-Elmer LS-50B fluorometer (excitation 436 nm, ratiometric emission at 480 and 535 nm). Baseline fluorescence is determined using lipoparticles not expressing the 1-TM sensor/reporter. Heat-destroyed ligand, and/or irrelevant ligands are used as negative controls. Anti-EGFR antibodies replacing the target ligands are used as positive controls. One skilled in the art would recognize that this ligand detection assay could be applied to any ligand simply by varying the receptor component of the 1-TM sensor/reporter fusion protein.

Example 108

Use of Lipoparticles Containing ZZ-TM and 1-TM Sensor/Reporters to Detect Ligand The goal of this experiment is to use lipoparticles containing both a ZZ-TM and a 1-TM sensor/reporter to detect the presence of a target ligand in samples. The use of antibody-bearing ZZ-TM sensor/reporters in combination with 1-TM sensor/reporters will increase the specificity of the ligand detection assay compared with using one sensor/reporter alone. ZZ-TM antibody-capture fusion proteins containing a YFP domain are constructed. A 1-TM receptor (EGFR) fused to CFP is constructed as described above. One skilled in the art would recognize that alternative 1-TM domains, or alternative fluorescent or luminescent protein domains could also be incorporated into lipoparticles. Lipoparticles containing both of these sensor/reporters are produced by standard methods as described herein. ZZ-TM sensor/reporters are made target specific by the addition of an anti-EGF MAb. The fluorescent protein domains undergo FRET when acceptor and donor pairs are brought into close proximity by MAb-ZZ-TM and 1-TM receptor binding to the same ligand molecule. Aliquots of the antibody-primed ZZ-TM/1-TM lipoparticles (containing 1 μg of protein) are placed into stirred cuvettes, and 1 pg to 1 μg of EGF in 1 ml HBS added. Fluorescence is recorded in real-time using a Perkin-Elmer LS-50B fluorometer (excitation 436 nm, ratiometric emission at 480 and 535 nm). Baseline fluorescence is determined using lipoparticles not expressing the sensor/reporter proteins. Heat-destroyed ligand and/or irrelevant ligands are used as negative controls. One skilled in the art would recognize that the basic ligand detection assay could be applied to any ligand simply by varying the receptor component of the 1-TM sensor/reporter and the antibody specificity of the ZZ-TM sensor/reporter, and that alternative detection formats (e.g. flow cytometry, optical biosensors) could also be used. The fluorescent protein CFP can be fused to either the 1-TM protein or on the ZZ-TM protein, so long as an appropriate acceptor protein (YFP) is fused to the complementary protein.

Example 109

Detection of Pathogens Using Flow-Cell Based Technology

Lipoparticles containing the ZZ-TM fusion protein are produced as described above. The ZZ-TM sensor/reporters are made target specific by capturing an anti-DEN E protein MAb as described above. Monomeric or dimeric DEN E protein, or virions expressing DEN E protein are amine-coupled to a carboxymethyldextran surface. Alternative coupling techniques, such as, but not limited to capture with a specific antibody or avidin-biotin interactions could also be used and other biochip surfaces could also be used. A suspension of antibody-primed ZZ-TM lipoparticles (1 pg to 1 µg) in HBS is passed through a flow-cell and fluorescence is monitored in real-time using ultra-sensitive assays based on evanescent field excitation (commonly known as TIRF) (Evans, et al. (2003), Neuron, 38:145-7, Wakelin, et al. (2003), J Microsc, 209:143-8). Fused silicon microscope slides derivatized with carboxymethyldextran are mounted on an inverted microscope stage in a small-volume (100 µl) lab-assembled flow cell that allows control over the injection and flow of analyte solutions. Derivitization commonly involves aminopropylsilanization followed by an EDC/NHS reaction of carboxymethyldextran with this aminated surface (Wakelin, et al. (2003), J Microsc, 209:143-8). Fluorescence excitation of captured lipoparticle sensors is induced by the evanescent field of a prism-coupled, internally reflected light source. Fluorescence emission is collected via a microscope objective focused on the derivatized slide surface and detected by a microscope mounted camera through appropriate emission filters. Alternatively, one skilled in the art would recognize a similar approach through the employment of derivatized fiber optics for evanescent excitation and collection of fluorescence with a sheath-based flow cell (Epstein, et al. (2003), Chem Soc Rev, 32:203-14, Marazuela, et al. (2002), Anal Bioanal Chem, 372:664-82). Negative controls include flow cells to which no antigen has been coupled and/or lipoparticles containing no ZZ-TM sensor/reporter. Variations based on this basic pathogen-detection assay are possible, such as coupling of the lipoparticles to the biochip and flowing solutions of the antigen through the flow cell. The assay could be applicable to any infectious agent or other antigen, simply by varying the specificity of the antibody captured by the ZZ-TM sensor/reporter.

Example 110

Detection of Target Protein in Tissue Sections

Lipoparticles containing the ZZ-TM fusion protein are produced as described above. The ZZ-TM sensor/reporters are made target specific by capturing an anti-mouse megalin MAb as described above. Megalin is a membrane protein found in a variety of tissues, including renal tubules, intestine, and thyroid, where it facilitates the trans-epithelial transport of a variety of hormones, vitamins and other molecules. Fixed sections of mouse kidney are incubated in suspensions of antibody-primed ZZ-TM lipoparticles (containing from 1 pg to 1 µg protein) at 37° C. for 1 hour. Sections are washed and visualized by fluorescent microscopy to detect FRET-induced signals. This basic immunohistochemistry procedure could be applied to any cell target simply by varying the specificity of the antibody captured by the ZZ-TM sensor, or by using a target-specific 1-TM sensor/reporter.

Example 111

Detection of Lipoparticle Signaling by Protein Reconstitution

This example detects 1-TM (single transmembrane) receptor signaling in lipoparticles using protein fragment complementation. The basis for protein fragment complementation assay is the reconstitution of a functional protein, such as an enzyme or a fluorescent protein, from rationally-designed inactive fragments fused to target proteins, such as membrane receptors. Interaction of the target proteins allows the folding of the reporter fragments into a functional protein, the activity of which is then detected. Two fusion proteins are constructed using standard cloning techniques. One fusion protein consists of the extracellular and transmembrane domains of the 1-TM receptor EGFR, with one half of the fluorescent protein GFP fused at its cytoplasmic tail (EGFR/GFPf1). The other fusion protein consists of identical EGFR domains fused to the complementary half of GFP (EGFR/GFPf2). Lipoparticles, simultaneously expressing both of these fusion proteins, are produced by methods already described, and suspended in HBS. An antibody recognizing EGFR will be added, and fluorescence measured in a stirred cuvette fluorometer. One skilled in the art would recognize that alternative transmembrane domains, including PDGFR, EPOR, and Tva could also be used, and that other inactive but complementary protein reporter fragments, including alternative fluorescent proteins (e.g. CFP, YFP), and enzymes (luciferase, β-lactamase, dihydrofolate reductase) could also be included (Galarneau, et al. (2002), Nat Biotechnol, 20:619-22, Luker, et al. (2004), Methods Enzymol, 385:349-60, Massoud, et al. (2004), Faseb J, Michnick (2001), Curr Opin Struct Biol, 11:472-7, Pelletier, et al. (1999), Nat Biotechnol, 17:683-90, Pelletier, et al. (1998), Proc Natl Acad Sci USA, 95:12141-6, Remy, et al. (2004), Mol Cell Biol, 24:1493-504).

Example 112

Incorporation of Gag/Fluorescent Protein Fusion Reporters into Lipoparticles

Gag is the one retroviral protein necessary and sufficient for lipoparticle production. In normal retroviruses, Gag is normally expressed as a fusion protein with enzymatic proteins (Pol). However, as Pol proteins are not necessary for lipoparticle formation, their sequence can be substituted with a variety of alternative genes, including those for fluorescent reporter proteins (Bennett, et al. (1991), J Virol, 65:272-80, McDonald, et al. (2002), J. Cell Biol., 159: McDonald, et al. (2003), Science, 300:1295-7, Weldon, et al. (1990), J Virol, 64:4169-79). Approximately 1,000-2,000 Gag proteins form the structural core of each lipoparticle (Knipe, et al. (2001)), so proteins fused to Gag are highly represented.

Figure 20:
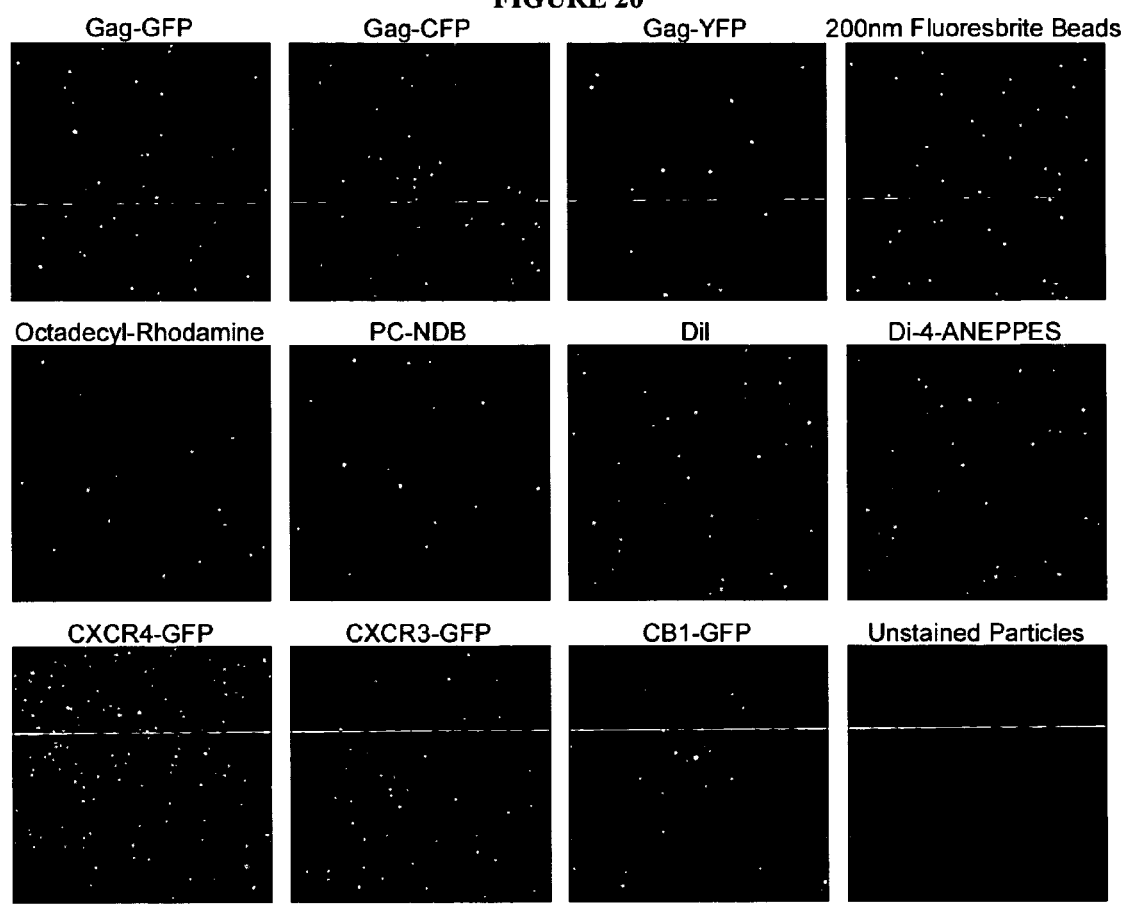
FIG. 20. Fluorescent Lipoparticles visualized by epifluorescence microscopy, 100× magnification. Lipoparticles were imaged for fluorescence using different fluorescent proteins (GFP, YFP, CFP) or dyes (octadecyl-rhodamine, phosphatidyl choline-NDB, diI, Di-4-ANEPPES), and using three different strategies (Gag-fusion protein, lipophilic dye incorporation, or membrane protein-fusion proteins). 200 nm Fluoresbrite beads and nonfluorescent particles (green channel shown, red channel was similarly blank) are shown as controls., All images were acquired with an epifluorescent Nikon microscope with a 100× lens.

Standard cloning techniques were used to fuse enhanced GFP (eGFP) to the C-terminus (base pair 1955) of the MoMLV Gag protein. Lipoparticles containing the Gag/GFP fusion were produced in HEK293 cells using methods described herein. The Gag/GFP fusion protein was evaluated by molecular weight confirmation using Western blot analysis, and its successful incorporation into lipoparticles was confirmed by direct microscopic visualization of lipoparticle fluorescence (FIG. 20) using epifluorescent illumination under an oil-immersion 100× lens (Nikon). Similarly, Gag/CFP and Gag/YFP fusion proteins were also created and incorporated into lipoparticles (FIG. 20). Lipoparticles were also constructed with both Gag/CFP and Gag/YFP simultaneously by co-expressing the Gag fusion proteins during production. Incorporation of both fluorophores was verified by fluorescence of both CFP and YFP in these particles as measured with an LS-50B Perkin Elmer fluorometer.

One skilled in the art would recognize that additional fluorescent (e.g. Green Fluorescent Protein (GFP), Yellow Fluorescent Protein (YFP), Blue Fluorescent Protein (BFP), Cyan Fluorescent Protein (CFP), DsRED, AsRED, AmCyan, HcRed, ZsGreen, ZsYellow, or variants thereof) and non-fluorescent proteins (e.g. esterases, proteases, kinases, G proteins, alkaline phosphatase, peroxidase, beta lactamase) could be similarly incorporated into lipoparticles by fusion to Gag, and that fluorescent and non-fluorescent proteins could be fused to other lipoparticle-integrated proteins (either native viral or artificially expressed proteins), and thus be co-incorporated, either individually or in combinations.

Example 113

Incorporation of Membrane Protein/Fluorescent Protein Fusion Reporters into Lipoparticles GFP was fused to the carboxy-(cytoplasmic) terminus of CXCR4 using standard cloning strategies. Lipoparticles containing the CXCR4/GFP fusion protein were produced in HEK293 cells using methods described herein. The presence of the CXCR4/GFP fusion within producer cells and lipoparticles was verified by direct microscopic visualization of fluorescent lipoparticles (FIG. 20). Three other membrane proteins fused to GFP were similarly incorporated into lipoparticles, including CCR5, CXCR3, and cannibanoid receptor 1 (CB1) (FIG. 20).

One skilled in the art would recognize that additional fluorescent and non-fluorescent proteins, including alternative fluorescent proteins (e.g. CFP, YFP, dsRed) and enzymes (e.g. alkaline phosphatase, horseradish peroxidase, beta-galactosidase, and other oxidases, kinases, and proteases), could be incorporated into lipoparticles by similarly fusing them to CXCR4 or other membrane proteins (e.g. CCR5, CD4).

Example 114

Incorporation of Lipophilic Dyes into Lipoparticle Membranes

Lipophilic dyes preferentially partition into lipid substrates, such as phospholipid membranes, simplifying their incorporation into lipoparticles when compared to water-soluble dyes. The membrane potential probe di-4-ANEPPS (Montana, et al. (1989), Biochemistry, 28:4536-4539, Rohr, et al. (1994), Biophysical Journal, 67:1301-1315, Venema, et al. (1993), Biochim Biophys Acta, 1146:87-96) was obtained as a powder, dissolved in ethanol, and added to an aqueous suspension of lipoparticles to a final concentration of 5 µM. Incorporation of the dye into lipoparticle membranes, which occurs almost instantaneously, was evaluated by fluorescent microscopy. Four other lipophilic dyes were similarly incorporated into lipoparticles, including octadecyl rhodamine, phosphatidyl choline-NDB, Nile Red, and diI (FIG. 20). In cases where the dye demonstrated high background, excess dye was removed by purification of the lipoparticles through a G50 spin column.

One skilled in the art would recognize that alternative strategies for the incorporation of di-4-ANEPPS and numerous other lipophilic dyes or other lipophilic substances (e.g. labeled or unlabeled fatty acids, phospholipids, sphingolipids, steroids, triacylglycerols, octadecyl rhodamine, lipophilic fluoresceins, coumarins, dialkylcarbocyanine probes, and dialkylaminostyryl probes) could also be employed to obtain similar results.

Example 115

Incorporation of AM-Ester Dye Reporters into Lipoparticle Interiors

The lipid bilayers of cell membranes (and lipoparticles) are normally impermeable to hydrophilic molecules such as water soluble fluorescent dyes. However, by coupling them to acetoxymethyl ester (AM-ester) groups, water soluble dyes can freely diffuse through lipid bilayers. This approach is commonly used to introduce water-soluble fluorescent dyes into cells, where they become trapped after removal of the AM-ester group by the action of cellular esterases. The same strategy is employed to load water-soluble dyes into modified, esterase-containing lipoparticles. A Gag/esterase fusion protein is generated by standard cloning techniques, using a human hepatic carboxylesterase (Pindel, et al. (1997), J Biol Chem, 272:14769-75). Gag/esterase-lipoparticles are produced in HEK293 cells using methods already described. The presence of the Gag/esterase fusion within lipoparticles is verified by Western blot analysis for the Gag fusion protein. Gag/esterase-lipoparticles are suspended in an aqueous solution of 10 µM calcein-AM (Molecular Probes). Fluorescence of calcein is quenched in its AM-ester form, but is released when the ester bond is cleaved. The removal of ester groups from calcein-AM molecules as they diffuse into lipoparticles is monitored by measuring increased fluorescent emission in a stirred-cuvette fluorometer. Retention of calcein within lipoparticles is confirmed by direct visualization using fluorescent microscopy. Lipoparticles not containing an esterase serve as negative controls.

One skilled in the art would recognize that alternative esterases could be incorporated into lipoparticles using this or similar techniques, or by fusion to other lipoparticle protein constituents. One skilled in the art would recognize that alternative water-soluble fluorescent AM-ester dyes (e.g. Fura-2, SNARF-1, SBFI, PBFI, DAF-FM, or other AM-ester dyes listed in the Molecular Probes handbook, all of which are incorporated by reference herein (Haugland (2003))) could be incorporated into Gag-esterase lipoparticles individually or in combinations by similar means.

Example 116

Mechanical Encapsulation of Membrane-Impermeable Reporters into Lipoparticles

Non-lipophilic probes and reporters that cannot be chemically modified to enable diffusion across lipid bilayers require mechanical delivery into membrane-bound spaces. Quantum dots (lipid membrane-impermeable, fluorescent reporters) are 3-6 nm spheres exhibiting high intensity and long-lived fluorescent characteristics. Quantum dots are incorporated into lipoparticles using electroporation, which causes pores (approximately 10 nm) to transiently open (for millisecond periods) in lipid membranes, allowing entry of external molecules and particles. lipoparticles are suspended in solutions of concentrated quantum dots and subjected to electroporation (200-2,000 V, 1-5 pulses of 1-20 msec duration each), conditions previously used for cells and liposomes (non-living, lipid spheres). Excess, non-incorporated quantum dots are removed by passing lipoparticles through sucrose cushions, and lipoparticle-incorporated fluorescence is visualized by microscopy and quantified using a fluorometer. Controls can include lipoparticles that have not been electroporated. One skilled in the art would recognize that alternative membrane-impermeable fluorescent and non-fluorescent molecules and particles (e.g. Phen-Green, lucigenin, OPA, radioactivity, paramagnetic beads, Raman probes (DSNB), gold) could be encapsulated in lipoparticles using similar strategies.

Example 117

Incorporation of Modified Lipids into Lipoparticle Membranes

Phospholipids, the major structural constituent of cell membranes, are glycerol-derived molecules comprised of a phosphorylalcohol molecule (the polar head), and two fatty acyl groups (non-polar tails). When phospholipids in solution are exposed to lipid membranes (such as cell membranes, liposomes, and lipoparticles), their non-polar tails partition into the membrane, leaving the polar head group, and molecules conjugated to it, exposed on the membrane surface. A variety of molecules, including proteins such as avidin, and small molecules such as biotin, may be conjugated to the phosphorylalcohol group of phospholipids.

Lipoparticle surfaces were biotinylated by allowing biotin-conjugated phosphoethanolamine (biotin-PE, Avanti Polar Lipids) to partition into lipoparticle membranes. To determine optimal lipoparticle biotinylation conditions, aliquots of lipoparticles were mixed with increasing amounts of biotin-PE at molar ratios of 1 thousand to 2.5 million (relative to lipoparticles), and reactions allowed to equilibrate for 1 hour. The functional characteristics of biotin-PE lipoparticles were then assessed.

Figure 21:
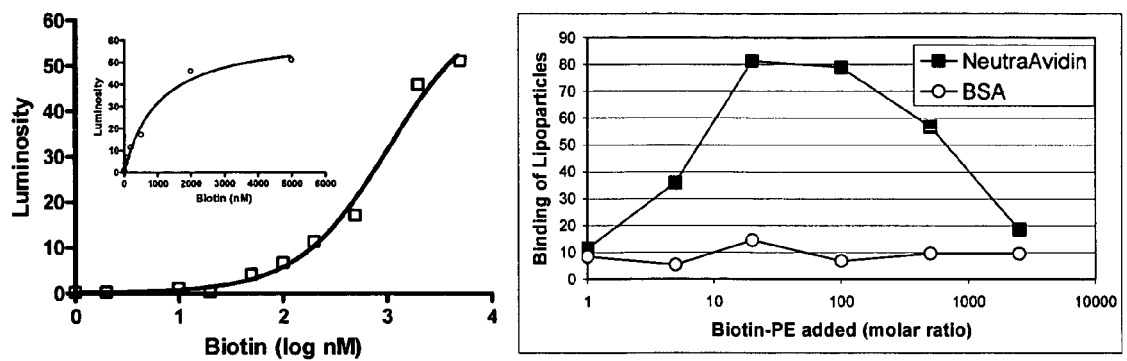
FIG. 21. Biotin can be incorporated into Lipoparticles. Lipoparticles containing the modified membrane lipid, biotin-phosphatidylethanolamine (biotin-PE), were created. Biotin-PE (Avanti Polar Lipids) was added to purified lipoparticles, and allowed to partition into the membrane. (Left Panel). Biotinylated lipoparticles were attached to a high-capacity protein-binding surface and probed with fluorescently labeled streptavidin. Binding of a constant amount of fluorescently labeled streptavidin (Molecular Probes) was dependent upon the concentration of biotin-PE used in lipoparticle preparation, and was saturable. The binding curve is also depicted on a linear scale (inset). (Right Panel) Binding by Neutravidin-coated ELISA plate wells (Pierce) of biotinylated lipoparticles prepared using a range of biotin-PE:lipoparticle ratios was measured by virus capture ELISA (VELISA) in which Gag from captured lipoparticles is measured. Values on the x-axis are in thousands. Binding reached a maximum at a biotin-PE:lipoparticle ratio of 100,000. The decrease in binding at higher ratios is presumably due to competition for Neutravidin binding sites by excess, unincorporated biotin-PE.

The ability of biotinylated lipoparticles to bind avidin derivatives in solution was evaluated. Lipoparticles were immobilized on glass slides by adsorption, excess biotin-PE removed by washing, and non-specific adsorption sites blocked for 20 minutes using 0.1% solutions of BSA. The slides were then exposed to a molar excess of fluorescently labeled streptavidin (50 nM in HBS) for 30 minutes and washed several times with buffer. Lipoparticles were imaged at 100× magnification on a microscope, and their luminosity determined from digital images using Canvas (Deneba software) image analysis software. Curves describing the dynamics of lipoparticle incorporation of biotin-PE were constructed by plotting average lipoparticle luminosity (directly proportional to the molar concentration of incorporated biotin-PE), against the total molar concentration of biotin-PE used in each biotinylation reaction. The incorporation of biotin-PE by fixed numbers of lipoparticles was found to be both concentration dependent and saturable (FIG. 21).

The ability of biotinylated lipoparticles in suspension to be captured by avidin-coated substrates was then evaluated. High-capacity protein-binding wells were coated with NeutrAvidin (Pierce), a deglycosolated version of avidin with a near-neutral pI to minimize non-specific binding, or BSA overnight. Lipoparticle/biotin-PE solutions (as above) were placed in the wells, which were centrifuged (1000 g, 90 min) before unbound particles were removed by washing. Binding of Lipoparticles by the neutravidin wells was quantified using an assay for the viral core protein, Gag. Neutravidin-bound lipoparticles were released and lysed using Triton X-100, transferred to new high binding ELISA plate wells, and allowed to adsorb to the well surfaces overnight. Total Gag concentration (proportional to the original neutravidin-bound lipoparticle concentration) was determined by ELISA using a rabbit anti-Gag primary antibody, an HRP conjugated anti-rabbit IgG secondary antibody, and Pico chemiluminescent substrate (Pierce). The concentration of bound lipoparticles was then plotted against the lipoparticle:biotin-PE ratio used in each biotinylation reaction (FIG. 21). Binding of biotinylated lipoparticles was biotin-PE concentration-dependent to a maximum (a molar ratio of approximately 1:100 000) after which binding decreased, presumably due to competitive interference by excess, unincorporated biotin-PE.

This demonstrates that a molar ratio of lipoparticle:biotin-PE between 1:20,000 and 1:100 000 produced optimal avidin binding by biotinylated Lipoparticles. One skilled in the art would recognize that alternative biotin-conjugated lipids or amphiphiles, differing, among other ways, in the structure of the lipid-biotin linkages, lipid head-group, acyl chain length, number, or structure, or non-glycerol based lipids, could also be used to biotinylate lipoparticle surfaces in a similar manner, and that other molecules such as enzymes, small molecules, or fluorescent proteins, when coupled to phospholipids may also be linked to lipoparticle membranes in a similar manner.

Example 118

Covalent Attachment of Molecules to Lipoparticle Surfaces

Figure 22:
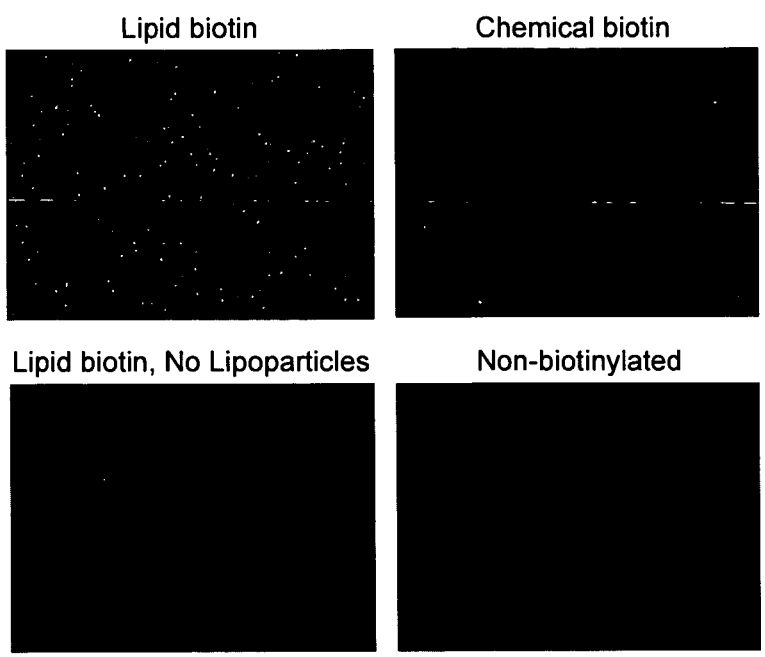
FIG. 22. Visualization of biotinylated lipoparticles. Lipoparticles were adsorbed to a microscope coverslip, blocked with 3% BSA, and exposed to a 50 nM solution of Alexa-Streptavidin (Molecular Probes) in a 100 µl volume for 20 minutes before the surface was rinsed three times with 10 mM Hepes pH 7 100 mM NaCl and imaged. Both chemically and lipid (DPPE-biotin) biotinylated lipoparticles produced punctuate fluorescent images through Alexa-Streptavidin binding, whereas non-biotinylated lipoparticles did not bind the fluorescent protein. The same coverslip surface exposed to lipid biotin alone did not demonstrate any streptavidin binding.

Cell membranes, including those from which lipoparticles are derived, naturally contain protein and carbohydrate constituents that can be non-specifically targeted by reactive molecules that form covalent bonds with molecular groups such as aldehydes and amines. Lipoparticle surfaces were biotinylated in this way using amine coupling. Aliquots of lipoparticles were suspended in buffered solutions (PBS pH 8.0 buffer) containing approximately 1,000-fold excess (relative to the total lipoparticle protein content)sulfo-NHS-biotin (amine reactive). After 1 hour, excess biotin was removed using size exclusion (Sephadex G50) spin chromatography, using a buffer containing 0.1% Pluronics F127 to reduce non-specific binding of the lipoparticles. Biotinylation of lipoparticles was evident by specific binding of fluorescently labeled streptavidin, which recognized lipoparticles only when biotinylated (FIG. 22). Lipoparticles were adsorbed to a microscope coverslip, blocked with 3% BSA, and exposed to a 50 nM solution of Alexa-Streptavidin (Molecular Probes) in a 100 μl volume for 20 minutes before the surface was rinsed three times with 10 mM Hepes pH 7 100 mM NaCl and imaged. Both chemically and lipid (DPPE-biotin) biotinylated lipoparticles produced punctate fluorescent images through Alexa-Streptavidin binding, whereas non-biotinylated lipoparticles did not bind the fluorescent protein. The same coverslip surface exposed to lipid biotin alone did not demonstrate any streptavidin binding.

Lipoparticles were similarly biotinylated using a carbohydrate-reactive biotin kit (Pierce) that links biotin to surface carbohydrates on the lipoparticle by biotin-hydrazide (carbohydrate reactive, pH 5.5 MES buffer). Lipoparticles were also biotinylated by mixing lipoparticles with biotinylated WGA (Vector Laboratories). The WGA lectin binds strongly to the lipoparticle surface. Biotinylated-WGA binding to lipoparticles was evident through enhanced lipoparticle attachment to streptavidin coated BIACORE chips during biosensing experiments.

Other reactive groups or methods for linking biotin to the Lipoparticle surface could also be used, including, but not limited to, carboxyl or sulfhydryl-coupling to membrane proteins, or the use of biotin-conjugated proteins with an affinity for Lipoparticle surface moieties, such as biotin-conjugated lectins. One skilled in the art would recognize that minor alterations to buffer composition, reactant ratios, reaction conditions and reaction duration could result in comparable products. In addition to biotin, other molecules, including magnetic particles, quantum dots, gold particles, or radioactive substances, could also be linked to lipoparticle surfaces using similar approaches. These other substances could be used to provide lipoparticles with unique interactive and detection properties and functions, such as detection by MRI, detection by electron microscopy, or detection by radiography or PET.

Example 119

Linkage of Reporters to the Lipoparticle Exterior

Streptavidin-coated quantum dots (Quantum Dot Corp) are added to aliquots of biotinylated lipoparticles, and allowed to bind to the lipoparticle surface. Unbound quantum dots are removed by passing lipoparticles through a sucrose cushion. Fluorescence of the lipoparticles is visualized by microscopy and quantified using a fluorometer. Controls can include non-biotinylated Lipoparticles. One skilled in the art would recognize that other avidin-, streptavidin-, or neutravidin-bound molecules or reporters could be linked to the surface of biotinylated lipoparticles in a similar manner. One skilled in the art would recognize that a lipoparticle expressing avidin or streptavidin on its surface could be used similarly to 'capture' biotinylated targets. One could also label with fluorescent lectin WGA or biotinylated lectin WGA. Other materials and proteins could also be linked to the lipoparticle exterior, such as antibodies.

Example 110

Incorporation of Enzymes into Lipoparticles

Figure 23:
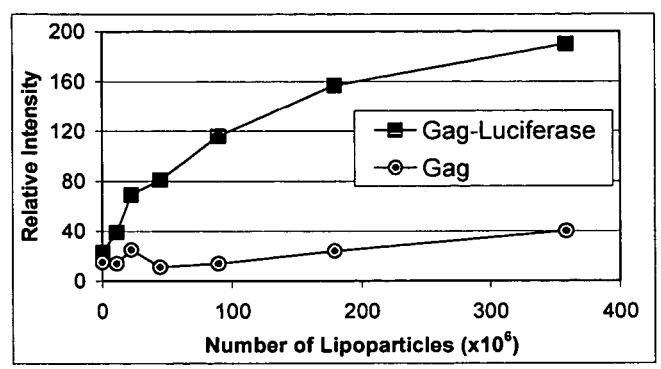
FIG. 23. Functional enzymes can be incorporated into Lipoparticles. The luciferase reporter enzyme (60 kDa) was included in lipoparticles by using a Gag-luciferase fusion protein for particle production. Detection of concentration-dependent luciferase activity (Promega Steady Glo Luciferase Assay System) in lysed particles demonstrates retention of function by the incorporated enzyme. Luciferase activity of conventional lipoparticles are shown as a negative control.

Enzymatic reporters, such as luciferase, catalyze reactions resulting in the detectable chemical modification of a substrate. Luciferase is one of the most sensitive reporters known (detectable to $10^{-20}$ moles under ideal conditions). Luciferase-containing lipoparticles were created by producing lipoparticles using a Gag/luciferase fusion protein as described herein for Gag-GFP fusion protein lipoparticles. In order to test the functional activity of the incorporated enzyme, lipoparticles were permeabilized using small amounts of detergent (1% Triton X-100) to allow access of substrate and co-factors (luciferin, ATP, coenzyme A) to luciferase. Permeabilized lipoparticles were suspended in a substrate buffer (Promega Steady-Glo Luciferase Assay System), and luciferase activity was measured using a Wallac Victor2V luminometer. Permeabilized lipoparticles not containing luciferase, and lipoparticles suspended in buffer solutions without the substrate, were used as negative controls. Results using increasing amounts of lipoparticles demonstrated that luciferase-containing lipoparticles retained luciferase activity, and that lipoparticles without luciferase did not contain any substantial luciferase activity (FIG. 23). Lipoparticles were also tested without permeabilization and did not display any significant luciferase activity. Lipoparticles were also permeabilized using melittin (a pore-forming peptide), freeze-thawing, Lubrol, NP-20, CHAPS, and beta-octylglucoside.

One skilled in the art would recognize that alternative means of physically associating enzymes with lipoparticles, such as fusion to other protein constituents including membrane proteins, as outlined herein, incorporation of enzymatic membrane proteins such as BACE, or linkage to the lipoparticle surface such as via biotin-streptavidin interactions as outlined herein, could also be used. Internally encapsulated enzymes could also be cleaved from Gag, or other proteins to which they are fused, if a protease target site is incorporated into the fusion linker, and a protease such as MoMLV Pol is also included in the lipoparticle. One skilled in the art would recognize that alternative signaling, or non-signaling enzymatic proteins (e.g. alkaline phosphatase, GTPases, ATPases, horseradish peroxidase, beta-galactosidase, DNA and RNA polymerases, lipid-active enzymes such as phospholipase A and C, and other oxidases, kinases, and proteases) could be incorporated in a similar manner, either individually or in combinations. One skilled in the art would recognize that alternative methods for poration of lipoparticles could also be employed, including sonication, vortex mixing, use of pore-forming peptides (e.g. melittin, streptolysin-O), polyethylene glycol, and low concentrations of alkanes.

Example 111

Poration and Permeabilization of Lipoparticles

Lipoparticles containing appropriately sized pores would be permeable to small molecules that would not normally be capable of crossing the lipid bilayer, while larger molecules, such as Gag or trapped reporters, would remain caged within the Lipoparticle. Melittin is a cationic, amphipathic peptide derived from the venom of the European honeybee. It partitions to the aqueous-lipid interface of cell membranes where it induces disruption of the lipid bilayer, aggregation (pore formation), and formation of voltage-gated channels. It has been used in large unilamellar vesicles (100 nm) to create pores with estimated radii of between 0.3 to 5 nm (Rex, S. 1996. Biophys Chem 58: 75-85).

Figure 24:
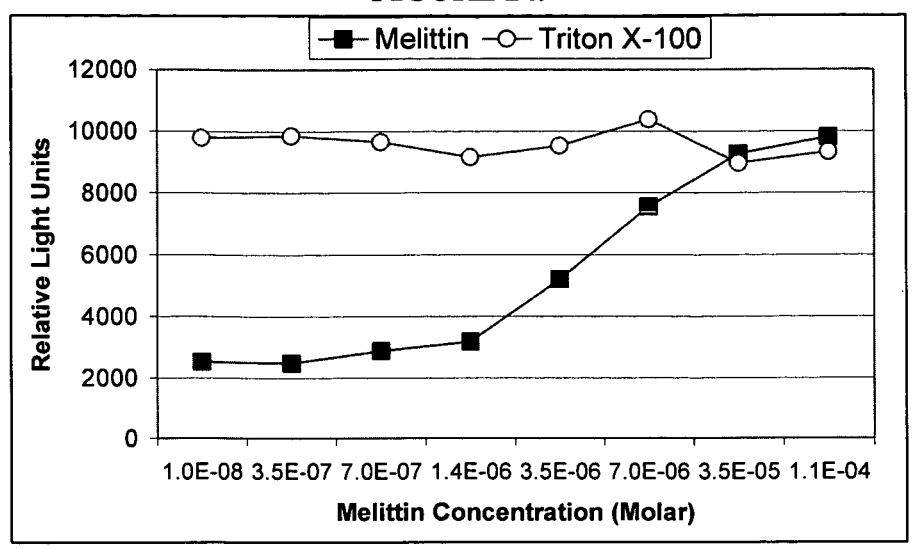
FIG. 24. Melittin poration of Lipoparticles. Lipoparticles were constructed to contain a luciferase enzyme inside the lipoparticle. Upon addition of increasing amounts of melittin peptide, the lipoparticles were permeabilized and luciferase substrate was allowed to enter and produce a signal. To insure the integrity of the luciferase, after each addition of melittin, the same sample was lysed with Triton X-100 (circles) and again measured. The results indicate that all samples contain luciferase, but only sample with sufficient pores induced by mellitin were able to react with the luciferase substrates. Luciferase activity was measured using a Wallac Victor2V and mixing lipoparticles with the Promega Steady Glo Luciferase Assay System.

Lipoparticles containing a Gag-luciferase fusion protein were prepared as described herein. Melittin, ranging from 0.3 to 105 uM in final concentration, was added to solutions of Gag/luciferase-lipoparticles (MOPS pH 6.5 buffer), mixed, and incubated for 30 minutes. A 5 µl aliquot of the Lipoparticle solution was then transferred to a 96-well plate containing 50 µl of Luciferase assay reagent (Promega Steady Glo Luciferase Assay System) which contains the necessary reagents for enzymatic activity, including luciferin, ATP, and $Mg^{2+}$. Luminescence was measured for 1 second integrations in a Wallac Victor2V. When sufficient melittin was added to the Lipoparticles, pore formation resulted in influx of luciferin and ATP into the lipoparticle interior, and an increase of the luminescent signal (FIG. 24). Triton X-100 was used to lyse luciferase-lipoparticles as a positive control.

One skilled in the art would recognize that numerous means of transiently or permanently permeabilizing or porating lipoparticles could be employed to similar effect. These include, but are not limited to sonication or vortexing, laser-generated stress waves (Graier W F, et al. 1998. J Physiol 506, 109-125), use of pore-forming proteins and peptides (e.g. streptolysin-O, aerolysin, maltoporin), pore-forming channels (P2X7), polyethylene glycol, concentrated calcium, and low concentrations of alkanes. The pore-forming channel P2X7 could also be incorporated into lipoparticles. P2X7 creates a 900 Da pore upon addition of 5 mM ATP (or BzBzATP or BzBzGTP) and can then re-close when exposed to divalent cations such as magnesium or calcium. Permeabilized lipoparticles could act as targeted or untargeted probes of local microenvironments, by allowing the interaction of trapped reporters with small molecules in the local vicinity.

Example 112

Linkage of Lipoparticles to Beads

Figure 25:
FIG. 25. Affinity binding of Lipoparticles. Lipoparticles, derived directly from the cell surface, naturally possess binding qualities similar to cellular membranes. Cell membranes, for example, are known to adhere to wheat germ agglutinin (WGA), a lectin that binds the abundant cell surface carbohydrate, N-acetylglucosamine. Fluorescent lipoparticles (constructed using Gag-GFP) were exposed to WGA agarose beads and control Protein A (ProA) agarose beads. Fluorescent lipoparticles were observed by microscopy to bind the WGA beads [A], but not the ProA beads [B], demonstrating their ability to label targets in a specific manner.

Wheat Germ Agglutinin (WGA) is a dimeric, 36 kDa protein which selectively binds the terminal N-acetylglucosamine of oligosaccharides including glycolipids that occur abundantly in most mammalian cell membranes (and lipoparticles). WGA, bound to 4% cross-linked agarose beads are available from a variety of vendors, including Vector Laboratories. In order to demonstrate the ability to link lipoparticles to these beads, 10 µl of fluorescent GFP-LipoProbes (lipoparticles constructed using a GFP/Gag fusion protein) were diluted to 100 µl in HBS buffer and mixed with 3 µl of either WGA agarose beads, or control Protein A (ProA) agarose beads and allowed to incubate with gentle rocking for 30 minutes. The beads were spun for 2 minutes at 3 k rpm, and washed with 1 ml of HBS buffer. Binding of LipoProbes to the beads was monitored directly by fluorescent microscopy (FIG. 25). LipoProbes were observed to bind the WGA agarose beads, but not the control beads.

One skilled in the art would recognize that a variety of core bead matrices could be used as alternatives to 4% agarose, including other agarose formats, polymers such as polystyrene, divinylbenzene, and polyvinyltoluene, poly-Lysine, and latexes such as sulfate-, carboxyl-, and chloromethyl-latex. Alternative bead-surface coupling groups to WGA could also be used, including, but not limited to other lectins such as ConA and DBA, aldehyde- and amine-reactive groups, ATP binding sites, carboxyl- and hydroxyl-reactive groups, thiols, phenyls and imidazoles, antibodies and other binding proteins, Protein A, Protein G, Protein L, and streptavidin. Specialty core matrices possessing intrinsic coupling and reporting properties, such as dyed or fluorescent microspheres, quantum dot beads, and magnetic beads could also be used. Where necessary and appropriate, lipoparticles could be engineered to contain surface molecules that specifically interact with bead coupling groups. Bead-coupled lipoparticles could be used for binding analyses such as scintillation proximity assays and immunobinding assays, affinity chromatography and protein purification applications, flow cytometry, and multiplexed binding assays.

Example 113

Co-Localization of Multiple Reporters within Lipoparticles

Carboxy-SNARF1 (Molecular Probes) is a pH-sensitive dye reporter with an excitation wavelength of 488 nm. Its emission spectrum undergoes a pH-dependent shift, and is typically monitored at two wavelengths, 580 nm and 640 nm. Alexa-fluor 488 (Molecular Probes) is a general-purpose, pH-insensitive, photostable fluorescein substitute with an absorption maximum at 488 nm, and an emission spectrum that is typically detected at 520 nm. These two reporters are simultaneously incorporated into lipoparticles. Lipoparticles containing a Gag/carboxylesterase and surface biotinylation, both of which are described herein, are produced. Carboxy-SNARF1-AM acetate is incorporated by incubating the dye with the lipoparticles, wherein the esterase cleaves the AM-ester bond and trap the SNARF1. An Alexa-fluor 488-biotin conjugate is linked to the surface of the lipoparticles. Unbound or unincorporated molecules are removed by passing lipoparticles through sucrose cushions, and lipoparticle fluorescence (at 520 nm, 580 nm and 640 nm) assessed by microscopy and in a stirred-cuvette fluorometer. One skilled in the art would recognize that a variety of reporter dyes and proteins could be incorporated into lipoparticles in combination using these, or alternative, methods.

Example 114

Incorporation of an Antibody-Anchoring ZZ-TM Fusion Protein into Lipoparticles for Targeting The targeting component comprises a variable target-recognition domain (an antibody), an anchor for fixation to the lipoparticle surface (a 1-TM protein domain), and a domain to link these two functional units (an antibody-binding protein, fused to the 1-TM anchor). The Tva-ZZ fusion protein (courtesy of Dr. Paul Bates) is a 1-TM sensor comprising the following contiguous domains (from amino- to carboxy-termini): a leader sequence, two Staphylococcal protein A Z-domains, and the transmembrane domain of the single transmembrane protein Tva. When expressed within the membrane of a lipoparticle, the exterior Z-domains of the ZZ-TM fusion are capable of 'capturing' antibody by binding their constant (Fc) domains, and expressing them in the correct orientation for target recognition and binding.

Figure 26:
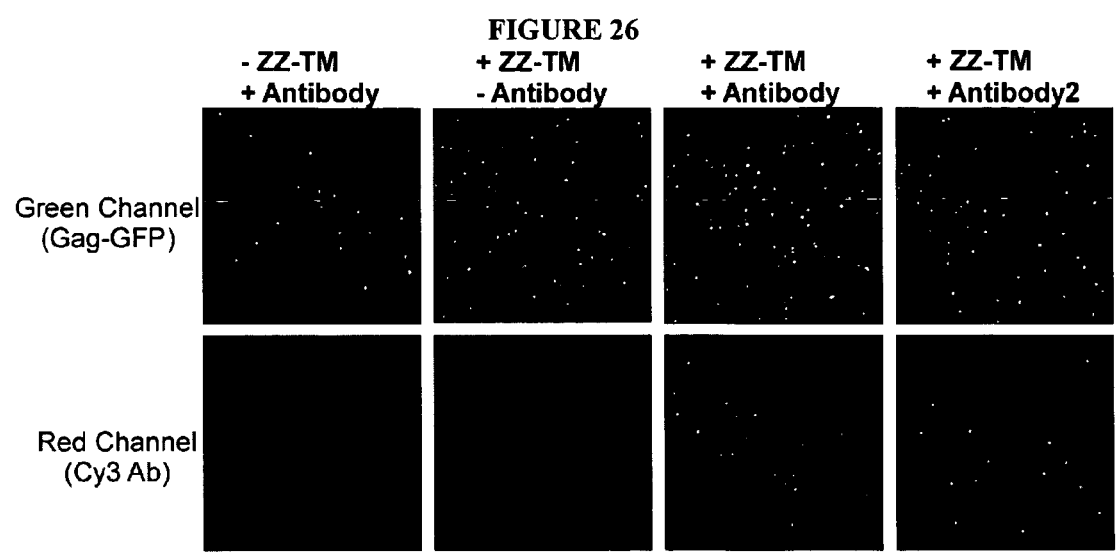
FIG. 26. A transmembrane-anchored form of the ZZ binding domain from Protein A (Tva-ZZ) was incorporated into lipoparticles made using a Gag-GFP core. The lipoparticles were then exposed to a primary antibody that could bind the ZZ domain (or none). All lipoparticles were then exposed to a red secondary fluorescent antibody (Goat antibody not capable of binding ZZ directly). The presence of lipoparticles in all panels is shown in the top row, imaging for the Gag-GFP using the green channel. The lipoparticles containing ZZ-TM were capable of binding two different antibodies, as shown by imaging of the Cy3-labeled antibody in the red channel (bottom row, two right panels). Lipoparticles not containing ZZ-TM or not exposed to the antibody did not show any fluorescence in the red channel (bottom row, left two panels).

Lipoparticles containing Tva-ZZ were produced in HEK-293 cells using methods previously described. The presence of Tva-ZZ in Lipoparticles was verified by binding of fluorescent antibodies to the lipoparticles and visualizing the fluorescently-labeled lipoparticles by microscopy (FIG. 26). The incorporation of Tva-ZZ was also confirmed by VELISA, capturing Tva-ZZ lipoparticles onto wells coated with an antibody and detecting the presence of Gag.

One skilled in the art would recognize that alternative antibody-binding domains (e.g. Protein G, Protein L), or 1-TM anchoring backbones (e.g. CD4, PDGFR, EGFR), could also be used to create the ZZ-TM recognition protein. One skilled in the art would recognize that additional methods of incorporating functional membrane protein anchors into the lipoparticles are also possible, including avidin-biotin linkage, amine coupling, genetic fusion of Fv fragments onto reporters, or incorporation of naturally expressed 1-TM receptors. One skilled in the art would recognize that the recognition domain of the ZZ-TM targeting component could comprise any monoclonal or polyclonal antibody, and that the target specificity could be defined simply by changing the epitope-recognition characteristics of the 'captured' antibody. One skilled in the art would recognize that the bead could be made to contain any number of molecules on its surface, including antibodies, antibody fragments, fluorescent molecules, peptides, proteins, small molecules, or organic compounds, that may be complementary to membrane proteins on the lipoparticle. Alternative target recognition domains, including ligand-specific binding proteins, could also be linked to a membrane anchor in a similar manner.

Example 115

Incorporation of Modifying Proteins to Provide Micro-Environmental Sensitivity of Lipoparticle Probes The goal of this experiment is to co-incorporate a modifying component, the membrane protein ion channel, TRPV1, into the lipoparticle membrane, and the calcium-sensitive reporter, FURA-2, into the lipoparticle interior. The Transient Receptor Potential Channel V1 (also known as the vanilloid receptor 1 (VR1)), is a 95 kDa $Ca^{++}$-ion channel that opens in response to heat and binding of appropriate ligands (capsaicin, resiniferatoxin, and anandamide) (Caterina, et al. (1997), Nature, 389:816-24, Clapham (2003), Nature, 426:517-24). Fura-2 is one of the most commonly used fluorescent reporters of calcium ions within living cells. On binding $Ca^{++}$ (Kd 0.14 µM), Fura-2 undergoes a change in its excitation spectrum that can be detected either as an increase in fluorescence or, most commonly, as an increase in the 340/380 nm excitation ratio (Molecular Probes Handbook (2003)). Lipoparticles containing the TRPV1 modifying component undergo selective and active $Ca^{++}$ internalization upon channel activation (by heat or ligand). The FURA-2 signaling component in the lipoparticle interior allows these lipoparticles to act as caged sensors of microenvironmental calcium flux. Lipoparticles containing an esterase are produced from a Gag/carboxylesterase fusion protein. A Fura-2-AM ester is incorporated into the TRPV1-lipoparticles where it is trapped after removal of the AM ester group by the action of the Gag/carboxylesterase. Unincorporated Fura-2 AM is removed by passing lipoparticles through sucrose cushions. Aliquots of these lipoparticles are suspended in buffered solutions containing various concentrations of calcium. TRPV1 is activated by heating to 43° C. and/or by addition of a TRPV1 ligand (e.g. capsaicin), and fluorescence monitored by microscopy and in a stirred-cuvette fluorometer. One skilled in the art would recognize that alternative calcium-sensitive reporters, such as the bioluminescent calcium-sensitive enzyme, aequorin, could be included in lipoparticles. Other ion channels responding to other desired stimuli, or alternative modifying proteins (such as surface enzymes) could also be included. A variety of reporters, such as pH sensitive dyes, or membrane-potential reporters, could also be co-integrated to create lipoparticle probes. Any number of these probes, either individually or in combinations, could be incorporated into lipoparticles.

Example 116

Use of Lipoparticles as Receptor-Directed Immunofluorescent Probes

Figure 27:
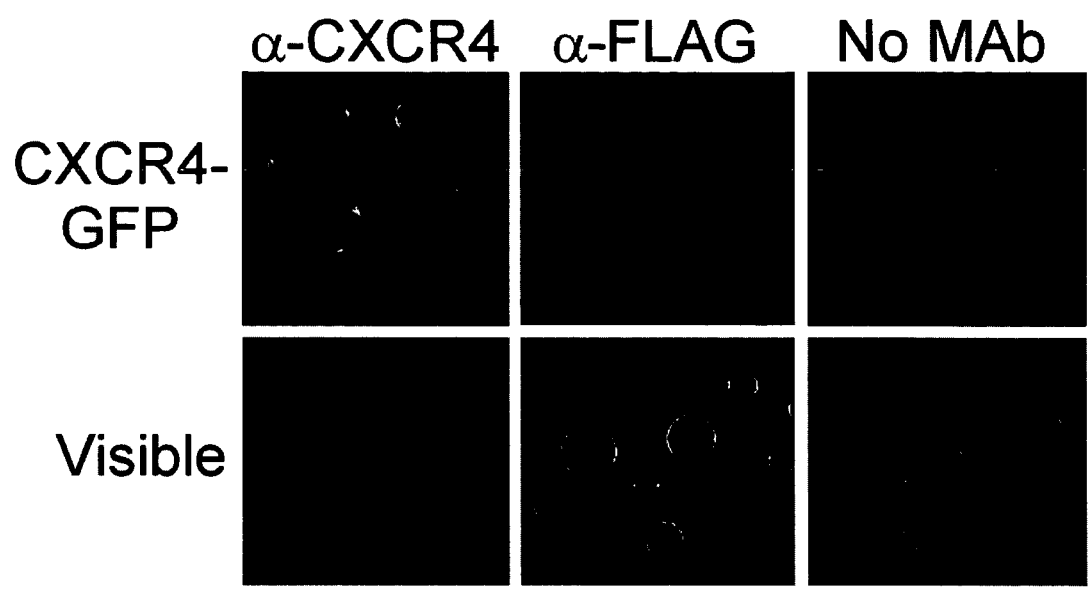
FIG. 27. Lipoparticles can act as Specific Probes Using Membrane-embedded Proteins. Lipoparticles can be targeted to desired locations using the characteristics of membrane proteins embedded in their surfaces. Fluorescent lipoparticles (Gag-GFP), containing the seven-transmembrane protein CXCR4, were used to probe ProA beads bearing a variety of antibodies. Beads (3-10 μm) were visualized using fluorescent light (top panels) or white light (bottom panels) and a 10× objective. CXCR4-containing lipoparticles were bound by anti-CXCR4 ProA beads, but not by ProA beads bearing an irrelevant antibody (anti-FLAG), or by ProA beads bearing no antibody, demonstrating the specificity of binding by the lipoparticle membrane-embedded protein.

Lipoparticles containing the CXCR4 membrane protein were produced using a Gag/GFP fusion protein. Separately, ProA beads were mixed with either an anti-CXCR4 antibody (recognizes a conformational domain on the extracellular side of the receptor), an anti-FLAG antibody (negative control), or no antibody at all. An aliquot of the CXCR4 GFP-lipoparticles were mixed with the beads, non-bound probes removed by washing, and the beads visualized by fluorescent microscopy. Results indicate that the lipoparticles bound only to the beads with the anti-CXCR4 antibody (FIG. 27). Minimal or no staining of the beads was observed with the negative control antibody (FLAG) and with the no antibody control. One skilled in the art would recognize that a variety of alternative fluorescent or non-fluorescent reporters could have been used. Similarly, lipoparticle probes could be used to detect proteins in other cell and tissue sample formats, such as other adherent cell cultures or cell suspensions, in paraformaldehyde or other processed tissue sections, or in tissue explants. Lipoparticle probes could also be used to detect targets using other formats such as flow cytometry, ELISA, and western blot analysis (far western).

Example 117

Use of Lipoparticles as Antibody-Directed Immunofluorescent Probes

Lipoparticles can be used as antibody-directed Immunofluorescent probes. Lipoparticles containing a ZZ-TM targeting fusion protein are produced using a Gag/GFP fusion protein. These lipoparticles are made target-specific by ZZ-TM binding of a monoclonal antibody (12G5) that recognizes the extracellular domain of the G protein-coupled receptor CXCR4. CXCR4 is transiently expressed in HEK-293 cells using standard transfection techniques. 24-48 h post-transfection, an aliquot of the CXCR4-specific GFP-lipoparticles is added to the culture, non-bound probes removed by washing, and the cells visualized by fluorescent microscopy. Negative controls will include lipoparticles expressing irrelevant antibodies, lipoparticles without ZZ-TM, and cells not expressing CXCR4.

One skilled in the art would recognize that a variety of alternative fluorescent or non-fluorescent reporters could be included, and that other cell or tissue proteins could be detected simply by altering the antibody captured by the ZZ-TM targeting protein. Similarly, lipoparticle probes could be used to detect proteins in other cell and tissue sample formats, such as other adherent cell cultures or cell suspensions, in paraformaldehyde or other processed tissue sections, or in tissue explants. Lipoparticle probes could also be used to detect targets using other immunochemistry-based detection modalities such as flow cytometry, ELISA, and western blot analysis (far western). The targeting membrane protein on the lipoparticle may be an antibody bound to an incorporated ZZ-TM protein, or could be a cellular membrane protein.

Example 118

Detection of pH Using a Lipoparticle Probe

Fluorescent dyes provide increased sensitivity for optical pH determination compared with conventional pH-sensitive dyes, and the incorporation of fluorescent dyes into Lipoparticles confers advantages of spatial localization when compared with electrode-based techniques. Lipoparticles are produced and the alkylated pH-sensitive blue fluorescent dye, 4-heptadecyl-7-hydroxycoumarin (pKa range from 6.35-11.15 depending on the ionic composition of the membrane) is allowed to partition into lipoparticle membranes, as described previously. Fluorescence is measured in a stirred-cuvette fluorometer under pH conditions ranging from pH 4-12. Similarly, fluorescence can also be measured using a microscope under epifluorescent illumination and while changing the pH in the solution above the lipoparticles.

One skilled in the art would recognize that alternative pH-sensitive dyes, such as fluorescein, FITC, Oregon Green, SNARF-1/AM, and SNAFL could similarly be loaded into Lipoparticle membranes by this, or alternative incorporation methods. Reactive pH-sensitive dyes could be incorporated into lipoparticles by conjugation to other lipophilic molecules such as phospholipids, or by reactive processes such as esterification or covalent attachment to Lipoparticle components. AM-esters could be allowed to diffuse directly across lipoparticle membranes, while pH-sensitive proteins, such as PHFluorin or other pH sensitive GFP-modifications (Hanson, et al. (2002), Biochemistry, 41:15477-88), could be incorporated into lipoparticles by fusion to Gag or a membrane protein as previously described.

By incorporating alternative dyes or reporters into them, Lipoparticles capable of detecting a variety of environmental conditions can be created for use in cells and tissues as well as in biological and environmental samples. The Molecular Probes Handbook (Haugland (2003)) details the properties of thousands of these reporters and indicators, all of which are incorporated by reference herein. For example, calcium ions can be detected using Fura-2, Indo-1, Fluo-3, Rhod-2, Fura-C18, Fura-FF-C18, Calcium Green, Calcium Orange, Oregon Greens, FFP18 (Gomez-Reino, et al. (1999), Arthritis & Rheumitism, 42:989-992), and aequorin protein. Magnesium can be detected by incorporating mag-indo-1 or mag-fura-2. Chloride ions can be detected using indicators such as SPQ, MQAE, MEQ, and L-6868, while sodium and potassium ions can be detected using such reporters as SBFI and PBFI, both of which are available as AM-esters, or the membrane-permeant Sodium Green tetra-acetate. Other metal ions can be detected by incorporating FluoZin-1 or FuraZin-1 (Zn2+), Phen Green FL (Cu+2, Fe, Hg, Pb, Cd, Ni), NewportGreen (Ni+2, Zn), while rhodamine 6G can be used to detect hypohalites (ClO—). Chelators and ionophores such as nitrophenyl EGTA, DMNP-EDTA, Diazo-2, BAPTA-AM, TPEN (chelates Zn, Cu, Fe), or the ionophore 4-Bromo A-23187 can also be incorporated into Lipoparticles. Environmental contaminants could also be detected by incorporation of appropriate reporters. For example, thiols and cyanide can be detected by the fluorescence of CBQCA. A variety of agents capable of detecting reactive oxygen species are available, including M-7913, MCLA, dihydrocalcein-AM, malachite green, Amplex Red, diphenyl-1-pyrenylphosphosine (DPPP) and coelenterazine, and nitric oxides can be detected by DAF-FM, SNAP, 2,3-diaminoapthalene, and SBD methylhydrazine. Oxidation and reduction can be monitored using agents such as resazurin, dodecyl resazurin, dihydrorhodamine, or dihydrofluoresceins. Any of these dyes can be incorporated into lipoparticles individually or in combination.

Such reporters could be incorporated into Lipoparticles by any of the methods outlined previously, or using combinations of these methods. These include, but are not limited to, fusion to Gag-, membrane-, or other lipoparticle proteins, partitioning of lipophilic dyes or lipid-conjugates within the membrane, encapsulation within the lipoparticle by diffusion of AM-esters or lipoparticle poration or permeabilization, and linkage or covalent attachment to the lipoparticle surface.

Example 119

Microinjection of Lipoparticles into Cells

Intracellular Lipoparticles bearing a variety of targeting and signaling components are capable of localizing desired subcellular structures and events, and reporting them through emission of detectable luminescent or fluorescent signals. The compartmentalization of functional components within the lipoparticle vehicle enables the Lipoparticle to contain and localize reporters to target sites and minimize non-specific background emissions, to limit general disruption to the cytoplasmic equilibrium, and to utilize high concentrations of potentially toxic reporters (e.g. ion chelators). Lipoparticles bearing user-specified effector proteins and other modifying components (e.g. ion channels, enzymes) are capable of selective and specific delivery of active molecules to subcellular locations, and of microenvironmental perturbation.

Labeled lipoparticles are prepared by producing lipoparticles using a Gag/GFP fusion protein as outlined herein, and are suspended in $Ca^{++}$-free HBS. HEK-293 cells, grown to confluence, are microinjected to approximately one-tenth of the cell volume with an aliquot of Gag-GFP Lipoparticles, using a back-loaded glass needle controlled with a Narshige micromanipulator. Placement is monitored before, during and after the procedure (up to two hours) by direct microscopic visualization using epifluorescent illumination. One skilled in the art would recognize that a variety of alternative placement techniques, such as those utilizing biolistics, endocytosis pathways, and protein transfection, could also be used to introduce Lipoparticles into cells.

Example 120

Detection of Cytosolic Fluctuations in $Ca^{++}$ Concentration Using Lipoparticles Lipoparticles are constructed by producing TRPV1-containing lipoparticles using a Gag/carboxylesterase-fusion protein as outlined herein, suspending them in $Ca^{++}$-free HBS, and loading them with the $Ca^{++}$ reporter, FURA-2. HEK-293 cells are grown to confluence, transferred to coverslips, and allowed to adhere. Lipoparticles are microinjected into 20 cells per coverslip, as described herein. Cells are stimulated with heat (heating to 43° C. activates TRPV1 in the Lipoparticles) and treated with TRAP-6, an agonist of the thrombin G-protein coupled receptor. Activation of the thrombin receptor initiates $Ca^{++}$ flux within the cell, causing $Ca^{++}$ entry into Lipoparticles through the open TRPV1 channels. Interaction of $Ca^{++}$ with the trapped Lipoparticle reporter, FURA-2, causes fluorescent emission, which is recorded in real time using a CCD camera mounted on a Nikon TE2000 inverted microscope using a 100× objective.

One skilled in the art would recognize that alternative means of activating TRPV1, including the use of ligands such as capsaicin, resiniferatoxin, and anandamide, and that alternative methods of stimulating this, and other cell signaling pathways, such as forskolin treatment, could similarly be used. A variety of cytoplasmic structures (e.g. cytoskeleton, membrane structures, transcription machinery) and events (e.g. cell signaling, enzyme activity, change in membrane potential, transcription and translation) could be monitored by altering the targeting, signaling and modifying components of the Lipoparticle appropriately. For example, the inclusion of the antibody-based ZZ-TM targeting component could localize and confine Lipoparticles to specific subcellular locations or events. The simultaneous combination of various targeting and signaling components could allow for the monitoring of cytoplasmic Lipoparticles using multimodal detection systems. Other modifications to the lipoparticle vehicle or components, such as PEGylation or polymerization of lipids, and fixation of proteins, could enhance or alter LipoProbe function within cells. Lipoparticles could also be used with a diverse range of other target cell formats, such as alternative secondary cell culture lines, primary cell cultures or isolates, permeabilized cells, and tissue explants or sections.

Example 121

Use of Lipoparticles as Modified Labeled Viruses

The purified virus is biotinylated and linked to streptavidin quantum dots, as described herein. Macrophages are prepared from healthy human volunteers using standard methods of practice. Labeled HIV is layered over the cells, and the interaction of the virus with the macrophages monitored in real time using a fluorescent microscope at 100× magnification and using a warmed microscope slide stage. Lipoparticles containing quantum dots but not expressing HIV Env are used as negative controls.

Labeled HIV virus can also be followed in vivo. A suspension of labeled HIV (containing quantum dots) in 50 µl of sterile HBS is injected intravenously into female CD1 mice (8 weeks of age). Mice are euthanized 24 hours later, conventional blood smears made, and histological sections of liver, spleen, kidney, lungs, lymph nodes, intestine, and brain prepared, and examined using fluorescent microscopy. Data are expressed as the proportion of tissue and cell populations exhibiting the quantum dot markers. Virions are expected to migrate to a number of tissues and cell types, including macrophages, dendritic cells, lymph nodes, and the liver. Toxicity, immune response, and the ability to target desired tissues and cells form the criteria for assessing the performance of Lipoparticles in live animals.

One skilled in the art would recognize that Lipoparticles expressing a variety of viral (e.g. MLV Envelope) and non-viral membrane proteins (e.g. EGFR, Fas-ligand, TNF receptor, Integrins), and containing a variety of reporters could be used ex vivo (with isolated cells or tissues) or in vivo in a similar manner. Lipoparticles could also be used to monitor protein and other active molecular interactions with primary or immortalized cells in culture. Lipoparticles could be used to monitor the effect of isolated viral or cell components on cell functions such as processing and phagocytosis in macrophages, or on whole-organism processes such as viral migration and tissue trafficking. These measurements could be made in real time, in whole animals (in vivo imaging), or as end-point measurements.

Example 122

Method of Hybridizing a Nucleic Acid Probe to a Lipoparticle

A large variety of fluorescent dyes that are capable of binding nucleic acids are available commercially. These dyes interact with features of DNA or RNA superstructure (e.g. SYBR green and DAPI bind the minor groove of double-stranded DNA) or with the nucleotide bases (e.g. YoYo1 and propidium iodide interchelate between the bases). These dyes are commonly used to monitor cell cycle activity in mammalian cells, and can be used to label nucleic acids within viruses and viral-derived structures such as lipoparticles. Retroviral structures that do not incorporate their own genomes will incorporate host cell RNA instead.

Figure 28:
FIG. 28. Visualization of lipoparticles stained with a nucleic acid dye. Lipoparticles adsorbed to a microscope coverslip, blocked with BSA, and exposed to a 20 mM solution of Alexa-Streptavidin (Molecular Probes) before the surface was rinsed with HBS and imaged. Both chemically and lipid (DPPE-biotin) biotinylated lipoparticles produced punctuate fluorescent images through Alexa-Streptavidin binding, whereas non-biotinylated lipoparticles did not bind the fluorescent protein. The same coverslip surface exposed to lipid biotin alone did not demonstrate any streptavidin binding.

Lipoparticles were produced from HEK-293 cells using methods previously described, and suspended in 10 nM solutions of YOYO-1 in HBS. After 20 min, Lipoparticles were visualized using fluorescence microscopy (FIG. 28). The stained lipoparticles could be visualized as fluorescent spots. One skilled in the art would recognize that alternative nucleic acid-specific fluorescent dyes could also be used, including, but not limited to, SYBR green, PicoGreen, SYTOX-1, ethidium bromide, DAPI, YO-PRO-1, TOTO-1, POPO-3, and propidium iodide. The lipoparticle may be stained with such dyes either before or after permeabilization with agents such as detergents or pore-forming peptides, or by mechanical means such as electroporation or sonication.

Example 123

Altering the Biochemistry of the Lipoparticle Interior

Lipoparticles can be used to monitor micro-environmental conditions, such as ion concentration, utilizing such sensing and modifying components as membrane ion channels, and to deliver molecules to specified extra- or intra-cellular sites. The efficiency and sensitivity of these Lipoparticle functions may be modified by characteristics of the lipoparticle contents, such as ion concentration, which are, to some extent, user-definable. The ionic content of lipoparticles can be altered by treating them with appropriate aqueous solutions. Although the lipid bilayer of lipoparticles is generally considered to be impermeable, ions will equilibrate across it over time. By soaking lipoparticles in solutions of high ion concentration, the ion content of the lipoparticles can be increased, and conversely, it can be decreased by soaking lipoparticles in solutions of low ion concentration. Lipoparticles (1 µg) are suspended in HBS containing 150 mM $CaCl_2$ and stored in darkness at 4° C. At 24 hour intervals, aliquots are passed through G50 Sephadex columns and re-suspended in HBS without $CaCl_2$. Lipoparticle fluorescence (indicating interior $Ca^{+2}$ accumulation) is measured in a stirred cuvette fluorometer by adding calcein, a fluorescent dye that fluoresces brightly in the presence of calcium. Lipoparticles without added $CaCl_2$ are used as a negative control. One skilled in the art would recognize that other biochemical characteristics of the lipoparticle interior, such as the concentration of other ions or small molecules, could also be altered by similar means.

Example 124

Stabilizing Lipoparticle Structure

Fixation of complex biological structures, such as cells and tissues, with aldehyde solutions such as formaldehyde and paraformaldehyde, results from the formation of methylene bridges between protein nitrogen atoms. This cross-linking preserves protein structural integrity, and forms an insoluble matrix that traps carbohydrates and lipids without altering their chemical composition. Fixation of lipoparticle protein or membrane constituents can alter their longevity and behavior in a number of applications such as immuno-probing. Lipoparticles containing the chemokine receptor CXCR4 are constructed by previously described methods. Aliquots of CXCR4-lipoparticles (1 µg total protein) are suspended in a 5% solution of paraformaldehyde in HBS, and aldehyde binding is allowed to proceed for 24 hours. Lipoparticles are then soaked in HBS, with several changes of solution, for 24 hours to remove unbound aldehyde molecules. Lipoparticles are passed through sucrose cushions and resuspended in fresh HBS. The structural integrity of the membrane proteins is verified by VELISA using conformationally-dependent MAbs, as described herein. The ability of CXCR4 to bind its cognate ligand, SDF-1, is also assessed by biosensor analysis. Unfixed lipoparticles containing CXCR4, and lipoparticles containing no specific membrane protein are used as controls. One skilled in the art would recognize that fixation of other lipoparticle membrane or non-membrane protein constituents could also be achieved using the same procedure, and that alterations to the fixation conditions, such as time, temperature, or buffer composition, could produce essentially similar results. Other fixatives, such as alternative protein cross-linking aldehydes (e.g. glutaraldehyde), or lipid fixa-

Example 125

Incorporation of Activating Molecules

Lipoparticles can be constructed to be capable of selective delivery of an active molecule, ryanodine, to intracellular ryanodine receptors. The ryanodine receptor (RyR) is a multi-isoform, intracellular membrane $Ca^{++}$ channel responsible for regulation of cytoplasmic calcium concentration in a variety of cells, including muscle cells (where it is found in the sarcoplasmic reticulum), and brain cells. Ryanodine, an ester of pyrrole-α-carboxylic acid with ryandolol, is a plant alkaloid capable of binding to and altering the activity of RyRs. Lipoparticles containing the ZZ-TM targeting fusion protein are constructed by methods described herein. Aliquots of ZZ-TM Lipoparticles are re-suspended in HBS containing 1 mmol/L of BODIPY-FL-X ryanodine (Molecular Probes), electroporated into lipoparticles. Unincorporated ryanodine is removed by passing lipoparticles through a Sephadex G50 spin column, resuspending in HBS. Lipoparticle fluorescence is measured in a stirred cuvette fluorometer, and monitored by direct visualization using fluorescence microscopy. FL-Ryanodine-ZZ-TM lipoparticles are made target specific using a monoclonal antibody (RDI-RYANRabm; Research Diagnostics Inc.) that recognizes RyR-1 and RyR-2 in a broad range of species and tissue types. HEK-293 cells are grown to confluence, transferred to coverslips, and allowed to adhere. Lipoparticles are microinjected into 20 cells per coverslip, and their intracellular distribution monitored in real time by direct visualization using fluorescent microscopy. Lipoparticles not containing a targeting antibody are used as controls. RyRs will be co-localized by double immunohistochemistry using a primary monoclonal antibody for RyR, and a fluorescently-labeled secondary antibody.

One skilled in the art would recognize that alternative methods for loading FL-ryanodine or other active compounds into Lipoparticles could also be used. One skilled in the art would recognize that a large variety of active compounds (e.g. terbium, bisindolylmaleimide, polymixin B, calmodulin, P2X receptor agonists (BzBzGTP and BzBzATP)), either native or modified (e.g. fluorescently tagged, caged), could alternatively be incorporated into the lipoparticle interior, or onto the lipoparticle surface, by this, or other methods. Using similar strategies, substrates can also be incorporated into lipoparticles, such as ELF97 (a fluorescent substrate), caspase-3 peptide substrates, DiFMUP phosphatase substrate, or other substrates that change color and/or fluorescence when altered by an enzyme such as beta galatosidase, a protease, a phospholipase, a kinase, or that respond to thiols, phosphates, pyrophosphates, or free phosphate, could also be incorporated into lipoparticles (Haugland (2003)). Lipoparticles could be used for the selective intracellular delivery of active molecules to a variety of cell and tissue formats, including cultured cells, tissue sections or explants, and in vivo.

Example 126

Detection of Lipoparticle-Virus Fusion

Lipoparticles can be used to monitor the process of receptor-mediated viral fusion using Lipoparticles containing viral envelope proteins ("effectors") and Lipoparticles containing viral receptors ("targets"). Gag/CFP-Lipoparticles containing the murine leukemia virus envelope protein (MLV-Env) are constructed. Separately, Gag/YFP-Lipoparticles containing murine Tva, a member of the LDL-superfamily of membrane proteins and a cognate host cell receptor for MLV, are also constructed. Gag/CFP and Gag/YFP are capable of fluorescence resonant energy transfer (FRET) if the fluorophores come into close proximity (<50 Å). This is possible in a mixing assay only if Lipoparticle membranes fuse as a result of MLV-Env interaction with Tva. Aliquots of each Lipoparticle preparation are mixed in HBS, and fluorescence is monitored in a stirred-cuvette fluorometer. When the particles fuse, FRET can be measured. Lipoparticles prepared with both Gag/CFP and Gag/YFP in the same particle are used as positive controls. Gag/CFP and Gag/YFP Lipoparticles lacking either or both membrane proteins are used as negative controls.

One skilled in the art would recognize that a variety of alternative methods for detecting the mixing of Lipoparticle contents can also be used to indicate fusion of lipoparticles. These include, but are not limited to, alternative FRET pairs (e.g. rhodamine and NBD, BODIPY and rhodamine, BODIPY and Texas Red), BRET pairs, dye/quencher pairs (e.g. ANTS/DPX and $Tb^{3+}$/DPA), dye/substrate pairs (e.g. Fluo-3 and calcium), and enzyme/fluorescent substrate pairs (e.g. carboxylesterase and calcein-AM). Alternatively, lipoparticle fusion can be detected by including reporters that indicate the mixing of membrane lipids. For example, FRET can occur from mixture of a donor phospholipid conjugate (e.g. NBD-PE) with an acceptor phospholipid conjugate (e.g. Rhodamine-PE). Other examples of detection systems can include octadecyl rhodamine B self-quenching and pyrene excimer formation, as described in the Molecular Probes handbook (Haugland (2003)). The viral-host cell interaction to be studied can be varied simply by including the desired viral and mammalian protein targets/targeting components. The system can be used to identify previously unknown viral host cell receptors, to monitor viral-host cell interaction kinetics, or to screen potential pharmaceutical inhibitors of viral-cell fusion.

Example 127

Detection of Lipoparticle Binding to Cells by FRET

FRET technology can be combined with the lipoparticle for detection of binding of the lipoparticle containing one receptor to cells containing a complementary receptor. Lipoparticles containing the membrane protein HIV Envelope are labeled with the fluorescent phospholipid rhodamine-PE. Separately, HEK-293 cells expressing CD4 on their surface are labeled with a phospholipid conjugated to the NBD fluorophore. When labeled particles are mixed with labeled cells, FRET occurs only when Env binds CD4. FRET is detected in using a Wallac Victor2V with samples in 96-well microplates. Labeled lipoparticles without Env and similarly labeled cells without CD4 can serve as negative controls. Such a system can be used to screen a library of candidate molecules for inhibitors of the membrane protein interactions.

One skilled in the art would recognize that the lipoparticle used here could be a live, replication-competent virus isolated from cells or a pseudotyped virus containing a viral Envelope protein. Similarly, the cells could be composed of cell lines, primary cells, or isolated tissues. On skilled in the art would also recognize that multiple additional fluorophores that serve as FRET pairs could also be used, including lipophilic dyes that can come into close proximity upon binding of lipoparticles.

Example 128

Detection of Ligand Binding to Lipoparticles by FRET

FRET technology can be used with the lipoparticle for detection of binding of a ligand to a receptor on the lipoparticle membrane. Lipoparticles containing the GPCR CXCR4 are labeled with the fluorescent phospholipid rhodamine-PE. Separately, the chemokine SDF is labeled with an NBD fluorophore. When labeled SDF is mixed with labeled lipoparticles, FRET will occur only when SDF binds to CXCR4. Labeled lipoparticles without CXCR4 and similarly labeled but non-specific chemokines can serve as negative controls. FRET is detected in using a Wallac Victor2V with samples in 96-well microplates. Such a system can be used to screen a library of candidate molecules for inhibitors of the ligand-receptor interaction. One skilled in the art would recognize that multiple additional fluorophores that serve as FRET pairs could also be used.

Example 129

Detection of Ligand Binding by Polarization

Lipoparticles can be used to detect binding of fluorophore-coupled HOE140 to lipoparticles expressing B2 bradykinin receptors by measuring fluorescent emission polarity. When fluorophores are exposed to polarized light such as a laser, molecules with their absorption transition vectors aligned parallel to the excitation vector will be selectively excited. During the period between excitation and emission, each fluorescent molecule will rotate such that light emission vectors will become randomized. As the speed of this molecular rotation is dependent upon the molecular weight of the fluorescent particle, fluorophores with lower molecular weights will be characterized by a more highly randomized emission vector distribution than those with higher molecular weights. A shift in the fluorescent emission polarity can be exploited to monitor the binding of relatively low molecular weight, fluorescently-labeled ligands (such as peptides and steroids) to relatively high molecular weight receptors or lipoparticles containing these receptors (the shift in polarity associated with the size differential between ligands and receptors expressed in lipoparticles would be extreme). Lipoparticles containing the B2 bradykinin receptor, a G-protein coupled receptor, are produced in HEK-293 cells. Aliquots of the B2-lipoparticles are suspended in HBS, added to the wells of 96-well plates and BODIPY TMR dye-labeled HOE140 (Molecular Probes) added in increasing concentrations. BODIPY dyes generally interfere less with receptor-binding affinity, possess greater molecular-weight range polarization sensitivity, and are less influenced by intrinsic sample fluorescence than other, more conventional dyes such as fluorescein and rhodamine. Fluorescence polarity is measured in real time using a Wallac Victor2V fluorescence plate reader (Perkin Elmer). Lipoparticles not containing any specific receptor are used as negative controls.

One skilled in the art would recognize that various other fluorescent labels can also be used as alternatives to BODIPY, and that a variety of ligand-receptor interactions can be similarly monitored by varying the ligand and the receptor incorporated into the lipoparticle. The binding of unlabeled ligands can similarly be monitored by adding a soluble, labeled ligand binder. The assay can be used to monitor binding kinetics of ligand-receptor interactions in the presence or absence of potential inhibitors, such as in high-throughput drug screening applications.

Example 130

Detection of Ligand Binding by Microscopy

Lipoparticles expressing the G-protein-coupled melanocortin receptor, MC4, are prepared. MC4-lipoparticles are immobilized on glass slides by adsorption, and non-specific adsorption sites blocked for 20 minutes using a 1% solution of BSA in HBS. Individual slides are then exposed to HBS solutions containing increasing concentrations of fluorescently labeled Fluo-NDP-αMSH (a fluorescein-labeled analog of the 13-mer MC4 agonist NDP-αMSH; Advanced Bioconcept Co.). After 45 minutes, slides are washed several times with buffer, and imaged at 100× magnification on a fluorescent microscope. Fluorescence intensity is quantified from digital images using Canvas software. Lipoparticles not containing any specific receptor are used as negative controls.

Additional fluorescent molecules, listed in the Molecular Probes Handbook (Haugland (2003)) and incorporated by reference herein could also be used. Such molecules include fibrinogen, gelatin, Type IV collagen, casein, cytochalasin B, Lipopolysaccharide (LPS), endostatin, fMLF receptor peptide, alpha-MSH (Melanocyte stimulating hormone) peptide, dexamethasone, Low-density lipoprotein (LDL), epidermal growth factor (EGF), transferrin, lactoferrin, fibrinogen, ovalbumin, bovine serum albumin, soybean trypsin inhibitor, Histone H, alpha crystalline, hyaluronic acid, mucin, subunit B of cholera toxin, chemotactic peptides, insulin, and heparin. Fluorescent molecules also include probes that bind to ion channels such as the L-type Ca+2 channel, intracellular Ca-channels, calcium pump, Na+/H+antiporter, Na+ channel, Na/K+ ATPase, Ca+-activated K+ channel, ATP-dependent K-channel, Glutamate gated Cl-channel. Fluorescent molecules also include probes that bind to neurotransmitter receptors such as alpha-Bungarotoxin (Nicotinic ACHR), acetylcholinesterase substrate, muscarinic acetylcholine receptor, pirenzepine fluorescent antagonist, prazosin (alpha1-adrenergic receptor), CGP 12177 (beta-adrenergic receptor), and muscimol (GABA-A receptor). Fluorescent molecules also include neuropeptides such as substance P, neuromedin C, angiotensin II, Naloxone, and naltrexone.

One skilled in the art would recognize that additional fluorescent or luminescent tags could be used as alternatives to fluorescein, and that the binding of ligands to a variety of receptors could be monitored in a similar manner by varying the receptor content of the immobilized lipoparticles. The use of confocal microscopy could overcome the need to wash slides, and allow monitoring of ligand to receptors in real time. The use of TIRF microscopy or flow cells could improve sensitivity. Alternative formats such as microfluidic flow cells and plates could also be used.

Example 131

Detection of Lipoparticles by Flow Cytometry

Figure 29:
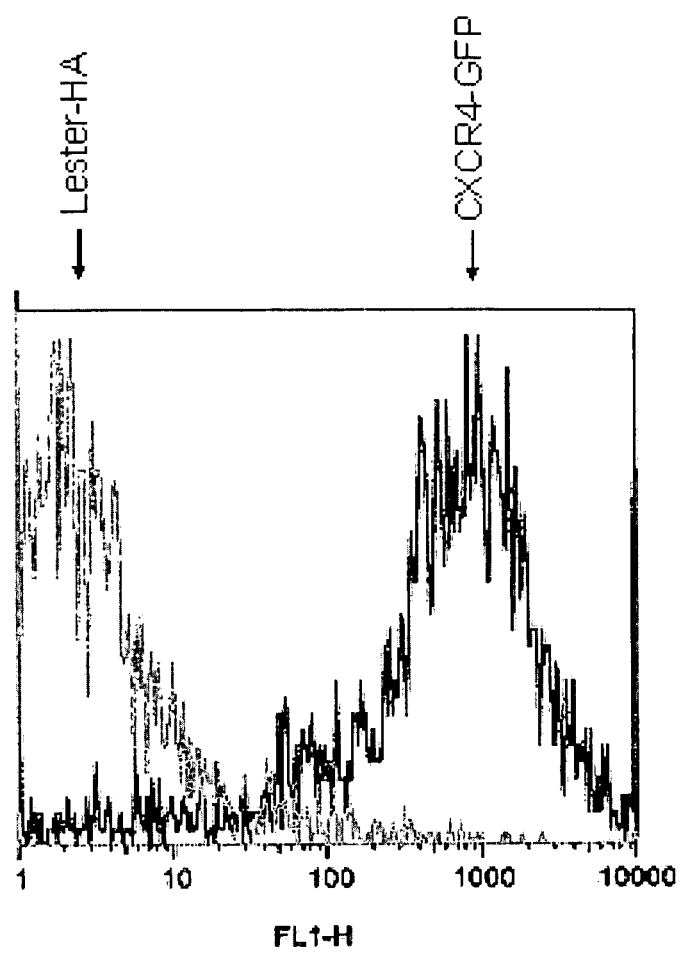
FIG. 29. Lipoparticles can be analyzed by flow cytometry. Two populations of lipoparticles, one incorporating fluorescently tagged CXCR4 (CXCR4-GFP), and the other incorporating control CXCR4 (a construct called Lestr-HA) were simultaneously analyzed by flow cytometry. Particles were gated using forward scatter, and fluorescence was detected at 488 nm excitation and 530 nm emission. Fluorescently labeled lipoparticles were characterized by higher fluorescence intensity compared with control non-fluorescent particles, demonstrating that labeled lipoparticles can be specifically identified using flow cytometry.

Flow cytometry is a technology in which simultaneous measurements of multiple characteristics are made on individual objects (such as cells or beads). A fluidics system manipulates the objects for interrogation, an optics system generates and collects light emissions, and an electronics component records the optical signals into digital recordings for analysis. Although some parameters of flow cytometry can be limited by resolution, other characteristics, such as side scatter and fluorescence intensity, can be measured for objects <200 nm. Lipoparticles containing a fluorescent fusion membrane protein, CXCR4/GFP, were produced and suspended in HBS. The Lipoparticle suspension was analyzed using a FACSCalibur flow cytometer (BD Biosciences), and gated using side scatter and fluorescent emission intensity (530 nm for the Lipoparticle gating reporter, GFP, after excitation at 488 nm). Lipoparticles containing a non-fluorescent version of CXCR4 (Lestr-HA) were used as a negative control. Results analyzed with CellQuest software indicate that fluorescent lipoparticles could be easily distinguished from non-fluorescent lipoparticles by flow cytometry (FIG. 29). 200 nm Fluoresbrite YG beads (Polysciences) were also used as a positive control.

One skilled in the art would recognize that a variety of reporters, incorporated by a number of methods, as described herein, could also be used to detect and identify lipoparticles for gating. These include fluorescent proteins fused to the structural core protein Gag, or to membrane proteins within the Lipoparticle, lipid-soluble fluorescent dyes, AM-ester dyes, or fluorescent dyes conjugated to the Lipoparticle surface using streptavidin-biotin linkage or covalent attachment. One skilled in the art would also realize that the number of fluorescent events counted by the flow cytometer is directly proportional to the number of lipoparticles in the sample, providing an estimate of the number of lipoparticles in the sample.

Example 132

Detection of Ligand Binding by Flow Cytometry

Commercial flow cytometers, in addition to detecting light diffraction (forward and side scatter) as an indication of size and internal granularity, are capable of making multiple, simultaneous measurements of fluorescent light emission intensity. Lipoparticles are constructed by producing lipoparticles containing CXCR4 using a Gag/GFP fusion protein as described herein. Aliquots of CXCR4-Gag/GFP-Lipoparticles (1 μg of protein) are suspended in HBS and 100 ng-100 ug solutions of APC-conjugated 12G5 antibody (a monoclonal antibody recognizing a conformational epitope on CXCR4) is added. After 30 minutes at room temperature, the Lipoparticle suspensions are passed through a FACSCalibur flow cytometer (BD Biosciences), and gated using fluorescence emission in FL1 (530 nm, for the Lipoparticle gating reporter, GFP) and side scatter. Fluorescence intensity in FL2 (661 nm for the APC-conjugated antibody) is measured. Gag/GFP-Lipoparticles containing a ZZ-TM antibody-binding protein with captured APC-antibody is used as a positive control. Lipoparticles not containing CXCR4 and unconjugated 12G5 antibody are used as negative controls. The specific binding of the antibody 12G5 to the receptor CXCR4 on the lipoparticle is detected.

One skilled in the art would recognize that Lipoparticles containing either no or alternative gating reporters (e.g. other Gag- or membrane protein-fusions, lipophilic dyes, other dyes and reporters encapsulated within the lipoparticle interior, or captured on the lipoparticle surface) could similarly be used. A wide variety of alternative target ligands (e.g. other receptor ligands, pathogen antigens, cancer markers, pathogen-specific antibodies, auto-immune antibodies) could similarly be detected by changing the recognition characteristics of the targeting component (e.g. other membrane receptors, antibody-bound ZZ-TM targeting protein) and the target reporter. The ligand to be detected may be fluorescently labeled for direct detection of binding or unlabeled and used for competition of a labeled ligand (e.g. for drug screening). The presence of target ligand could be expressed either semi-quantitatively (target reporter fluorescence intensity as a function of gating reporter fluorescence intensity), or quantitatively (using standard solutions of known target concentration). Multimodal detection is also possible by simultaneously combining multiple compatible targeting and signaling (gating and target recognition) components within the lipoparticle vehicle. One skilled in the art would also realize that the number of fluorescent events counted by the flow cytometer is directly proportional to the number of receptors in the sample, providing an estimate of the number of receptors in the sample.

Example 133

Detection and Quantitation of Anti-Viral Antibodies in Serum

Lipoparticles can be used to detect and quantify anti-viral antibodies in serum. HIV Env is a single-transmembrane protein that forms trimers in its functional and antigenically-correct form. The ability to identify and distinguish antibodies against trimeric Env versus monomeric Env would provide a better characterization of the neutralizing antibodies present in a patient's serum. Env-Lipoparticles are produced and biotinylated and attached to streptavidin-coated Luminex beads. Bead/lipoparticle sets are mixed with serum derived from patients infected with the pathogen, or with serum from uninfected controls, and the antibody is allowed to bind for 1 hour at room temperature, and then washed with PBS buffer. A fluorescent secondary anti-human IgG antibody is added and allowed to bind for 30 minutes at room temperature. Bead sets are washed and then flowed through a FACSCalibur flow-cytometer (Becton Dickinson), gating the fluorescent beads (with lipoparticles attached) using side scatter and bead-incorporated fluorescence. Each bead set can be distinguished by a unique optical signature (each bead incorporates a unique set of fluorescent markers). Viral-specific antibody is quantified by the relative intensity of the reporter antibody signal. Specific quantitation may be made relative to standards of known quantity, or by minimal detectable titration of the serum.

One skilled in the art would recognize that additional bead types and means of attachment, including alternative biotin-avidin linkage strategies, covalent attachment, or binding to lectins, could be used. In addition, fluorescent dyes and reporters may be incorporated into lipoparticles in various ways, by associating them with the core protein, membrane proteins, within the membrane lipid, or encapsulating them within the lipoparticle interior, either in place of or in addition to bead fluorescence. When lipoparticles are labeled, the efficiency of lipoparticle conjugation to bead sets could be determined by the detection of lipoparticle-associated dye emission. The system may be optimized to use several distinct viral antigens, separately or simultaneously, for the detection of stage of infection, or viral strain, as well as for sub-typing of immunoglobulin class by the use of reporter antibodies specific for IgG, IgM, or IgA. One skilled in the art would recognize that antibodies to other viral membrane antigens, including EBV gp340, gp84, and gp150, RSV G- or F-protein, or Influenza virus HA or NA, could also be detected in a similar manner.

Example 134

Multiplex Detection of Respiratory Viral Infections

Influenza and respiratory syncytial virus (RSV) account for the majority of viral respiratory tract infections, particularly in the very young. Infections are not clinically distinguishable from one another, the seasons of highest risk of infection overlap, and there is a broad range of overlapping clinical manifestations, necessitating laboratory techniques for definitive diagnosis. There is currently no technique on the market for the simultaneous detection of antibodies for these pathogens, and the ability to characterize the serological profile of a patient presenting with suspected viral respiratory disease will lead to more rapid and accurate diagnosis, and more rapid instigation of appropriate therapy. Lipoparticles containing the haemagluttinin and neuraminidase influenza viral membrane glycoproteins (HANA-lipoparticles) and lipoparticles containing the G- and F-envelope glycoproteins of RSV (GFRSV-lipoparticles) are prepared, biotinylated, and attached to optically-unique Luminex beads. Bead/lipoparticle sets are mixed with antibody-containing serum derived from human patients infected with either RSV or influenza (or both), washed, and then mixed with a fluorescent secondary anti-human IgG antibody. Bead sets are gated using side scatter and the unique fluorescent signal of each bead set, which will differentiate GFRSV-lipoparticles from HANA-lipoparticles. Viral-specific antibodies are quantitated from the intensity of the fluorescent signal from the secondary antibody in each gate. One skilled in the art would recognize that antibodies to other viral membrane antigens could also be detected in a similar manner.

Example 135

Detection of Serum Response to Viral-Encoded Host Cell Membrane Proteins

Lipoparticles can be used to develop a methodology for the detection of a serum response to ORF74, a GPCR encoded by human herpesvirus 8 (HHV8), and expressed on the surface of infected cells. HHV8 infection is associated with a number of neoplastic diseases, including Kaposi's sarcoma and pleural effusion lymphoma. There are currently a number of methods for the detection of both lytic and latent viral antigens, however, the ability to detect an antibody response against host-cell expressed viral proteins will aid in the differentiation of active and ongoing infection with HHV8. Lipoparticles expressing ORF74 are prepared, biotinylated, and attached to Luminex beads. Bead/lipoparticle sets are mixed with antibody-containing serum derived from human patients infected with HHV8, or with serum from uninfected controls, washed, and then mixed with a fluorescent secondary anti-human IgG antibody. ORF74-Lipoparticles/beads are separated and distinguished using flow cytometry, and ORF74-specific antibodies quantitated from the intensity of the fluorescent signal from the secondary antibody in each gate. One skilled in the art would recognize that antibodies to other viral-encoded membrane antigens, such as US28, UL32 and UL78 from CMV, or U12 and U51 from HH6 and HHV7, could be detected in a similar manner.

Example 136

Detection and Quantitation of Autoimmune Antibodies in Serum

Lipoparticles can be used to detect auto-antibodies to the thyrotropin (thyroid-stimulating hormone) receptor (TSHR) in serum. TSHR, the largest of the hormone receptors, is a seven-transmembrane G protein-coupled glycoprotein expressed in multiple tissues. Autoantibodies directed against this protein are implicated in both autoimmune hypothyroidism (Hashimoto thyroiditis) and autoimmune hyperthyroidism (Graves disease). The ability to routinely detect these antibodies in serum will complement more cumbersome confirmatory diagnostic techniques such as the measurement of radioiodine uptake. Lipoparticles incorporating TSHR are prepared, biotinylated, and attached to Luminex beads. Bead/lipoparticle sets are mixed with antibody-containing serum derived from human patients with autoimmune thyroid disease, or with healthy control serum, washed, and then mixed with a fluorescent secondary anti-human IgG antibody. TSHR-Lipoparticles/Beads are separated and distinguished, and TSH-R-specific antibodies quantitated from the intensity of the fluorescent signal from the secondary antibody in each gate. One skilled in the art would recognize that auto-antibodies directed against other membrane antigens, including acetylcholine receptors (myasthenia gravis) and calcium channels (Lambert-Eaton) could also be detected in a similar manner.

Example 137

Screening Hybridomas for Monoclonal Antibody Production

Lipoparticles can be used to simultaneously screen hybridoma cultures for the presence of monoclonal antibodies recognizing the Epstein-Barr virus (EBV) membrane glycoproteins gp340, gp84, and gp150. Monoclonal antibody production is a laborious and time-consuming procedure. The ability to utilize structurally intact membrane proteins (as opposed to synthetic peptides) to screen cultures will allow the more reliable isolation of conformationally-dependent antibodies. The ability to simultaneously detect and quantitate monoclonal antibodies produced by multiple hybridoma cultures will be a valuable time-saving feature. Hybridomas are produced as described elsewhere (Harlow, et al. (1989)), using whole, killed EBV inoculates. Three sets of lipoparticles, expressing the EBV membrane proteins gp340, gp84, and gp150 are produced, biotinylated, and attached to optically-unique Luminex bead sets. EBV-Bead/lipoparticle sets are mixed, singly, or in combination for 1 hour at room temperature with supernatant from 7-day hybridoma cultures, washed, and then mixed with anti-mouse fluorescent secondary antibody. Bead sets undergo flow cytometric analysis, gating upon side scatter and the unique fluorescent signal of each bead set, which will differentiate gp340-lipoparticles, gp84-lipoparticles, and gp150-lipoparticles. Monoclonal antibodies are quantitated from the intensity of the fluorescent signal from the secondary antibody in each gate. One skilled in the art would recognize that monoclonal antibodies directed against other membrane proteins, including human membrane proteins, could also be detected in a similar manner.

Example 138

Mapping Epitopes on Integral Membrane Proteins

Lipoparticles can be used to develop a system for the mapping of epitopes of the G protein-coupled receptor CCR2b. The characterization of monoclonal antibody interactions with structurally distinct epitopes of CCR2b enables these antibodies to be used to identify functional components of the receptor, including ligand binding sites. Hybridomas and monoclonal antibodies directed against CCR2b are produced as described previously. Lipoparticles incorporating wild-type and selective variants of CCR2b (containing CCR5 region substitutes (Rucker, et al. (1996), Cell, 87:437-446)) are produced, biotinylated, and attached to Luminex beads as described previously. Bead/lipoparticle sets are mixed with a monoclonal antibody directed against CCR2b, washed, and then mixed with fluorescent anti-mouse fluorescent secondary antibody. Bead sets undergo flow cytometric analysis as previously described, gating upon side scatter and the unique fluorescent signal of each bead set, which will differentiate wild-type CCR2b-lipoparticles, substituted mutant CCR2b-lipoparticles, and deleted mutant CCR2b-lipoparticles. Monoclonal antibodies are quantitated from the intensity of the fluorescent signal from the secondary antibody in each gate. One skilled in the art would recognize that monoclonal antibody interaction with other intact and structurally altered antigens could also be detected in a similar manner.

Example 139

Multiplex Detection of Unlabeled Ligands in Biological Fluids

Lipoparticles can be used to develop a multiplex detection system for unlabeled ligands of the G protein-coupled receptor CCR5 and CCR1. CCR5 binds the naturally-occurring chemokine ligands MIP1α, MIP1β and RANTES with nanomolar affinity. Chemokine receptors characteristically demonstrate wide ligand promiscuity, and some of these same ligands (e.g. MIP1α) are also known to bind other chemokine receptors, for example CCR1. The ability to detect and distinguish such natural ligands in biological fluids would be useful for diagnostic and research purposes. A system that can detect ligand-receptor interaction would also be useful for the identification of different, previously unrecognized receptor-ligand pairs. Two sets of lipoparticles are prepared, incorporating CCR5 or CCR1. Lipoparticles are attached to Luminex beads, pairing CCR5 lipoparticles with one uniquely colored bead set and CCR1 lipoparticles with a different uniquely colored bead set. Bead/lipoparticle sets are mixed with human serum for one hour, washed in Hepes buffered saline, and then mixed with fluorescently-labeled anti-MIP1α, anti-MIP1β, and anti-RANTES antibodies, each fluorescently labeled with a different color. Bead sets undergo flow cytometric analysis as previously described, gating upon side scatter and the unique fluorescent signal of each bead set. The unique fluorescent pattern of each Luminex bead set differentiates CCR5- from CCR1-containing beads. Binding of ligands to each receptor is quantitated from the intensity of the fluorescent signal from the fluorescently labeled antibody against each chemokine ligand. One skilled in the art would recognize that ligands of other membrane receptors could also be detected in a similar manner. On skilled in the art would recognize that additional membrane proteins could be analyzed in a similar manner, either individually or in multiplexed format.

Example 140

Purification of a Protein

Lipoparticles can be used as a vehicle for the in vitro production of the soluble protein sulfated glycoprotein-1 (SGP-1, also known as prosaposin). Conventional protein expression systems often possess limitations in their ability to produce sufficient quantities of some proteins (in the case of eukaryotic expression systems) or appropriately processed forms (in the case of prokaryotic expression systems) for structural analyses such as crystallography. Lipoparticles allow the production of large (milligram) quantities of highly concentrated proteins using mammalian cells to ensure physiologically appropriate post-translational modifications. A Gag/SGP-1 fusion plasmid will be constructed as previously described. The fusion gene will contain a consensus enterokinase protease cleavage site (see, for example, Jenny R J et al. Protein Expr Purif. 2003 September; 31(1):1-11; and Yuan L D et al. Protein Expr Purif. 2002 July; 25(2):300-4.) interposed between the Gag and SGP-1 domains. Lipoparticles are produced in HEK-293 cells using the Gag/SGP-1 fusion in a manner similar to that described previously for other Gag-fusion proteins. Harvested lipoparticles are lysed in a 1% solution of CHAPSO detergent, and the lysate passed through a sepharose affinity column covalently coupled with anti-Gag IgG. After washing with two column-volumes of buffer, Gag/SGP is eluted using high salt and/or low pH elution buffer, and concentrated by a centrifugation filter (Centricon™). The presence and purity of the Gag/SGP in the resultant filtrate is verified by polyacrylamide gel electrophoresis, and western blot using anti-Gag and anti-SGP antibodies. SGP can be released from the Gag partner as desired by treatment with enterokinase (Roche). One skilled in the art would recognize that any soluble protein, such as a kinase, phosphatase, or fluorescent protein, could be similarly expressed and purified using this technique.

Example 141

Lipoparticle Ligand Fishing

Lipoparticles bound to a bead substrate can be used to capture ligands for molecular identification. The identification of potential receptor ligands in complex biological mixtures such as blood serum presents a major challenge in pairing of orphan receptors and ligands. Affinity chromatography is a useful method for such "ligand fishing" applications. The characteristics of Lipoparticles significantly simplify affinity chromatography techniques for membrane proteins. Lipoparticles containing no specific membrane proteins ('null'-lipoparticles), and Lipoparticles containing the membrane receptor CCR5 are produced by techniques previously described. Both sets of Lipoparticles are surface-biotinylated as outlined previously. Neutravidin beads (Pierce) are suspended in HBS, biotinylated Lipoparticles are added, and lipoparticles are allowed to bind for 1 hour at room temperature. The lipoparticle-coated beads are packed into two separate glass columns, one containing the null-Lipoparticles and one containing the CCR5-Lipoparticles, and allowed to equilibrate by flowing through five column-volumes of HBS. Supernatant from the FC36.12 cell line (used originally to isolate the chemokines RANTES, MIP1α, and MIP1β as inhibitory factors of HIV (Cocchi, et al. (1995), Science, 270:1811-1815)) are applied to the null-Lipoparticle column, and the flow-through is collected. This column removes compounds that bind non-specifically to the beads and/or non-target components of the Lipoparticles. The null-Lipoparticle column can be regenerated by washing with HBS containing 2M NaCl, or other high salt solutions, or by washing with pH extremes. The collected flow through is applied to the CCR5-lipoparticle column, washed with five column volumes of buffer, and the flow through discarded. Molecules that have specifically bound to the Lipoparticle-incorporated CCR5 are eluted from the column using buffer containing 1M NaCl, and collected in fractions. This eluate is analyzed by SDS-PAGE gel with silver staining, as well as by mass spectroscopy, to analyze the protein content of the eluate. Ligands specific for CCR5 are isolated. This technique could be used to identify ligands, in a variety of sample formats, for any membrane protein by linking the appropriate Lipoparticles to the bead substrate. The technique could also be applied to chemical libraries for the identification of potential pharmaceutical agents that interact with membrane proteins.

Example 142

Measurement of an Arrayed Library with Lipoparticles

Lipoparticles are coated onto a poly-lysine slide by spraying onto the slide surface a solution of CXCR4-Lipoparticles and 1% sucrose (a stabilizer). The Lipoparticles are allowed to dry and are stored at 4 C. until ready to use. When ready for use, the slide is arrayed with a library of antibodies using a microarrayer. The antibodies are allowed to bind to the Lipoparticles and are then washed away. The binding of the antibodies is then detected by coating the entire slide with a fluorescent secondary antibody that recognizes the first antibody. The slide is washed and spots that have bound antibody are detected by visualizing fluorescent spots.

One skilled in the art would recognize that the library may be composed of antibodies, hybridoma supernatants, drug candidates, or peptides. One skilled in the art would also recognize that the library arrayed onto the Lipoparticles may also contain glycerol to prevent drying of the spots. Alternatively, Lipoparticles are coated by covering the entire slide with a solution of Lipoparticles in 1% sucrose, allowing Lipoparticles to attach for 1 hour, and then removing the Lipoparticle solution. The Lipoparticles may or may not be allowed to dry.

Example 143

Identifying a Binding Partner Using Phage Display

Immobilized Lipoparticles containing Kv1.3 (Aim 1.3) are used as specific target molecules to select phage displaying reactive scFV fragments ("panning"). Because phage panning is essentially a ligand binding reaction, biochemical parameters influencing binding specificity and affinity (e.g. NaCl concentration, pH, etc.) can be manipulated to control the stringency of selection. The values for these parameters are selected on the basis of round of phage selection (later rounds of selection can be higher stringency to isolate more specific or higher affinity phage) and the library (phage libraries created for specific antigens can contain larger numbers of phage and with greater binding affinities).

In the first round of panning, non-specific binding sites on immobilized Lipoparticles are blocked using Blotto (2% skimmed milk in PBS) and $10^{12}$-$10^{13}$ phage are added. Non-biotinylated Lipoparticles without Kv1.3 are also be included during phage binding to competitively adsorb phage that bind non-specifically to components of the Lipoparticle surface. After allowing binding to proceed for 2 h at room temperature, the beads are magnetically separated and washed extensively with PBS. Bound phage are eluted by Trypsin digestion, which cleaves the specific scFV-Kv1.3 interactions but leaves most non-specific interactions intact (hence improving phage selectivity), and does not affect phage coat proteins necessary for subsequent bacterial infection. The eluted phage are recovered in their host strain bacteria (TG1 E. coli) and expanded with the use of a helper strain of phage (KM13 provides phage proteins in trans that are replaced in phage libraries by antibody inserts). Two more rounds of panning can conducted to select for the most specific and highest affinity binders.

Phage isolated after the third round of panning are tested for reactivity to cells expressing Kv1.3 on their surface. Cells are grown to confluence in 96-well microplates and transiently transfected with a plasmid expressing Kv1.3. Non-specific binding sites are blocked with 3% BSA in PBS, and isolated phage are added. After removing unbound phage by washing, bound phage are detected using an anti-phage (M13) secondary MAb coupled to a reporter (HRP). Cells used for screening (quail QT6 cells) are of heterologous origin than the cells used to produce Lipoparticles (human HEK-293 cells) to reduce the probability of detecting phage against unwanted proteins. Cells lacking Kv1.3 are used as negative controls. Flow cytometry may be used as an alternative detection method. Phage that react with cells expressing Kv1.3 are sequenced to determine the encoded antibodies, and scFv fragments are isolated from bacterial periplasmic space (expressed as a scFv-pIII fusion protein from TG-1 E. coli, or as isolated scFv from the HB2151 non-suppressor strain of E. coli).

Western blotting is used to determine if the isolated MAbs are directed to linear or conformational epitopes of receptors (MAbs that react with denatured protein are nearly always to linear epitopes). Lysates of QT6 cells expressing Kv1.3 are separated by SDS-PAGE under denaturing conditions. The proteins are transferred to PVDF membranes, which is cut into strips, and exposed to isolated scFv. Reactivity of a MAb to a receptor by Western blot is indicative of recognition of a linear epitope within the receptor.

One of the most useful functions of any MAb is the ability to recognize and block important structural and/or functional determinants in a target protein. This ability to inhibit function directly enables humanized MAbs to serve as therapeutic agents, a role that polyclonal antibodies, intracellular-epitope antibodies, and linear-epitope antibodies are typically not capable of performing. The ability of selected phage to recognize conformational epitopes in Kv1.3-expressing cells is determined from their ability to competitively inhibit ligand binding. Briefly, quail QT6 cells expressing Kv1.3 are pre-incubated with phage-derived scFv's prior to addition of radiolabeled Charybdotoxin. The ability of each phage to competitively inhibit radioligand binding under a variety of conditions is determined. One skilled in the art would recognize that phage panning could also be conducted against whole virus or virus-like particles.

Example 144

Detection of GPCR Activation 3 ug CXCR4-Lipoparticles are suspended in a solution of 500 nM FL-GTP-γS. 10 uM melittin peptide is added to porate the Lipoparticles. One skilled in the art would recognize that alternative permeabilization conditions may also be employed, and that alternative methods for incorporation of FL-GTP-γS can also be used. These include, but are not limited to, poration using mild sonication or electroporation. Controls can include Lipoparticles without CXCR4 and CXCR4-Lipoparticles without melittin. To test GPCR signaling, CXCR4-Lipoparticles in a buffer containing 50 mM Hepes 8.0, 1 mM EDTA, 20 mM $MgCl_2$, 100 mM NaCl, and 1 mM DTT are stimulated with the CXCR4 agonist SDF-1. Stimulation of CXCR4 causes Gα to irreversibly bind FL- GTP-γS, allowing the BODIPY fluorophore to emit a detectable fluorescent signal. Fluorescence emission is not altered in null-Lipoparticles, or in Lipoparticles treated with a CXCR4 antagonist such as the antibody 12G5. Fluorescence is measured in real-time, beginning prior to addition of SDF-1, using a Perkin Elmer LS-50B fluorometer (excitation 485, emission 530). One skilled in the art would recognize that alternative guanine-nucleotides could be incorporated into Lipoparticles in a similar manner, including MANT-GTP, MANT-GMPPNP, BODIPY-FL-GTP, BODIPY-R6G-GTP, BODIPY-TR-GTP, BODIPY FL GMPPNP, BODIPY FL GTP-γ-S thioester, TNP-GTP (2'-(or 3'-)O-(trinitrophenyl) guanosine 5'-triphosphate), BzBzGTP (2'-(or 3'-)O-(4-benzoylbenzoyl)guanosine 5'-triphosphate), S-(DMNPE-caged) GTP-γ-S, or Europium-GTPγS. One skilled in the art would also recognize that the Lipoparticles within this example could be modified prior to stimulation with agonist to permit signaling components to interact. Such modification could include, but is not limited to, disruption by sonication, vortexing, or detergent; or poration using melittin, Streptolysin-O, polyethylene glycol, high amounts of calcium, or low amounts of alkanes. As an alternative to fluorescence emission, fluorescence polarization or FRET could also be used to detect binding of fluorescent GTPγS to the G protein within the Lipoparticle.

Example 145

Detection of GPCR Activation by FRET

YFP is fused to the carboxy-terminus of CXCR4 and CFP fused to the carboxy terminus of Gag. Fusion proteins are created using standard cloning methodology. Lipoparticles containing both proteins together are constructed. The fusion proteins are incorporated into these Lipoparticles as described herein. One skilled in the art would recognize that additional or alternative GPCRs, G proteins, and fluorescent protein labels could similarly be incorporated. One skilled in the art would recognize that the GPCR could contain the CFP protein and the Gag could contain the YFP protein. In some embodiments, the Lipoparticle is also constructed to contain a G protein, for example Gag-Gprotein. To test their function, the labeled Lipoparticles are exposed to the CXCR4 agonist SDF-1. Ligand binding by CXCR4 causes a conformational change in CXCR4 that induces a change in the relative proximity of the CFP and YFP tags, causing a change in the fluorescent emission from the CFP-YFP FRET pair. Fluorescence emission is not altered in null-Lipoparticles, or in Lipoparticles treated with a CXCR4 antagonist such as the antibody 12G5. Fluorescence is measured in real-time, beginning prior to the addition of SDF-1, using a Perkin Elmer LS-50B fluorometer.

Example 146

Generation of an Antibody Against a Gag-Fusion Protein

Luciferase is incorporated into Lipoparticles as described herein by fusing luciferase to Gag. Gag-luciferase lipoparticles are produced and purified. 300 ug of luciferase-containing lipoparticles are injected into mice as described herein. Polyclonal and monoclonal antibodies to luciferase-containing lipoparticles are generated as described in examples herein. The serum is screened for reactivity against luciferase using purified luciferase protein, and either polyclonal antibodies will be collected or hybridomas established for monoclonal antibody production.

Example 147

Creation of an Array of Viruses

HIV-1 virions from the strains JRFL, IIIB, and 89.6 are prepared by purifying viruses through sucrose cushions. The viruses are resuspended in 50 mM Hepes 7.0 containing 5% sucrose. Spots of viruses are arrayed on a polylysine slide using a microarrayer. The viruses are allowed to dry and the slide is stored at −20 C. until further use. When ready for use, the slide is brought to room temperature. An antibody against HIV-1 Envelope (b12) is used to probe the slide, using a fluorescent secondary antibody for detection. Reactivity of the antibody with viruses on the slide, a indicated by fluorescent spots, is indicative of the epitope contained within that strain of HIV-1. Reactivity of a broadly neutralizing antibody such as b 12 against a panel of diverse HIV-1 strains is indicative of the antibody's potency as part of a humoral immune response against the virus, a critical part of determining a test vaccine's potential. One skilled in the art would recognize that the viruses herein may be modified, such as with a fluorophore, biotin, avidin, streptavidin, or WGA to facilitate attachment and/or detection. One skilled in the art would also recognize that the probe used to detect the virus array may be a monoclonal antibody, a polyclonal serum, a phage, a lipoparticle, a protein, a peptide, an organic molecule, or an inorganic molecule. One skilled in the art would also recognize that other stabilizers could also be used, including glucose, glycerol, gelatin, or trehalose.

Example 148

Detection of an Array of Binding Partners Using a Lipoparticle

An array of antibodies is prepared by microarraying different monoclonal antibodies onto a surface. The array is then probed using a fluorescently labeled (Gag-GFP) lipoparticle containing the GPCR CXCR4. Spots that bind the lipoparticle, as visualized by fluorescence of the spot, indicate that CXCR4 has interacted specifically with a MAb at that spot. The identity of the MAb is known from the location on the array.

One skilled in the art would recognize that the array could consist of any number of molecules, including monoclonal antibodies, hybridoma supernatant, polyclonal antibodies, serum, phage, other lipoparticles, proteins, peptides, organic molecules, or inorganic molecules. One skilled in the art would also recognize that fluorescently labeled viruses or virus-like particles could also be used. Other means of labeling and detecting the particles could also be used, including fluorescence, luminescence, radioactivity, or magnetism.

Example 149

Creation of a Microarray of Lipoparticles

Figure 30:
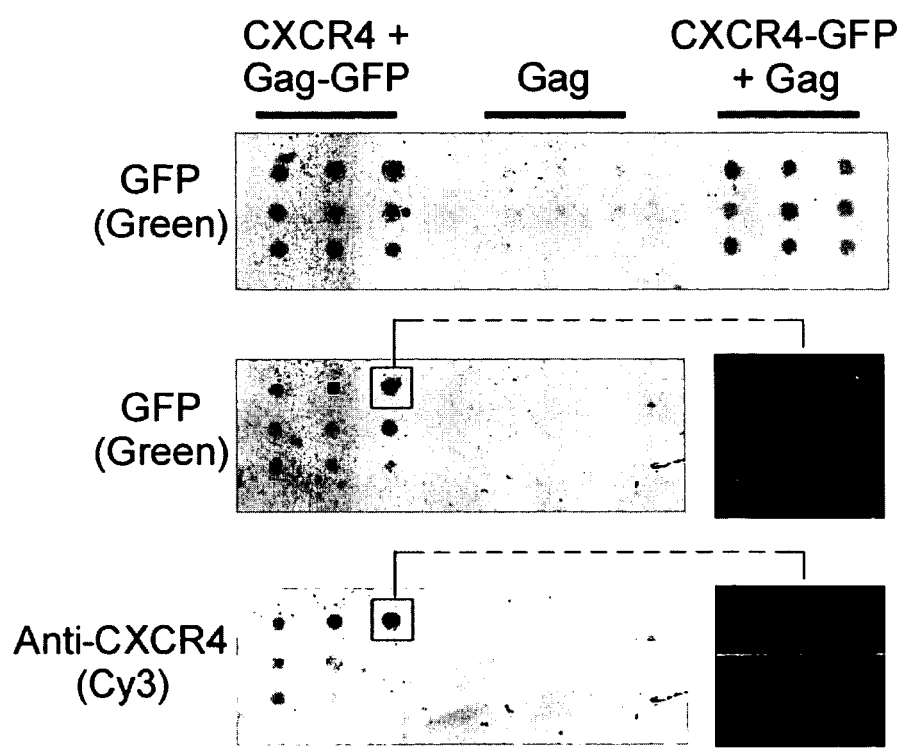
FIG. 30. Lipoparticles can be spotted on a microarray. Lipoparticles were constructed with either a fluorescent core (Gag-GFP), a fluorescent membrane protein (CXCR4-GFP), or non-fluorescent versions of the same (Gag and CXCR4). Sucrose was added to lipoparticles to a final concentration of 5%. Spots of lipoparticles were then arrayed on a polylysine slide using a microarray device. The lipoparticles were allowed to dry and were stored at 4 C. until further use. Fluorescence in the green channel was visualized by imaging the lipoparticles with a FITC filter on an AlphaArray 7500i (top panel). The slide was then probed with a conformation-dependent anti-CXCR4 MAb (447.08). Binding of this primary antibody was detected using a Cy3-labeled secondary antibody (red channel). After staining, the array was again visualized using both green and red filters (middle and bottom panels). Green spots (middle panel) indicated that the lipoparticles were still bound to the slide, and red spots (bottom panel) indicated that CXCR4 within the lipoparticles was present and structurally intact. Control Gag particles without CXCR4 or GFP demonstrated little or no background.

Lipoparticles were constructed with either a fluorescent core (Gag-GFP), a fluorescent membrane protein (CXCR4-GFP), or non-fluorescent versions of the same (Gag and CXCR4). Lipoparticles were prepared and purified as described herein. Sucrose was added to Lipoparticles to a final concentration of 5%. Spots of Lipoparticles were then arrayed on a polylysine slide using a microarrayer. The Lipoparticles were allowed to dry and were stored at 4 C. until further use. Fluorescence in the green channel was visualized by imaging the Lipoparticles with a FITC filter on an AlphaInnotech AlphaArray 7500i (FIG. 30). The slide was then probed with a conformation-dependent anti-CXCR4 MAb (447.08). Binding of this primary antibody was detected using a Cy3-labeled secondary antibody. Slides were washed with PBS after incubation with each antibody. After staining, the array was again visualized using both green and red filters. Green spots indicated that the Lipoparticles were still bound to the slide, and red spots indicated that CXCR4 within the Lipoparticles was present and structurally intact. Control Gag particles without CXCR4 or GFP demonstrated little or no background.

The disclosures of each and every patent, patent application, publication, and accession number cited herein are hereby incorporated herein by reference in their entirety. The appended sequence listing is hereby incorporated herein by reference in its entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A lipoparticle comprising
an external lipid bilayer;
an enveloped retroviral structural protein; and
a multiple membrane spanning protein,
wherein said enveloped retroviral structural protein is an uncleaved gag protein and wherein the multiple membrane spanning protein that is incorporated into the lipoparticle does not bind to the gag protein,
provided that the only viral proteins in the lipoparticle are structural proteins.

2. The lipoparticle of claim 1 wherein said multiple membrane spanning protein is a G protein coupled receptor.

3. The lipoparticle of claim 1, wherein said Gag is from murine leukemia virus, rous sarcoma virus, HIV, SIV, avian leukemia virus, or equine anemia virus.

4. A composition comprising an isolated lipoparticle of claim 1 attached to a biosensor surface.

5. The lipoparticle of claim 1, further comprising a G-protein.

6. The lipoparticle of claim 5, wherein said G-protein is a modified G-protein.

7. The lipoparticle of claim 6, wherein said modified G-protein comprises a fusion protein.

8. The lipoparticle of claim 7, wherein said fusion protein comprises a fluorescent protein, a linker, a viral protein, membrane protein, a protease cleavage sequence, or combinations thereof.

9. The lipoparticle of claim 2, wherein said G protein coupled receptor (GPCR) is a modified GPCR.

10. The lipoparticle of claim 9, wherein said modified GPCR comprises a fusion protein.

11. The lipoparticle of claim 10, wherein said fusion protein comprises a fluorescent protein, a linker, a viral protein, membrane protein, a protease cleavage sequence, or combinations thereof.

12. The lipoparticle of claim 5 further comprising a GTP analog.

13. The lipoparticle of claim 12 wherein said GTP analog is a fluorescent GTP analog.

14. An immunogen comprising a lipoparticle according to claim 1.

15. A method of eliciting an immune response to a multiple membrane spanning protein, said method comprising the introduction of the lipoparticle of claim 1 to an animal.

16. The lipoparticle of claim 1, wherein said multiple membrane spanning protein is an ion channel protein.

17. The lipoparticle of claim 1, wherein said multiple membrane spanning protein is a transporter protein.

18. A lipoparticle comprising
an external lipid bilayer;
an enveloped retroviral structural protein; and
a multiple membrane spanning protein,
wherein said enveloped retroviral structural protein is an unmodified, uncleaved gag protein and, provided that the only viral proteins in the lipoparticle are structural proteins.

19. A lipoparticle comprising
an external lipid bilayer;
an enveloped retroviral structural protein; and a multiple membrane spanning protein,
wherein said enveloped retroviral structural protein is an uncleaved gag protein and wherein said gag protein does not comprise a heterologous tag,
provided that the only viral proteins in the lipoparticle are structural proteins.

* * * * *

SEQUENCE LISTING

```
<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: Protease cleavage sequence

<400> SEQUENCE: 1

Ser Ala Ala Trp Pro
1               5

<210> SEQ ID NO 2
<211> LENGTH: 5
<212> TYPE: PRT
<213> ORGANISM: Artificial Sequence
<220> FEATURE:
<223> OTHER INFORMATION: Protease cleavage sequence

<400> SEQUENCE: 2

Thr Ala Ala Tyr Pro
1               5

<210> SEQ ID NO 3
<211> LENGTH: 5
<212> TYPE: PRT
<213> ORGANISM: Artificial Sequence
<220> FEATURE:
<223> OTHER INFORMATION: Protease cleavage sequence

<400> SEQUENCE: 3

Ser Ala Ala Phe Pro
1               5

<210> SEQ ID NO 4
<211> LENGTH: 5
<212> TYPE: PRT
<213> ORGANISM: Artificial Sequence
<220> FEATURE:
<223> OTHER INFORMATION: Protease cleavage sequence

<400> SEQUENCE: 4

Ser Val Ala Tyr Pro
1               5

<210> SEQ ID NO 5
<211> LENGTH: 5
<212> TYPE: PRT
<213> ORGANISM: Artificial Sequence
```

```
<220> FEATURE:
<223> OTHER INFORMATION: Protease cleavage sequence

<400> SEQUENCE: 5

Ser Ala Gly Tyr Pro
1               5

<210> SEQ ID NO 6
<211> LENGTH: 5
<212> TYPE: PRT
<213> ORGANISM: Artificial Sequence
<220> FEATURE:
<223> OTHER INFORMATION: Protease cleavage sequence
<220> FEATURE:
<221> NAME/KEY: misc_feature
<222> LOCATION: (5)..(5)
<223> OTHER INFORMATION: X is any amino acid residue

<400> SEQUENCE: 6

Asp Asp Asp Lys Xaa
1               5

<210> SEQ ID NO 7
<211> LENGTH: 5
<212> TYPE: PRT
<213> ORGANISM: Artificial Sequence
<220> FEATURE:
<223> OTHER INFORMATION: Protease cleavage sequence
<220> FEATURE:
<221> NAME/KEY: MISC_FEATURE
<222> LOCATION: (5)..(5)
<223> OTHER INFORMATION: Xaa is any amino acid residue

<400> SEQUENCE: 7

Glu Glu Glu Lys Xaa
1               5
```